(12) United States Patent
Birkus et al.

(10) Patent No.: US 10,966,999 B2
(45) Date of Patent: *Apr. 6, 2021

(54) 3'3' CYCLIC DINUCLEOTIDES WITH PHOSPHONATE BOND ACTIVATING THE STING ADAPTOR PROTEIN

(71) Applicant: INSTITUTE OF ORGANIC CHEMISTRY AND BIOCHEMISTRY ASCR, V.V.I., Prague (CZ)

(72) Inventors: Gabriel Birkus, Prague (CZ); Ondrej Pav, Prague (CZ); Tomas Jandusik, Prague (CZ); Ivan Rosenberg, Prague (CZ); Radim Nencka, Prague (CZ)

(73) Assignee: INSTITUTE OF ORGANIC CHEMISTRY AND BIOCHEMISTRY ASCR, V.V.I., Prague (CZ)

(*) Notice: Subject to any disclaimer, the term of this patent is extended or adjusted under 35 U.S.C. 154(b) by 0 days.

This patent is subject to a terminal disclaimer.

(21) Appl. No.: 16/225,986

(22) Filed: Dec. 19, 2018

(65) Prior Publication Data

US 2019/0183917 A1 Jun. 20, 2019

Related U.S. Application Data

(60) Provisional application No. 62/608,373, filed on Dec. 20, 2017, provisional application No. 62/725,858, filed on Aug. 31, 2018.

(51) Int. Cl.

| | | |
|---|---|---|
| *A61K 31/7084* | (2006.01) | |
| *A61K 39/39* | (2006.01) | |
| *A61P 35/00* | (2006.01) | |
| *A61P 31/18* | (2006.01) | |
| *A61K 31/708* | (2006.01) | |
| *A61K 45/06* | (2006.01) | |
| *C07H 21/02* | (2006.01) | |

(52) U.S. Cl.
CPC ........ *A61K 31/7084* (2013.01); *A61K 31/708* (2013.01); *A61K 39/39* (2013.01); *A61K 45/06* (2013.01); *A61P 31/18* (2018.01); *A61P 35/00* (2018.01); *C07H 21/02* (2013.01)

(58) Field of Classification Search
USPC .......................................................... 514/38
See application file for complete search history.

(56) References Cited

U.S. PATENT DOCUMENTS

| | | | |
|---|---|---|---|
| 4,943,593 A | 7/1990 | Palfreyman et al. | |
| 4,965,288 A | 10/1990 | Palfreyman et al. | |
| 4,997,854 A | 3/1991 | Kagan et al. | |
| 5,021,456 A | 6/1991 | Palfreyman et al. | |
| 5,059,714 A | 10/1991 | Palfreyman et al. | |
| 5,120,764 A | 6/1992 | McCarthy et al. | |
| 5,182,297 A | 1/1993 | Palfreyman et al. | |
| 5,252,608 A | 10/1993 | Palfreyman et al. | |
| 5,866,567 A * | 2/1999 | Ohkawa | C07D 401/14 514/220 |
| 6,319,494 B1 | 11/2001 | Capon et al. | |
| 7,446,190 B2 | 11/2008 | Sadelain et al. | |
| 7,741,465 B1 | 6/2010 | Eshhar et al. | |
| 8,450,321 B2 | 5/2013 | Mitchell et al. | |
| 8,513,184 B2 | 8/2013 | Appleby et al. | |
| 8,691,809 B2 | 4/2014 | Howbert et al. | |
| 8,722,054 B2 | 5/2014 | Apelian et al. | |
| 9,089,520 B2 | 7/2015 | Brenner | |
| 9,181,288 B2 | 11/2015 | Hartman et al. | |
| 9,186,337 B2 | 11/2015 | Baker et al. | |
| 9,670,205 B2 | 6/2017 | Aktoudianakis et al. | |
| 9,884,866 B2 | 2/2018 | Ferguson et al. | |
| 2004/0248871 A1 | 12/2004 | Farjanel et al. | |
| 2008/0234251 A1 | 9/2008 | Doherty et al. | |
| 2008/0306050 A1 | 12/2008 | Doherty et al. | |
| 2009/0047249 A1 | 2/2009 | Graupe et al. | |
| 2009/0142345 A1 | 6/2009 | Satou et al. | |
| 2010/0015178 A1 | 1/2010 | Combs et al. | |
| 2010/0029585 A1 | 2/2010 | Howbert et al. | |
| 2010/0143301 A1 | 6/2010 | Desai et al. | |
| 2011/0092485 A1 | 4/2011 | Howbert et al. | |
| 2011/0098248 A1 | 4/2011 | Halcomb et al. | |
| 2011/0118235 A1 | 5/2011 | Howbert et al. | |

(Continued)

FOREIGN PATENT DOCUMENTS

| | | |
|---|---|---|
| WO | 2003/099840 | 12/2003 |
| WO | 2004/096286 A2 | 11/2004 |

(Continued)

OTHER PUBLICATIONS

Zhang et al, Molecular Cell, 2013, 51, 226-235.*
Pressova et al, Biopolymers, 2010, 93, 277-289.*
Gaffney et al, Org. Lett, 2010, 12(14), 3269-3271.*
European Patent Office, International Search Report and Written Opinion for PCT International Patent Application No. PCT/IB2018/060382, dated Mar. 14, 2018, 11 pages.
European Patent Office, International Search Report and Written Opinion for PCT International Patent Application No. PCT/IB2018/060381, dated Mar. 14, 2018, 9 pages.

(Continued)

*Primary Examiner* — Ganapathy Krishnan
(74) *Attorney, Agent, or Firm* — Notaro, Michalos & Zaccaria P.C.

(57) ABSTRACT

Provided herein are the 3'3' cyclic phosphonate dinucleotides of general formula J, their pharmaceutically acceptable salts, a pharmaceutical composition containing them and combinations of said substances and other medicaments or pharmaceuticals. The disclosure also relates to the use of said compounds for the treatment or prevention of diseases or conditions modifiable by STING protein modulation, such as cancer or viral, allergic and inflammatory diseases. In addition, these substances can be used as adjuvants in vaccines.

20 Claims, No Drawings
Specification includes a Sequence Listing.

(56) References Cited

U.S. PATENT DOCUMENTS

| | | |
|---|---|---|
| 2011/0287011 A1 | 11/2011 | Gurney et al. |
| 2012/0082658 A1 | 4/2012 | Hershberg |
| 2012/0219615 A1 | 8/2012 | Hershberg et al. |
| 2013/0079327 A1 | 3/2013 | Yamamoto et al. |
| 2013/0165489 A1 | 6/2013 | Cocklin et al. |
| 2013/0217880 A1 | 8/2013 | Yamamoto et al. |
| 2013/0251673 A1 | 9/2013 | Hartman et al. |
| 2013/0267517 A1 | 10/2013 | Guo et al. |
| 2013/0344029 A1 | 12/2013 | Aciro et al. |
| 2013/0344030 A1 | 12/2013 | Steadman et al. |
| 2014/0030221 A1 | 1/2014 | Aciro et al. |
| 2014/0045849 A1 | 2/2014 | McGowan et al. |
| 2014/0066432 A1 | 3/2014 | Howbert et al. |
| 2014/0073642 A1 | 3/2014 | McGowan et al. |
| 2014/0088085 A1 | 3/2014 | Burgess et al. |
| 2014/0171432 A1 | 6/2014 | Kanouni et al. |
| 2014/0178337 A1 | 6/2014 | Hartman et al. |
| 2014/0194469 A1 | 7/2014 | Nie et al. |
| 2014/0213591 A1 | 7/2014 | Chen et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0275084 A1 | 9/2014 | Kanouni et al. |
| 2014/0275092 A1 | 9/2014 | Albrecht et al. |
| 2014/0275167 A1 | 9/2014 | Hartman |
| 2014/0330015 A1 | 11/2014 | Yamamoto et al. |
| 2014/0341976 A1 | 11/2014 | Dubensky et al. |
| 2014/0343032 A1 | 11/2014 | Guo et al. |
| 2014/0350031 A1 | 11/2014 | Mc et al. |
| 2014/0371195 A1 | 12/2014 | Labelle et al. |
| 2014/0371214 A1 | 12/2014 | Labelle et al. |
| 2015/0031687 A1 | 1/2015 | Guo et al. |
| 2015/0132258 A1 | 5/2015 | Hartman |
| 2015/0175616 A1 | 6/2015 | Blomgren et al. |
| 2015/0197533 A1 | 7/2015 | Hartman et al. |
| 2015/0210682 A1 | 7/2015 | Han et al. |
| 2015/0225355 A1 | 8/2015 | Hartman |
| 2015/0252057 A1 | 9/2015 | Guo et al. |
| 2015/0259324 A1 | 9/2015 | Hartman et al. |
| 2015/0274652 A1 | 10/2015 | Hartman |
| 2015/0315159 A1 | 11/2015 | Hartman |
| 2016/0039808 A1 | 2/2016 | Kanouni et al. |
| 2016/0102096 A1 | 4/2016 | Boesen et al. |
| 2016/0122344 A1 | 5/2016 | Han et al. |
| 2016/0137652 A1 | 5/2016 | Beck et al. |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2016/0289229 A1 | 10/2016 | Aktoudianakis et al. |
| 2017/0044206 A1 | 2/2017 | Altman et al. |
| 2017/0121328 A1 | 5/2017 | Hartman et al. |
| 2017/0121329 A1 | 5/2017 | Hartman et al. |
| 2017/0158724 A1 | 6/2017 | Adams et al. |
| 2017/0334882 A1 | 11/2017 | Hartman et al. |
| 2017/0334898 A9 | 11/2017 | Guo et al. |
| 2018/0030053 A1 | 2/2018 | Fu et al. |
| 2018/0065929 A1 | 3/2018 | Vandyck et al. |
| 2018/0065938 A1 | 3/2018 | Chin et al. |
| 2018/0086755 A1 | 3/2018 | Chin et al. |
| 2018/0258132 A1 | 9/2018 | Adams et al. |

FOREIGN PATENT DOCUMENTS

| | | |
|---|---|---|
| WO | 2005113556 A1 | 12/2005 |
| WO | 2006015261 A2 | 2/2006 |
| WO | 2006/110157 A2 | 10/2006 |
| WO | WO 2007/054279 A2 * | 5/2007 |
| WO | 2008005542 A2 | 1/2008 |
| WO | 2008005555 A1 | 1/2008 |
| WO | 2009017833 A2 | 2/2009 |
| WO | 2009062285 A1 | 5/2009 |
| WO | 2010130034 A1 | 11/2010 |
| WO | 2011008709 A1 | 1/2011 |
| WO | 2011097513 A1 | 8/2011 |
| WO | 2011161699 A2 | 12/2011 |
| WO | 2012003497 A1 | 1/2012 |
| WO | 2012003498 A1 | 1/2012 |
| WO | 2012027721 A2 | 3/2012 |
| WO | 2012079000 A4 | 8/2012 |
| WO | 2012145728 A1 | 10/2012 |
| WO | 2012168944 A1 | 12/2012 |
| WO | 2013006738 A1 | 1/2013 |
| WO | 2013006792 A1 | 1/2013 |
| WO | 2013027802 A1 | 2/2013 |
| WO | 2013034933 A1 | 3/2013 |
| WO | 2013052699 A2 | 4/2013 |
| WO | 2013091096 A1 | 6/2013 |
| WO | 2013096744 A1 | 6/2013 |
| WO | 2013112741 A1 | 8/2013 |
| WO | 2013116562 A1 | 8/2013 |
| WO | 2013144129 A1 | 10/2013 |
| WO | 2013144704 A1 | 10/2013 |
| WO | 2013159064 A1 | 10/2013 |
| WO | 2013173223 A1 | 11/2013 |
| WO | 2013185052 A1 | 12/2013 |
| WO | 2013132317 A9 | 1/2014 |
| WO | 2014023813 A1 | 2/2014 |
| WO | 2014033167 A1 | 3/2014 |
| WO | 2014033170 A1 | 3/2014 |
| WO | 2014033176 A1 | 3/2014 |
| WO | 2014037480 A1 | 3/2014 |
| WO | 2014047624 A1 | 3/2014 |
| WO | 2014056953 A1 | 4/2014 |
| WO | 2014073738 A1 | 5/2014 |
| WO | 2014076221 A1 | 5/2014 |
| WO | 2009035791 A9 | 6/2014 |
| WO | 2014093936 A1 | 6/2014 |
| WO | 2014100323 A1 | 6/2014 |
| WO | 2014100765 A1 | 6/2014 |
| WO | 2014100767 A1 | 6/2014 |
| WO | 2014128189 A1 | 8/2014 |
| WO | 2014131847 A1 | 9/2014 |
| WO | 2014151634 A1 | 9/2014 |
| WO | 2014161888 A1 | 10/2014 |
| WO | 2014164708 A1 | 10/2014 |
| WO | 2014179760 A1 | 11/2014 |
| WO | 2014184350 A1 | 11/2014 |
| WO | 2014184365 A1 | 11/2014 |
| WO | 2014189806 A1 | 11/2014 |
| WO | 2014201409 A1 | 12/2014 |
| WO | 2014189805 A8 | 1/2015 |
| WO | 2015011281 A1 | 1/2015 |
| WO | 2015014815 A1 | 2/2015 |
| WO | 2015019284 A2 | 2/2015 |
| WO | 2015023958 A1 | 2/2015 |
| WO | 2015033299 A1 | 3/2015 |
| WO | 2015033301 A1 | 3/2015 |
| WO | 2015033303 A1 | 3/2015 |
| WO | 2015034820 A1 | 3/2015 |
| WO | 2015036927 A1 | 3/2015 |
| WO | 2015044900 A1 | 4/2015 |
| WO | 2015057655 A1 | 4/2015 |
| WO | 2015057659 A1 | 4/2015 |
| WO | 2015059212 A1 | 4/2015 |
| WO | 2015077354 A1 | 5/2015 |
| WO | 2015088045 A1 | 6/2015 |
| WO | 2015095780 A1 | 6/2015 |
| WO | 2015118057 A1 | 8/2015 |
| WO | 2015119944 A1 | 8/2015 |
| WO | 2015134605 A1 | 9/2015 |
| WO | 2015157386 A1 | 10/2015 |
| WO | 2015160641 A2 | 10/2015 |
| WO | 2015162075 A1 | 10/2015 |
| WO | 2015168269 A1 | 11/2015 |
| WO | 2015168279 A1 | 11/2015 |
| WO | 2015173164 A1 | 11/2015 |
| WO | 2015179615 A1 | 11/2015 |
| WO | 2015185565 A1 | 12/2015 |
| WO | 2015188085 A1 | 12/2015 |
| WO | 2016012470 A1 | 1/2016 |
| WO | 2016019232 A1 | 2/2016 |
| WO | 2016023511 A1 | 2/2016 |
| WO | 2016023877 A1 | 2/2016 |
| WO | 2016029077 A1 | 2/2016 |

(56) References Cited

FOREIGN PATENT DOCUMENTS

| | | |
|---|---|---|
| WO | 2016033570 A1 | 3/2016 |
| WO | 2016039749 A1 | 3/2016 |
| WO | 2016055553 A1 | 4/2016 |
| WO | 2016057624 A1 | 4/2016 |
| WO | 2016057924 A1 | 4/2016 |
| WO | 2016075661 A1 | 5/2016 |
| WO | 2016077518 A1 | 5/2016 |
| WO | 2016090190 A1 | 6/2016 |
| WO | 2016091698 A1 | 6/2016 |
| WO | 2016096174 A1 | 6/2016 |
| WO | 2016096577 A1 | 6/2016 |
| WO | 2016096778 A1 | 6/2016 |
| WO | 2016100236 A2 | 6/2016 |
| WO | 2016100285 A1 | 6/2016 |
| WO | 2016100608 A1 | 6/2016 |
| WO | 2016102438 A1 | 6/2016 |
| WO | 2016107536 A1 | 7/2016 |
| WO | 2016107832 A1 | 7/2016 |
| WO | 2016107833 A1 | 7/2016 |
| WO | 2016120186 A1 | 8/2016 |
| WO | 2016120305 A1 | 8/2016 |
| WO | 2016126646 A1 | 8/2016 |
| WO | 2016128335 A1 | 8/2016 |
| WO | 2016141092 A1 | 9/2016 |
| WO | 2016142250 A1 | 9/2016 |
| WO | 2016142833 A1 | 9/2016 |
| WO | 2016142835 A1 | 9/2016 |
| WO | 2016142852 A1 | 9/2016 |
| WO | 2016142886 A2 | 9/2016 |
| WO | 2016142894 A1 | 9/2016 |
| WO | 2016145102 A1 | 9/2016 |
| WO | 2016149351 A1 | 9/2016 |
| WO | 2016161268 A1 | 10/2016 |
| WO | 2016168619 A1 | 10/2016 |
| WO | 2016177655 A1 | 11/2016 |
| WO | 2016180743 A1 | 11/2016 |
| WO | 2016195982 A2 | 12/2016 |
| WO | 2016196388 A1 | 12/2016 |
| WO | 2017001307 A1 | 1/2017 |
| WO | 2017001655 A1 | 1/2017 |
| WO | 2017001853 A1 | 1/2017 |
| WO | 2017007701 A1 | 1/2017 |
| WO | 2017013046 A1 | 1/2017 |
| WO | 2017016960 A1 | 2/2017 |
| WO | 2017017042 A1 | 2/2017 |
| WO | 2017017043 A1 | 2/2017 |
| WO | 2017017624 A1 | 2/2017 |
| WO | 2017027434 A1 | 2/2017 |
| WO | 2017027645 A1 | 2/2017 |
| WO | 2017027646 A1 | 2/2017 |
| WO | 2017034986 A1 | 3/2017 |
| WO | 2017038909 A1 | 3/2017 |
| WO | 2017040233 A1 | 3/2017 |
| WO | 2017046112 A1 | 3/2017 |
| WO | 2017047769 A1 | 3/2017 |
| WO | 2017048950 A1 | 3/2017 |
| WO | 2017048954 A1 | 3/2017 |
| WO | 2017048962 A1 | 3/2017 |
| WO | 2017049166 A1 | 3/2017 |
| WO | 2017061466 A1 | 4/2017 |
| WO | 2017061532 A1 | 4/2017 |
| WO | 2017066227 A1 | 4/2017 |
| WO | 2017070089 A1 | 4/2017 |
| WO | 2017076346 A1 | 5/2017 |
| WO | 2017079669 A1 | 5/2017 |
| WO | 2017087678 A2 | 5/2017 |
| WO | 2017087777 A1 | 5/2017 |
| WO | 2017093933 A1 | 6/2017 |
| WO | 2017100108 A1 | 6/2017 |
| WO | 2017106607 A1 | 6/2017 |
| WO | 2017106634 A1 | 6/2017 |
| WO | 2017106740 A1 | 6/2017 |
| WO | 2017112730 A1 | 6/2017 |
| WO | 2017123657 A1 | 7/2017 |
| WO | 2017123669 A1 | 7/2017 |
| WO | 2017161349 A1 | 9/2017 |
| WO | 2017163264 A1 | 9/2017 |
| WO | 2017175147 A1 | 10/2017 |
| WO | 2017175156 A1 | 10/2017 |
| WO | 2017176608 A1 | 10/2017 |
| WO | 2017184735 A1 | 10/2017 |
| WO | 2017184746 A1 | 10/2017 |
| WO | 2017186711 A1 | 11/2017 |
| WO | 2017190669 A1 | 11/2017 |
| WO | 2017192961 A1 | 11/2017 |
| WO | 2017198744 A1 | 11/2017 |
| WO | 2017202703 A1 | 11/2017 |
| WO | 2017202704 A1 | 11/2017 |
| WO | 2017202798 A1 | 11/2017 |
| WO | 2017205464 A1 | 11/2017 |
| WO | 2017211791 A1 | 12/2017 |
| WO | 2017214395 A1 | 12/2017 |
| WO | 2017216054 A1 | 12/2017 |
| WO | 2017216685 A1 | 12/2017 |
| WO | 2017216686 A1 | 12/2017 |
| WO | 2017219931 A1 | 12/2017 |
| WO | 2017222976 A1 | 12/2017 |
| WO | 2018001944 A1 | 1/2018 |
| WO | 2018001952 A1 | 1/2018 |
| WO | 2018002319 A1 | 1/2018 |
| WO | 2018005586 A1 | 1/2018 |
| WO | 2018005881 A1 | 1/2018 |
| WO | 2018005883 A1 | 1/2018 |
| WO | 2018009466 A1 | 1/2018 |
| WO | 2018009505 A1 | 1/2018 |
| WO | 2018009648 A1 | 1/2018 |
| WO | 2018009652 A1 | 1/2018 |
| WO | 2018011100 A1 | 1/2018 |
| WO | 2018011160 A1 | 1/2018 |
| WO | 2018011162 A1 | 1/2018 |
| WO | 2018011163 A1 | 1/2018 |
| WO | 2018013789 A1 | 1/2018 |
| WO | 2018013887 A1 | 1/2018 |
| WO | 2018013908 A1 | 1/2018 |
| WO | 2018019297 A1 | 2/2018 |
| WO | 2018022282 A1 | 2/2018 |
| WO | 2018026620 A1 | 2/2018 |
| WO | 2018026971 A1 | 2/2018 |
| WO | 2018031434 A1 | 2/2018 |
| WO | 2018036941 A1 | 3/2018 |
| WO | 2018038877 A1 | 3/2018 |
| WO | 2018043747 A1 | 3/2018 |
| WO | 2018044783 A1 | 3/2018 |
| WO | 2018044963 A1 | 3/2018 |
| WO | 2018045144 A1 | 3/2018 |
| WO | 2018045150 A1 | 3/2018 |
| WO | 2018045204 A1 | 3/2018 |
| WO | 2018045911 A1 | 3/2018 |
| WO | 2018046460 A1 | 3/2018 |
| WO | 2018047081 A1 | 3/2018 |
| WO | 2018049089 A1 | 3/2018 |
| WO | 2018051254 A1 | 3/2018 |
| WO | 2018051255 A1 | 3/2018 |
| WO | 2017075477 A8 | 4/2018 |
| WO | 2018060323 A1 | 4/2018 |
| WO | 2018065360 A1 | 4/2018 |
| WO | 2018067423 A1 | 4/2018 |
| WO | 2018073754 A1 | 4/2018 |
| WO | 2018078149 A1 | 5/2018 |
| WO | 2018080903 A1 | 5/2018 |
| WO | 2018085750 A2 | 5/2018 |
| WO | 2018086593 A1 | 5/2018 |
| WO | 2018089695 A1 | 5/2018 |
| WO | 2018095426 A1 | 5/2018 |
| WO | 2018098203 A1 | 5/2018 |
| WO | 2018118664 A1 | 6/2018 |
| WO | 2018118665 A1 | 6/2018 |
| WO | 2018118826 A1 | 6/2018 |
| WO | 2018118848 A1 | 6/2018 |
| WO | 2018119013 A1 | 6/2018 |
| WO | 2018119221 A1 | 6/2018 |
| WO | 2018119236 A1 | 6/2018 |
| WO | 2018119263 A1 | 6/2018 |
| WO | 2018119266 A1 | 6/2018 |

(56) References Cited

FOREIGN PATENT DOCUMENTS

| | | |
|---|---|---|
| WO | 2018119286 A1 | 6/2018 |
| WO | 2018100558 A3 | 7/2018 |
| WO | 2018138685 A2 | 8/2018 |
| WO | 2018152450 A1 | 8/2018 |
| WO | 2018172206 A1 | 9/2018 |
| WO | 2018198076 A1 | 11/2018 |
| WO | 2019023459 A1 | 1/2019 |
| WO | 2019034866 A1 | 2/2019 |
| WO | 2019046496 A1 | 3/2019 |
| WO | 2019046498 A1 | 3/2019 |
| WO | 2019046500 A1 | 3/2019 |
| WO | 2019046511 A1 | 3/2019 |
| WO | 2019051488 A1 | 3/2019 |
| WO | 2019055750 A1 | 3/2019 |
| WO | 2019074887 A1 | 4/2019 |
| WO | 2019079261 A1 | 4/2019 |
| WO | 2019092660 A1 | 5/2019 |
| WO | 2019118839 A1 | 6/2019 |
| WO | 2019125974 A1 | 6/2019 |
| WO | 2019129880 A1 | 7/2019 |
| WO | 2019160884 A1 | 8/2019 |
| WO | 2019175776 A1 | 9/2019 |
| WO | 2019180683 A1 | 9/2019 |
| WO | 2019185476 A1 | 10/2019 |
| WO | 2019185477 A1 | 10/2019 |

OTHER PUBLICATIONS

European Patent Office, International Search Report and Written Opinion for PCT International Patent Application No. PCT/IB2018/060383, dated Mar. 14, 2018, 9 pages.

Aerschot, et al., "Synthesis and antiviral activity evaluation of 3'-fluoro-3'-deoxyribonucleosides: broad-spectrum antiviral activity of 3'-fluoro-3'-deoxyadenosine", Antiviral Research, 1989, pp. 133-150, vol. 12.

Brubaker, et al., "Innate Immune Pattern Recognition: A Cell Biological Perspective", Annual Review of Immunology, Mar. 2015, pp. 257-290, vol. 33.

Burdette, et al., "STING is a direct innate immune sensor of cyclic-di-GMP", Nature, 2011, pp. 515-518, vol. 478.

Cohen, et al., "Renal-Cell Carcinoma", N Engl J Med, Dec. 8, 2005, pp. 2477-2490, vol. 353.

Corrales, et al., "Direct Activation of STING in the Tumor Microenvironment Leads to Potent and Systemic Tumor Regression and Immunity", Cell Rep, 2015, pp. 1018-1030, vol. 11.

Diamond, et al., "Type I interferon is selectively required by dendritic cells for immune rejection of tumors", J Exp Med, 2011, pp. 1989-2003, vol. 208.

Dubensky, et al., "Rationale, progress and development of vaccines utilizing STING-activating cyclic dinucleotide adjuvants", Ther Adv Vaccines, 2013, pp. 131-143, vol. 1.

Foster, et al., "Deuterium Isotope Effects in Studies of Drug Metabolism", Trends in Pharmacological Sciences, vol. 5., Dec. 1984, pp. 524-527.

Fuertes, et al., "Host type I IFN signals are required for antitumor CD8+ T cell responses through CD8a+ dendritic cells", J Exp Med, 2011, pp. 2005-2016, vol. 208.

Gallucci, et al., "Natural adjuvants: Endogenous activators of dendritic cells", Nature Medicine, vol. 5, No. 11, Nov. 1999, pp. 1249-1255.

Gillerman, et al., "An Improved One-Pot Synthesis of Nucleoside 5'-Triphosphate Analogues", Nucleos. Nucleot. Nucl., 2010, pp. 245-256, vol. 29.

Kelly, et al., "9-[(Phosphonoalkyl)Benzyl]guanines. Multisubstrate Analogue Inhibitors of Human Erythrocyte Purine Nucleoside Phosphorylase", Journal of Medicinal Chemistry, vol. 36., 1993, pp. 3455-3463.

Kim, et al., "Regiospecific and Highly Stereoselective Electrophilic Addition to Furanoid Glycals: Synthesis of Phosphonate Nucleotide Analogues with Potent Activity against HIV", Journal of Organic Chemistry, vol. 56, No. 8., 1991, pp. 2642-2647.

Kovacs, et al., "Solid Phase Synthesis of 2', 5'-Oligoadenylates Containing 3'-Fluorinated Ribose", Nucleosides & Nucleotides, vol. 14, No. 6., 1995, pp. 1259-1267.

Lin, et al., "Interferons: Success in anti-viral immunotherapy", Cytokine Growth Factor, 2014, pp. 369-376, vol. 25.

Musella, et al., "Type-I-interferons in infection and cancer: Unanticipated dynamics with therapeutic implications", Oncoimmunology, 2017, 6:e1314424.

Paces Ondrej, et al., "A new linker for solid-phase synthesis of oligonucleotides with terminal phosphate group", Collection of Czechoslovak Chemical Communications, vol. 73, No. 1., Jan. 2008, pp. 32-43.

Pav, et al., "Activation of human RNase L by 2'-and 5'-O-methylphosphonate-modified oligoadenylates", Bioorganic & Medicinal Chemistry Letters, vol. 22., 2012, pp. 181-185.

Pav, et al., "Synthesis of oligoribonucleotides with phosphonate-modified linkages", Organic & Biomolecular Chemistry, vol. 9., 2011, pp. 6120-6126.

Pressova, et al., "Oligomerization of adenosin-5'-0-ylmethylphosphonate, an isopolar AMP analogue: Evaluation of the route to short oligoadenylates", Biopolymers, Mar. 1, 2010, pp. 277-289, vol. 93, No. 3.

Takeuchi, et al., "Pattern Recognition Receptors and Inflammation", Cell, 2010, pp. 805-820, vol. 140.

Tsao, et al., "Management of Cutaneous Melanoma", The New England Journal of Medicine, Sep. 2, 2004, pp. 998-1012, vol. 351, No. 10.

Unterholzner, "The interferon response to intracellular DNA: Why so many receptors?", Immunobiology, 2013, pp. 1312-1321, vol. 218.

Venkatachalam, et al., "Effect of change in nucleoside structure on the activation and antiviral activity of phosphoramidate derivatives", Bioorganic & Medicinal Chemistry, 2005, pp. 5408-5423, vol. 13.

Zhang, et al., "Cyclic GMP-AMP Containing Mixed Phosphodiester Linkages Is an Endogenous High-Affinity Ligand for STING", Molecular Cell, 2013, pp. 226-235, vol. 51.

European Patent Office, International Search Report and Written Opinion for PCT International Patent Application No. PCT/IB2019/052778, dated Jul. 18, 2019, 11 pages.

European Patent Office, International Search Report and Written Opinion for PCT International Patent Application No. PCT/IB2019/052764, dated Jul. 8, 2019, 14 pages.

European Patent Office, International Search Report and Written Opinion for PCT International Patent Application No. PCT/IB2019/052777, dated Jul. 24, 2019, 13 pages.

European Patent Office, International Search Report and Written Opinion for PCT International Patent Application No. PCT/IB2019/053616, dated Sep. 20, 2019, 15 pages.

\* cited by examiner

3'3' CYCLIC DINUCLEOTIDES WITH PHOSPHONATE BOND ACTIVATING THE STING ADAPTOR PROTEIN

CROSS-REFERENCES TO RELATED APPLICATIONS

This application claims priority to U.S. Provisional Application No. 62/608,373, filed Dec. 20, 2017, and U.S. Provisional Application No. 62/725,858, filed Aug. 31, 2018, both of which are incorporated herein in their entirety for all purposes.

SEQUENCE LISTING

This application contains a Sequence Listing which has been submitted electronically in ASCII format and is hereby incorporated by reference in its entirety. Said ASCII copy, created on Nov. 20, 2018) is named 052838-535001WO_Sequence_Listing_ST25.txt and is 14,654 bytes in size.

FIELD

The present disclosure relates to 3'3' cyclic di-nucleotides and derivatives thereof that may be useful in the treatment of diseases in which modulation of STING adaptor protein (Stimulator of Interferon Genes) is beneficial, for example, inflammation, allergic and autoimmune diseases, cancer, and viral infections such as chronic hepatitis B and human immunodeficiency virus, and in the preparation of immunogenic compositions or vaccine adjuvants.

BACKGROUND

The innate immune system recognizes the presence of pathogen or disruption of the homeostasis of the host by a battery of Pattern Recognition Receptors (PRRs) which detect a small set of ligands associated with pathogens or damage. These ligands are generally called Pathogen or Damage Associated Molecular Patterns (PAMPs and DAMPs) (Takeuchi O et al, *Cell,* 2010:140, 805-820). A number of PRRs have been identified over the past two decades including Toll-like receptors, retinoic acids inducible gene (RIG-I)-like receptors, nucleotide-binding oligomerization domain-like (NOD) receptors, C-type lectin receptors and cytosolic DNA sensors (Brubaker S W et al, *Annu Rev Immunol,* 2015:33, 257-290). Recognition of PAMPs and DAMPs by PRRs ultimately leads to the upregulation of cytokines and chemokines, including interferons, and recruitment of immune cells to the sites of infection. All these processes slow down pathogen replication and contribute to the development of adaptive immunity.

Cellular DNA is normally restricted to the nucleus and mitochondria of healthy cells. DNA present in cytosol, therefore, represents a signal indicating the presence of pathogen or disruption of the host homeostasis. The sensing of exogenous DNA is initiated by several DNA sensors such as DNA-dependent activator of IRFs (DAI) or DEAD box polypeptide 41 (DDX41). They signal via adaptor protein STING (Stimulator Of Interferon Genes, also called TMEM173, MITA, ERIS) (Unterholzner L, *Immunology,* 2013: 218, 1312-1321) by recruiting protein kinase TBK1 that triggers activation of the transcription factors NFκ-B (nuclear factor kappa B) and IRF-3 (interferon regulatory factor 3). Activation of STING ultimately results in release of type I and III interferons and variety of cytokines and chemokines such as IL-6, TNF-α and INF-γ.

Alternatively, STING can be activated by the second messenger cyclic dinucleotides (CDNs)(Burdette et al. Nature 2011: 478, 515-518). CDNs with affinity to STING contain two purine nucleotide monophosphates linked with either two 3'-5' (3'3'-CDNs), two 2'-5' (2'2'-CDNs) or 2'-5' and 3'-5' phosphodiester bonds (2'3'-CDNs). The prototype 2'3' cGAMP (c[G(2',5')pA(3',5')p]) is a product of the activation of host cGAS in the presence of pathogen or self dsDNA and it has the highest binding affinity to STING of all linkage isomers (Zhang et al, Molecular Cell 2013:51, 226-235).

The type I interferons (IFNs) are immune-regulatory cytokines that play a pivotal role in viral immunity. They induce dendritic cell (DC) and macrophage maturation and activation (Galluci et al, *Nat Med,* 1999:5, 1249-1255) and promote T- and B-cell survival, activation and differentiation. Furthermore they activate numerous intracellular pathways that inhibit virus replication. The clinical utility of type I interferons has been demonstrated by their usefulness in treatment of chronic hepatitis B and C (Lin and Young, *Cytokine Growth Factor Rev,* 2014:25, 369-376).

In addition, interferons have shown utility in treatment of human cancers (Cohen et al, *N Engl J Med,* 2005:353, 2477-2490, Tsao et al, *N Engl J Med,* 2004:351, 998-1012). They can directly inhibit proliferation of tumor cells and may be synergistic with many approved anticancer agents. Furthermore, type-I-IFNs can act on immune cells to induce antitumor response (Musella et al, Oncoimmunology 2017: 6:e1314424). Type I IFN signaling was shown to be important in tumor-initiated T cell priming in mice and animals lacking the IFN-α/β receptor in dendritic cells were unable to reject immunogenic tumors, and were defective in antigen cross-presentation to CD8+ T cells (Fuertes et al, *J Exp Med,* 2011:208, 2005-2016, Diamond et al, *J Exp Med,* 2011:208: 1989-2003). Consistently with these observations, intratumoral injection of STING agonists has been recently shown to induce regression of established tumors in mice and generated substantial systemic immune responses capable of rejecting distant metastases and providing long-lived immunologic memory (Corrales et al, Cell Rep, 2015:11, 1018-1030).

CDNs are believed to promote priming of both cellular and humoral immunity. For example, CDNs were shown to be an effective adjuvant in animal models (Dubensky et al, Ther Adv Vaccines, 2013:1, 131-143.

Patent publications WO 2014/093936, WO 2014/189805, WO 2013/185052, US 2014/03441976, WO 2015/077354, WO 2015/185565, WO 2016/145102, WO 2017/093933, WO 2017/027646, WO 2017/027645, WO 2017/175156, WO 2017/175147, WO 2017/123657, WO 2018/013908, WO 2018/013887, WO2018/009652, WO 2018/009648, and WO 2018/009466 disclose certain CDNs and their use in inducing an immune response.

BRIEF SUMMARY

In an aspect, this disclosure describes novel 3'3' cyclic phosphonate di-nucleotides and derivatives thereof that bind to and activate protein STING and, consequently, stimulate the signal transduction pathway that induces interferons and other cytokines/chemokines. One advantage compared to previously disclosed CDNs arises from the replacement of a phosphoester bond with a phosphonate bond that is resistant toward hydrolysis by phosphodiesterases present in tissues and bodily fluids. Such compounds may find utility as an anti-viral and anti-cancer agent, act as adjuvants in vaccines or may be used in the treatment of allergic or other inflammatory diseases.

In one embodiment, the present disclosure provides a compound of Formula (J):

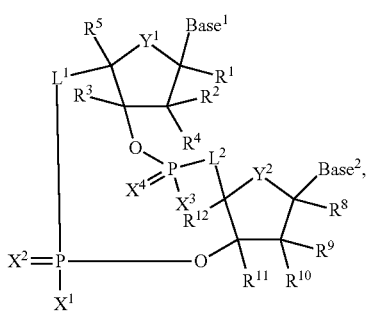

(J)

or an enantiomer, or pharmaceutically acceptable salt thereof, wherein
$L^1$ is —C($R^6R^7$)—O— and $L^2$ is —C($R^{13}R^{14}$)—O—,
$L^1$ is —C($R^6R^7$)—O— and $L^2$ is —O—C($R^{13}R^{14}$)—,
$L^1$ is —O—C($R^6R^7$)— and $L^2$ is —C($R^{13}R^{14}$)—O—,
$L^1$ is —C($R^6R^7$)—$K^1$—C($R^6R^7$)— and $L^2$ is —C($R^{13}R^{14}$)—$K^1$—C($R^{13}R^{14}$)—,
$L^1$ is —C($R^6R^7$)—$K^1$—C($R^6R^7$)— and $L^2$ is —O—C($R^{13}R^{14}$)—,
$L^1$ is —O—C($R^6R^7$)— and $L^2$ is —C($R^{13}R^{14}$)—$K^1$—C($R^{13}R^{14}$)—,
$L^1$ is —CH(O$R^{15}$)— and $L^2$ is —CH(O$R^{15}$)—,
$L^1$ is —CH(O$R^{15}$)— and $L^2$ is —O—C($R^{13}R^{14}$)—, or
$L^1$ is —O—C($R^6R^7$)— and $L^2$ is —CH(O$R^{15}$)—;
$Y^1$ and $Y^2$ are each independently —O—, —S—, or —CH$_2$—;
$X^1$ and $X^3$ are each independently OH, SH, O$R^{15}$, S$R^{15}$, or N($R^{15}$)$_2$;
$X^2$ and $X^4$ are each independently O or S;
$R^1$, $R^5$, $R^8$ and $R^{12}$ are each independently H, CN, N$_3$, F, Cl, Br, I, COO$R^{15}$, CON($R^{15}$)$_2$, $C_1$-$C_6$ alkyl, $C_2$-$C_6$ alkenyl, $C_2$-$C_6$ alkynyl, O$R^{15}$, S$R^{15}$, or N($R^{15}$)$_2$;
$R^2$, $R^3$, $R^4$, $R^9$, $R^{10}$ and $R^{11}$ are each independently H, OH, F, Cl, Br, I, CN, N$_3$, $C_1$-$C_6$ alkyl, $C_2$-$C_6$ alkenyl, $C_2$-$C_6$ alkynyl, O$R^{15}$, S$R^{15}$, or N($R^{15}$)$_2$;
$R^6$, $R^7$, $R^{13}$ and $R^{14}$ are each independently H, CN, N$_3$, F, Cl, Br, I, COO$R^{15}$, CON($R^{15}$)$_2$, O$R^{15}$, S$R^{15}$, N($R^{15}$)$_2$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;
each $R^{15}$ is independently H, —C(=Z)$R^{16}$, —C(=Z)O$R^{16}$, —C(=Z)S$R^{16}$, —C(=Z)N($R^{16}$)$_2$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;
each $R^{16}$ is independently H, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;
each Z is independently O, S, or N$R^{15}$;
$K^1$ is a variable that represents —O—, —S—, —S(O)—, —S(O)$_2$—, —NH—, or —N$R^{15}$—;

Base$^1$ and Base$^2$ are each independently:

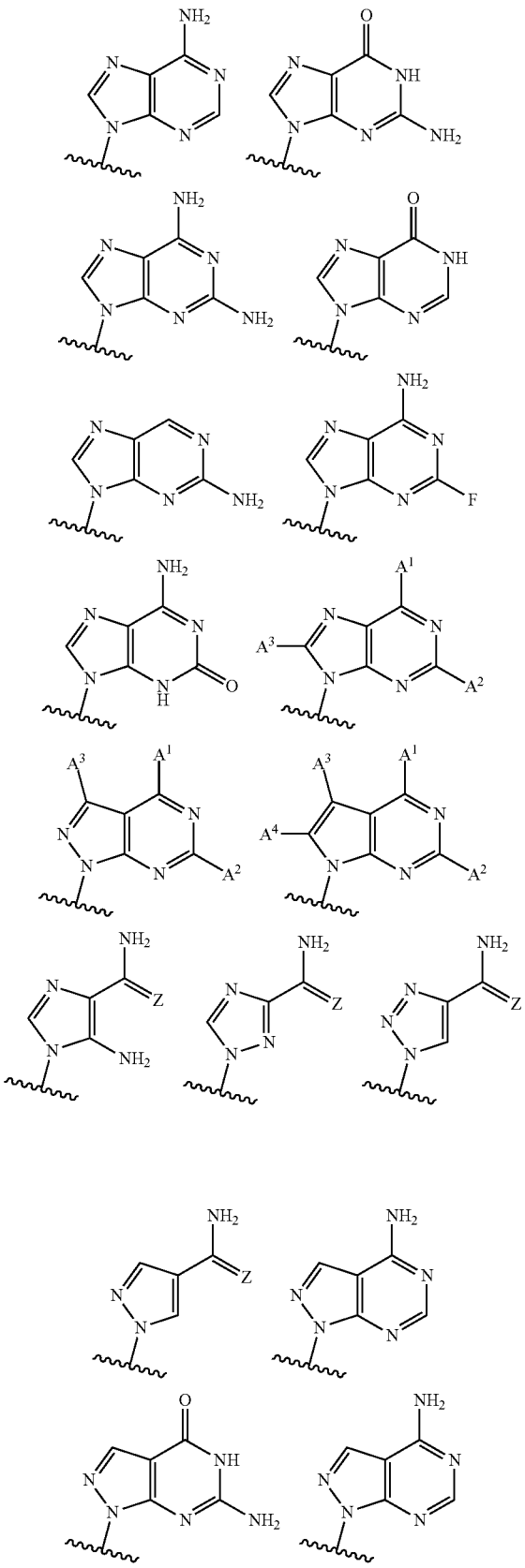

-continued

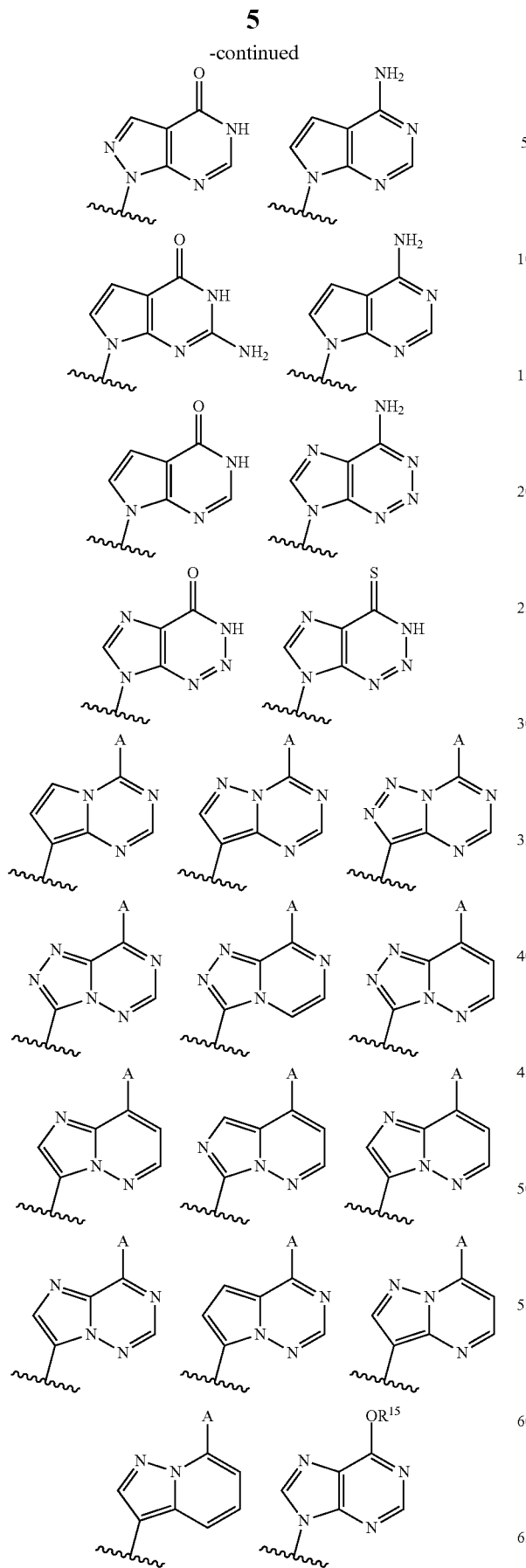

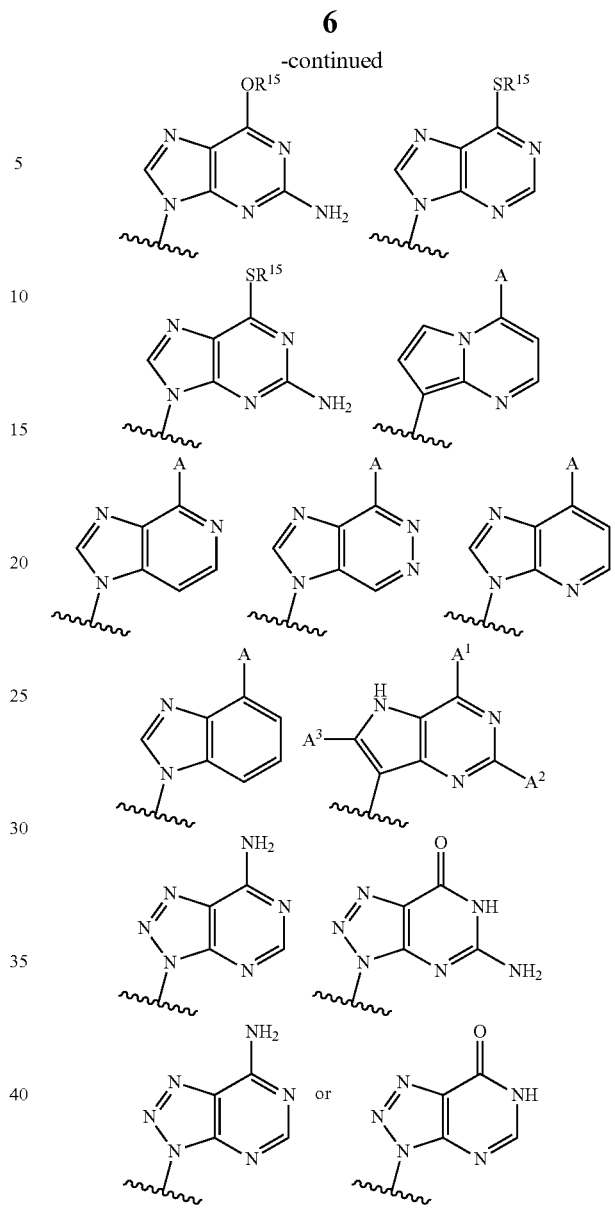

wherein
A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$; and wherein the $C_1$-$C_6$ alkyl, $C_2$-$C_6$ alkenyl, $C_2$-$C_6$ alkynyl, $C_2$-$C_{10}$ heterocycloalkyl, $C_6$-$C_{10}$ aryl, or $C_2$-$C_{10}$ heteroaryl independently in each instance is optionally substituted with 1, 2, or 3 —OH; —SH; —$NH_2$; =O; =NH; =S; halogen; —$N_3$; $C_6$-$C_{10}$ aryl optionally substituted with 1, 2, or 3 —OH, —CN, —O(C=O)$OR^B$, —O(C=O)$R^B$, or —COO$R^B$; unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)$OR^B$; —O(C=O)$R^B$; or —COO$R^B$; wherein $R^B$ is H or unsubstituted $C_1$-$C_6$ alkyl.

The present disclosure includes a pharmaceutical composition comprising the cyclic dinucleotide of Formula (J), or an enantiomer, or pharmaceutically acceptable salt thereof, and a pharmaceutically acceptable carrier, excipient, and/or diluent.

Also provided is a method of treating or preventing a disease or disorder, e.g., a method of treating or preventing a viral infection, hepatitis B virus infection, HIV infection, hyperproliferative disease or cancer, comprising administering to a human or animal in need thereof a therapeutically effective amount of a cyclic dinucleotide of Formula (J), or an enantiomer, or pharmaceutically acceptable salt thereof, or a pharmaceutical composition of any of the foregoing.

Further provided is a method of enhancing the efficacy of a vaccine, comprising administering a therapeutically effective amount of a cyclic dinucleotide of Formula (J), or an enantiomer, or pharmaceutically acceptable salt thereof, or a pharmaceutical composition of any of the foregoing.

Additionally, provided herein is a method of modulating the activity of STING adaptor protein to induce production of a type I interferon, cytokine and/or chemokine dependent on the STING adaptor protein, e.g., inducing a STING adaptor protein-dependent type I interferon, cytokine or chemokine in a human or animal, comprising administering a therapeutically effective amount of a cyclic dinucleotide of Formula (J), or an enantiomer, or pharmaceutically acceptable salt thereof, or a pharmaceutical composition of any of the foregoing.

DETAILED DESCRIPTION

I. General

The disclosure provides novel 3'3' cyclic dinucleotides, comprising at least one phosphonate group, that bind to and modulate the activity of, e.g., activate, the STING protein. The dinucleotides have at least one 4' linkage that is a variant of the naturally occurring methylene phosphate, i.e., the naturally occurring 4'-$CH_2$—O—P—, attachment to the sugar.

II. Definitions

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or "$C_u$-$C_v$" indicates that the following group has from u to v carbon atoms, where u and v are integers. For example, "$C_{1-6}$ alkyl" or "$C_1$-$C_6$ alkyl" indicates that the alkyl group has from 1 to 6 carbon atoms.

"Alkyl" is a linear or branched saturated monovalent hydrocarbon. For example, an alkyl group can have 1 to 10 carbon atoms (i.e., $C_{1-10}$ alkyl) or 1 to 8 carbon atoms (i.e., $C_{1-8}$ alkyl) or 1 to 6 carbon atoms (i.e., $C_{1-6}$ alkyl) or 1 to 4 carbon atoms (i.e., $C_{1-4}$ alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —CH($CH_3$)$_2$), 1-butyl (n-Bu, n-butyl, —$CH_2CH_2CH_2CH_3$), 2-methyl-1-propyl (i-Bu, i-butyl, —$CH_2$CH($CH_3$)$_2$), 2-butyl (s-Bu, s-butyl, —CH($CH_3$)$CH_2CH_3$), 2-methyl-2-propyl (t-Bu, t-butyl, —C($CH_3$)$_3$), 1-pentyl (n-pentyl, —$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), 1-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$), and octyl (—($CH_2$)$_7CH_3$). Alkyl groups can be unsubstituted or substituted.

"Alkoxy" refers to the group —O-alkyl, where alkyl is as defined above. For example, $C_{1-4}$ alkoxy refers to an —O-alkyl group having 1 to 4 carbons.

"Alkenyl" is a linear or branched monovalent hydrocarbon radical with at least one carbon-carbon double bond. For example, an alkenyl group can have 2 to 8 carbon atoms (i.e., $C_2$-8 alkenyl) or 2 to 6 carbon atoms (i.e., $C_2$-6 alkenyl) or 2 to 4 carbon atoms (i.e., $C_{2-4}$ alkenyl). Examples of alkenyl groups include, but are not limited to, ethenyl (—CH=$CH_2$), allyl (—$CH_2$CH=$CH_2$), and —$CH_2$—CH=CH—$CH_3$. Alkenyl groups can be unsubstituted or substituted.

"Alkynyl" is a linear or branched monovalent hydrocarbon radical with at least one carbon-carbon triple bond. For example, an alkynyl group can have 2 to 8 carbon atoms (i.e., $C_{2-8}$ alkynyl) or 2 to 6 carbon atoms (i.e., $C_{2-6}$ alkynyl) or 2 to 4 carbon atoms (i.e., $C_{2-4}$ alkynyl). Examples of alkynyl groups include, but are not limited to, acetylenyl (—C≡CH), propargyl (—$CH_2$C≡CH), and —$CH_2$—C≡C—$CH_3$. Alkynyl groups can be unsubstituted or substituted.

Alkylamino is —HNR$_b$ group, where R$_b$ is an alkyl.

Alkylthio is —SR$_b$ group, where R$_b$ is an alkyl.

"Halo" or "halogen" as used herein refers to fluoro (—F), chloro (—Cl), bromo (—Br) and iodo (—I).

"Haloalkyl" as used herein refers to an alkyl as defined herein, wherein one or more hydrogen atoms of the alkyl are independently replaced by a halo substituent, which may be the same or different. For example, $C_1$-4 haloalkyl is a $C_1$-4 alkyl wherein one or more of the hydrogen atoms of the $C_1$-4 alkyl have been replaced by a halo substituent. Examples of haloalkyl groups include but are not limited to fluoromethyl, fluorochloromethyl, difluoromethyl, difluorochloromethyl, trifluoromethyl, 1,1,1-trifluoroethyl and pentafluoroethyl.

"Aryl" as used herein refers to a single all carbon aromatic ring or a multiple condensed all carbon ring system wherein at least one of the rings is aromatic. For example, in certain embodiments, an aryl group has 6 to 20 carbon atoms, 6 to 14 carbon atoms, or 6 to 12 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is also to be understood that when reference is made to a certain atom-range membered aryl (e.g., 6-10 membered aryl), the atom range is for the total ring atoms of the aryl. For example, a 6-membered aryl would include phenyl and a 10-membered aryl would include naphthyl and 1,2,3,4-tetrahydronaphthyl. Non-limiting examples of aryl groups include, but are not limited to, phenyl, indenyl, naphthyl, 1,2,3,4-tetrahydronaphthyl, anthracenyl, and the like. Aryl groups can be unsubstituted or substituted.

"Heteroaryl" as used herein refers to a single aromatic ring that has at least one atom other than carbon in the ring, wherein the atom is selected from the group consisting of oxygen, nitrogen and sulfur; "heteroaryl" also includes multiple condensed ring systems that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2, 3 or 4 rings) wherein a heteroaryl group, as defined above, is condensed with one or more rings selected from heteroaryls (to form for example 1,8-naphthyridinyl), heterocycles, (to form for example 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has about 1-20 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). It also to be understood that when a reference is made to a certain atom-range membered heteroaryl (e.g., a 5 to 10 membered heteroaryl), the atom range is for the total ring atoms of the heteroaryl and includes carbon atoms and heteroatoms. For example, a 5-membered heteroaryl would include a thiazolyl and a 10-membered heteroaryl would include a quinolinyl. Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, and triazolyl. Heteroaryl groups can be unsubstituted or substituted.

"Cycloalkyl" refers to a single saturated or partially unsaturated all carbon ring having 3 to 20 annular carbon atoms (i.e., $C_{3-20}$ cycloalkyl), for example from 3 to 12 annular atoms, for example from 3 to 10 annular atoms, or 3 to 8 annular atoms, or 3 to 6 annular atoms, or 3 to 5 annular atoms, or 3 to 4 annular atoms. The term "cycloalkyl" also includes multiple condensed, saturated and partially unsaturated all carbon ring systems (e.g., ring systems comprising 2, 3 or 4 carbocyclic rings). Accordingly, cycloalkyl includes multicyclic carbocyles such as a bicyclic carbocycles (e.g., bicyclic carbocycles having about 6 to 12 annular carbon atoms such as bicyclo[3.1.0]hexane and bicyclo[2.1.1]hexane), and polycyclic carbocycles (e.g tricyclic and tetracyclic carbocycles with up to about 20 annular carbon atoms). The rings of a multiple condensed ring system can be connected to each other via fused, spiro and bridged bonds when allowed by valency requirements. Non-limiting examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl and 1-cyclohex-3-enyl. Cycloalkyl groups can be unsubstituted or substituted.

"Heterocyclyl" or "heterocycle" or "heterocycloalkyl" as used herein refers to a single saturated or partially unsaturated non-aromatic ring or a non-aromatic multiple ring system that has at least one heteroatom in the ring (i.e., at least one annular heteroatom selected from oxygen, nitrogen, and sulfur). Unless otherwise specified, a heterocyclyl group has from 3 to about 20 annular atoms, for example from 3 to 12 annular atoms, for example from 3 to 10 annular atoms, or 3 to 8 annular atoms, or 3 to 6 annular atoms, or 3 to 5 annular atoms, or 4 to 6 annular atoms, or 4 to 5 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The rings of the multiple condensed ring (e.g. bicyclic heterocyclyl) system can be connected to each other via fused, spiro and bridged bonds when allowed by valency requirements. Heterocycles include, but are not limited to, azetidine, aziridine, imidazolidine, morpholine, oxirane (epoxide), oxetane, thietane, piperazine, piperidine, pyrazolidine, piperidine, pyrrolidine, pyrrolidinone, tetrahydrofuran, tetrahydrothiophene, dihydropyridine, tetrahydropyridine, quinuclidine, 2-oxa-6-azaspiro[3.3]heptan-6-yl, 6-oxa-1-azaspiro[3.3]heptan-1-yl, 2-thia-6-azaspiro[3.3]heptan-6-yl, 2,6-diazaspiro[3.3]heptan-2-yl, 2-azabicyclo[3.1.0]hexan-2-yl, 3-azabicyclo[3.1.0]hexanyl, 2-azabicyclo[2.1.1]hexanyl, 2-azabicyclo[2.2.1]heptan-2-yl, 4-azaspiro[2.4]heptanyl, 5-azaspiro[2.4]heptanyl, and the like. Heterocyclyl groups can be unsubstituted or substituted.

"Oxo" as used herein refers to =O.

"Substituted" as used herein refers to substitution with one or more substituents (e.g., 1, 2, 3, or 4 or more) selected from the group consisting of —OH, —SH, —NH$_2$, =O, =NH, =S, EN, halogen, —N$_3$, $C_{1-6}$ alkyl, $C_{1-6}$ alkoxy, $C_{1-6}$ alkylthio, $C_{1-6}$ alkylamino, $C_{1-6}$ dialkylamino, —CN, —O(C=O)OR$^B$, —O(C=O)R$^B$ and —COOR$^B$, where R$^B$ is hydrogen or $C_1$ to $C_6$ alkyl.

A "compound of the present disclosure" includes compounds disclosed herein, for example a compound of the present disclosure includes compounds of Formula (J), (I), (Ia), (IIa), (IIIa), (IIIb), (IIIc), (IVa), (IVb), and/or (IVc), including the compounds of the Examples.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom and/or preventing a worsening of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" as used herein means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable cancer (e.g., a hepatocellular carcinoma) in the subject). The subject may be an individual at risk of developing the disease or disorder, such as an individual who has one or more risk factors known to be associated with development or onset of the disease or disorder. Thus, in certain embodiments, the term "preventing a cancer" refers to administering to a subject who does not have a detectable cancer an anti-cancer therapeutic substance. It is understood that the subject for anti-cancer preventative therapy may be an individual at risk of developing cancer. It is also understood that prevention does not require a 100% success rate. In some instances, prevention may be understood as a reduction of the risk of cancer, but not a complete elimination of the occurrence of a cancer.

In certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus. It is also understood that prevention does not require a 100% success rate. In some instances, prevention may be understood as a reduction of the risk of infection, but not a complete elimination the occurrence of an infection.

"Modulation" or "modulating" the activity of a protein, e.g., a STING adaptor protein, as used herein refers to alteration of the activity such that the activity increases or decreases. In some embodiments, the modulation increases the activity.

As used herein, the term "viral infection" describes a diseased state in which a virus invades healthy cells, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "enhancing" refers to any form of increase in the immunogenic activity of an effective dosage of a vaccine as a result of administering to an animal or a human a therapeutically effective dose of a compound of the disclosure, e.g., a cyclic dinucleotide of Formula (J), (I), (Ia), (IIa), (IIIa), (IIIb), (IIIc), (IVa), (IVb), and/or (IVc) wherein said compound is administered at any time prior to, simultaneous with, or just after administration to the same animal or human of the effective dosage of a vaccine.

"Animal" as used herein refers to a non-human mammal, for example, a domestic animal such as a pig, a cow, a horse, a dog, a cat, a rat, or a mouse, or a non-human primate such as a cynomolgus monkey or chimpanzee.

"At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

"Therapeutically effective amount" or "effective amount" as used herein refers to an amount that is effective to elicit the desired biological or medical response, including the amount of a compound that, when administered to a subject for treating a disease, is sufficient to effect such treatment for the disease. The effective amount will vary depending on the compound, the disease, and its severity and the age, weight, etc., of the subject to be treated. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

In some embodiments, a therapeutically effective amount of a compound provided herein or pharmaceutically acceptable salt thereof, may (i) reduce the number of diseased cells; (ii) reduce tumor size; (iii) inhibit, retard, slow to some extent, and preferably stop the diseased cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with cancer or hyperproliferative disease. In some embodiments, a therapeutically effective amount is sufficient to ameliorate, palliate, lessen, and/or delay one or more of symptoms of cancer or hyperproliferative disease.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Co-administration" as used herein refers to administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure. Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the subject.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The compounds described herein may be prepared and/or formulated as pharmaceutically acceptable salts or when appropriate as a free base. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

Provided are also compounds described herein or pharmaceutically acceptable salts, isomers, or a mixture thereof, in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomer, or a mixture thereof when administered to a mammal. See, e.g., Foster, "Deuterium Isotope Effects in Studies of Drug Metabolism", Trends Pharmacol. Sci., 5(12):524-527 (1984). Such compounds are synthesized by means well known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) can generally be prepared by conventional techniques known to those skilled in the art or by processes analogous to those described in the Examples as set out below using an appropriate isotopically-labeled reagent in place of the non-labeled reagent previously employed.

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

"Stereoisomer" as used herein refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Tautomer" as used herein refers to a proton shift from one atom of a molecule to another atom of the same molecule. The present disclosure includes tautomers of any said compounds.

"Solvate" as used herein refers to the result of the interaction of a solvent and a compound. Solvates of salts of the compounds described herein are also provided. Hydrates of the compounds described herein are also provided.

"Hydrate" as used herein refers to a compound of the disclosure that is chemically associated with one or more molecules of water.

"Prodrug" as used herein refers to a derivative of a drug that upon administration to the human body is converted to the parent drug according to some chemical or enzymatic pathway. In some embodiments, a prodrug is a biologically inactive derivative of a drug that upon administration to the human body is converted to the biologically active parent drug according to some chemical or enzymatic pathway. Prodrugs for phosphonate and phosphates are known in the art. Exemplary prodrugs that can be used with the compounds of the disclosure include esters, such as alkyl (e.g, methyl or ethyl), benzyl (e.g., 4-OAc or 4-OMe substituted benzyl), acyloxyalkyl (e.g., pivaloyloxymethyl (POM)), alkoxycarbonyloxy alkyl (e.g., isopropyloxycarbonyloxymethyl (POC)), S-acylthioalkyl (e.g., an S-acyl-2-thioethyl (SATE) such as S-pivaloyl-2-thioethyl), steroidal (e.g., cholesteryl), glycerol fatty alcohol (e.g., —CH$_2$OCH$_2$(CH$_2$)$_{14}$CH$_3$) esters, and amidates, such as amino acid amidates (e.g., alanine O-alkyl ester amidate).

III. COMPOUNDS

In an aspect, provided herein is a compound, i.e., a cyclic dinucleotide, of formula (J):

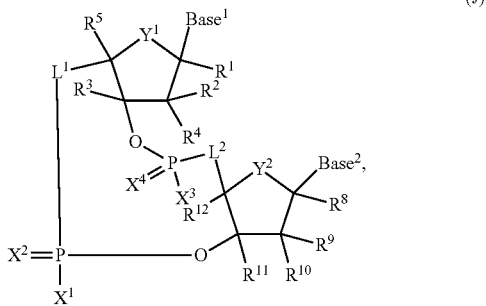

(J)

or a regioisomer, enantiomer, or pharmaceutically acceptable salt thereof,
wherein
L$^1$ is —C(R$^6$R$^7$)—O— and L$^2$ is —C(R$^{13}$R$^{14}$)—O—,
L$^1$ is —C(R$^6$R$^7$)—O— and L$^2$ is —O—C(R$^{13}$R$^{14}$)—,
L$^1$ is —O—C(R$^6$R$^7$)— and L$^2$ is —C(R$^{13}$R$^{14}$)—O—,
L$^1$ is —C(R$^6$R$^7$)—K$^1$—C(R$^6$R$^7$)— and L$^2$ is —C(R$^{13}$R$^{14}$)—K$^1$—C(R$^{13}$R$^{14}$)—,
L$^1$ is —C(R$^6$R$^7$)—K$^1$—C(R$^6$R$^7$)— and L$^2$ is —O—C(R$^{13}$R$^{14}$)—,
L$^1$ is —O—C(R$^6$R$^7$)— and L$^2$ is —C(R$^{13}$R$^{14}$)—K$^1$—C(R$^{13}$R$^{14}$)—,
L$^1$ is —CH(OR$^{15}$)— and L$^2$ is —CH(OR$^{15}$)—,
L$^1$ is —CH(OR$^{15}$)— and L$^2$ is —O—C(R$^{13}$R$^{14}$)—, or
L$^1$ is —O—C(R$^6$R$^7$)— and L$^2$ is —CH(OR$^{15}$)—;
Y$^1$ and Y$^2$ are each independently —O—, —S—, or —CH$_2$—;
X$^1$ and X$^3$ are each independently OH, SH, OR$^{15}$, SR$^{15}$, or N(R$^{15}$)$_2$;
X$^2$ and X$^4$ are each independently O or S;
R$^1$, R$^5$, R$^8$ and R$^{12}$ are each independently H, CN, N$_3$, F, Cl, Br, I, COOR$^{15}$, CON(R$^{15}$)$_2$, C$_1$-C$_6$ alkyl, C$_2$-C$_6$ alkenyl, C$_2$-C$_6$ alkynyl, OR$^{15}$, SR$^{15}$, or N(R$^{15}$)$_2$;

R$^2$, R$^3$, R$^4$, R$^9$, R$^{10}$ and R$^{11}$ are each independently H, OH, F, Cl, Br, I, CN, N$_3$, C$_1$-C$_6$ alkyl, C$_2$-C$_6$ alkenyl, C$_2$-C$_6$ alkynyl, OR$^{15}$, SR$^{15}$, or N(R$^{15}$)$_2$;
R$^6$, R$^7$, R$^{13}$ and R$^{14}$ are each independently H, CN, N$_3$, F, Cl, Br, I, COOR$^{15}$, CON(R$^{15}$)$_2$, OR$^{15}$, SR$^{15}$, N(R$^{15}$)$_2$, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_{10}$ heteroaryl;
each R$^{15}$ is independently H, —C(=Z)R$^{16}$, —C(=Z)OR$^{16}$, —C(=Z)SR$^{16}$, —C(=Z)N(R$^{16}$)$_2$, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_0$ heteroaryl;
each R$^{16}$ is independently H, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_{10}$ heteroaryl;
each Z is independently O, S, or NR$^{15}$;
K$^1$ is a variable that represents —O—, —S—, —S(O)—, —S(O)$_2$—, —NH—, or —NR$^{15}$—;
Base$^1$ and Base$^2$ are each independently:

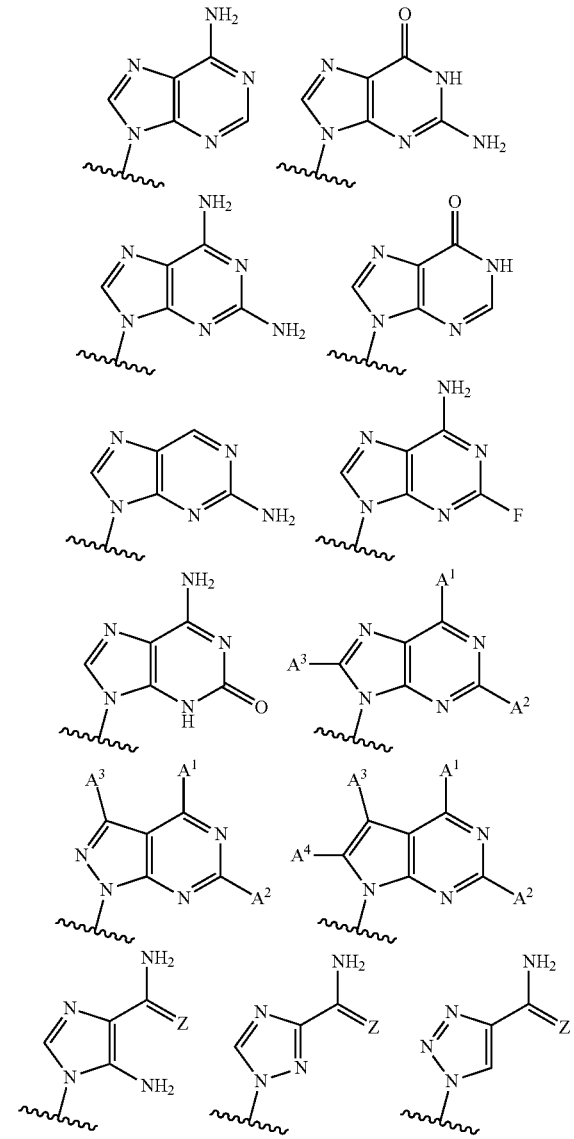

-continued
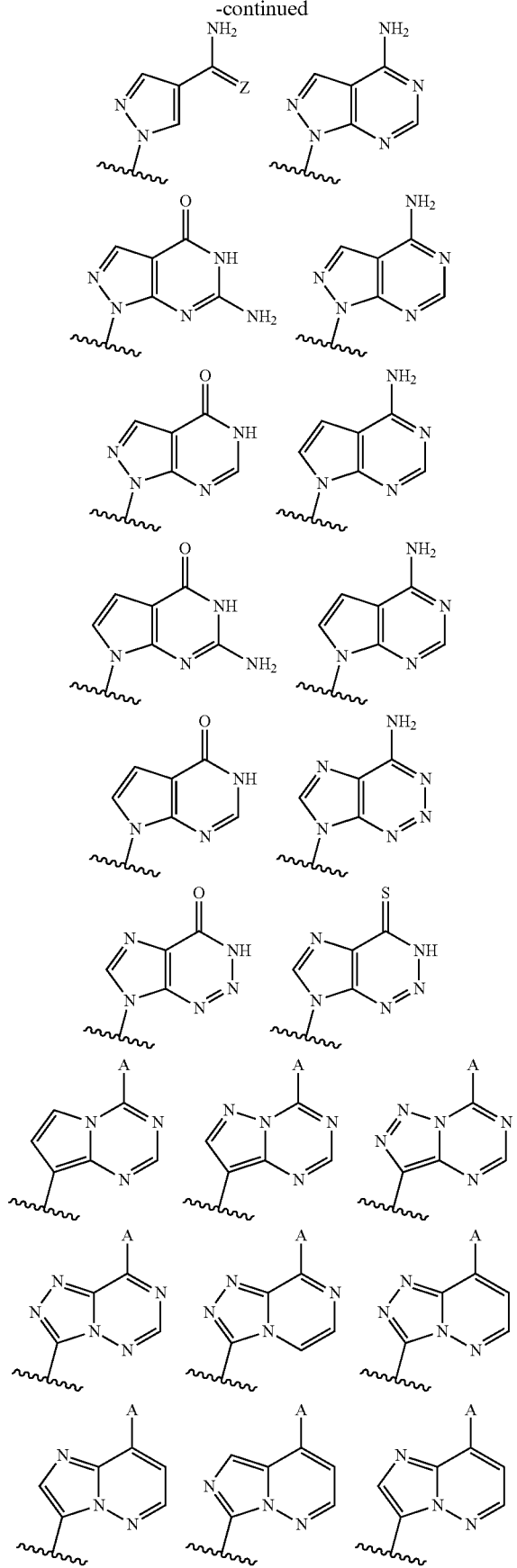
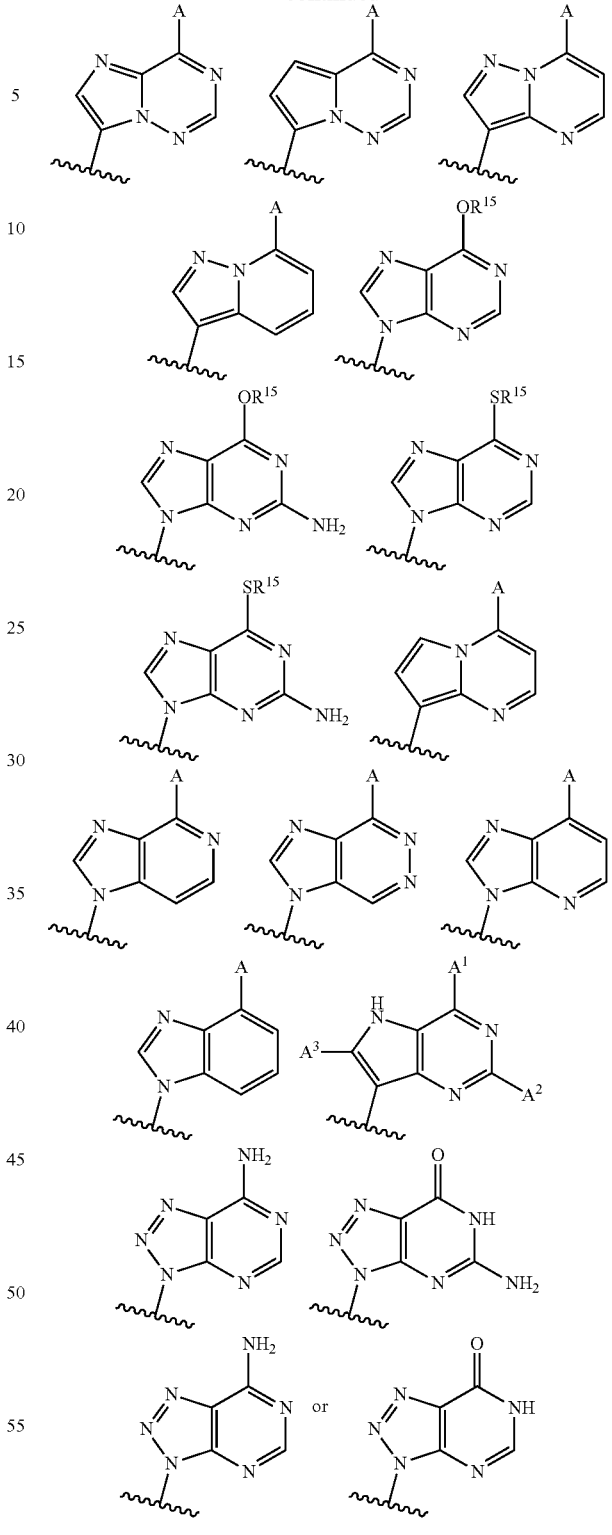
wherein
A, A¹, A², A³ and A⁴ are each independently H, OH, SH, F, Cl, Br, I, $NH_2$, $OR^{15}$, $SR^{15}$, $NHR^{15}$, $N(R^{15})_2$, or $R^{16}$; and wherein the $C_1$-$C_6$ alkyl, $C_2$-$C_6$ alkenyl, $C_2$-$C_6$ alkynyl, $C_2$-$C_{10}$ heterocycloalkyl, $C_6$-$C_{10}$ aryl, or $C_2$-$C_{10}$ heteroaryl independently in each instance is optionally substituted with 1, 2, or 3 —OH; —SH; —$NH_2$; =O; =NH;

=S; halogen; —N₃; $C_6$-$C_{10}$ aryl optionally substituted with 1, 2, or 3 —OH, —CN, —O(C=O)OR$^B$, —O(C=O)R$^B$, or —COOR$^B$; unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)OR$^B$;

—O(C=O)R$^B$; or —COOR$^B$; wherein R$^B$ is H or unsubstituted $C_1$-$C_6$ alkyl.

In some embodiments, the compound is a compound of formula (J), or an enantiomer, or pharmaceutically acceptable salt thereof.

In some embodiments, the compound of formula (J) has a structure of formula (IIa):

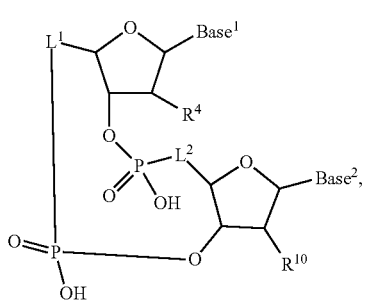

(IIa)

or an enantiomer, or pharmaceutically acceptable salt thereof.

In some embodiments, the compound of formula (J) has a structure of formula (I):

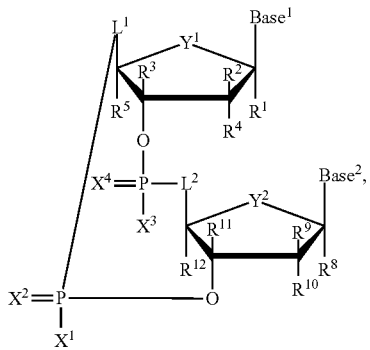

(I)

or an enantiomer, or pharmaceutically acceptable salt thereof.

In some embodiments of the compound of formula (J) and/or (I), $L^1$ is —C(R$^6$R$^7$)—O— while $L^2$ is —C(R$^{13}$R$^{14}$)—O— or —O—C(R$^{13}$R$^{14}$)—;
or
$L^1$ is —C(R$^6$R$^7$)—K$^1$—C(R$^6$R$^7$)— while $L^2$ is —C(R$^{13}$R$^{14}$)—K$^1$—C(R$^{13}$R$^{14}$)— Or —O—C(R$^{13}$R$^{14}$)—; or
$L^1$ is —CH(OR$^{15}$)— while $L^2$ is —CH(OR$^{15}$)— or —O—C(R$^{13}$R$^{14}$)—;

$Y^1$ and $Y^2$ are each independently selected from the group consisting of —O—, —S—, and —CH₂—;

$X^1$ and $X^3$ are each independently selected from the group consisting of OH, SH, OR$^{15}$, SR$^{15}$, and N(R$^{15}$)₂;

$X^2$ and $X^4$ are each independently selected from the group consisting of O and S;

$R^1$, $R^5$, $R^8$ and $R^{12}$ are each independently selected from the group consisting of H, CH₂F, CHF₂, CF₃, CN, N₃, F, Cl, Br, I, COOR$^{15}$, CON(R$^{15}$)₂, CH₂OH, $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, OR$^{15}$, SR$^{15}$, and N(R$^{15}$)₂;

$R^2$, $R^3$, $R^4$, $R^9$, $R^{10}$ and $R^{11}$ are each independently selected from the group consisting of H, OH, F, Cl, Br, I, CN, N₃, $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, OR$^{15}$, SR$^{15}$, and N(R$^{15}$)₂;

$R^6$, $R^7$, $R^{13}$ and $R^{14}$ are each independently selected from the group consisting of H, CH₂F, CHF₂, CF₃, CN, N₃, F, Cl, Br, I, COOR$^{15}$, CON(R$^{15}$)₂, CH₂OH, CH₂N3, OR$^{15}$, SR$^{15}$, N(R$^{15}$)₂, $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, $C_3$-$C_7$ cycloalkyl, $C_2$-$C_{10}$ heterocycloalkyl, $C_2$-$C_{10}$ substituted heterocycloalkyl, $C_2$-$C_{10}$ aryl, $C_2$-$C_{10}$ substituted aryl, $C_2$-$C_{10}$ heteroaryl, and $C_2$-$C_{10}$ substituted heteroaryl;

each R$^{15}$ is independently selected from the group consisting of H, —C(=Z)R$^{16}$, —C(=Z)OR$^{16}$, —C(=Z)SR$^{16}$, —C(=Z)N(R$^{16}$)₂, $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, $C_3$-$C_7$ cycloalkyl, $C_2$-$C_{10}$ heterocycloalkyl, $C_2$-$C_{10}$ substituted heterocycloalkyl, $C_6$-$C_{10}$ aryl, $C_6$-$C_{10}$ substituted aryl, $C_2$-$C_{10}$ heteroaryl, and $C_2$-$C_{10}$ substituted heteroaryl;

each R$^{16}$ is independently selected from the group consisting of H, $C_1$-$C_6$ alkyl, $C_2$-$C_6$ alkenyl, $C_2$-$C_6$ alkynyl, $C_1$-$C_6$ substituted alkyl, $C_2$-$C_6$ substituted alkenyl, $C_2$-$C_6$ substituted alkynyl, $C_3$-$C_7$ cycloalkyl, $C_2$-$C_{10}$ heterocycloalkyl, $C_2$-$C_{10}$ substituted heterocycloalkyl, $C_6$-$C_{10}$ aryl, $C_6$-$C_{10}$ substituted aryl, $C_2$-$C_{10}$ heteroaryl, and $C_2$-$C_{10}$ substituted heteroaryl;

each Z is independently selected from the group consisting of O, S, and NR$^{15}$;

$K^1$ is a variable that is selected from the group consisting of —O—, —S—, —S(O)—, —S(O)₂—, —NH—, and —NR$^{15}$—;

Base$^1$ and Base$^2$ are each independently selected from the group consisting of:

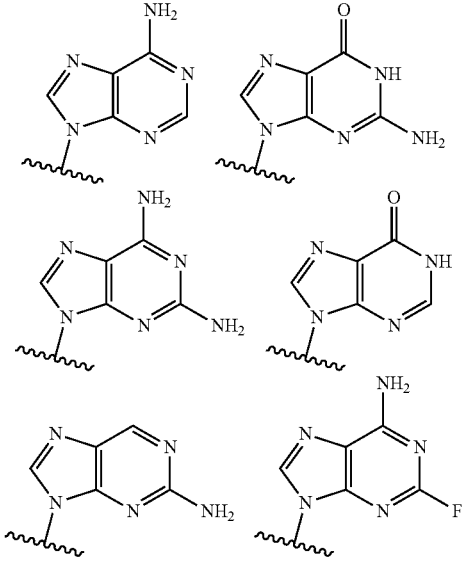

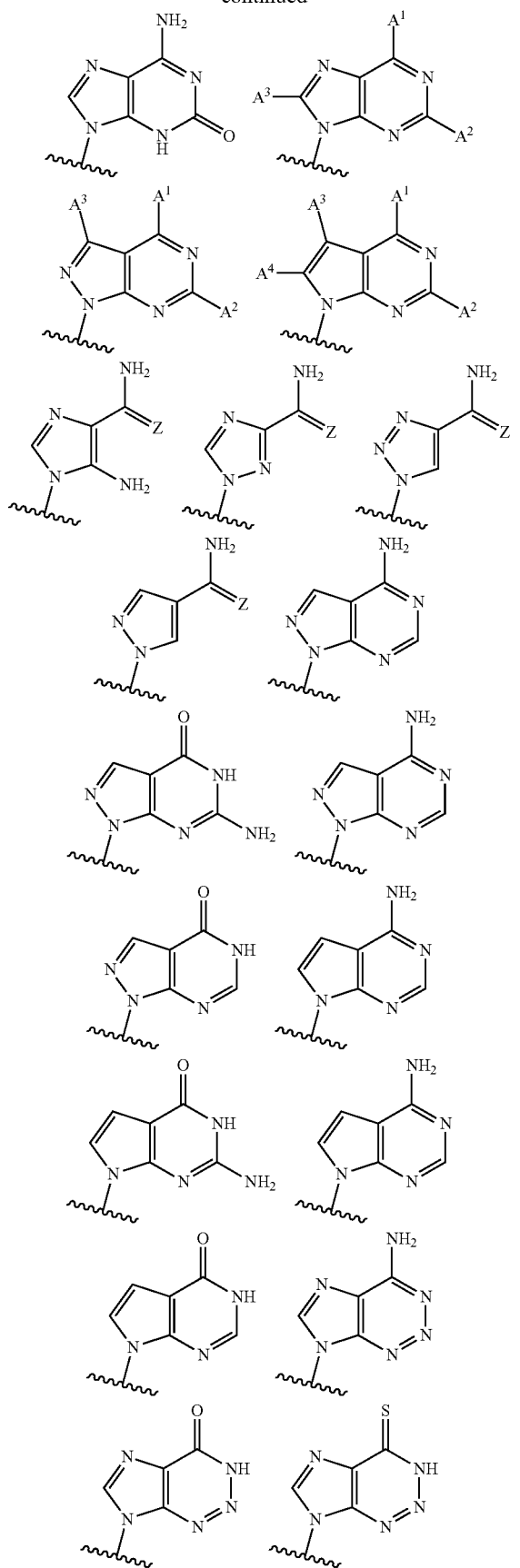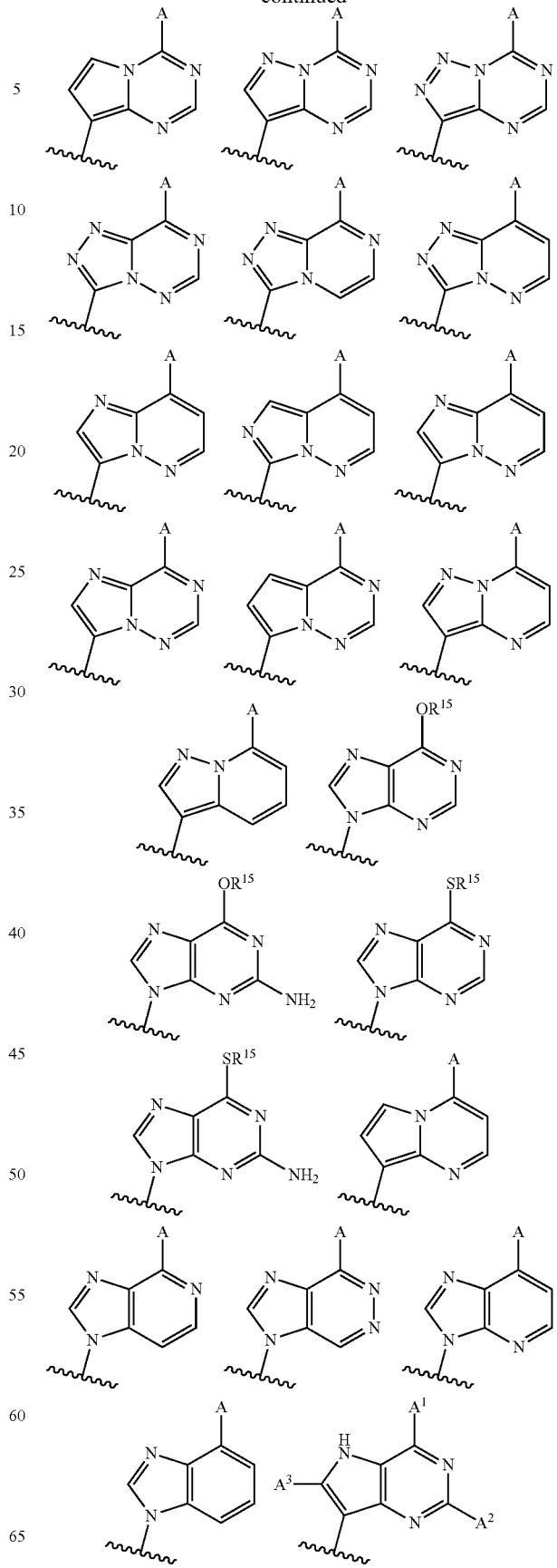

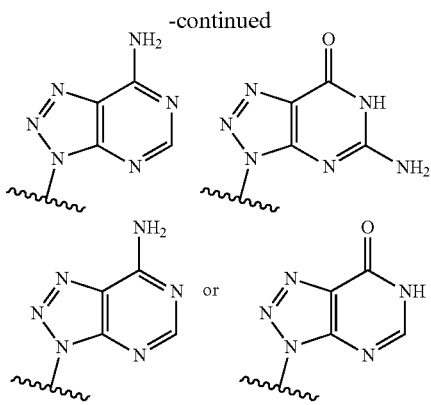

wherein

A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$.

In some embodiments of the compound of formula (I), alkyl is a linear or branched $C_1$ to $C_6$, preferably $C_2$ to $C_6$, hydrocarbon chain; for example methyl, ethyl, n-propyl, isopropyl, n-butyl, sec-butyl, tert-butyl, amyl, t-amyl, n-pentyl, n-hexyl and the like, unsubstituted or substituted with one or more substituents selected from the group consisting of —OH, —SH, —$NH_2$, =O, =NH, =S, EN, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN and —COOR$_p$, where R$_p$ is hydrogen or $C_1$ to $C_6$ alkyl.

In some embodiments of the compound of formula (I), alkenyl is a linear or branched $C_2$ to $C_6$ hydrocarbon chain containing at least one double bond, for example ethenyl, allyl, 2-butynyl, 3-butenyl, 2-pentenyl, 3-pentenyl, 2-hexenyl, 3-hexenyl, 4-hexenyl and the like; wherein the alkenyl may be substituted with one or more substituents selected from the group consisting of —OH, —SH, —$NH_2$, =O, =NH, =S, EN, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN and —COOR$_p$, where R$_p$ is hydrogen or $C_1$ to $C_6$ alkyl.

In some embodiments of the compound of formula (I), alkynyl is a linear or branched $C_2$ to $C_6$ hydrocarbon chain containing at least one triple bond, and may optionally also contain a double bond; for example ethynyl or propynyl, wherein the alkynyl may be substituted with one or more substituents selected from the group consisting of —OH, —SH, —$NH_2$, =O, =NH, =S, EN, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN and —COOR$_p$, where R$_p$ is hydrogen or $C_1$ to $C_6$ alkyl.

In some embodiments of the compound of formula (I), cycloalkyl is a cyclic hydrocarbon chain preferably having 3 to 9 carbon atoms, for example cyclopropyl, cyclobutyl, cyclopentyl, cyclohexyl; optionally, it may be in the form of condensed rings or bridged rings.

In some embodiments of the compound of formula (I), heterocycle or heterocyclyl or heterocycloalkyl is a hydrocarbon group containing from 2 to 10, preferably 4 to 10, carbon atoms, and at least one heteroatom, preferably one to two heteroatoms selected from the group consisting of O, S, N, and containing at least one saturated or partially unsaturated ring system having from 3 to 12 ring members and from 1 to 4 heteroatoms of N, O and S. In some embodiments, additional heteroatoms can also be useful, including, but not limited to, B, Al, Si and P. In some embodiments, the heteroatoms can also be oxidized, such as, but not limited to, —S(O)— and —S(O)$_2$—. In some embodiments, heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. In some embodiments, heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. In some embodiments, heterocycloalkyl groups can also be fused to aromatic or non-aromatic ring systems to form members including, but not limited to, indoline. In some embodiments, heterocycloalkyl groups can be further substituted with one or more substituents selected from the group consisting of —OH, —SH, —$NH_2$, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN, —CR$_p$=O and —COOR$_p$, where R$_p$ is hydrogen or $C_1$ to $C_6$ alkyl.

In some embodiments of the compound of formula (I), alkoxy is —OR$_a$ group, where R$_a$ is a $C_1$-$C_4$ alkyl.

In some embodiments of the compound of formula (I), alkylamino is —HNR$_b$ group, where R$_b$ is a $C_1$-$C_4$ alkyl.

In some embodiments of the compound of formula (I), alkylthio is —SR$_b$ group, where R$_b$ is a $C_1$-$C_4$ alkyl.

In some embodiments of the compound of formula (I), aryl is a hydrocarbon group containing 6 to 10 carbon atoms and containing at least one aromatic ring which may be substituted by one or more substituents selected from the group consisting of OH, —SH, —$NH_2$, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN, —CR$_p$=O and —COOR$_p$, where R$_p$ is hydrogen or $C_1$ to $C_6$ alkyl.

In some embodiments of the compound of formula (I), heteroaryl is a hydrocarbon group containing from 2 to 10, preferably 4 to 10, carbon atoms, and at least one heteroatom, preferably one to two heteroatoms selected from the group consisting of O, S, N, and containing at least one aromatic ring. In some embodiments, heteroaryl can be further substituted with one or more substituents selected from the group consisting of —OH, —SH, —$NH_2$, halogen, —$N_3$, $C_1$ to $C_6$ alkyl, $C_1$ to $C_6$ alkoxy, $C_1$ to $C_6$ alkylthio, $C_1$ to $C_6$ alkylamino, $C_1$ to $C_6$ dialkylamino, —CN, —CR$_p$=O and —COOR$_p$, where R$_p$ is hydrogen or $C_1$ to $C_6$ alkyl. In certain embodiments, the heteroaryl is selected from the group of pyrrole, furan, thiophene, imidazole, thiazole, oxazole, indole and pyridine.

In some embodiments of the compound of formula (J) and/or (I), $R^1$, $R^2$, $R^3$, $R^5$, $R^8$, $R^9$, $R^{11}$, and $R^{12}$ are each independently H, OH, F, Cl, Br, I, CN, $N_3$, or $C_1$-$C_6$ alkyl. In some embodiments, $R^1$, $R^2$, $R^3$, $R^5$, $R^8$, $R^9$, $R^{11}$, and $R^{12}$ are each independently H, OH, F, CN, or $C_1$-$C_6$ alkyl. In some embodiments, $R^1$, $R^2$, $R^3$, $R^5$, $R^8$, $R^9$, $R^{11}$, and $R^{12}$ are each independently H, CN, or $C_1$-$C_6$ alkyl. In some embodiments, $R^1$, $R^2$, $R^3$, $R^5$, $R^8$, $R^9$, $R^{11}$, and $R^{12}$ are each H.

In some embodiments of the compound of formula (J) and/or (I), $Y^1$ and $Y^2$ are each independently —$CH_2$— or —O—. In some embodiments, $Y^1$ is —$CH_2$— and $Y^2$ is —O—. In some embodiments, $Y^1$ and $Y^2$ are each —O—.

In some embodiments of the compound of formula (J) and/or (I), $X^1$ and $X^3$ are each independently $OR^{15}$ or SH. In some embodiments, $X^1$ and $X^3$ are each independently $OR^{15}$. In some embodiments, $R^{15}$ is $C_1$-$C_6$ alkyl optionally substituted with 1 or 2 —O(C=O)$OR^B$; —O(C=O)$R^B$; or —$COOR^B$, for example, $R^{15}$ can be a $C_1$-$C_6$ alkyl substituted with a —O(C=O)$OR^B$. In some embodiments, $R^B$ is a $C_1$-$C_6$ alkyl, such as methyl, ethyl, n-propyl, isopropyl, n-butyl, tert-butyl, sec-butyl, n-pentyl, n-hexyl, sec-hexyl, or tert-hexyl. In some embodiments, $X^1$ and $X^3$ are each $OR^{15}$, wherein $R^{15}$ is $CH_2$ substituted with an —O(C=O)$R^B$, wherein $R^B$ is tert-butyl. In some embodiments, $X^1$ and $X^3$ are each $OR^{15}$, wherein $R^{15}$ is $CH_2$ substituted with an —O(C=O)$OR^B$, wherein $R^B$ is isopropyl. In some embodiments, $X^1$ is OH or SH, and $X^3$ is OH. In some embodiments, $X^1$ and $X^3$ are each OH. In some embodiments, $X^1$ is SH and $X^3$ is OH.

In some embodiments of the compound of formula (J) and/or (I), $X^2$ and $X^4$ are each O.

In some embodiments, the compound of formula (J), (I), and/or (IIa) has a structure of formula (Ia):

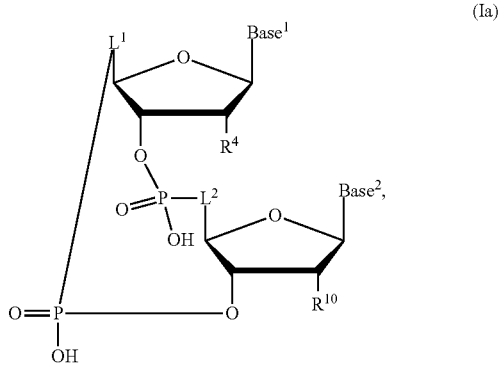

(Ia)

or an enantiomer, or pharmaceutically acceptable salt thereof.

As depicted in the formula (J), (I), (Ia), and/or (IIa), the connection of the atoms in $L^1$ and $L^2$ are as read from left to right. For example, in a compound of formula (IIa), when $L^2$ is —O—C($R^{13}R^{14}$)—, the oxygen atom is attached to the phosphorus atom and the carbon in —C($R^{13}R^{14}$)— is attached to the tetrahydrofuran ring, as distinct from when $L^2$ is —C($R^{13}R^{14}$)—O—, wherein the oxygen atom is attached to the tetrahydrofuran ring, and the carbon in —C($R^{13}R^{14}$)— is attached to the phosphorus atom.

In some embodiments of the compound of formula (J), (I), (Ia), and/or (IIa), $L^1$ and $L^2$ are each independently —CH($OR^{15}$)—, —C($R^6R^7$)—O—, —O—C($R^6R^7$)—, or —C($R^6R^7$)—$K^1$—C($R^6R^7$)—, wherein at least one of $L^1$ and $L^2$ is —CH($OR^{15}$), —C($R^6R^7$)—O—, or —C($R^6R^7$)—$K^1$—C($R^6R^7$)—. In some embodiments, $L^1$ and $L^2$ are each independently —CH($OR^{15}$)—, —C($R^6R^7$)—O—, —O—C($R^6R^7$)—, or —C($R^6R^7$)—$K^1$—C($R^6R^7$)—, wherein at least one of $L^1$ and $L^2$ is not —O—$CH_2$—. In some embodiments, $L^1$ and $L^2$ are each independently —C($R^6R^7$)—O—, —O—C($R^6R^7$)—, or —C($R^6R^7$)—$K^1$—C($R^6R^7$)—, wherein at least one of $L^1$ and $L^2$ is, —C($R^6R^7$)—O— or —C($R^6R^7$)—$K^1$—C($R^6R^7$)—. In some embodiments, $L^1$ is —C($R^6R^7$)—O— and $L^2$ is —C($R^{13}R^{14}$)—O—, $L^1$ is —C($R^6R^7$)—O— and $L^2$ is —O—C($R^{13}R^{14}$)—, $L^1$ is —O—C($R^6R^7$)— and $L^2$ is —C($R^{13}R^{14}$)—O—, $L^1$ is —C($R^6R^7$)—$K^1$—C($R^6R^7$)— and $L^2$ is —C($R^{13}R^{14}$)—$K^1$—C($R^{13}R^{14}$)—, $L^1$ is —C($R^6R^7$)—$K^1$—C($R^6R^7$)— and $L^2$ is —O—C($R^{13}R^{14}$)—, or $L^1$ is —O—C($R^6R^7$)— and $L^2$ is —C($R^{13}R^{14}$)—$K^1$—C($R^{13}R^{14}$)—. In some embodiments, $L^1$ is —C($R^6R^7$)—O— and $L^2$ is —C($R^{13}R^{14}$)—O—, $L^1$ is —C($R^6R^7$)—O— and $L^2$ is —O—C($R^{13}R^{14}$)—, $L^1$ is —O—C($R^6R^7$)— and $L^2$ is —C($R^{13}R^{14}$)—O—, $L^1$ is —C($R^6R^7$)—O— and $L^2$ is —C($R^{13}R^{14}$)—O—, or $L^1$ is —C($R^6R^7$)—$K^1$—C($R^6R^7$)— and $L^2$ is —O—C($R^{13}R^{14}$)—. In some embodiments, $L^1$ is —C($R^6R^7$)—O— and $L^2$ is —O—C($R^{13}R^{14}$)— or —C($R^{13}R^{14}$)—O—. In some embodiments, $L^1$ is —C($R^6R^7$)—O— and $L^2$ is —O—C($R^{13}R^{14}$)—, or $L^1$ is —O—C($R^6R^7$)— and $L^2$ is —C($R^{13}R^{14}$)—O—. In some embodiments, $L^1$ is —C($R^6R^7$)—O— and $L^2$ is —O—C($R^{13}R^{14}$)—. In some embodiments, $L^1$ is —O—C($R^6R^7$)— and $L^2$ is —C($R^{13}R^{14}$)—O—. In some embodiments, at least one of $L^1$ and $L^2$ is not —O—$CH_2$—.

In some embodiments of the compound of formula (J), (I), (Ia), and/or (IIa), $K^1$ is —O—.

In some embodiments, the compound of formula (J), (I), (Ia), and/or (IIa) has a structure of formula (IIIa):

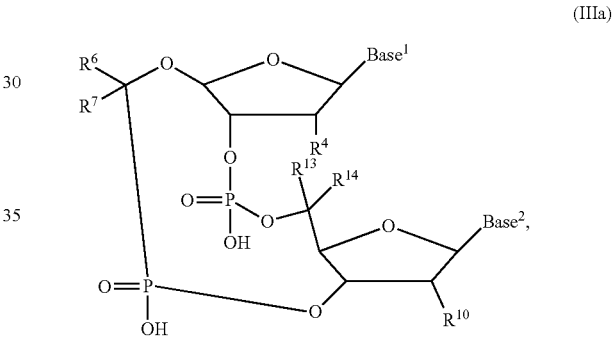

(IIIa)

or an enantiomer, or pharmaceutically acceptable salt thereof.

In some embodiments, the compound of formula (J), (I), (Ia), (IIa), and/or (IIIa) has a structure of formula (IVa):

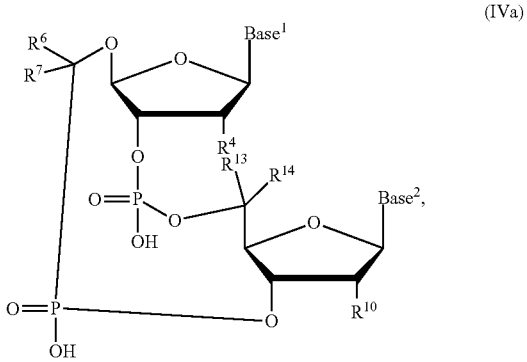

(IVa)

or an enantiomer, or pharmaceutically acceptable salt thereof.

In some embodiments, the compound of formula (J), (I), (Ia), and/or (IIa) has a structure of formula (IIIb):

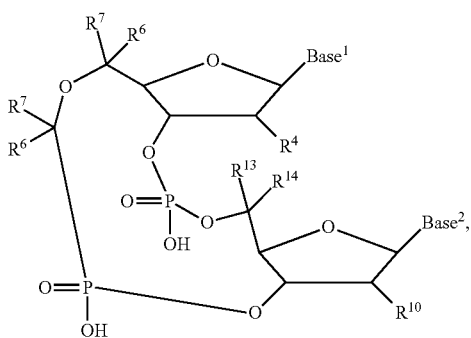

(IIIb)

or an enantiomer, or pharmaceutically acceptable salt thereof.

In some embodiments, the compound of formula (J), (I), (Ia), (IIa), and/or (IIIb) has a structure of formula (IVb):

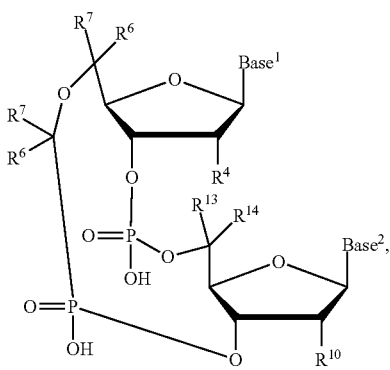

(IVb)

or an enantiomer, or pharmaceutically acceptable salt thereof.

In some embodiments, the compound of formula (J), (I), (Ia), and/or (IIa) has a structure of formula (IIIc):

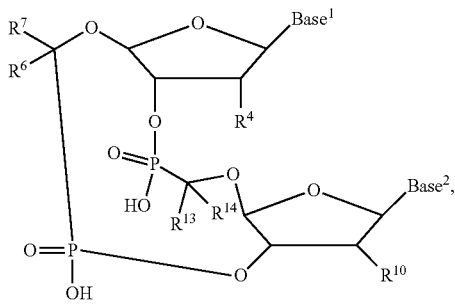

(IIIc)

or an enantiomer, or pharmaceutically acceptable salt thereof.

In some embodiments, the compound of formula (J), (I), (Ia), (IIa) and/or (IIIc) has a structure of formula (IVc):

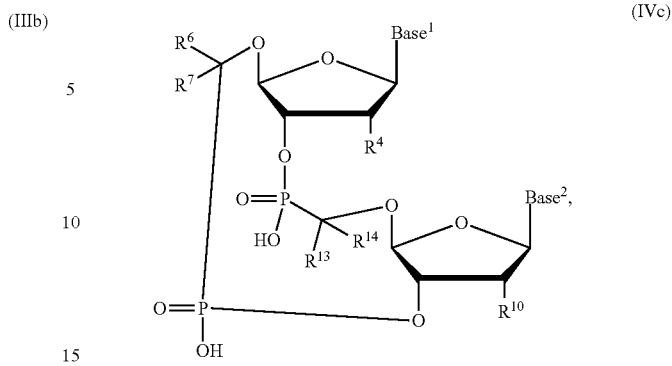

(IVc)

or an enantiomer, or pharmaceutically acceptable salt thereof.

In some embodiments of the compound of formula (J), (I), (Ia), (IIa), (IIIa), (IIIb), (IIIc), (IVa), (IVb), and/or (IVc), $R^6$ and $R^7$ are each independently H, CN, $N_3$, F, Cl, Br, I, $COOR^{15}$, $CON(R^{15})_2$, $OR^{15}$, $SR^{15}$, $N(R^{15})_2$, or $C_1$-$C_6$ alkyl. In some embodiments, $R^6$ and $R^7$ are each independently H, CN, F, Cl, $COOR^{15}$, $CON(R^{15})_2$, $OR^{15}$, $SR^{15}$, $N(R^{15})_2$, or $C_1$-$C_6$ alkyl, wherein each $R^{15}$ is independently H or $C_1$-$C_6$ alkyl. In some embodiments, $R^6$ and $R^7$ are each independently H, CN, $N_3$, F, Cl, Br, I, $CH_2OH$, or $CH_2N_3$. In some embodiments, $R^6$ and $R^7$ are each independently H or $C_1$-$C_6$ alkyl. In some embodiments, $R^6$ and $R^7$ are each H.

In some embodiments of the compound of formula (J), (I), (Ia), (IIa), (IIIa), (IIIb), (IIIc), (IVa), (IVb), and/or (IVc), $R^6$, $R^7$, $R^{13}$ and $R^{14}$ are each independently H, CN, $N_3$, F, Cl, Br, I, $COOR^{15}$, $CON(R^{15})_2$, $OR^{15}$, $SR^{15}$, $N(R^{15})_2$, or $C_1$-$C_6$ alkyl. In some embodiments, $R^6$, $R^7$, $R^{13}$ and $R^{14}$ are each independently H, CN, F, Cl, $COOR^{15}$, $CON(R^{15})_2$, $OR^{15}$, $SR^{15}$, $N(R^{15})_2$, or $C_1$-$C_6$ alkyl, wherein each $R^{15}$ is independently H or $C_1$-$C_6$ alkyl. In some embodiments, $R^6$, $R^7$, $R^{13}$ and $R^{14}$ are each independently H, CN, $N_3$, F, Cl, Br, I, $CH_2OH$, or $CH_2N_3$. In some embodiments, $R^6$, $R^7$, $R^{13}$ and $R^{14}$ are each independently H or $C_1$-$C_6$ alkyl. In some embodiments, $R^6$, $R^7$, $R^{13}$ and $R^{14}$ are each H.

In some embodiments of the compound of formula (J), (I), (Ia), (IIa), (IIIa), (IIIb), (IIIc), (IVa), (IVb), and/or (IVc), $R^{10}$ is H, OH, F, Cl, Br, I, CN, $N_3$, or $C_1$-$C_6$ alkyl. In some embodiments, $R^{10}$ is H, OH, F, Cl, Br, I, CN, $N_3$, $OR^{15}$, $SR^{15}$, or $N(R^{15})_2$. In some embodiments, $R^{10}$ is H, OH, F, CN, $N_3$, $OR^{15}$, $SR^{15}$, or $N(R^5)_2$. In some embodiments, $R^{10}$ is H, OH, F, CN, $OR^{15}$, $SR^{15}$, or $N(R^{15})_2$, wherein $R^{15}$ is each independently H or $C_1$-$C_6$ alkyl. In some embodiments, $R^{10}$ is H, OH, F, Cl, CN, or $C_1$-$C_6$ alkyl. In some embodiments, $R^{10}$ is H, OH, or F. In some embodiments, $R^{10}$ is H. In some embodiments, $R^{10}$ is OH. In some embodiments, $R^{10}$ is F.

In some embodiments of the compound of formula (J), (I), (Ia), (IIa), (IIIa), (IIIb), (IIIc), (IVa), (IVb), and/or (IVc), $R^4$ is H, OH, F, Cl, Br, I, CN, $N_3$, or $C_1$-$C_6$ alkyl. In some embodiments, $R^4$ is H, OH, F, Cl, Br, I, CN, $N_3$, $OR^{15}$, $SR^{15}$, or $N(R^{15})_2$. In some embodiments, $R^4$ is H, OH, F, CN, $N_3$, $OR^{15}$, $SR^{15}$, or $N(R^{15})_2$. In some embodiments, $R^4$ is H, OH, F, CN, $OR^{15}$, $SR^{15}$, or $N(R^{15})_2$, wherein $R^{15}$ is each independently H or $C_1$-$C_6$ alkyl. In some embodiments, $R^4$ is H, OH, F, Cl, CN, or $C_1$-$C_6$ alkyl. In some embodiments, $R^4$ is H, OH, or F. In some embodiments, $R^4$ is H. In some embodiments, $R^4$ is OH. In some embodiments, $R^4$ is F.

In some embodiments of the compound of formula (J), (I), (Ia), (IIa), (IIIa), (IIIb), (IIIc), (IVa), (IVb), and/or (IVc), $R^4$ and $R^{10}$ are each independently H, OH, F, Cl, Br, I, CN, $N_3$, or $C_1$-$C_6$ alkyl. In some embodiments, $R^4$ and $R^{10}$ are each independently H, OH, F, Cl, Br, I, CN, $N_3$, $OR^{15}$, $SR^{15}$, or $N(R^{15})_2$. In some embodiments, $R^4$ and $R^{10}$ are each independently H, OH, F, CN, $N_3$, $OR^{15}$, $SR^{15}$, or $N(R^{15})_2$. In some embodiments, $R^4$ and $R^{10}$ are each independently H, OH, F, CN, $OR^{15}$, $SR^{15}$, or $N(R^{15})_2$, wherein $R^{15}$ is each independently H or $C_1$-$C_6$ alkyl. In some embodiments, $R^4$ and $R^{10}$ are each independently H, OH, F, or CN. In some embodiments, $R^4$ and $R^{10}$ are each independently H, OH, or F. In some embodiments, $R^4$ is OH, and $R^{10}$ is H, OH, or F. In some embodiments, $R^4$ and $R^{10}$ are each independently H or OH. In some embodiments, $R^4$ and $R^{10}$ are each independently OH or F. In some embodiments, $R^4$ and $R^{10}$ are each OH. In some embodiments, $R^4$ is H, and $R^{10}$ is OH. In some embodiments, $R^4$ is OH, and $R^{10}$ is H. In some embodiments, $R^4$ is OH, and $R^{10}$ is F.

In some embodiments of the compound of formula (J), (I), (Ia), (IIa), (IIIa), (IIIb), (IIIc), (IVa), (IVb), and/or (IVc), $R^{15}$ is H, $-C(=Z)R^{16}$, $-C(=Z)OR^{16}$, $-C(=Z)SR^{16}$, $-C(=Z)N(R^{16})_2$, $C_1$-$C_6$ alkyl, $C_2$-$C_6$ alkenyl, $C_2$-$C_6$ alkynyl, or $C_3$-$C_7$ cycloalkyl. In some embodiments, $R^{15}$ is H, $-C(=Z)R^{16}$, $-C(=Z)OR^{16}$, $-C(=Z)SR^{16}$, $-C(=Z)N(R^{16})_2$, or $C_1$-$C_6$ alkyl. In some embodiments, $R^{15}$ is H, $-C(=Z)R^{16}$, $-C(=Z)OR^{16}$, $-C(=Z)N(R^{16})_2$, or $C_1$-$C_6$ alkyl. In some embodiments, $R^{15}$ is H, $-C(=Z)OR^{16}$, or $C_1$-$C_6$ alkyl optionally substituted with $C_6$-$C_{10}$ aryl optionally substituted with 1, 2, or 3 $-$OH, $-$CN, $-$O(C=O)$OR^B$, $-$O(C=O)$R^B$, or $-$COO$R^B$, wherein $R^B$ is an unsubstituted $C_1$-$C_6$ alkyl. In some embodiments, $R^{15}$ is $C_1$-$C_6$ alkyl optionally substituted with 1 or 2 $-$O(C=O)$OR^B$; $-$O(C=O)$R^B$; or $-$COO$R^B$, for example, $R^{15}$ can be a $C_1$-$C_6$ alkyl substituted with a $-$O(C=O)$OR^B$. In some embodiments, $R^B$ is a $C_1$-$C_6$ alkyl, such as methyl, ethyl, n-propyl, isopropyl, n-butyl, tert-butyl, sec-butyl, n-pentyl, n-hexyl, sec-hexyl, or tert-hexyl.

In some embodiments of the compound of formula (J), (I), (Ia), (IIa), (IIIa), (IIIb), (IIIc), (IVa), (IVb), and/or (IVc), $R^{16}$ is $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl. In some embodiments, $R^{16}$ is $C_1$-$C_6$ alkyl, $C_6$-$C_{10}$ aryl, or $C_2$-$C_{10}$ heteroaryl, which are each optionally substituted with 1, 2, or 3 $-$OH, $-$CN, $-$O(C=O)$OR^B$, $-$O(C=O)$R^B$, or $-$COO$R^B$, wherein $R^B$ is an unsubstituted $C_1$-$C_6$ alkyl.

In some embodiments of the compound of formula (J), (I), (Ia), (IIa), (IIIa), (IIIb), (IIIc), (IVa), (IVb), and/or (IVc), Base¹ and Base² are each independently:

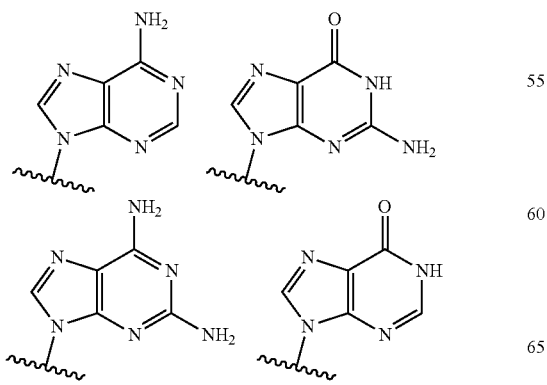

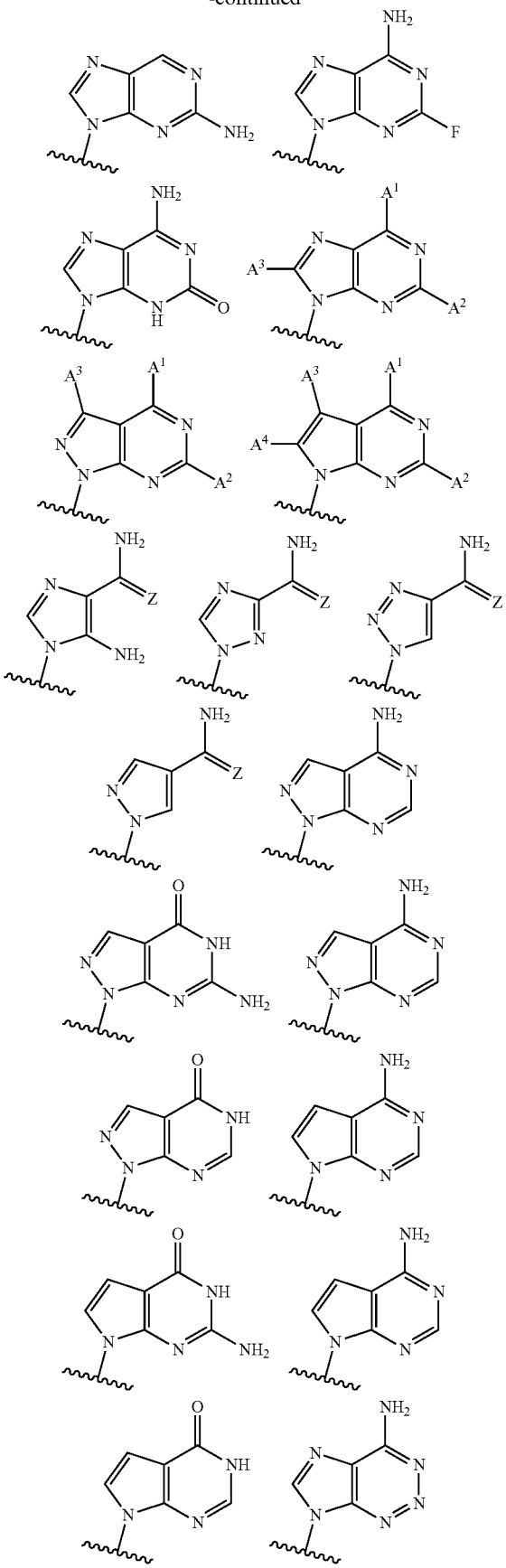

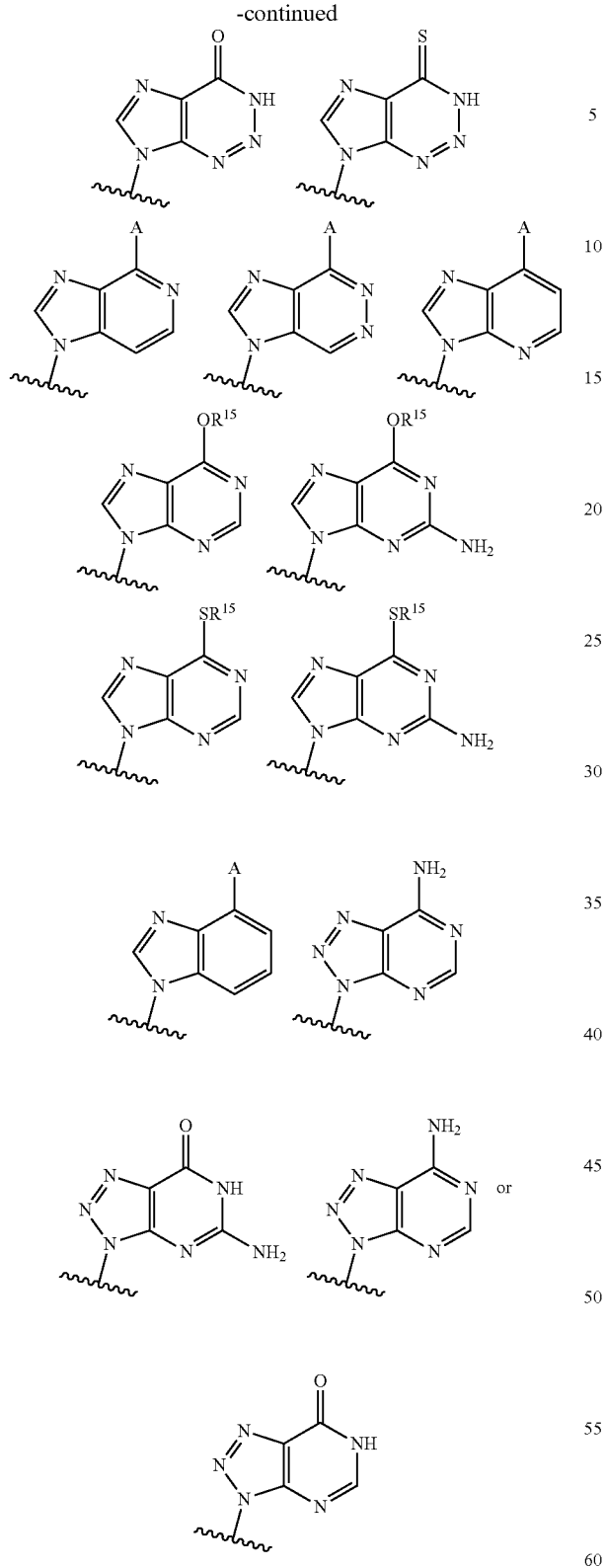
wherein
A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$.
In some embodiments, Base¹ and Base² are each independently:

wherein
A, A$^1$, A$^2$, A$^3$ and A$^4$ are each independently H, OH, SH, F, Cl, Br, I, NH$_2$, OR$^{15}$, SR$^{15}$, NHR$^{15}$, N(R$^{15}$)$_2$, or R$^{16}$.
In some embodiments, Base$^1$ and Base$^2$ are each independently:
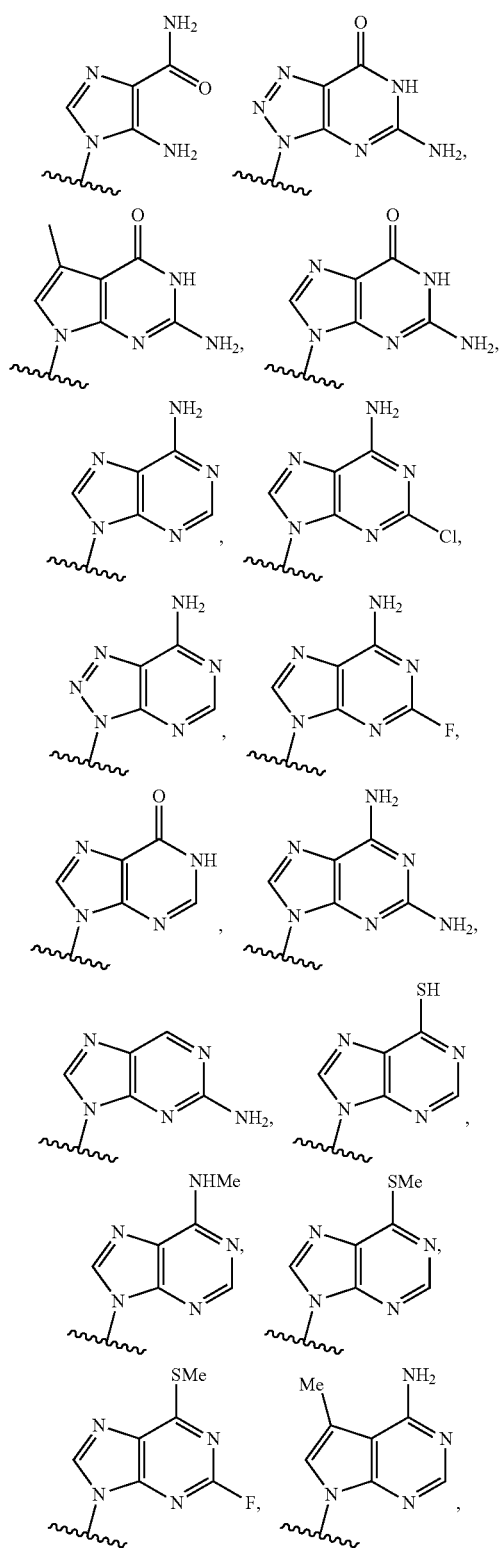
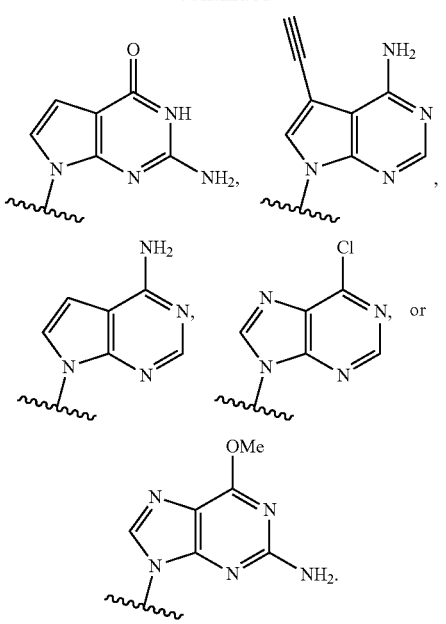
In some embodiments, Base$^1$ and Base$^2$ are each independently:
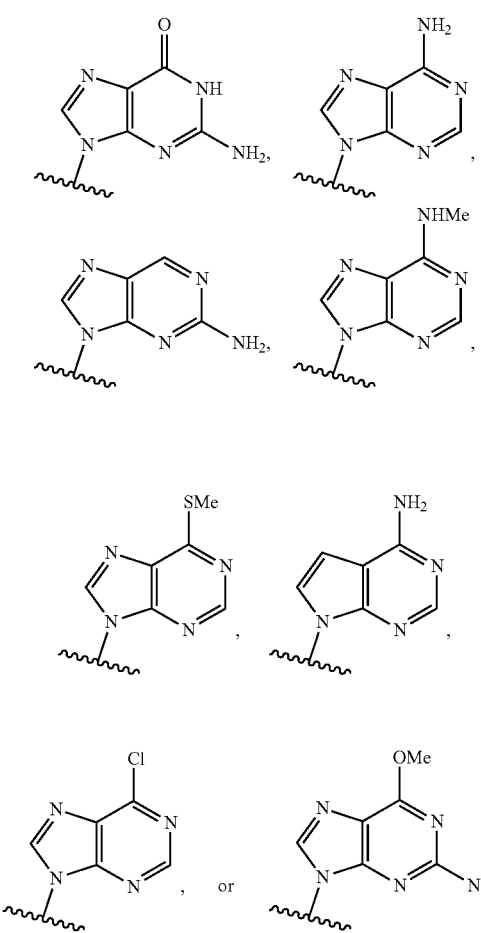

In some embodiments, Base¹ is:
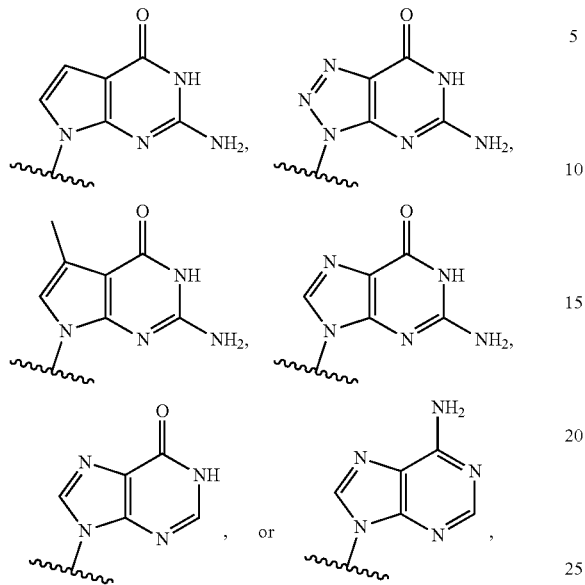
and Base² is:
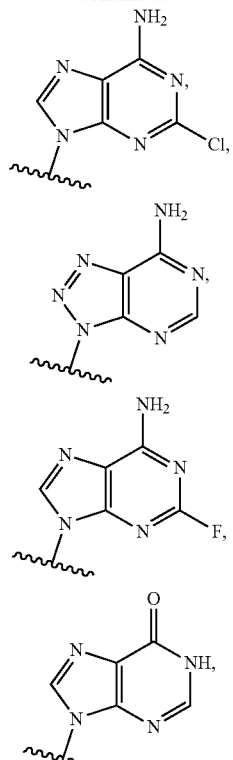
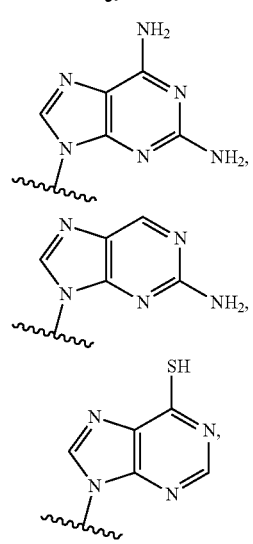
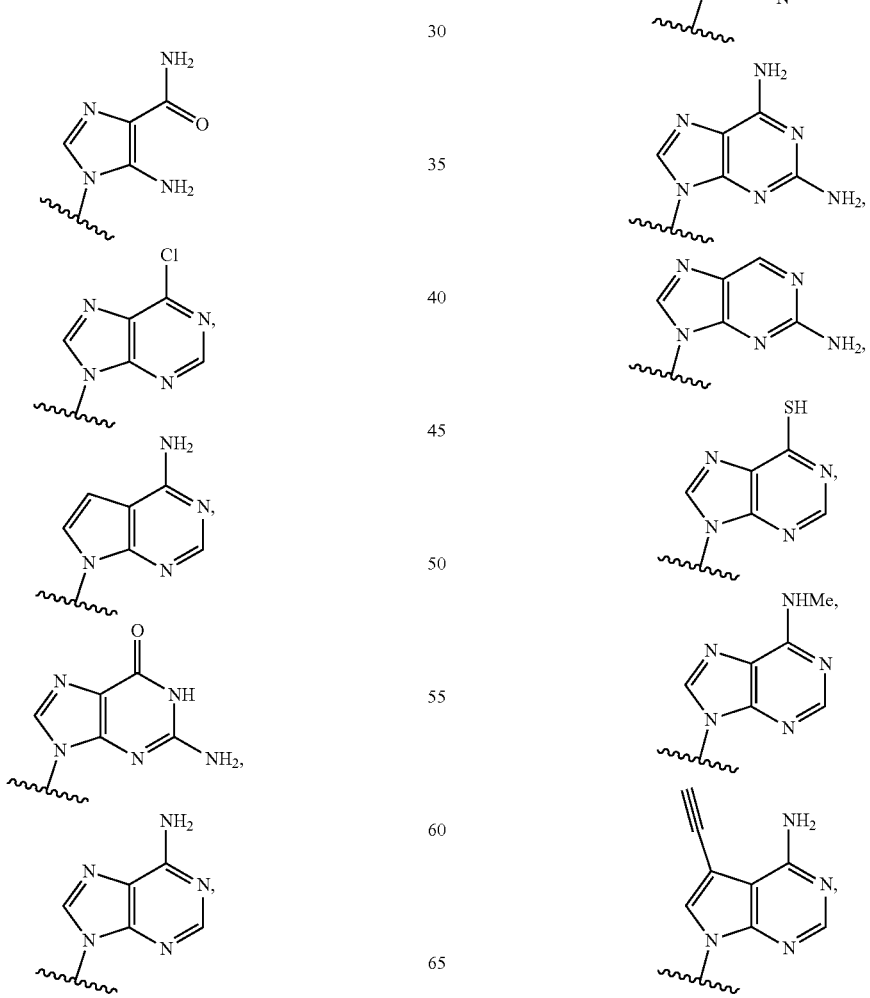

-continued
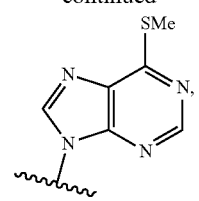
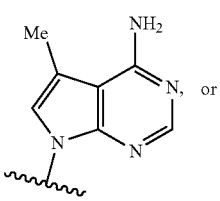
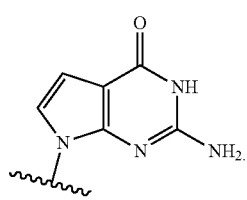
In some embodiments, Base¹ is:
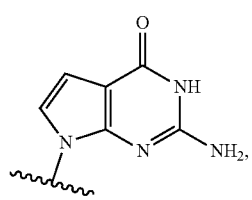 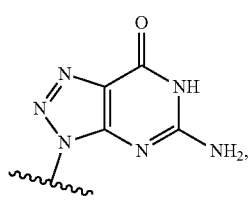
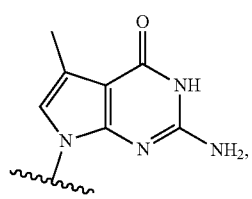 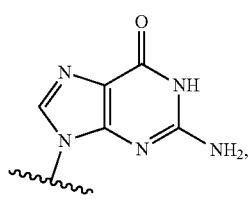
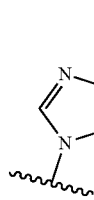 or 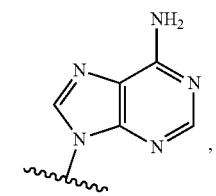,
and Base² is
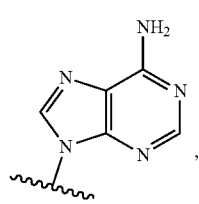 [SMILES: *n1cnc2c(N)ncnc21],
In some embodiments, Base¹ is
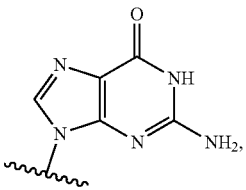 [SMILES: *n1cnc2c(=O)[nH]c(N)nc21]
and Base² is:
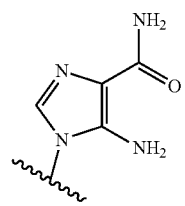
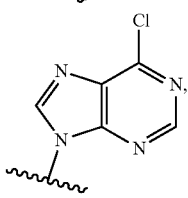
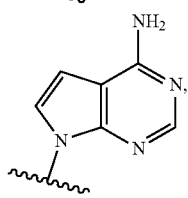
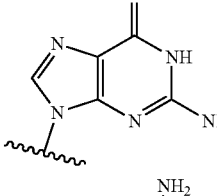
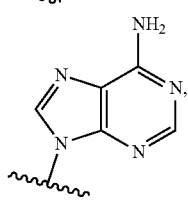
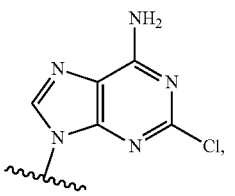
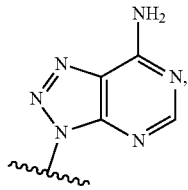

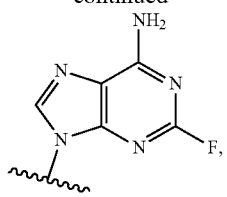
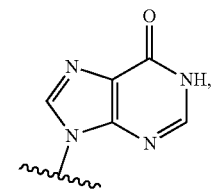
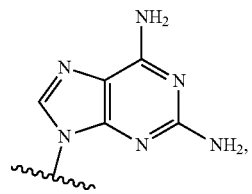
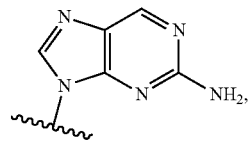
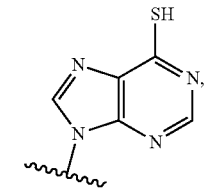
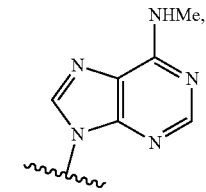
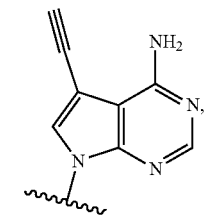
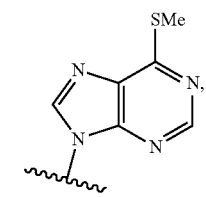
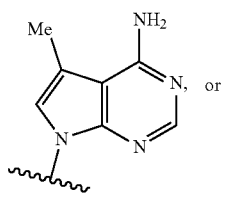
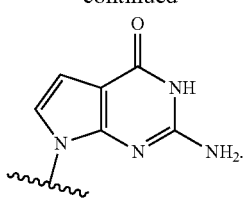
In some embodiments, Base$^1$ is
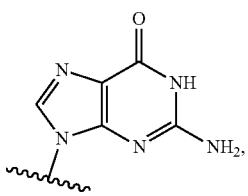 [SMILES: *n1cnc2c(=O)[nH]c(N)nc21]
and Base$^2$ is
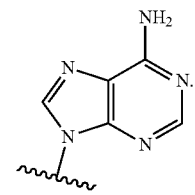 [SMILES: *n1cnc2c(N)ncnc21]
In some embodiments, Base$^1$ is
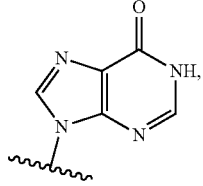 [SMILES: *n1cnc2c(=O)[nH]cnc21]
and Base$^2$ is
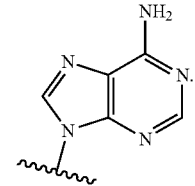
In some embodiments of the compound of formula (J), (I), (Ia), (IIa), (IIIa), (IIIb), (IIIc), (IVa), (IVb), and/or (IVc), the compound has a structure:

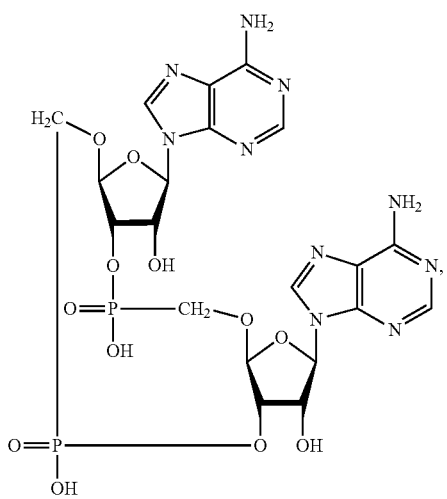
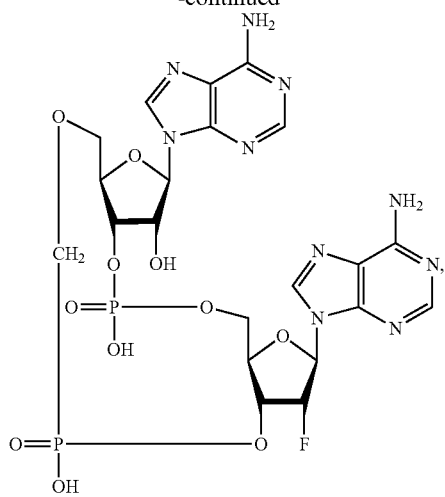
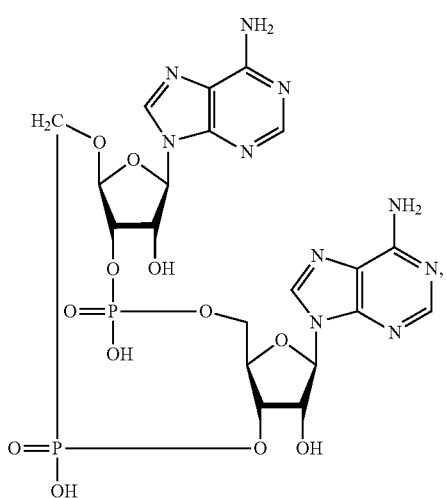
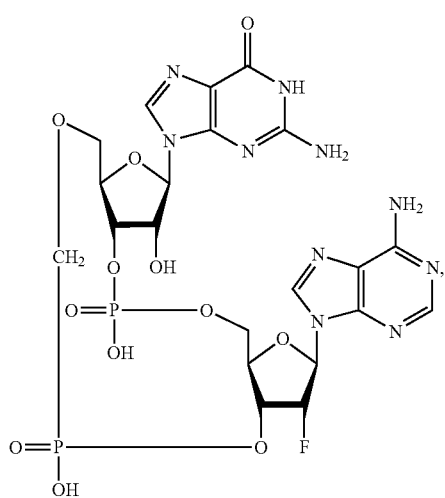
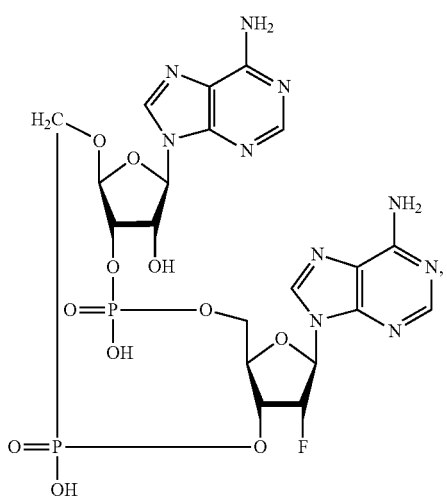
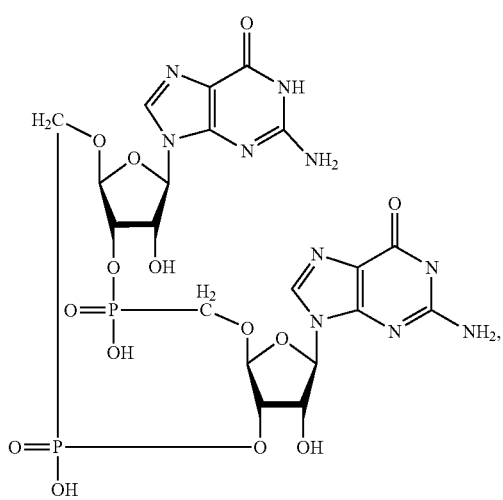

43
-continued
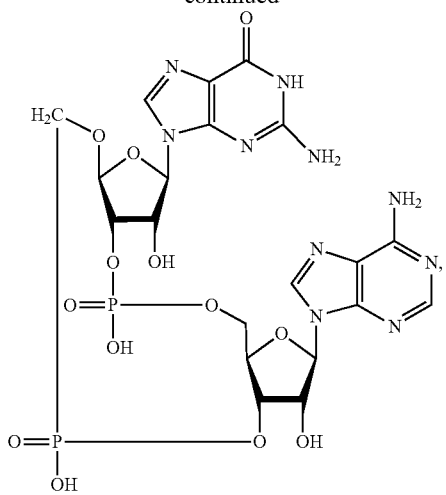
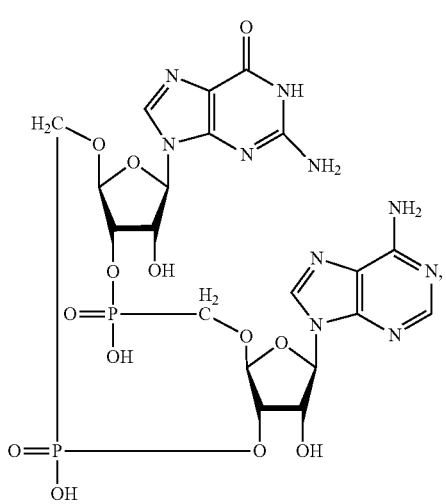
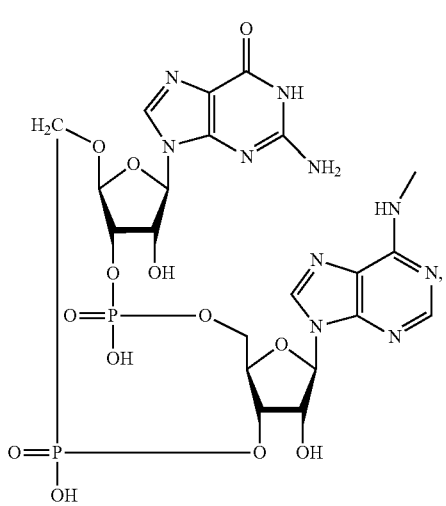
44
-continued
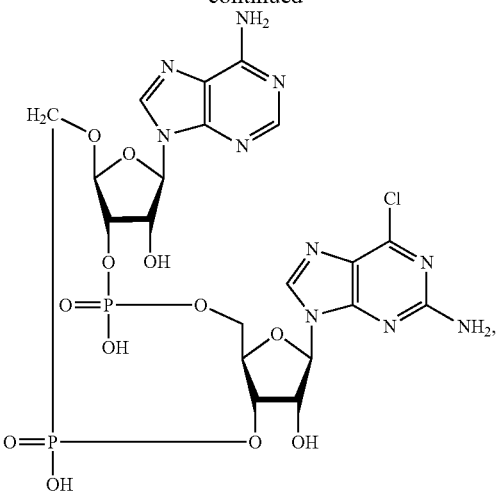
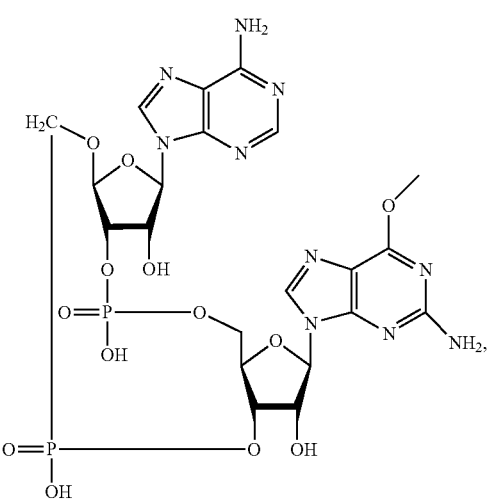
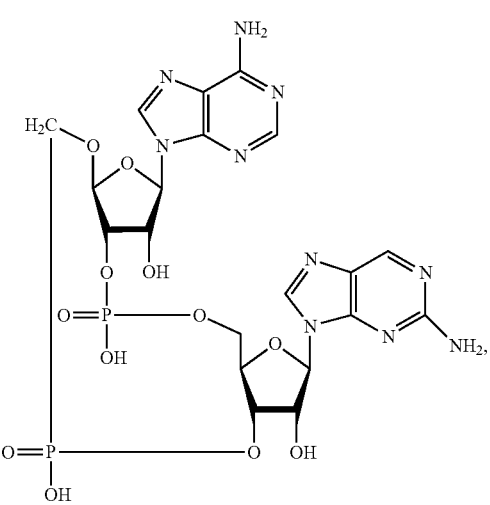

45
-continued
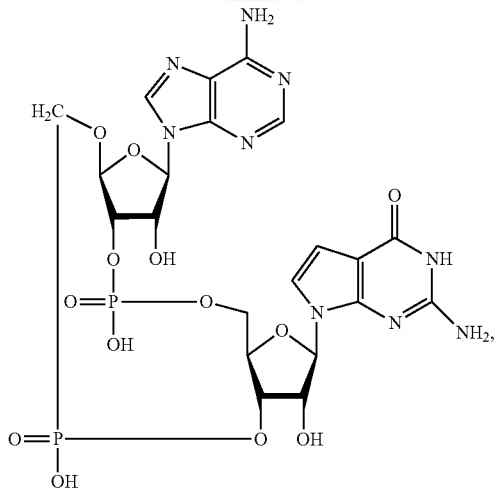
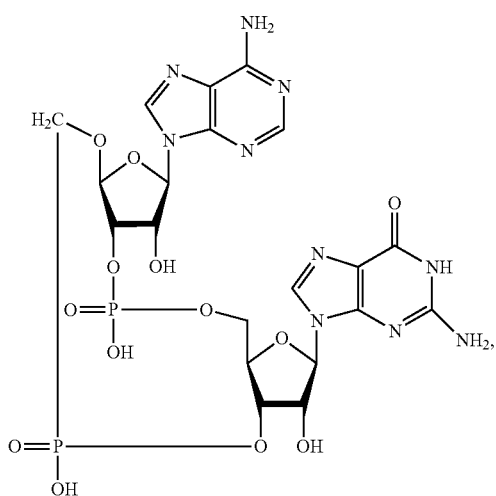
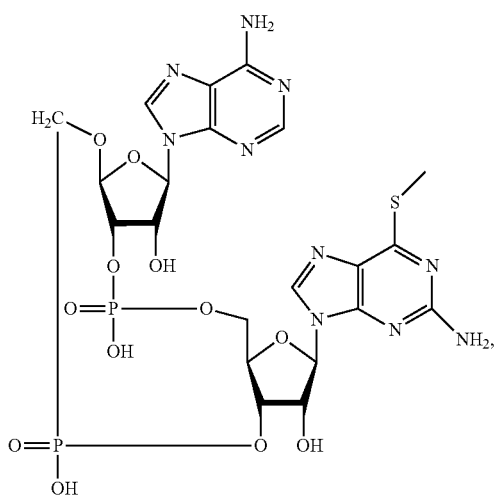
46
-continued
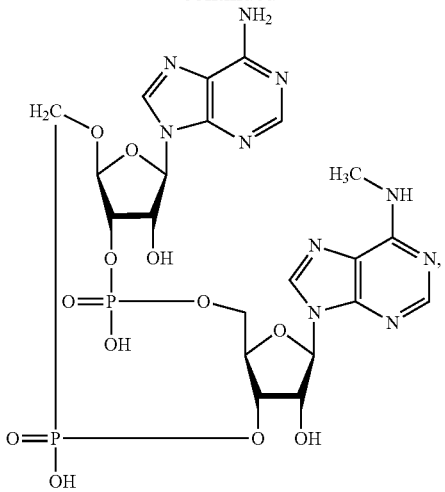
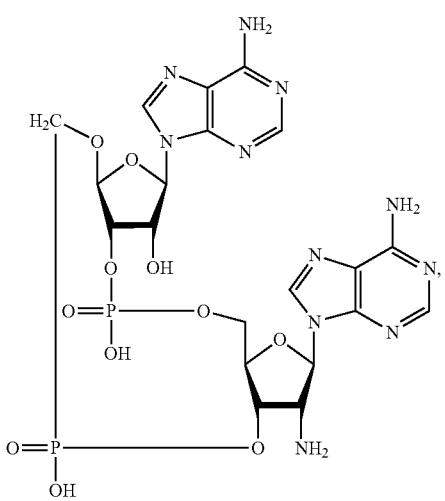
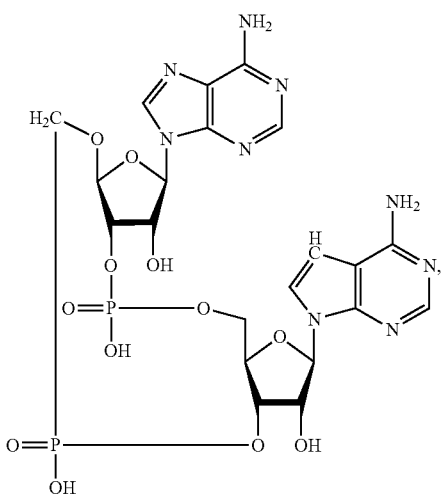

-continued
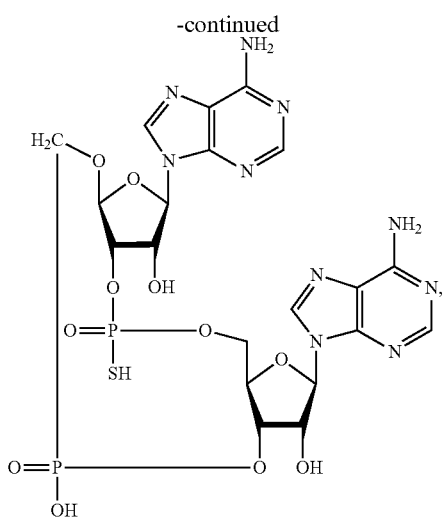
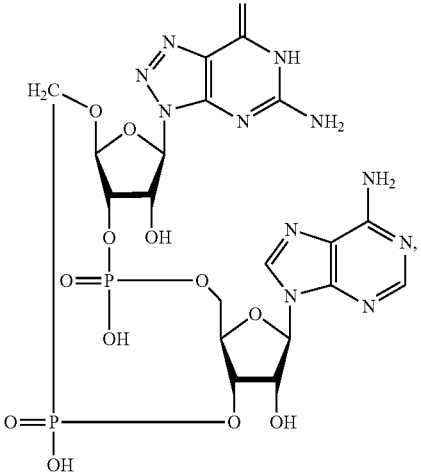
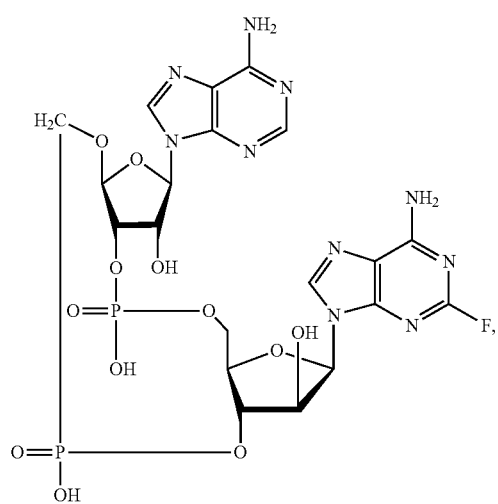
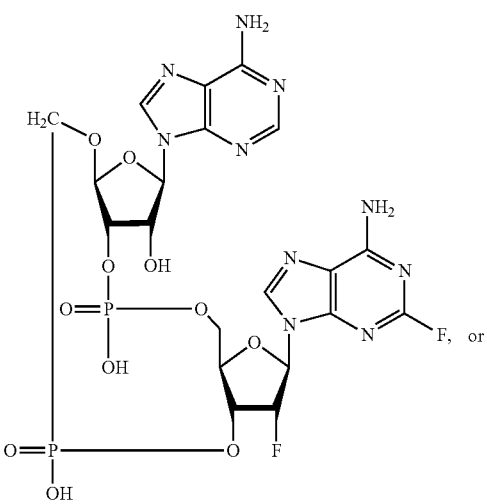
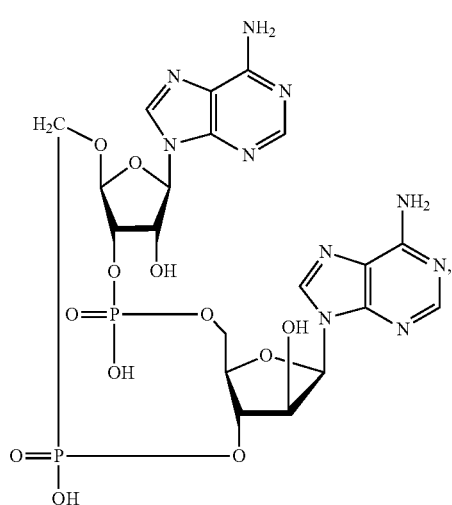
or an enantiomer, or pharmaceutically acceptable salt thereof.
In some embodiments, the compound of formula (J), (I), (Ia), (IIa), (IIIa), (IIIb), (IIIc), (IVa), (IVb), and/or (IVc) has a structure:

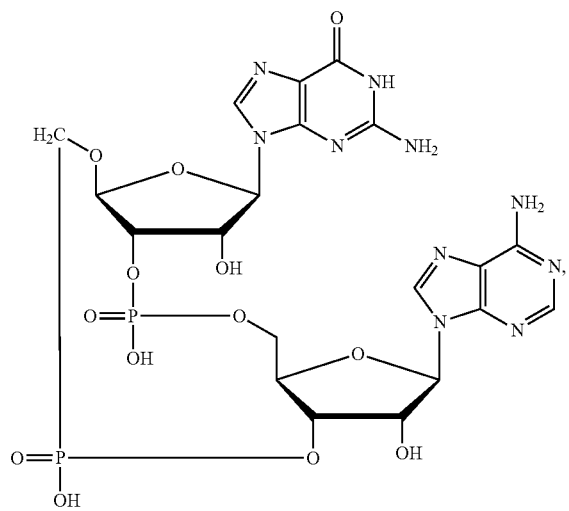

or a pharmaceutically acceptable salt thereof.

In some embodiments, the compound of formula (J), (I), (Ia), (IIa), (IIIa), (IIIb), (IIIc), (IVa), (IVb), and/or (IVc) has a structure:

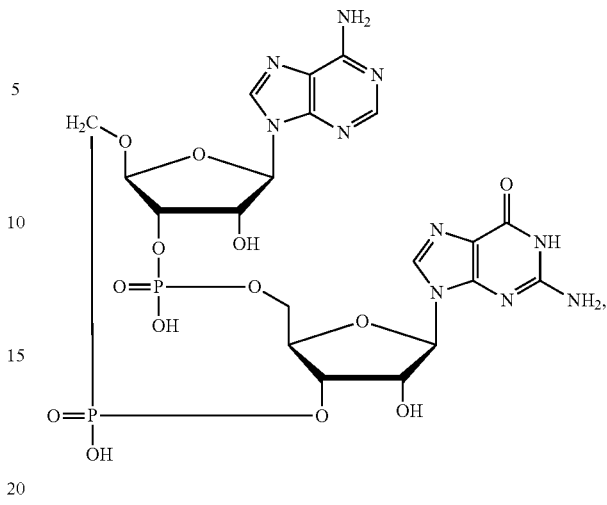

or a pharmaceutically acceptable salt thereof.

In some embodiments, the compound of formula (J), (I), (Ia), (IIa), (IIIa), (IIIb), (IIIc), (IVa), (IVb), and/or (IVc) has a structure:

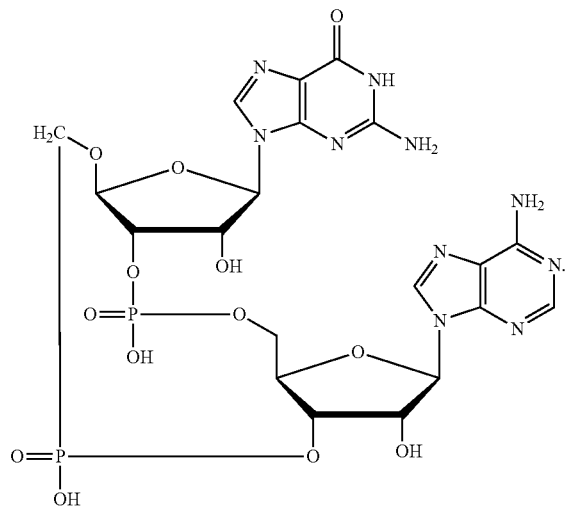

In some embodiments, the compound of formula (J), (I), (Ia), (IIa), (IIIa), (IIIb), (IIIc), (IVa), (IVb), and/or (IVc) has a structure:

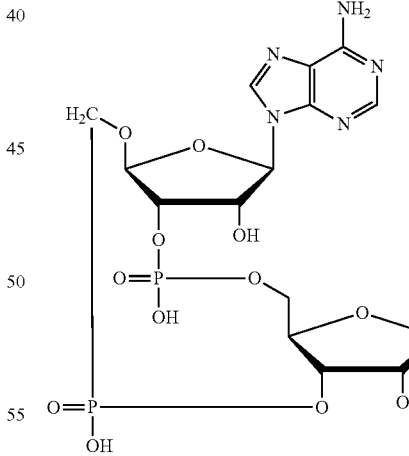

In some embodiments, the compound of formula (J), (I), (Ia), (IIa), (IIIa), (IIIb), (IIIc), (IVa), (IVb), and/or (IVc) has a structure:

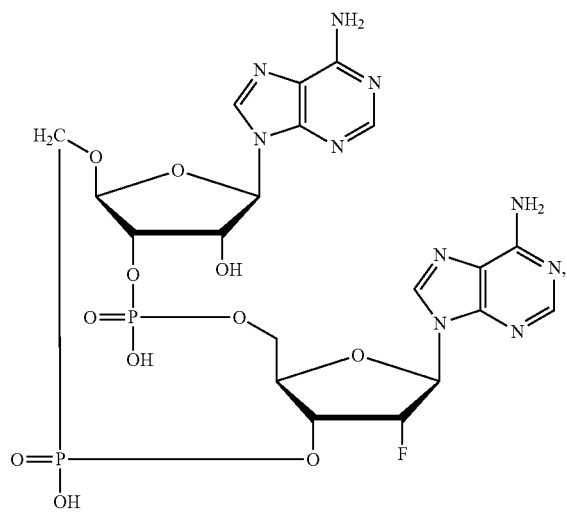

or a pharmaceutically acceptable salt thereof.

In some embodiments, the compound of formula (J), (I), (Ia), (IIa), (IIIa), (IIIb), (IIIc), (IVa), (IVb), and/or (IVc) has a structure:

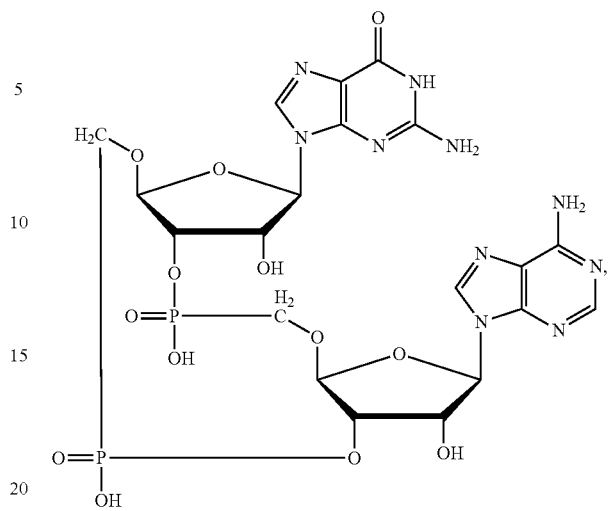

or a pharmaceutically acceptable salt thereof.

In some embodiments, the compound of formula (J), (I), (Ia), (IIa), (IIIa), (IIIb), (IIIc), (IVa), (IVb), and/or (IVc) has a structure:

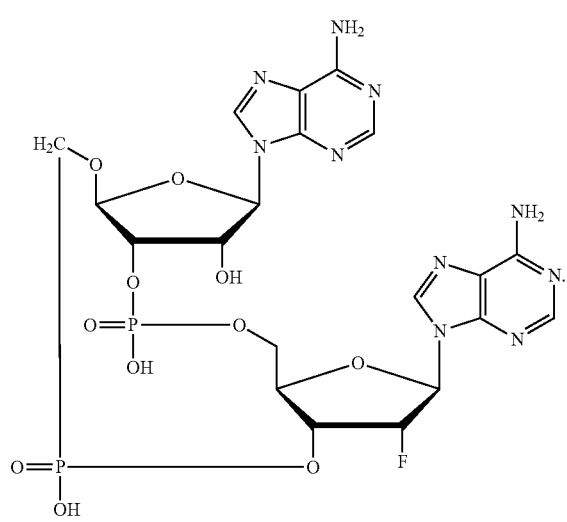

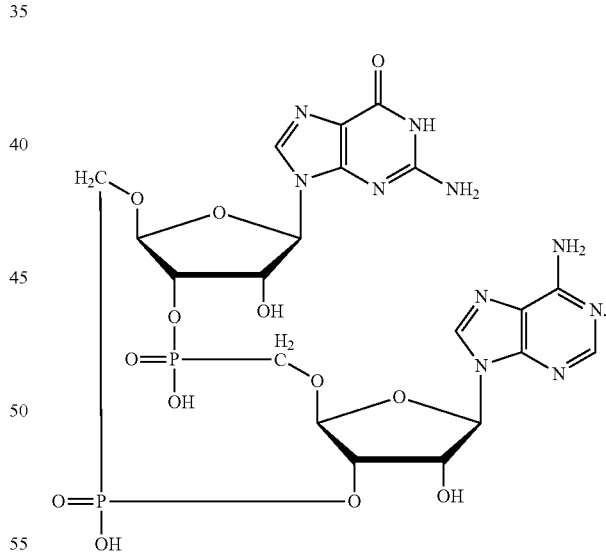

In some embodiments, the compound of formula (J), (I), (Ia), (IIa), (IIIa), (IIIb), (IIIc), (IVa), (IVb), and/or (IVc) has a structure:

In some embodiments, the compound of formula (J), (I), (Ia), (IIa), (IIIa), (IIIb), (IIIc), (IVa), (IVb), and/or (IVc) has a structure:

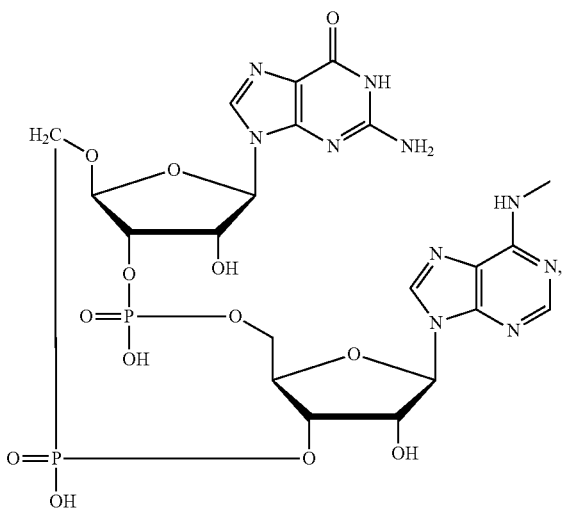

or a pharmaceutically acceptable salt thereof.

In some embodiments, the compound of formula (J), (I), (Ia), (IIa), (IIIa), (IIIb), (IIIc), (IVa), (IVb), and/or (IVc) has a structure:

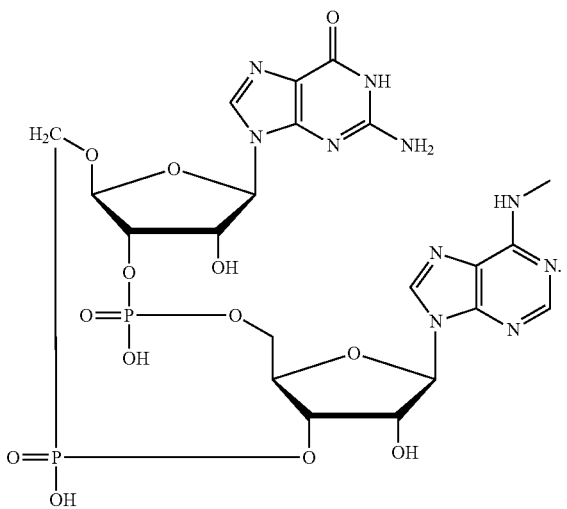

IV. Compositions

In certain embodiments, the present disclosure provides a pharmaceutical composition comprising a compound of the present disclosure (e.g. a compound of Formula (J), (I), (Ia), (IIa), (IIIa), (IIIb), (IIIc), (IVa), (IVb), and/or (IVc)), or a pharmaceutically acceptable salt thereof, and a pharmaceutically acceptable excipient.

In certain embodiments, the pharmaceutical composition comprises one or more additional therapeutic agent, as more fully set forth below.

Pharmaceutical compositions comprising the compounds disclosed herein, or pharmaceutically acceptable salts thereof, may be prepared with one or more pharmaceutically acceptable excipients which may be selected in accord with ordinary practice. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like. In certain embodiments, the composition is provided as a solid dosage form, including a solid oral dosage form.

The compositions include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, sachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

In certain embodiments, a composition comprising a compound of the present disclosure (e.g. a compound of Formula (J), (I), (Ia), (IIa), (IIIa), (IIIb), (IIIc), (IVa), (IVb), and/or (IVc)), or a pharmaceutically acceptable salt thereof in one variation does not contain an agent that affects the rate at which the active ingredient is metabolized. Thus, it is understood that compositions comprising a compound of the present disclosure in one aspect do not comprise an agent that would affect (e.g., slow, hinder or retard) the metabolism of a compound of the present disclosure or any other active ingredient administered separately, sequentially or simultaneously with a compound of the present disclosure. It is also understood that any of the methods, kits, articles of manufacture and the like detailed herein in one aspect do not comprise an agent that would affect (e.g., slow, hinder or retard) the metabolism of a compound of the present disclosure or any other active ingredient administered separately, sequentially or simultaneously with a compound of the present disclosure.

The disclosure further includes a pharmaceutical composition as described above for use in modulating STING protein activity, to induce STING-dependent production of type I interferons, cytokines or chemokines.

The disclosure further includes a pharmaceutical composition as described above for use in treating or preventing viral infection, infection caused by hepatitis B virus, by HIV, hyperproliferative disease or cancer.

In some embodiments, the pharmaceutical compositions described above are for use in a human or an animal.

The disclosure further includes compounds of Formula (J), (I), (Ia), (IIa), (IIIa), (IIIb), (IIIc), (IVa), (IVb), and/or (IVc), for administration as a single active ingredient of a pharmaceutically acceptable composition which can be prepared by conventional methods known in the art, for example by binding the active ingredient to a pharmaceutically acceptable, therapeutically inert organic and/or inorganic carrier or excipient, or by mixing therewith.

In one aspect, provided herein is the use of a compound of Formula (J), (I), (Ia), (IIa), (IIIa), (IIIb), (IIIc), (IVa), (IVb), and/or (IVc), as a second or other active ingredient having a synergistic effect with other active ingredients in known drugs, or administration of the compound of Formula (J), (I), (Ia), (IIa), (IIIa), (IIIb), (IIIc), (IVa), (IVb), and/or (IVc), together with such drugs.

The compound of Formula (J), (I), (Ia), (IIa), (IIIa), (IIIb), (IIIc), (IVa), (IVb), and/or (IVc) of this disclosure may also be used in the form of a prodrug or other suitably modified form which releases the active ingredient in vivo.

V. Methods

In one embodiment, provided herein is a method of treating a disease or disorder, comprising administering to a human or animal in need thereof a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

Also provided is a method of modulating the activity of STING protein, comprising administering a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

The Stimulator of interferon genes (STING) adaptor protein, also known as STING, STING protein, transmembrane protein 173 (TMEM173), MPYS, mediator of IRF3 activation (MITA), or endoplasmic reticulum interferon stimulator (ERIS), is a protein that in humans is encoded by the TMEM173 gene (UniProt code Q86WV6; NCBI Reference Sequences: NP_938023.1 (isoform 1) and NP_001288667 (isoform 2)). STING adaptor protein is believed to function as both a direct cytosolic DNA sensor (CDS) and an adaptor protein in Type I interferon signaling through different molecular mechanisms. STING adaptor protein has been shown to activate downstream transcription factors STAT6 and IRF3 through TBK1, and NF-κB through IKKβ, which can effect an antiviral response or innate immune response against an intracellular pathogen. STING adaptor protein plays a role in innate immunity by inducing type I interferon production when cells are infected with intracellular pathogens, such as viruses, mycobacteria and intracellular parasites. Type I interferon, mediated by STING adaptor protein, protects infected cells and nearby cells from local infection by autocrine and paracrine signaling.

Further provided is a method of preventing or treating a disease or condition responsive to the modulation of STING adaptor protein, comprising administering to a human or animal in need thereof a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

Further provided is a method of inducing a STING adaptor protein-dependent type I interferon, cytokine or chemokine in a human or animal, comprising administering a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

Activation of STING adaptor protein in turn activates protein kinase TBK1, which subsequently activates downstream transcription factors NF-κB and IRF-3. Activation of STING adaptor protein ultimately is believed to result in the release of type I and III interferons as well as a variety of cytokines and chemokines such as IL-6, TNF-α and INF-γ. Accordingly, induction of a STING adaptor protein-dependent type I interferon, cytokine or chemokine in a human or animal results in the activation of one or more of NF-κB, IRF-3, a type I interferon, a type III interferon, IL-6, TNF-α, and INF-γ in said human or animal.

Further provided is a method of treating or preventing viral infection, e.g., infection by hepatitis B or HIV, comprising administering to a human or animal in need thereof a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

Viral infections that can be treated or prevented by the methods of the present disclosure can be any infection caused by a virus, e.g., a virus from the Hepadnaviridae family of viruses, e.g., hepatitis B; or any retrovirus, e.g., an alpharetrovirus, such as Rous sarcoma virus; a betaretrovirus, such as simian retrovirus; a deltaretrovirus, such as bovine leukemia virus or human T-lymphotrophic virus (HTLV) including HTLV-1, HTLV-2, and HTLV-3; a gammaretrovirus, such as murine leukemia virus or feline leukemia virus; or a lentivirus, such as human immunodeficiency virus (HIV) including HIV-1 and HIV-2, simian immunodeficiency virus, equine infectious anemia virus, bovine immunodeficiency virus, rabbit endogenous lentivirus type K (RELIK), or feline immunodeficiency virus.

Further provided is a method of treating or preventing a hyperproliferative disease or cancer, comprising administering to a human or animal in need thereof a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

Hyperproliferative diseases include diseases caused by excessive growth of non-cancer cells. Such conditions include but are not limited to psoriasis, actinic keratoses, and seborrheic keratoses, warts, keloids, and eczema.

Cancers that can be treated or prevented by the methods of the disclosure include solid tumors and lymphomas, including but not limited to adrenal cancer, bladder cancer, bone cancer, brain cancer, breast cancer, colon cancer, colorectal cancer, eye cancer, head-and-neck cancer, kidney cancer such as renal cell carcinoma, liver cancer, lung cancer such as non-small cell lung cancer, ovarian cancer, pancreatic cancer, prostate cancer, skin cancer such as squamous cell carcinoma and melanoma, thyroid cancer, uterine cancer, vaginal cancer, and myeloma such as multiple myeloma. The cancer can be naïve, or relapsed and/or refractory.

In some embodiments, the cancer is Burkitt's lymphoma, Hodgkin's lymphoma, non-Hodgkin's lymphoma (NHL), indolent non-Hodgkin's lymphoma (iNHL), refractory iNHL, multiple myeloma (MM), chronic myeloid leukemia (CML), acute lymphocytic leukemia (ALL), B-cell ALL, acute myeloid leukemia (AML), chronic lymphocytic leukemia (CLL), small lymphocytic lymphoma (SLL), myelodysplastic syndrome (MDS), myeloproliferative disease (MPD), mantle cell lymphoma (MCL), follicular lymphoma (FL), Waldestrom's macroglobulinemia (WM), T-cell lymphoma, B-cell lymphoma, diffuse large B-cell lymphoma (DLBCL), or marginal zone lymphoma (MZL). In one embodiment, the cancer is minimal residual disease (MRD). In some embodiments, the cancer is selected from Hodgkin's lymphoma, non-Hodgkin's lymphoma (NHL), indolent non-Hodgkin's lymphoma (iNHL), and refractory iNHL. In some embodiments, the cancer is indolent non-Hodgkin's lymphoma (iNHL). In some embodiments, the cancer is refractory iNHL. In some embodiments, the cancer is chronic lymphocytic leukemia (CLL). In some embodiments, the cancer is diffuse large B-cell lymphoma (DLBCL).

In some embodiments, the cancer is a solid tumor selected from the group consisting of pancreatic cancer; bladder cancer; colorectal cancer; breast cancer, including metastatic breast cancer; prostate cancer, including androgen-dependent and androgen-independent prostate cancer; kidney or renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma, hepatic carcinoma, rectal cancer, penile carcinoma, vulval cancer, thyroid cancer, salivary gland carcinoma, endometrial or uterine carcinoma, hepatoma, hepatocellular cancer, liver cancer, gastric or stomach cancer including gastrointestinal cancer, cancer of the peritoneum, squamous carcinoma of the lung, gastroesophagal cancer, biliary tract cancer, gall bladder cancer, colorectal/appendiceal cancer, squamous cell cancer (e.g., epithelial squamous cell cancer).

Any of the methods of treatment provided herein may be used to treat cancer at various stages. By way of example, the cancer stage includes but is not limited to early, advanced, locally advanced, remission, refractory, reoccurred after remission and progressive.

Subjects

Any of the methods of treatment provided herein may be used to treat a subject (e.g., human) who has been diagnosed with or is suspected of having cancer. As used herein, a subject refers to a mammal, including, for example, a human.

In some embodiments, the subject may be a human who exhibits one or more symptoms associated with cancer or hyperproliferative disease. In some embodiments, the subject may be a human who exhibits one or more symptoms associated with cancer. In some embodiments, the subject is at an early stage of a cancer. In other embodiments, the subject is at an advanced stage of cancer.

In some embodiments, the subject may be a human who is at risk, or genetically or otherwise predisposed (e.g., risk factor) to developing cancer or hyperproliferative disease who has or has not been diagnosed. As used herein, an "at risk" subject is a subject who is at risk of developing cancer. The subject may or may not have detectable disease, and may or may not have displayed detectable disease prior to the treatment methods described herein. An at risk subject may have one or more so-called risk factors, which are measurable parameters that correlate with development of cancer, which are described herein. A subject having one or more of these risk factors has a higher probability of developing cancer than an individual without these risk factor(s). These risk factors may include, for example, age, sex, race, diet, history of previous disease, presence of precursor disease, genetic (e.g., hereditary) considerations, and environmental exposure. In some embodiments, the subjects at risk for cancer include, for example, those having relatives who have experienced the disease, and those whose risk is determined by analysis of genetic or biochemical markers.

In addition, the subject may be a human who is undergoing one or more standard therapies, such as chemotherapy, radiotherapy, immunotherapy, surgery, or any combination thereof. Accordingly, one or more compounds provided herein may be administered before, during, or after administration of chemotherapy, radiotherapy, immunotherapy, surgery or combination thereof.

In some embodiments, the subject may be a human who is (i) substantially refractory to at least one chemotherapy treatment, or (ii) is in relapse after treatment with chemotherapy, or both (i) and (ii). In some embodiments, the subject is refractory to at least two, at least three, or at least four chemotherapy treatments (including standard or experimental chemotherapies).

Further provided is a method of enhancing the efficacy of a vaccine, comprising administering to a human or animal in need thereof a therapeutically effective amount of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof.

The disclosure includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use as a medicament in a human or animal.

The disclosure includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in treating a disease or disorder in a human or animal.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in modulating the activity of STING protein.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in the prevention or treatment of a disease or condition in a human or animal responsive to the modulation of the STING protein.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof alone or in combination with one or more therapeutically active substances, for use in STING dependent induction of a type I interferon, cytokine or chemokine in a human or animal.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof, alone or in combination with one or more therapeutically active agents for use in the treatment or prevention of viral infection in a human or animal.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof, alone or in combination with one or more therapeutically active substances, for use in the treatment or prevention of infection caused by hepatitis B virus or HIV in a human or animal.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof alone or in combination with one or more therapeutically active agents, for use in the treatment or prevention of a hyperproliferative disease or cancer in a human or animal.

The disclosure further includes a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in enhancing vaccine efficacy in a human or animal.

The disclosure further includes a pharmaceutical composition comprising a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in modulating STING protein activity, to induce STING-dependent production of a type I interferon, cytokine or chemokine in a human or animal.

The disclosure further includes a pharmaceutical composition comprising a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for use in treating or preventing viral infection, infection caused by hepatitis B virus, by HIV, hyperproliferative disease or cancer in a human or animal.

The disclosure further includes the use of a cyclic dinucleotide provided herein, including compounds of Formula (J), (I), (Ia), (IIa), (IIIa), (IIIb), (IIIc), (IVa), (IVb), and/or (IVc), or an enantiomer, or pharmaceutically acceptable salt thereof for the production of a medicament for the treatment or prevention of infection caused by hepatitis B virus, by HIV, of hyperproliferative disease or cancer.

VI. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intratumoral, intrathecal and epidural), and the like. It will be appreciated that the preferred route may vary with for example the condition of the recipient. An advantage of certain compounds disclosed herein is that they are orally bioavailable and can be dosed orally.

A compound of the present disclosure, may be administered to an individual in accordance with an effective dosing regimen for a desired period of time or duration, such as at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

The compound may be administered to an individual (e.g., a human) in a therapeutically effective amount. In certain embodiments, the compound is administered once daily.

The compound can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 mg to about 30 mg per day, or such as from about 30 mg to about 300 mg per day.

A compound of the present disclosure may be combined with one or more additional therapeutic agents in any dosage amount of the compound of the present disclosure (e.g., from 1 mg to 1000 mg of compound). Therapeutically effective amounts may include from about 1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose. Other therapeutically effective amounts of the compound of the present disclosure are about 100, 125, 150, 175, 200, 225, 250, 275, 300, 325, 350, 375, 400, 425, 450, 475, or about 500 mg per dose. Other therapeutically effective amounts of the compound of the present disclosure are about 100 mg per dose, or about 125, 150, 175, 200, 225, 250, 275, 300, 350, 400, 450, or about 500 mg per dose. A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month.

Kits that comprise a cyclic dinucleotide of Formula (J), (I), (Ia), (IIa), (IIIa), (IIIb), (IIIc), (IVa), (IVb), and/or (IVc), or an enantiomer, or pharmaceutically acceptable salt thereof, or a pharmaceutical composition containing any of the above, are also included in the present disclosure.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

VII. Combination Therapy

In certain embodiments, a method for treating or preventing an infectious disease, a viral infection, hepatitis B infection, HIV infection, cancer, or a hyperproliferative disease in a human having or at risk of having the disease is provided, comprising administering to the human a therapeutically effective amount of a compound disclosed herein, e.g., a compound of Formula (J), (I), (Ia), (IIa), (IIIa), (IIIb), (IIIc), (IVa), (IVb), and/or (IVc), or a pharmaceutically acceptable salt thereof, in combination with a therapeutically effective amount of one or more (e.g., one, two, three, four, one or two, one to three, or one to four) additional therapeutic agents. In one embodiment, a method for treating an infectious disease, a viral infection, hepatitis B infection, HIV infection, cancer, or a hyperproliferative disease in a human having or at risk of having the disease is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating a viral infection, comprising administering to a subject in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating the viral infection. In some embodiments, the viral infection is a hepatitis B infection. In some embodiments, the viral infection is a HIV infection.

In certain embodiments, a compound disclosed herein, or a pharmaceutically acceptable salt thereof, is combined with one, two, three, four, or more additional therapeutic agents. In certain embodiments, a compound disclosed herein, or a pharmaceutically acceptable salt thereof, is combined with two additional therapeutic agents. In other embodiments, a compound disclosed herein, or a pharmaceutically acceptable salt thereof, is combined with three additional therapeutic agents. In further embodiments, a compound disclosed herein, or a pharmaceutically acceptable salt thereof, is combined with four additional therapeutic agents. The one, two, three, four, or more additional therapeutic agents can be different therapeutic agents selected from the same class of therapeutic agents, and/or they can be selected from different classes of therapeutic agents.

Administration of Combination Therapy

In certain embodiments, a compound disclosed herein is administered with one or more additional therapeutic agents. Co-administration of a compound disclosed herein with one or more additional therapeutic agents generally refers to simultaneous or sequential administration of a compound disclosed herein and one or more additional therapeutic agents, such that therapeutically effective amounts of the compound disclosed herein and the one or more additional therapeutic agents are both present in the body of the subject. When administered sequentially, the combination may be administered in two or more administrations.

Co-administration of a compound disclosed herein with one or more additional therapeutic agents generally refers to simultaneous or sequential administration of a compound disclosed herein and one or more additional therapeutic agents, such that therapeutically effective amounts of each agent are present in the body of the patient.

In certain embodiments, a compound as disclosed herein (e.g., any compound of Formula I) may be combined with one or more (e.g., one, two, three, four, one or two, one to three, or one to four) additional therapeutic agents in any dosage amount of the compound of Formula I (e.g., from 10 mg to 1000 mg of compound).

Co-administration includes administration of unit dosages of the compounds disclosed herein before or after administration of unit dosages of one or more additional therapeutic agents. The compound disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound disclosed herein.

In certain embodiments, a compound disclosed herein is combined with one or more additional therapeutic agents in a unitary dosage form for simultaneous administration to a subject, for example as a solid dosage form for oral administration.

In certain embodiments a compound of Formula (J), (I), (Ia), (IIa), (IIIa), (IIIb), (IIIc), (IVa), (IVb), and/or (IVc), is formulated as a tablet, which may optionally contain one or more other compounds useful for treating the disease being treated. In certain embodiments, the tablet can contain another active ingredient for treating a viral disease, e.g., hepatitis B virus or HIV.

In certain embodiments, such tablets are suitable for once daily dosing.

In one embodiment, pharmaceutical compositions comprising a compound disclosed herein, or a pharmaceutically acceptable salt thereof, in combination with one or more (e.g., one, two, three, one or two, or one to three) additional therapeutic agents, and a pharmaceutically acceptable carrier, diluent, or excipient are provided.

In one embodiment, kits comprising a compound disclosed herein, or a pharmaceutically acceptable salt thereof, in combination with one or more (e.g., one, two, three, four, one or two, or one to three, or one to four) additional therapeutic agents are provided.

Viral Combination Therapy

The compounds described herein may be used or combined with one or more of a antiviral agents including abacavir, aciclovir, adefovir, amantadine, amprenavir, arbidol, atazanavir, artipla, brivudine, cidofovir, combivir, edoxudine, efavirenz, emtricitabine, enfuvirtide, entecavir, fomvirsen, fosamprenavir, foscarnet, fosfonet, ganciclovir, gardasil, ibacitabine, immunovir, idoxuridine, imiquimod, indinavir, inosine, integrase inhibitors, interferons, including interferon type III, interferon type II, interferon type I, lamivudine, lopinavir, loviride, MK-0518, maraviroc, moroxydine, nelfinavir, nevirapine, nexavir, nucleoside analogues, oseltamivir, penciclovir, peramivir, pleconaril, podophyllotoxin, protease inhibitors, reverse transcriptase inhibitors, ribavirin, rimantadine, ritonavir, saquinavir, stavudine, tenofovir, tenofovir disoproxil, tipranavir, trifluridine, trizivir, tromantadine, truvada, valganciclovir, vicriviroc, vidarabine, viramidine, zalcitabine, zanamivir, zidovudine, and combinations thereof.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide. A compound as disclosed herein (e.g., a compound of Formula J) may be combined with the agents provided herein in any dosage amount of the compound (e.g., from 50 mg to 500 mg of compound) the same as if each combination of dosages were specifically and individually listed.

In certain embodiments, a compound disclosed herein, or a pharmaceutically acceptable salt thereof, is combined with 100-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil. In certain embodiments, a compound disclosed herein, or a pharmaceutically acceptable salt thereof, is combined with 250 mg tenofovir disoproxil fumarate, tenofovir disoproxil hemifumarate, or tenofovir disoproxil. In certain embodiments, a compound disclosed herein, or a pharmaceutically acceptable salt thereof, is combined with 150 mg tenofovir disoproxil fumarate, tenofovir disoproxil hemifumarate, or tenofovir disoproxil. A compound as disclosed herein (e.g., a compound of Formula J) may be combined with the agents provided herein in any dosage amount of the compound (e.g., from 50 mg to 500 mg of compound) the same as if each combination of dosages were specifically and individually listed.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating an HIV infection, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such tablets are suitable for once daily dosing.

In the above embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement $C_5a$ receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4× and romidepsin; and APH-0812.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide $C_{25}P$, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232. Latency Reversing Agents Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, and GSK-343.

Examples of HDAC inhibitors include romidepsin, vorinostat, and panobinostat.

Examples of PKC activators include indolactam, prostratin, ingenol B, and DAG-lactones.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series; Immune-based Therapies Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107, interleukin-15/Fc fusion protein, normferon, peginterferon alfa-2a, peginterferon alfa-2b, recombinant interleukin-15, RPI-MN, GS-9620, STING modulators, RIG-I modulators, NOD2 modulators, and IR-103.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670, 205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.) Phosphatidylinositol 3-kinase (PI3K) Inhibitors Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Examples of those targeting HIV in such a manner include bavituximab, UB-421, C2F5, 2G12, C4E10, C2F5+C2G12+ C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07. Example of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/ AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C$_5$, VAC-3S, multiclade DNA recombinant adenovirus-5 (rAdS), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multi-HIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B 11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS 1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAdS gag-pol env A/B/C vaccine, DNA.HTI and MVA.HTI.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, BanLec, deferiprone, Gamimune, metenkefalin, naltrexone, Prolastin, REP 9, RPI-MN, VSSP, Hlviral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, 1ND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene Therapy and Cell Therapy include the genetic modification to silence a gene; genetic approaches to directly kill the infected cells; the infusion of immune cells designed to replace most of the subject's own immune system to enhance the immune response to infected cells, or activate the subject's own immune system to kill infected cells, or find and kill the infected cells; genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systenms include EBT101,

CAR-T Cell Therapy

CAR-T cell therapy includes a population of immune effector cells engineered to express a chimeric antigen receptor (CAR), wherein the CAR comprises an HIV antigen-binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T cell or an NK cell. In some embodiments, the T cell is a CD4+ T cell, a CD8+ T cell, or a combination thereof.

Examples of HIV CAR-T include VC-CAR-T.

TCR-T cell therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin;

zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (e.g., a compound of formula J) may be combined with the agents provided herein in any dosage amount of the compound (e.g., from 1 mg to 500 mg of compound) the same as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (e.g., a compound of formula J) may be combined with the agents provided herein in any dosage amount of the compound (e.g., from 1 mg to 500 mg of compound) the same as if each combination of dosages were specifically and individually listed.

HBV Combination Therapy

In certain embodiments, a method for treating or preventing an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents. In one embodiment, a method for treating an HBV infection in a human having or at risk of having the infection is provided, comprising administering to the human a therapeutically effective amount of a compound disclosed herein, or a pharmaceutically acceptable salt thereof, in combination with a therapeutically effective amount of one or more (e.g., one, two, three, four, one or two, one to three, or one to four) additional therapeutic agents.

In certain embodiments, the present disclosure provides a method for treating an HBV infection, comprising administering to a patient in need thereof a therapeutically effective amount of a compound disclosed herein or a pharmaceutically acceptable salt thereof, in combination with a therapeutically effective amount of one or more (e.g., one, two, three, four, one or two, one to three, or one to four) additional therapeutic agents which are suitable for treating an HBV infection.

The compounds described herein may be used or combined with one or more of a chemotherapeutic agent, an immunomodulator, an immunotherapeutic agent, a therapeutic antibody, a therapeutic vaccine, a bispecific antibody and "antibody-like" therapeutic protein (such as DARTs®, Duobodies®, Bites®, XmAbs®, TandAbs®, Fab derivatives), an antibody-drug conjugate (ADC), gene modifiers or gene editors (such as CRISPR Cas9, zinc finger nucleases, homing endonucleases, synthetic nucleases, TALENs), cell therapies such as CAR-T (chimeric antigen receptor T-cell), and TCR-T (an engineered T cell receptor) agent or any combination thereof.

In certain embodiments, a compound of Formula (I) is formulated as a tablet, which may optionally contain one or more other compounds useful for treating HBV. In certain embodiments, the tablet can contain another active ingredient for treating HBV, such as 3-dioxygenase (IDO) inhibitors, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), core protein allosteric modulators, covalently closed circular DNA (cccDNA) inhibitors, cyclophilin inhibitors, cytotoxic T-lymphocyte-associated protein 4 (ipi4) inhibitors, DNA polymerase inhibitor, Endonuclease modulator, epigenetic modifiers, Farnesoid X receptor agonist, HBsAg inhibitors, HBsAg secretion or assembly inhibitors, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, immunomodulators, indoleamine-2 inhibitors, inhibitors of ribonucleotide reductase, Interleukin-2 ligand, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, Peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, and combinations thereof.

HBV Combination Drugs

Examples of combination drugs for the treatment of HBV include TRUVADA® (tenofovir disoproxil fumarate and emtricitabine); ABX-203, lamivudine, and PEG-IFN-alpha; ABX-203 adefovir, and PEG-IFNalpha; and INO-1800 (INO-9112 and RG7944).

Other HBV Drugs

Examples of other drugs for the treatment of HBV include alpha-hydroxytropolones, amdoxovir, beta-hydroxycytosine nucleosides, AL-034, CCC-0975, elvucitabine, ezetimibe, cyclosporin A, gentiopicrin (gentiopicroside), JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

HBV Vaccines

HBV vaccines include both prophylactic and therapeutic vaccines. Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, and DTaP-rHB-Hib vaccine.

Examples of HBV therapeutic vaccines include HBsAG-HBIG complex, ARB-1598, Bio-Hep-B, NASVAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2, TG-1050, NU-500, HBVax, im/TriGrid/ antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, and Lm HBV.

HBV DNA Polymerase Inhibitors

Examples of HBV DNA polymerase inhibitors include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-11-04-26, HIP-1302, tenofovir disoproxil aspartate, tenofovir disoproxil orotate, and HS-10234.

Immunomodulators

Examples of immunomodulators include rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), JNJ-440,WF-10,AB-452, ribavirin, IL-12, INO-9112, polymer polyethyleneimine (PEI), Gepon, VGV-1, MOR-22, CRV-431, JNJ-0535, TG-1050, ABI-H2158, BMS-936559,GS-9688, RO-7011785, RG-7854, AB-506, RO-6871765, AIC-649, and IR-103.

Toll-Like Receptor (TLR) Modulators

TLR modulators include modulators of TLR1, TLR2, TLR3, TLR4, TLR5, TLR6, TLR7, TLR8, TLR9, TLR10, TLR11, TLR12, and TLR13. Examples of TLR3 modulators include rintatolimod, poly-ICLC, RIBOXXON®, Apoxxim, RIBOXXIM®, IPH-33, MCT-465, MCT-475, and ND-1.1.

Examples of TLR7 modulators include GS-9620, GSK-2245035, imiquimod, resiquimod, DSR-6434, DSP-3025, IMO-4200, MCT-465, MEDI-9197, 3M-051, SB-9922, 3M-052, Limtop, D, telratolimod, SP-0509, TMX-30X, TMX-202, RG-7863, RG-7795, LHC-165, RG-7854, and the compounds disclosed in US20100143301 (Gilead Sciences), US20110098248 (Gilead Sciences), and US20090047249 (Gilead Sciences).

Examples of TLR8 modulators include motolimod, resiquimod, 3M-051, 3M-052, MCT-465, IMO-4200, VTX-763, VTX-1463, GS-9688 and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), US20130251673 (Novira Therapeutics), U.S. Pat. No. 9,670,205, US20160289229, U.S. patent application Ser. No. 15/692,161, and U.S. patent application Ser. No. 15/692,093.

Examples of TLR9 modulators include BB-001, BB-006, CYT-003, IMO-2055, IMO-2125, IMO-3100, IMO-8400, IR-103, IMO-9200, agatolimod, DIMS-9054, DV-1079, DV-1179, AZD-1419, leftolimod (MGN-1703), litenimod, and CYT-003-QbG10.

Examples of TLR7, TLR8 and TLR9 modulators include the compounds disclosed in WO2017047769 (Teika Seiyaku), WO2015014815 (Janssen), WO2018045150 (Gilead Sciences Inc), WO2018045144 (Gilead Sciences Inc), WO2015162075 (Roche),WO2017034986 (University of Kansas), WO2018095426 (Jiangsu Hengrui Medicine Co Ltd), WO2016091698 (Roche), WO2016075661 (GlaxoSmithKline Biologicals),WO2016180743 (Roche), WO2018089695 (Dynavax Technologies),WO2016055553 (ROche), WO2015168279 (Novartis), WO2016107536 (Medshine Discovery), WO2018086593 (Livo (Shanghai) Pharmaceutical),WO2017106607 (Merck),WO2017061532 (Sumitomo Dainippon Pharma), WO2016023511 (Chia Tai Tianqing Pharmaceutical), WO2017076346 (Chia Tai Tianqing Pharmaceutical), WO2017046112 (ROche), WO2018078149 (Roche),WO2017040233 (3M Co), WO2016141092 (Gilead Sciences), WO2018049089 (BristolMyers Squibb),WO2015057655 (Eisai Co Ltd), WO2017001307 (Roche), WO2018005586 (BristolMyers Squibb), WO201704023(3M Co),WO2017163264 (Council of Scientific and Industrial Research (India)), WO2018046460 (GlaxoSmithKline Biologicals), WO2018047081 (Novartis), WO2016142250 (Roche), WO2015168269 (Novartis),WO201804163 (Roche), WO2018038877 (3M Co), WO2015057659 (Eisai Co Ltd), WO2017202704 (Roche), WO2018026620 (BristolMyers Squibb),WO2016029077 (Janus Biotherapeutics), WO201803143 (Merck), WO2016096778 (Roche), WO2017190669 (Shanghai De Novo Pharmatech),U.S. Ser. No. 09/884,866 (University of Minnesota),WO2017219931 (Sichuan KelunBiotech Biopharmaceutical), WO2018002319 (Janssen Sciences), WO2017216054 (Roche),WO2017202703 (Roche),WO2017184735 (IFM Therapeutics), WO2017184746 (IFM Therapeutics), WO2015088045 (Takeda Pharmaceutical), WO2017038909 (Takeda Pharmaceutical),WO2015095780 (University of Kansas),WO2015023958 (University of Kansas)

Interferon Alpha Receptor Ligands

Examples of interferon alpha receptor ligands include interferon alpha-2b (INTRON A®), pegylated interferon alpha-2a (PEGASYS®), PEGylated interferon alpha-1b, interferon alpha 1b (HAPGEN®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-INTRON®), Bioferon, Novaferon, Inmutag (Inferon), MULTIFERON®, interferon alfa-nl (HUMOFERON®), interferon beta-1a (AVONEX®), Shaferon, interferon alfa-2b (Axxo), Alfaferone, interferon alfa-2b (BioGeneric Pharma), interferon-alpha 2 (CJ), Laferonum, VIPEG, BLAUFERON-A, BLAUFERON-B, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, PegiHep, interferon alfa 2b (Zydus-Cadila), interferon alfa 2a, Optipeg A, Realfa 2B, Reliferon, interferon alfa-2b (Amega), interferon alfa-2b (Virchow), ropeginterferon alfa-2b, rHSA-IFN alpha-2a (recombinant human serum albumin intereferon alpha 2a fusion protein), rHSA-IFN alpha 2b, recombinant human interferon alpha-(1b, 2a, 2b), peginterferon alfa-2b (Amega), peginterferon alfa-2a, Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b, SFR-9216, and Interapo (Interapa).

Hyaluronidase Inhibitors

Examples of hyaluronidase inhibitors include astodrimer.

Hepatitis B Surface Antigen (HBsAg) Inhibitors

Examples of HBsAg inhibitors include HBF-0259, PBHBV-001, PBHBV-2-15, PBHBV-2-1, REP-9AC, REP-9C, REP-9, REP-2139, REP-2139-Ca, REP-2165, REP-2055, REP-2163, REP-2165, REP-2053, REP-2031 and REP-006, and REP-9AC'.

Examples of HBsAg secretion inhibitors include BM601.

Cytotoxic T-lymphocyte-associated protein 4 (ipi4) inhibitors

Examples of Cytotoxic T-lymphocyte-associated protein 4 (ipi4) inhibitors include AGEN-2041, AGEN-1884, ipilumimab, belatacept, PSI-001, PRS-010, Probody mAbs, tremelimumab, and JHL-1155.

Cyclophilin Inhibitors

Examples of cyclophilin inhibitors include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

Examples of HBV viral entry inhibitors include Myrcludex B.

Antisense Oligonucleotide Targeting Viral mRNA

Examples of antisense oligonucleotide targeting viral mRNA include ISIS-HBVRx, IONIS-HBVRx, IONIS-GSK6-LRx, GSK-3389404, RG-6004.

Short Interfering RNAs (siRNA) and ddRNAi

Examples of siRNA include TKM-HBV (TKM-HepB), ALN-HBV, SR-008, HepB-nRNA, and ARC-520, ARC-521, ARB-1740, ARB-1467.

Examples of DNA-directed RNA interference (ddRNAi) include BB-HB-331.

Endonuclease Modulators

Examples of endonuclease modulators include PGN-514.

Ribonucelotide Reductase Inhibitors

Examples of inhibitors of ribonucleotide reductase include Trimidox.

HBV E Antigen Inhibitors

Examples of HBV E antigen inhibitors include wogonin.

Covalently Closed Circular DNA (cccDNA) Inhibitors

Examples of cccDNA inhibitors include BSBI-25, and CHR-101.

Farnesoid X Receptor Agonist

Examples of farnesoid x receptor agonist such as EYP-001, GS-9674, EDP-305, MET-409, Tropifexor, AKN-083, RDX-023, BWD-100, LMB-763, INV-3, NTX-023-1, EP-024297 and GS-8670

HBV Antibodies

Examples of HBV antibodies targeting the surface antigens of the hepatitis B virus include GC-1102, XTL-17, XTL-19, KN-003, IV Hepabulin SN, and fully human monoclonal antibody therapy (hepatitis B virus infection, Humabs BioMed).

Examples of HBV antibodies, including monoclonal antibodies and polyclonal antibodies, include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products), and Fovepta (BT-088).

Fully human monoclonal antibodies include HBC-34.

CCR2 Chemokine Antagonists

Examples of CCR2 chemokine antagonists include propagermanium.

Thymosin Agonists

Examples of thymosin agonists include Thymalfasin, recombinant thymosin alpha 1 (GeneScience)

Cytokines

Examples of cytokines include recombinant IL-7, CYT-107, interleukin-2 (IL-2, Immunex), recombinant human interleukin-2 (Shenzhen Neptunus), IL-15, IL-21, IL-24, and celmoleukin.

Nucleoprotein Modulators

Nucleoprotein modulators may be either HBV core or capsid protein inhibitors. Examples of nucleoprotein modulators include GS-4882, AB-423, AT-130, GLS4, NVR-1221, NVR-3778, AL-3778, BAY 41-4109, morphothiadine mesilate, ARB-168786, ARB-880, JNJ-379, RG-7907, HEC-72702, AB-506, ABI-H0731, JNJ-440, ABI-H2158 and DVR-23.

Examples of capsid inhibitors include the compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira).

Examples of transcript inhibitors include the compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Retinoic Acid-Inducible Gene 1 Stimulators

Examples of stimulators of retinoic acid-inducible gene 1 include SB-9200, SB-40, SB-44, ORI-7246, ORI-9350, ORI-7537, ORI-9020, ORI-9198, and ORI-7170, RGT-100.

NOD2 Stimulators

Examples of stimulators of NOD2 include SB-9200.

Phosphatidylinositol 3-Kinase (PI3K) Inhibitors

Examples of PI3K inhibitors include idelalisib, ACP-319, AZD-8186, AZD-8835, buparlisib, CDZ-173, CLR-457, pictilisib, neratinib, rigosertib, rigosertib sodium, EN-3342, TGR-1202, alpelisib, duvelisib, IPI-549, UCB-5857, taselisib, XL-765, gedatolisib, ME-401, VS-5584, copanlisib, CAI orotate, perifosine, RG-7666, GSK-2636771, DS-7423, panulisib, GSK-2269557, GSK-2126458, CUDC-907, PQR-309, INCB-40093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301,TAK-117, HMPL-689, tenalisib, voxtalisib, and CLR-1401.

Indoleamine-2,3-dioxygenase (IDO) Pathway Inhibitors

Examples of IDO inhibitors include epacadostat (1NCB24360), resminostat (4SC-201), indoximod, F-001287, SN-35837, NLG-919, GDC-0919, GBV-1028, GBV-1012, NKTR-218, and the compounds disclosed in US20100015178 (Incyte), US2016137652 (Flexus Biosciences, Inc.), WO2014073738 (Flexus Biosciences, Inc.), and WO2015188085 (Flexus Biosciences, Inc.).

PD-1 Inhibitors

Examples of PD-1 inhibitors include cemiplimab, nivolumab, pembrolizumab, pidilizumab, BGB-108, STI-A1014, SHR-1210, PDR-001, PF-06801591, IBI-308, GB-226, STI-1110, JNJ-63723283, CA-170, durvalumab, atezolizumab and mDX-400, JS-001, Camrelizumab, Sintilimab, Sintilimab, tislelizumab, BCD-100,BGB-A333 JNJ-63723283, GLS-010 (WBP-3055), CX-072, AGEN-2034, GNS-1480 (Epidermal growth factor receptor antagonist; Programmed cell death ligand 1 inhibitor), CS-1001, M-7824 (PD-L1/TGF-β bifunctional fusion protein), Genolimzumab, BMS-936559

PD-L1 Inhibitors

Examples of PD-L1 inhibitors include atezolizumab, avelumab, AMP-224, MEDI-0680, RG-7446, GX-P2, durvalumab, KY-1003, KD-033, MSB-0010718C, TSR-042, ALN-PDL, STI-A1014,GS-4224, CX-072, and BMS-936559.

Examples of PD-1 inhibitors include the compounds disclosed in WO2017112730 (Incyte Corp), WO2017087777 (Incyte Corp), WO2017017624, WO2014151634 (BristolMyers Squibb Co), WO201317322 (BristolMyers Squibb Co), WO2018119286 (Incyte Corp), WO2018119266 (Incyte Corp), WO2018119263 (Incyte Corp), WO2018119236 (Incyte Corp), WO2018119221 (Incyte Corp), WO2018118848 (BristolMyers Squibb Co), WO20161266460 (BristolMyers Squibb Co), WO2017087678 (BristolMyers Squibb Co), WO2016149351 (BristolMyers Squibb Co), WO2015033299 (Aurigene Discovery Technologies Ltd), WO2015179615 (Eisai Co Ltd; Eisai Research Institute), WO2017066227 (BristolMyers Squibb Co), WO2016142886 (Aurigene Discovery Technologies Ltd), WO2016142852 (Aurigene Discovery Technologies Ltd), WO2016142835 (Aurigene Discovery Technologies Ltd; Individual), WO2016142833 (Aurigene Discovery Technologies Ltd), WO2018085750 (BristolMyers Squibb Co), WO2015033303 (Aurigene Discovery Technologies Ltd), WO2017205464 (Incyte Corp), WO2016019232 (3M Co; Individual; Texas A&M University System), WO2015160641 (BristolMyers Squibb Co), WO2017079669 (Incyte Corp), WO2015033301 (Aurigene Discovery Technologies Ltd), WO2015034820 (BristolMyers Squibb Co), WO2018073754 (Aurigene Discovery Technologies Ltd), WO2016077518 (BristolMyers Squibb Co), WO2016057624 (BristolMyers Squibb Co), WO2018044783 (Incyte Corp), WO2016100608 (BristolMyers Squibb Co), WO2016100285 (BristolMyers Squibb Co), WO2016039749 (BristolMyers Squibb Co), WO2015019284 (Cambridge Enterprise Ltd), WO2016142894 (Aurigene Discovery Technologies Ltd), WO2015134605 (BristolMyers Squibb Co), WO2018051255 (Aurigene Discovery Technologies Ltd), WO2018051254 (Aurigene Discovery Technologies Ltd), WO2017222976 (Incyte Corp), WO2017070089 (Incyte Corp), WO2018044963 (BristolMyers Squibb Co), WO2013144704 (Aurigene Discovery Technologies Ltd), WO2018013789 (Incyte Corp), WO2017176608 (BristolMyers Squibb Co), WO2018009505 (BristolMyers Squibb Co), WO2011161699 (Aurigene Discovery Technologies Ltd), WO2015119944 (Incyte Corp; Merck Sharp & Dohme Corp), WO2017192961 (Incyte Corp), WO2017106634 (Incyte Corp), WO2013132317 (Aurigene Discovery Technologies Ltd), WO2012168944 (Aurigene Discovery Technologies Ltd), WO2015036927 (Aurigene Discovery Technologies Ltd),WO2015044900 (Aurigene Discovery Technologies Ltd), WO2018026971 (Arising International).

Recombinant Thymosin Alpha-1

Examples of recombinant thymosin alpha-1 include NL-004 and PEGylated thymosin alpha-1.

Bruton's Tyrosine Kinase (BTK) Inhibitors

Examples of BTK inhibitors include ABBV-105, acalabrutinib (ACP-196), ARQ-531, BMS-986142, dasatinib, ibrutinib, GDC-0853, PRN-1008, SNS-062, ONO-4059, BGB-3111, ML-319, MSC-2364447, RDX-022, X-022, AC-058, RG-7845, spebrutinib, TAS-5315, TP-0158, TP-4207, HM-71224, KBP-7536, M-2951, TAK-020, AC-0025, and the compounds disclosed in US20140330015 (Ono Pharmaceutical), US20130079327 (Ono Pharmaceutical), and US20130217880 (Ono Pharmaceutical).

KDM Inhibitors

Examples of KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

Examples of KDM1 inhibitors include the compounds disclosed in U.S. Pat. No. 9,186,337B2 (Oryzon Genomics), GSK-2879552, and RG-6016.

STING Agonists

Examples of STING agonists include SB-11285, AdVCA0848, STINGVAX, amd the compounds disclosed in WO 2018065360 ("Biolog Life Science Institute Forschungslabor und Biochemica-Vertrieb GmbH, Germany), WO 2018009466 (Aduro Biotech), WO 2017186711 (InvivoGen), WO 2017161349 (Immune Sensor), WO 2017106740 (Aduro Biotech), US 20170158724 (Glaxo Smithkiline), WO 2017075477 (Aduro Biotech), US 20170044206 (Merck), WO 2014179760 (University of California), WO2018098203 (Janssn), WO2018118665 (Merck), WO2018118664 (Merck), WO2018100558 (Takeda), WO2018067423 (Merck), WO2018060323 (Boehringer).

Non-Nucleoside Reverse Transcriptase Inhibitors (NNRTI)

Examples of NNRTI include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

Examples of hepatitis B virus replication inhibitors include isothiafludine, IQP-HBV, RM-5038, and Xingantie.

Arginase Inhibitors

Examples of Arginase inhibitors include CB-1158, C-201, and resminostat.

Gene Therapy and Cell Therapy

Gene therapy and cell therapy includes the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Gene Editors

Examples of genome editing systems include a CRISPR/Cas9 system, a zinc finger nuclease system, a TALEN system, a homing endonucleases system, and a meganuclease system; e.g., cccDNA elimination via targeted cleavage, and altering one or more of the hepatitis B virus (HBV) viral genes. Altering (e.g., knocking out and/or knocking down) the PreC, C, X, PreS1, PreS2, S, P or SP gene refers to (1) reducing or eliminating PreC, C, X, PreS1, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum and/or intraparenchymal levels of HBe, HBc, HBx, LHBs, MHBs, SHBs, Pol, and/or HBSP proteins. Knockdown of one or more of the PreC, C, X, PreS1, PreS2, S, P and/or SP gene(s) is performed by targeting the gene(s) within HBV cccDNA and/or integrated HBV DNA.

CAR-T Cell Therapy

CAR T cell therapy includes a population of immune effector cells engineered to express a chimeric antigen receptor (CAR), wherein the CAR comprises an HBV antigen-binding domain. The immune effector cell is a T cell or an NK cell. In some embodiments, the T cell is a CD4+ T cell, a CD8+ T cell, or a combination thereof. Cells can be autologous or allogeneic.

TCR-T Cell Therapy

TCR T cell therapy includes T cells expressing HBV-specific T cell receptors. TCR-T cells are engineered to target HBV derived peptides presented on the surface of virus-infected cells. In some embodiments, the T-cells express HBV surface antigen (HBsAg)-specific TCR. Examples of TCR-T therapy directed to treatment of HBV include LTCR-H2-1.

In another specific embodiment, a compound disclosed herein, or a pharmaceutically acceptable salt thereof, is combined with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In another specific embodiment, a compound disclosed herein, or a pharmaceutically acceptable salt thereof, is combined with an HBV DNA polymerase inhibitor and at least a second additional therapeutic agent selected from the group consisting of: immunomodulators, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In another specific embodiment, a compound disclosed herein, or a pharmaceutically acceptable salt thereof, is combined with an HBV DNA polymerase inhibitor and at least a second additional therapeutic agent selected from the group consisting of: HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In a particular embodiment, a compound disclosed herein, or a pharmaceutically acceptable salt thereof, is combined with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics),U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (*Flexus* Biosciences, Inc.), WO2014073738 (*Flexus* Biosciences, Inc.), WO2015188085 (*Flexus* Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

Cancer Combination Therapy

In one embodiment, the compound of the disclosure may be employed with other therapeutic methods of cancer treatment. Preferably, combination therapy with chemotherapeutic, hormonal, antibody, surgical and/or radiation treatments are contemplated.

In some embodiments, the further anti-cancer therapy is surgery and/or radiotherapy.

In some embodiments, the further anti-cancer therapy is at least one additional cancer medicament.

In some embodiments, there is provided a combination comprising a compound of Formula (J), (I), (Ia), (IIa), (IIIa), (IIIb), (IIIc), (IVa), (IVb), and/or (IVc), or a pharmaceutically acceptable salt thereof and at least one further cancer medicament.

In some embodiments, there is provided a combination comprising a compound of Formula (J), (I), (Ia), (IIa), (IIIa), (IIIb), (IIIc), (IVa), (IVb), and/or (IVc), or a pharmaceutically acceptable salt thereof and at least one further cancer medicament, for use in therapy.

In some embodiments, there is provided the use of a combination comprising a compound of Formula (J), (I), (Ia), (IIa), (IIIa), (IIIb), (IIIc), (IVa), (IVb), and/or (IVc), or a pharmaceutically acceptable salt thereof and at least one cancer medicament, in the manufacture of a medicament for the treatment of cancer.

Examples of further cancer medicaments include intercalating substances such as anthracycline, doxorubicin, idarubicin, epirubicin, and daunorubicin; topoisomerase inhibitors such as irinotecan, topotecan, camptothecin, lamellarin D, etoposide, teniposide, mitoxantrone, amsacrine, ellipticines and aurintricarboxylic acid; nitrosourea compounds such as carmustine (BCNU), lomustine (CCNU), and streptozocin; nitrogen mustards such as cyclophosphamide, mechlorethamine, uramustine, bendamustine, melphalan, chlorambucil, mafosfamide, trofosfamid and ifosfamide; alkyl sulfonates such as busulfan and treosulfan; alkylating agents such as procarbazin, dacarbazin, temozolomid and thiotepa; platinum analogues such as cisplatin, carboplatin, nedaplatin, oxaliplatin, satraplatin, and triplatin tetranitrate; microtubule disruptive drugs such as vinblastine, colcemid and nocodazole; antifolates like methotrexate, aminopterin, dichloromethotrexat, pemetrexed, raltitrexed and pralatrexate: purine analogues like azathioprine, mercaptopurine, thioguanine, fludarabine, fludarabine phosphate, pentostatin and cladribine; pyrimidine analogues like 5-fluorouracil, floxuridine, cytarabine, 6-azauracil, gemcitabine; steroids such as gestagene, androgene, glucocorticoids, dexamethasone, prednisolone, and prednisone; anti-cancer antibodies such as monoclonal antibodies, e.g., alemtuzumab, apolizumab, cetuximab, epratuzumab, galiximab, gemtuzumab, ipilimumab, labetuzumab, panitumumab, rituximab, trastuzumab, nimotuzumab, mapatumumab, matuzumab, rhMab ICR62 and pertuzumab, radioactively labeled antibodies and antibody-drug conjugates; anti-cancer peptides such as radioactively labeled peptides and peptide-drug conjugates; and taxane and taxane analogues such as paclitaxel and docetaxel.

In certain embodiments, a method for treating or preventing a hyperproliferative disorder or cancer in a human or animal having or at risk of having the hyperproliferative disorder or cancer is provided, comprising administering to the human or animal a therapeutically effective amount of a compound of Formula (J), (I), (Ia), (IIa), (IIIa), (IIIb), (IIIc), (IVa), (IVb), and/or (IVc) as disclosed herein, or a pharmaceutically acceptable salt thereof, in combination with a therapeutically effective amount of one or more (e.g., one, two, three, one or two, or one to three) additional therapeutic agents. In one embodiment, a method for treating a hyperproliferative disorder or cancer in a human or animal having or at risk of having the hyperproliferative disorder or cancer is provided, comprising administering to the human or animal a therapeutically effective amount of a compound disclosed herein, or a pharmaceutically acceptable salt thereof, in combination with a therapeutically effective amount of one or more (e.g., one, two, three, one or two, or one to three) additional therapeutic agents.

In certain embodiments, the present disclosure provides a method for treating a hyperproliferative disorder or cancer, comprising administering to a subject in need thereof a therapeutically effective amount of a compound disclosed herein, or a pharmaceutically acceptable salt thereof, in combination with a therapeutically effective amount of one or more additional therapeutic agents which are suitable for treating hyperproliferative disorder or cancer.

The compounds described herein may be used or combined with one or more of a chemotherapeutic agent, an anti-cancer agent, an anti-angiogenic agent, an anti-fibrotic agent, an immunotherapeutic agent, a therapeutic antibody, a bispecific antibody and "antibody-like" therapeutic protein (such as DARTs®, Duobodies®, Bites®, XmAbs®, TandAbs®, Fab derivatives), an antibody-drug conjugate (ADC), a radiotherapeutic agent, an anti-neoplastic agent, an anti-proliferation agent, an oncolytic virus, a gene modifier or editor (such as CRISPR/Cas9, zinc finger nucleases or synthetic nucleases, TALENs), a CAR (chimeric antigen receptor) T-cell immunotherapeutic agent, an engineered T cell receptor (TCR-T), or any combination thereof. These therapeutic agents may be in the forms of compounds, antibodies, polypeptides, or polynucleotides. In one embodiment, provided herein is a product comprising a compound described herein and an additional therapeutic agent as a combined preparation for simultaneous, separate, or sequential use in therapy.

The one or more therapeutic agents include, but are not limited to, an inhibitor, agonist, antagonist, ligand, modulator, stimulator, blocker, activator or suppressor of a gene, ligand, receptor, protein, or factor. Non-limiting examples of additional therapeutic agents include: Abelson murine leukemia viral oncogene homolog 1 gene (ABL, such as ABL1), Acetyl-CoA carboxylase (such as ACC1/2), activated CDC kinase (ACK, such as ACK1), Adenosine deaminase, adenosine receptor (such as A2B, A2a, A3), Adenylate cyclase, ADP ribosyl cyclase-1, adrenocorticotropic hormone receptor (ACTH), Aerolysin, AKT1 gene, Alk-5 protein kinase, Alkaline phosphatase, Alpha 1 adrenoceptor, Alpha 2 adrenoceptor, Alpha-ketoglutarate dehydrogenase (KGDH), Aminopeptidase N, AMP activated protein kinase, anaplastic lymphoma kinase (ALK, such as ALK1), Androgen receptor, Angiopoietin (such as ligand-1, ligand-2), Angiotensinogen (AGT) gene, murine thymoma viral oncogene homolog 1 (AKT) protein kinase (such as AKT1, AKT2, AKT3), apolipoprotein A-I (APOA1) gene, Apoptosis inducing factor, apoptosis protein (such as 1, 2), apoptosis signal-regulating kinase (ASK, such as ASK1), Arginase (I), Arginine deiminase, Aromatase, Asteroid homolog 1 (ASTE1) gene, ataxia telangiectasia and Rad 3 related (ATR) serine/threonine protein kinase, Aurora protein kinase (such as 1, 2), Axl tyrosine kinase receptor, Baculoviral IAP repeat containing 5 (BIRC5) gene, Basigin, B-cell lymphoma 2 (BCL2) gene, Bcl2 binding component 3, Bcl2 protein, BCL2L11 gene, BCR (breakpoint cluster region) protein and gene, Beta adrenoceptor, Beta-catenin, B-lymphocyte antigen CD19, B-lymphocyte antigen CD20, B-lymphocyte cell adhesion molecule, B-lymphocyte stimulator ligand, Bone morphogenetic protein-10 ligand, Bone morphogenetic protein-9 ligand modulator, Brachyury protein, Bradykinin receptor, B-Raf proto-oncogene (BRAF), Brc-Abl tyrosine kinase, Bromodomain and external domain (BET) bromodomain containing protein (such as BRD2, BRD3, BRD4), Bruton's tyrosine kinase (BTK), Calmodulin, calmodulin-dependent protein kinase (CaMK, such as CAMKII), Cancer testis antigen 2, Cancer testis antigen NY-ESO-1, cancer/testis antigen 1B (CTAG1) gene, Cannabinoid receptor (such as CB1, CB2), Carbonic anhydrase, casein kinase (CK, such as CKI, CKII), Caspase (such as caspase-3, caspase-7, Caspase-9), caspase 8 apoptosis-related cysteine peptidase CASP8-FADD-like regulator, Caspase recruitment domain protein-15, Cathepsin G, CCR5 gene, CDK-activating kinase (CAK), Checkpoint kinase (such as CHK1,CHK2), chemokine (C-C motif) (such as CCR2, CCR4, CCR5), chemokine (C-X-C motif) receptor (such as CXCR4, CXCR1 and CXCR2), Chemokine CC21 ligand, Cholecystokinin CCK2 receptor, Chorionic gonadotropin, c-Kit (tyrosine-protein kinase Kit or CD117), Claudin (such as 6, 18), cluster of differentiation (CD) such as CD4, CD27, CD29, CD30, CD33, CD37, CD40, CD40 ligand receptor, CD40 ligand, CD40LG gene, CD44, CD45, CD47, CD49b, CD51, CD52, CD55, CD58, CD66e, CD70 gene, CD74, CD79, CD79b, CD79B gene, CD80, CD95, CD99, CD117, CD122, CDw123, CD134, CDw137, CD158a, CD158b1, CD158b2, CD223, CD276 antigen; clusterin (CLU) gene, Clusterin, c-Met (hepatocyte growth factor receptor (HGFR)), Complement $C_3$, Connective tissue growth factor, COP9 signalosome subunit 5, CSF-1 (colony-stimulating factor 1 receptor), CSF2 gene, CTLA-4 (cytotoxic T-lymphocyte protein 4) receptor, Cyclin D1, Cyclin GI, cyclin-dependent kinases (CDK, such as CDK1, CDK1B, CDK2-9), cyclooxygenase (such as 1, 2), CYP2B1 gene, Cysteine palmitoyltransferase porcupine, Cytochrome P450 11B2, Cytochrome P450 17, cytochrome P450 17A1, Cytochrome P450 2D6, cytochrome P450 3A4, Cytochrome P450 reductase, cytokine signalling-1, cytokine signalling-3, Cytoplasmic isocitrate dehydrogenase, Cytosine deaminase, cytosine DNA methyltransferase, cytotoxic T-lymphocyte protein-4, DDR2 gene, Delta-like protein ligand (such as 3, 4), Deoxyribonuclease, Dickkopf-1 ligand, dihydrofolate reductase (DHFR), Dihydropyrimidine dehydrogenase, Dipeptidyl peptidase IV, discoidin domain receptor (DDR, such as DDR1), DNA binding protein (such as HU-beta), DNA dependent protein kinase, DNA gyrase, DNA methyltransferase, DNA polymerase (such as alpha), DNA primase, dUTP pyrophosphatase, L-dopachrome tautomerase, echinoderm microtubule like protein 4, EGFR tyrosine kinase receptor, Elastase, Elongation factor 1 alpha 2, Elongation factor 2, Endoglin, Endonuclease, Endoplasmin, Endosialin, Endostatin, endothelin (such as ET-A, ET-B), Enhancer of zeste homolog 2 (EZH2), Ephrin (EPH) tyrosine kinase (such as Epha3, Ephb4), Ephrin B2 ligand, epidermal growth factor, epidermal growth factor receptors (EGFR), epidermal growth factor receptor (EGFR) gene, Epigen, Epithelial cell adhesion molecule (EpCAM), Erb-b2 (v-erb-b2 avian erythroblastic leukemia viral oncogene homolog 2) tyrosine kinase receptor, Erb-b3 tyrosine kinase receptor, Erb-b4 tyrosine kinase receptor, E-selectin, Estradiol 17 beta dehydrogenase, Estrogen receptor (such as alpha, beta), Estrogen related receptor, Eukaryotic translation initiation factor 5A (EIF5A) gene, Exportin 1, Extracellular signal related kinase (such as 1, 2), Extracellular signal-regulated kinases (ERK), Factor (such as Xa, VIIa), farnesoid x receptor (FXR), Fas ligand, Fatty acid synthase (FASN), Ferritin, FGF-2 ligand, FGF-5 ligand, fibroblast growth factor (FGF, such as FGF1, FGF2, FGF4), Fibronectin, Fms-related tyrosine kinase 3 (Flt3), focal adhesion kinase (FAK, such as FAK2), folate hydrolase prostate-specific membrane antigen 1 (FOLH1), Folate receptor (such as alpha), Folate, Folate transporter 1, FYN tyrosine kinase, paired basic amino acid cleaving enzyme (FURIN), Beta-glucuronidase, Galactosyltransferase, Galectin-3, Ganglioside GD2, Glucocorticoid, glucocorticoid-induced TNFR-related protein GITR receptor, Glutamate carboxypeptidase II, glutaminase, Glutathione S-transferase P, glycogen synthase kinase (GSK, such as 3-beta), Glypican 3 (GPC3), gonadotropin-releasing hormone (GNRH), Granulocyte macrophage colony stimulating factor (GM-CSF) receptor, Granulocyte-colony stimulating factor (GCSF) ligand, growth factor receptor-bound protein 2 (GRB2), Grp78 (78 kDa glucose-regulated protein) calcium binding protein, molecular chaperone groEL2 gene, Heat shock protein (such as 27, 70, 90 alpha, beta), Heat shock protein gene, Heat stable enterotoxin receptor, Hedgehog protein, Heparanase, Hepatocyte growth factor, HERV-H LTR associating protein 2, Hexose kinase, Histamine H2 receptor, Histone methyltransferase (DOT1L), histone deacetylase (HDAC, such as 1, 2, 3, 6, 10, 11), Histone H1, Histone H3, HLA class I antigen (A-2 alpha), HLA class II antigen, Homeobox protein NANOG, HSPB 1 gene, Human leukocyte antigen (HLA), Human papillomavirus (such as E6, E7) protein, Hyaluronic acid, Hyaluronidase, Hypoxia inducible factor-1 alpha (HIFla), Imprinted Maternally Expressed Transcript (H19) gene, mitogen-activated protein kinase kinase kinase kinase 1 (MAP4K1), tyrosine-protein kinase HCK, I-Kappa-B kinase (IKK, such as IKKbe), IL-1 alpha, IL-1 beta, IL-12, IL-12 gene, IL-15, IL-17, IL-2 gene, IL-2 receptor alpha subunit, IL-2, IL-3 receptor, IL-4, IL-6, IL-7, IL-8, immunoglobulin (such as G, G1, G2, K, M), Immunoglobulin Fc receptor, Immunoglobulin gamma Fc receptor (such as I, III, IIIA), indoleamine 2,3-dioxygenase (IDO, such as IDO1), indoleamine pyrrole 2,3-dioxygenase 1 inhibitor, insulin receptor, Insulin-like growth factor (such as 1, 2), Integrin alpha-4/beta-1, integrin alpha-4/beta-7, Integrin alpha-5/beta-1, Integrin alpha-V/beta-3, Integrin alpha-V/beta-5, Integrin alpha-V/beta-6, Intercellular adhesion molecule 1 (ICAM-1), interferon (such as alpha, alpha 2, beta, gamma), Interferon inducible protein absent in melanoma 2 (AIM2), interferon type I receptor, Interleukin 1 ligand, Interleukin 13 receptor alpha 2, interleukin 2 ligand, interleukin-1 receptor-associated kinase 4 (IRAK4), Interleukin-2, Interleukin-29 ligand, isocitrate dehydrogenase (such as IDH1, IDH2), Janus kinase (JAK, such as JAKi, JAK2), Jun N terminal kinase, kallikrein-related peptidase 3 (KLK3) gene, Killer cell Ig like receptor, Kinase insert domain receptor (KDR), Kinesin-like protein KIF11, Kirsten rat sarcoma viral oncogene homolog (KRAS) gene, Kisspeptin (KiSS-1) receptor, KIT gene, v-kit Hardy-Zuckerman 4 feline sarcoma viral oncogene homolog (KIT) tyrosine kinase, lactoferrin, Lanosterol-14 demethylase, LDL receptor related protein-1, Leukotriene A4 hydrolase, Listeriolysin, L-Selectin, Luteinizing hormone receptor, Lyase, lymphocyte activation gene 3 protein (LAG-3), Lymphocyte antigen 75, Lymphocyte function antigen-3 receptor, lymphocyte-specific protein tyrosine kinase (LCK), Lymphotactin, Lyn (Lck/Yes novel) tyrosine kinase, lysine demethylases (such as KDM1, KDM2, KDM4, KDM5, KDM6, A/B/C/D), Lysophosphatidate-1 receptor, lysosomal-associated membrane protein family (LAMP) gene, Lysyl oxidase homolog 2, lysyl oxidase protein (LOX), lysyl oxidase-like protein (LOXL, such as LOXL2), Hematopoietic Progenitor Kinase 1 (HPKi), Hepatocyte growth factor receptor (MET) gene, macrophage colony-stimulating factor (MCSF) ligand, Macrophage migration inhibitory fact, MAGEC 1 gene, MAGEC2 gene, Maj or vault protein, MAPK-activated protein kinase (such as MK2), Mas-related G-protein coupled receptor, matrix metalloprotease (MMP, such as MMP2, MMP9), Mcl-1 differentiation protein, Mdm2 p53-binding protein, Mdm4 protein, Melan-A (MART-1) melanoma antigen, Melanocyte protein Pmel 17, melanocyte stimulating hormone ligand, melanoma antigen family A3 (MAGEA3) gene, Melanoma associated antigen (such as 1, 2, 3, 6), Membrane copper amine oxidase, Mesothelin, MET tyrosine kinase, Metabotropic glutamate receptor 1, Metalloreductase STEAPI (six transmembrane epithelial antigen of the prostate 1), Metastin, methionine aminopeptidase-2, Methyltransferase, Mitochondrial 3 ketoacyl CoA thiolase, mitogen-activate protein kinase (MAPK), mitogen-activated protein kinase (MEK, such as MEK1, MEK2), mTOR (mechanistic target of rapamycin (serine/threonine kinase), mTOR complex (such as 1,2), mucin (such as 1, 5A, 16), mut T homolog (MTH, such as MTH1), Myc proto-oncogene protein, myeloid cell leukemia 1 (MCL1) gene, myristoylated alanine-rich protein kinase C substrate (MARCKS) protein, NAD ADP ribosyltransferase, natriuretic peptide receptor C, Neural cell adhesion molecule 1, Neurokinin 1 (NK1) receptor, Neurokinin receptor, Neuropilin 2, NF kappa B activating protein, NIMA-related kinase 9 (NEK9), Nitric oxide synthase, NK cell receptor, NK3 receptor, NKG2 A B activating NK receptor, Noradrenaline transporter, Notch (such as Notch-2 receptor, Notch-3 receptor, Notch-4 receptor), Nuclear erythroid 2-related factor 2, Nuclear Factor (NF) kappa B, Nucleolin, Nucleophosmin, nucleophosmin-anaplastic lymphoma kinase (NPM-ALK), 2 oxoglutarate dehydrogenase, 2,5-oligoadenylate synthetase, O-methylguanine DNA methyltransferase, Opioid receptor (such as delta), Ornithine decarboxylase, Orotate phosphoribosyltransferase, orphan nuclear hormone receptor NR4A1, Osteocalcin, Osteoclast differentiation factor, Osteopontin, OX-40 (tumor necrosis factor receptor superfamily member 4 TNFRSF4, or CD134) receptor, P3 protein, p38 kinase, p38 MAP kinase, p53 tumor suppressor protein, Parathyroid hormone ligand, peroxisome proliferator-activated receptors (PPAR, such as alpha, delta, gamma), P-Glycoprotein (such as 1), phosphatase and tensin homolog (PTEN), phosphatidylinositol 3-kinase (PI3K), phosphoinositide-3 kinase (PI3K such as alpha, delta, gamma), phosphorylase kinase (PK), PKN3 gene, placenta growth factor,platelet-derived growth factor (PDGF, such as alpha, beta), Platelet-derived growth factor (PDGF, such as alpha, beta), Pleiotropic drug resistance transporter, Plexin B1, PLK1 gene, polo-like kinase (PLK), Polo-like kinase 1, Poly ADP ribose polymerase (PARP, such as PARP1, 2 and 3), Preferentially expressed antigen in melanoma (PRAME) gene, Prenyl-binding protein (PrPB), Probable transcription factor PML, Progesterone receptor, Programmed cell death 1 (PD-1), Programmed cell death ligand 1 inhibitor (PD-L1), Prosaposin (PSAP) gene, Prostanoid receptor (EP4), prostate specific antigen, Prostatic acid phosphatase, proteasome, Protein E7, Protein farnesyltransferase, protein kinase (PK, such as A, B, C), protein tyrosine kinase, Protein tyrosine phosphatase beta, Protooncogene serine/threonine-protein kinase (PIM, such as PIM-1, PIM-2, PIM-3), P-Selectin, Purine nucleoside phosphorylase, purinergic receptor P2X ligand gated ion channel 7 (P2X7), Pyruvate dehydrogenase (PDH), Pyruvate dehydrogenase kinase, Pyruvate kinase (PYK), 5-Alpha-reductase, Raf protein kinase (such as 1, B), RAF1 gene, Ras gene, Ras GTPase, RET gene, Ret tyrosine kinase receptor, retinoblastoma associated protein, retinoic acid receptor (such as gamma), Retinoid X receptor, Rheb (Ras homolog enriched in brain) GTPase, Rho (Ras homolog) associated protein kinase 2, ribonuclease, Ribonucleotide reductase (such as M2 subunit), Ribosomal protein S6 kinase, RNA polymerase (such as I, II), Ron (Recepteur d'Origine Nantais) tyrosine kinase, ROS1 (ROS proto-oncogene 1, receptor tyrosine kinase) gene, Rosi tyrosine kinase, Runt-related transcription factor 3, Gamma-secretase, S100 calcium binding protein A9, Sarco endoplasmic calcium ATPase, Second mitochondria-derived activator of caspases (SMAC) protein, Secreted frizzled related protein-2, Semaphorin-4D, Serine protease, serine/threonine kinase (STK), serine/threonine-protein kinase (TBK, such as TBK1), signal transduction and transcription (STAT, such as STAT-1, STAT-3, STAT-5), Signaling lymphocytic activation molecule (SLAM) family member 7, six-transmembrane epithelial antigen of the prostate (STEAP) gene, SL cytokine ligand, smoothened (SMO) receptor, Sodium iodide cotransporter, Sodium phosphate cotransporter 2B, Somatostatin receptor (such as 1, 2, 3, 4, 5), Sonic hedgehog protein, Son of sevenless (SOS), Specific protein 1 (Sp1) transcription factor, Sphingomyelin synthase, Sphingosine kinase (such as 1, 2), Sphingosine-1-phosphate receptor-1, spleen tyrosine kinase (SYK), SRC gene, Src tyrosine kinase, STAT3 gene, Steroid sulfatase, Stimulator of interferon genes (STING) receptor, stimulator of interferon genes protein, Stromal cell-derived factor 1 ligand, SUMO (small ubiquitin-like modifier), Superoxide dismutase, Survivin protein, Synapsin 3, Syndecan-1, Synuclein alpha, T cell surface glycoprotein CD28, tank-binding kinase (TBK), TATA box-binding protein-associated factor RNA polymerase I subunit B (TAF1B) gene, T-cell CD3 glycoprotein zeta chain, T-cell differentiation antigen CD6, T-cell immunoglobulin and mucin-domain containing-3 (TIM-3), T-cell surface glycoprotein CD8, Tec protein tyrosine kinase, Tek tyrosine kinase receptor, telomerase, Telomerase reverse transcriptase (TERT) gene, Tenascin, TGF beta 2 ligand, Thrombopoietin receptor, Thymidine kinase, Thymidine phosphorylase, Thymidylate synthase, Thymosin (such as alpha 1), Thyroid hormone receptor, Thyroid stimulating hormone receptor, Tissue factor, TNF related apoptosis inducing ligand, TNFR1 associated death domain protein, TNF-related apoptosis-inducing ligand (TRAIL) receptor, TNFSF11 gene, TNFSF9 gene, Toll-like receptor (TLR such as 1-13), topoisomerase (such as I, II, III), Transcription factor, Transferase, Transferrin, Transforming growth factor (TGF, such as beta) kinase, Transforming growth factor TGF-β receptor kinase, Transglutaminase, Translocation associated protein, Transmembrane glycoprotein NMB, Trop-2 calcium signal transducer, trophoblast glycoprotein (TPBG) gene, Trophoblast glycoprotein, Tropomyosin receptor kinase (Trk) receptor (such as TrkA, TrkB, TrkC), Tryptophan 5-hydroxylase, Tubulin, Tumor necrosis factor (TNF, such as alpha, beta), Tumor necrosis factor 13C receptor, tumor progression locus 2 (TPL2), Tumor protein 53 (TP53) gene, Tumor suppressor candidate 2 (TUSC2) gene, Tyrosinase, Tyrosine hydroxylase, tyrosine kinase (TK), Tyrosine kinase receptor, Tyrosine kinase with immunoglobulin-like and EGF-like domains (TIE) receptor, Tyrosine protein kinase ABL1 inhibitor, Ubiquitin, Ubiquitin carboxyl hydrolase isozyme L5, Ubiquitin thioesterase-14, Ubiquitin-conjugating enzyme E21 (UBE2I, UBC9), Urease, Urokinase plasminogen activator, Uteroglobin, Vanilloid VR1, Vascular cell adhesion protein 1, vascular endothelial growth factor receptor (VEGFR), V-domain Ig suppressor of T-cell activation (VISTA), VEGF-1 receptor, VEGF-2 receptor, VEGF-3 receptor, VEGF-A, VEGF-B, Vimentin, Vitamin D3 receptor, Proto-oncogene tyrosine-protein kinase Yes, Wee-1 protein kinase, Wilms' tumor antigen 1, Wilms' tumor protein, X-linked inhibitor of apoptosis protein, Zinc finger protein transcription factor or any combination thereof.

Non-limiting examples of additional therapeutic agents may be categorized by their mechanism of action into, for example, the following groups:

anti-metabolites/anti-cancer agents, such as pyrimidine analogs floxuridine, capecitabine, cytarabine, CPX-351 (liposomal cytarabine, daunorubicin), and TAS-118;

purine analogs, folate antagonists (such as pralatrexate), and related inhibitors;

antiproliferative/antimitotic agents including natural products, such as *vinca* alkaloids (vinblastine, vincristine) and microtubule disruptors such as taxane (paclitaxel, docetaxel), vinblastin, nocodazole, epothilones, vinorelbine (NAVELBINE®), and epipodophyllotoxins (etoposide, teniposide);

DNA damaging agents, such as actinomycin, amsacrine, busulfan, carboplatin, chlorambucil, cisplatin, cyclophosphamide (CYTOXAN®), dactinomycin, daunorubicin, doxorubicin, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA-hypomethylating agents, such as guadecitabine (SGI-110), ASTX727;

antibiotics such as dactinomycin, daunorubicin, doxorubicin, idarubicin, anthracyclines, mitoxantrone, bleomycins, plicamycin (mithramycin);

enzymes such as L-asparaginase which systemically metabolizes L-asparagine and deprives cells which do not have the capacity to synthesize their own asparagine;

antiplatelet agents;

DNAi oligonucleotides targeting Bcl-2, such as PNT2258;

agents that activate or reactivate latent human immunodeficiency virus (HIV), such as panobinostat and romidepsin;

asparaginase stimulators, such as crisantaspase (Erwinase®) and GRASPA (ERY-001, ERY-ASP), calaspargase pegol;

pan-Trk, ROS1 and ALK inhibitors, such as entrectinib, TPX-0005;

anaplastic lymphoma kinase (ALK) inhibitors, such as alectinib, ceritinib;

antiproliferative/antimitotic alkylating agents, such as nitrogen mustard cyclophosphamide and analogs (melphalan, chlorambucil, hexamethylmelamine, thiotepa), alkyl nitrosoureas (carmustine) and analogs, streptozocin, and triazenes (dacarbazine);

antiproliferative/antimitotic antimetabolites, such as folic acid analogs (methotrexate);

platinum coordination complexes (cisplatin, oxiloplatinim, and carboplatin), procarbazine, hydroxyurea, mitotane, and aminoglutethimide;

hormones, hormone analogs (estrogen, tamoxifen, goserelin, bicalutamide, and nilutamide), and aromatase inhibitors (letrozole and anastrozole);

anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents;

antisecretory agents (breveldin);

immunosuppressives, such as tacrolimus, sirolimus, azathioprine, and mycophenolate;

growth factor inhibitors, and vascular endothelial growth factor inhibitors;

fibroblast growth factor inhibitors, such as FPA14;

anti-VEGFR antibodies, such as IMC-$3C_5$, GNR-011, tanibirumab;

anti-VEGF/DDL4 antibodies, such as ABT-165;

anti-cadherins antibodies, such as HKT-288;

anti-CD70 antibodies, such as AMG-172; anti-leucine-rich repeat containing 15 (LRRC15) antibodies, such as ABBV-085. ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;

DNA interference oligonucleotides, such as PNT2258, AZD-9150;

anti-ANG-2 antibodies, such as MEDI3617, and LY3127804;

anti-ANG-1/ANG-2 antibodies, such as AMG-780;

anti-MET/EGFR antibodies, such as LY3164530;

anti-EGFR antibodies, such as ABT-414, AMG-595, necitumumab, ABBV-221, depatuxizumab mafodotin (ABT-414), tomuzotuximab, ABT-806, vectibix, modotuximab, RM-1929;

anti-CSF1R antibodies, such as emactuzumab, LY3022855, AMG-820, FPA-008 (cabiralizumab);

anti-CD40 antibodies, such as RG7876, SEA-CD40, APX-005M, ABBV-428;

anti-endoglin antibodies, such as TRC105 (carotuximab);

anti-CD45 antibodies, such as 1311-BC8 (lomab-B);

anti-HER3 antibodies, such as LJM716, GSK2849330;

anti-HER2 antibodies, such as margetuximab, MEDI4276, BAT-8001;

anti-HLA-DR antibodies, such as IMMU-114;

anti-IL-3 antibodies, such as JNJ-56022473;

anti-OX40 antibodies, such as MEDI6469, MEDI6383, MEDI0562 (tavolixizumab), MOXR0916, PF-04518600, RG-7888, GSK-3174998, INCAGN1949, BMS-986178, GBR-8383, ABBV-368;

anti-EphA3 antibodies, such as KB-004;

anti-CD20 antibodies, such as obinutuzumab, IGN-002;

anti-CD20/CD3 antibodies, such as RG7828;

anti-CD37 antibodies, such as AGS67E, otlertuzumab (TRU-016);

anti-ENPP3 antibodies, such as AGS-$16C_3F$;

anti-FGFR-3 antibodies, such as LY3076226, B-701;

anti-FGFR-2 antibodies, such as GAL-F2;

anti-$C_5$ antibodies, such as ALXN-1210;

anti-CD27 antibodies, such as varlilumab (CDX-1127);

anti-TROP-2 antibodies, such as IMMU-132 anti-NKG2a antibodies, such as monalizumab;

anti-VISTA antibodies, such as HMBD-002;

anti-PVRIG antibodies, such as COM-701;

anti-EpCAM antibodies, such as VB4-845;

anti-BCMA antibodies, such as GSK-2857916 anti-CEA antibodies, such as RG-7813;

anti-cluster of differentiation 3 (CD3) antibodies, such as MGDO15;

anti-folate receptor alpha antibodies, such as IMGN853;

MCL-1 inhibitors, such as AMG-176, S-64315, and AZD-5991, 483-LM, A-1210477, UMI-77, JKY-5-037;

epha2 inhibitors, such as MM-310;

anti LAG-3 antibodies, such as relatlimab (ONO-4482), LAG-525, MK-4280, REGN-3767;

raf kinase/VEGFR inhibitors, such as RAF-265;

polycomb protein (EED) inhibitors, such as MAK683;

anti-fibroblast activation protein (FAP)/IL-2R antibodies, such as RG7461;

anti-fibroblast activation protein (FAP)/TRAIL-$R^2$ antibodies, such as RG7386;

anti-fucosyl-GM1 antibodies, such as BMS-986012;

p38 MAP kinase inhibitors, such as ralimetinib;

PRMT1 inhibitors, such as MS203;

Sphingosine kinase 2 (SK2) inhibitors, such as opaganib;

FLT3-ITD inhibitors, such as BCI-332;

Nuclear erythroid 2-related factor 2 stimulators, such as omaveloxolone (RTA-408);

Tropomyosin receptor kinase (TRK) inhibitors, such as LOXO-195, ONO-7579;

anti-ICOS antibodies, such as JTX-2011, GSK3359609;

anti-DR5 (TRAIL2) antibodies, such as DS-8273;

anti-GD2 antibodies, such as APN-301;
anti-interleukin-17 (IL-17) antibodies, such as CJM-112;
anti-carbonic anhydrase IX antibodies, such as TX-250;
anti-CD38-attenukine, such as TAK573;
anti-Mucin 1 antibodies, such as gatipotuzumab;
Mucin 1 inhibitors, such as GO-203-2C;
MARCKS protein inhibitors, such as BIO-11006;
Folate antagonists, such as arfolitixorin;
Galectin-3 inhibitors, such as GR-MD-02;
Phosphorylated P68 inhibitors, such as RX-5902;
CD95/TNF modulators, such as ofranergene obadenovec;
PI3K/Akt/mTOR inhibitors, such as ABTL-0812;
pan-PIM kinase inhibitors, such as INCB-053914;
IL-12 gene stimulators, such as EGEN-001, tavokinogene telseplasmid;
Heat shock protein HSP90 inhibitors, such as TAS-116, PEN-866;
VEGF/HGF antagonists, such as MP-0250;
SYK tyrosine kinase/FLT3 tyrosine kinase inhibitors, such as TAK-659;
SYK tyrosine kinase/JAK tyrosine kinase inhibitors, such as ASN-002;
FLT3 tyrosine kinase inhibitor, such as FF-10101;
FLT3 tyrosine kinase agonist, such as CDX-301;
FLT3/MEK1 inhibitors, such as E-6201;
IL-24 antagonist, such as AD-IL24;
RIG-I agonists, such as RGT-100;
Aerolysin stimulators, such as topsalysin;
P-Glycoprotein 1 inhibitors, such as HM-30181A;
CSF-1 antagonists, such as ARRY-382, BLZ-945;
anti-Mesothelin antibodies, such as SEL-403;
Thymidine kinase stimulators, such as aglatimagene besadenovec;
Polo-like kinase 1 inhibitors, such as PCM-075;
TLR-7 agonists, such as TMX-101 (imiquimod);
NEDD8 inhibitors, such as pevonedistat (MLN-4924), TAS-4464;
Pleiotropic pathway modulators, such as avadomide (CC-122);
FoxM1 inhibitors, such as thiostrepton;
Anti-MUC 1 antibodies, such as Mab-AR-20.5;
anti-CD38 antibodies, such as isatuximab, MOR-202;
UBA1 inhibitors, such as TAK-243;
Src tyrosine kinase inhibitors, such as VAL-201;
VDAC/HK inhibitors, such as VDA-1102;
BRAF/PI3K inhibitors, such as ASN-003;
Elf4a inhibitors, such as rohinitib, eFT226;
TP53 gene stimulators, such as ad-p53;
PD-L1/EGFR inhibitors, such as GNS-1480;
Retinoic acid receptor alpha (RARt) inhibitors, such as SY-1425;
SIRT3 inhibitors, such as YC8-02;
Stromal cell-derived factor 1 ligand inhibitors, such as olaptesed pegol (NOX-A12);
IL-4 receptor modulators, such as MDNA-55;
Arginase-I stimulators, such as pegzilarginase;
Topoisomerase I inhibitor/hypoxia inducible factor-1 alpha inhibitors, such as PEG-SN38 (firtecan pegol);
Hypoxia inducible factor-1 alpha inhibitors, such as PT-2977, PT-2385;
CD122 agonists such as NKTR-214;
p53 tumor suppressor protein stimulators such as kevetrin;
Mdm4/Mdm2 p53-binding protein inhibitors, such as ALRN-6924;
kinesin spindle protein (KSP) inhibitors, such as filanesib (ARRY-520);
CD80-fc fusion protein inhibitors, such as FPT-155;
Menin and mixed lineage leukemia (MLL) inhibitors such as KO-539;
Liver x receptor agonists, such as RGX-104;
IL-10 agonists, such as AM-0010;
EGFR/ErbB-2 inhibitors, such as varlitinib;
VEGFR/PDGFR inhibitors, such as vorolanib;
IRAK4 inhibitors, such as CA-4948;
anti-TLR-2 antibodies, such as OPN-305;
Calmodulin modulators, such as CBP-501;
Glucocorticoid receptor antagonists, such as relacorilant (CORT-125134);
Second mitochondria-derived activator of caspases (SMAC) protein inhibitors, such as BI-891065;
Lactoferrin modulators, such as LTX-315;
Kit tyrosine kinase/PDGF receptor alpha antagonists such as DCC-2618;
KIT inhibitors, such as PLX-9486;
Exportin 1 inhibitors, such as eltanexor;
EGFR/ErbB2/Ephb4 inhibitors, such as tesevatinib;
anti-CD33 antibodies, such as IMGN-779;
anti-KMA antibodies, such as MDX-1097;
anti-TIM-3 antibodies, such as TSR-022, LY-3321367, MBG-453;
anti-CD55 antibodies, such as PAT-SC1;
anti-PSMA antibodies, such as ATL-101;
anti-CD100 antibodies, such as VX-15;
anti-EPHA3 antibodies, such as fibatuzumab;
anti-Erbb antibodies, such as CDX-3379, HLX-02, seribantumab;
anti-APRIL antibodies, such as BION-1301;
Anti-Tigit antidbodies, such as BMS-986207, RG-6058;
CHST15 gene inhibitors, such as STNM-01;
RAS inhibitors, such as NEO-100;
Somatostatin receptor antagonist, such as OPS-201;
CEBPA gene stimulators, such as MTL-501;
DKK3 gene modulators, such as MTG-201;
p70s6k inhibitors, such as MSC2363318A;
methionine aminopeptidase 2 (MetAP2) inhibitors, such as M8891, APL-1202;
arginine N-methyltransferase 5 inhibitors, such as GSK-3326595;
anti-programmed cell death protein 1 (anti-PD-1) antibodies, such as nivolumab (OPDIVO®, BMS-936558, MDX-1106), pembrolizumab (KEYTRUDA®, MK-3477, SCH-900475, lambrolizumab, CAS Reg. No. 1374853-91-4), pidilizumab, PF-06801591, BGB-A317, GLS-010 (WBP-3055), AK-103 (HX-008), MGA-012, BI-754091, REGN-2810 (cemiplimab), AGEN-2034, JS-001, JNJ-63723283, genolimzumab (CBT-501), LZM-009, BCD-100, LY-3300054, SHR-1201, BAT-1306, and anti-programmed death-ligand 1 (anti-PD-L1) antibodies such as BMS-936559, atezolizumab (MPDL3280A), durvalumab (MEDI4736), avelumab, CK-301, (MSB0010718C), MEDI0680, CX-072, CBT-502, PDR-001 (spartalizumab), TSR-042 (dostarlimab), JTX-4014, BGB-A333, SHR-1316, CS-1001 (WBP-3155, KN-035, IBI-308, FAZ-053, and MDX1105-01;
PD-L1/VISTA antagonists such as CA-170;
anti-PD-L1/TGF3 antibodies, such as M7824;
anti-transferrin antibodies, such as CX-2029;
anti-IL-8 (Interleukin-8) antibodies, such as HuMax-Inflam;
ATM (ataxia telangiectasia) inhibitors, such as AZD0156;
CHK1 inhibitors, such as GDC-0575, LY2606368 (prexasertib), SRA737, RG7741 (CHKI/2);

CXCR4 antagonists, such as BL-8040, LY2510924, burixafor (TG-0054), X4P-002, X4P-001-IO;
EXH2 inhibitors, such as GSK2816126;
HER2 inhibitors, such as neratinib, tucatinib (ONT-380);
KDM1 inhibitors, such as ORY-1001, IMG-7289, INCB-59872, GSK-2879552;
CXCR2 antagonists, such as AZD-5069;
GM-CSF antibodies, such as lenzilumab;
DNA dependent protein kinase inhibitors, such as MSC2490484A (nedisertib), VX-984, AsiDNA (DT-01);
protein kinase C (PKC) inhibitors, such as LXS-196, sotrastaurin;
Selective estrogen receptor downregulators (SERD), such as fulvestrant (Faslodex®), RG6046, RG6047, elacestrant (RAD-1901) and AZD9496;
Selective estrogen receptor covalent antagonists (SERCAs), such as H3B-6545;
selective androgen receptor modulator (SARM), such as GTX-024, darolutamide;
transforming growth factor-beta (TGF-beta) kinase antagonists, such as galunisertib;
anti-transforming growth factor-beta (TGF-beta) antibodies, such as LY3022859, NIS793, XOMA 089;
bispecific antibodies, such as MM-141 (IGF-1/ErbB3), MM-111 (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietins/VEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3);
Mutant selective EGFR inhibitors, such as PF-06747775, EGF816 (nazartinib), ASP8273, ACEA-0010, BI-1482694;
Anti-GITR (glucocorticoid-induced tumor necrosis factor receptor-related protein) antibodies, such as MEDI1873, FPA-154, INCAGN-1876, TRX-518, BMS-986156, MK-1248, GWN-323;
anti-delta-like protein ligand 3 (DDL3) antibodies, such as rovalpituzumab tesirine;
anti-clusterin antibodies, such as AB-16B5;
anti-Ephrin-A4 (EFNA4) antibodies, such as PF-06647263;
anti-RANKL antibodies, such as denosumab;
anti-mesothelin antibodies, such as BMS-986148, Anti-MSLN-MMAE;
anti-sodium phosphate cotransporter 2B (NaP2B) antibodies, such as lifastuzumab
anti-c-Met antibodies, such as ABBV-399;
Adenosine A2A receptor antagonists, such as CPI-444, AZD-4635, preladenant, PBF-509;
Alpha-ketoglutarate dehydrogenase (KGDH) inhibitors, such as CPI-613;
XPO1 inhibitors, such as selinexor (KPT-330);
Isocitrate dehydrogenase 2 (IDH2) inhibitors, such as enasidenib (AG-221);
IDH1 inhibitors such as AG-120, and AG-881 (IDH1 and IDH2), IDH-305, BAY-1436032;
interleukin-3 receptor (IL-3R) modulators, such as SL-401;
Arginine deiminase stimulators, such as pegargiminase (ADI-PEG-20);
antibody-drug conjugates, such as MLN0264 (anti-GCC, guanylyl cyclase C), T-DM1 (trastuzumab emtansine, Kadcycla), milatuzumab-doxorubicin (hCD74-DOX), brentuximab vedotin, DCDT2980S, polatuzumab vedotin, SGN-CD70A, SGN-CD19A, inotuzumab ozogamicin, lorvotuzumab mertansine, SAR3419, isactuzumab govitecan, enfortumab vedotin (ASG-22ME), ASG-15ME, DS-8201 ((trastuzumab deruxtecan), 225Ac-lintuzumab, U3-1402, 177Lu-tetraxetan-tetuloma, tisotumab vedotin, anetumab ravtansine, CX-2009, SAR-566658, W-0101, polatuzumab vedotin, ABBV-085;
claudin-18 inhibitors, such as claudiximab;
β-catenin inhibitors, such as CWP-291;
anti-CD73 antibodies, such as MEDI-9447 (oleclumab), CPX-006, IPH-53, BMS-986179;
CD73 antagonists, such as AB-680, PSB-12379, PSB-12441, PSB-12425;
CD39/CD73 antagonists, such as PBF-1662;
chemokine receptor 2 (CCR) inhibitors, such as PF-04136309, CCX-872, BMS-813160 (CCR2/CCR5)
thymidylate synthase inhibitors, such as ONX-0801;
ALK/ROS1 inhibtors, such as lorlatinib;
tankyrase inhibitors, such as G007-LK;
Mdm2 p53-binding protein inhibitors, such as CMG-097, HDM-201;
c-PIM inhibitors, such as PIM447;
BRAF inhibitors, such as dabrafenib, vemurafenib, encorafenib (LGX818), PLX8394;
sphingosine kinase-2 (SK2) inhibitors, such as Yeliva® (ABC294640);
cell cycle inhibitors, such as selumetinib (MEK1/2), and sapacitabine;
AKT inhibitors such as MK-2206, ipatasertib, afuresertib, AZD5363, and ARQ-092, capivasertib, triciribine;
anti-CTLA-4 (cytotoxic T-lymphocyte protein-4) inhibitors, such as tremelimumab, AGEN-1884, BMS-986218;
c-MET inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;
c-Met/VEGFR inhibitors, such as BMS-817378, TAS-115;
c-Met/RON inhibitors, such as BMS-777607;
BRAF/EGFR inhibitors, such as BGB-283;
bcr/abl inhibitors, such as rebastinib, asciminib;
MNK1/MNK2 inhibitors, such as eFT-508;
mTOR inhibitor/cytochrome P450 3A4 stimulators, such as TYME-88
lysine-specific demethylase-1 (LSD1) inhibitors, such as CC-90011;
Pan-RAF inhibitors, such as LY3009120, LXH254, TAK-580;
Raf/MEK inhibitors, such as RG7304;
CSF1R/KIT and FLT3 inhibitors, such as pexidartinib (PLX3397);
kinase inhibitors, such as vandetanib;
E selectin antagonists, such as GMI-1271;
differentiation inducers, such as tretinoin;
epidermal growth factor receptor (EGFR) inhibitors, such as osimertinib (AZD-9291);

topoisomerase inhibitors, such as doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114);

corticosteroids, such as cortisone, dexamethasone, hydrocortisone, methylprednisolone, prednisone, prednisolone;

growth factor signal transduction kinase inhibitors;

nucleoside analogs, such as DFP-10917;

Axl inhibitors, such as BGB-324 (bemcentinib), SLC-0211;

BET inhibitors, such as INCB-054329, INCB057643, TEN-010, AZD-5153, ABT-767, BMS-986158, CC-90010, GSK525762 (molibresib), NHWD-870, ODM-207,GSK-2820151, GSK-1210151A, ZBC246, ZBC260, ZEN3694, FT-1101, RG-6146, CC-90010, mivebresib, BI-894999, PLX-2853, PLX-51107, CPI-0610, GS-5829;

PARP inhibitors, such as olaparib, rucaparib, veliparib, talazoparib, ABT-767, BGB-290;

Proteasome inhibitors, such as ixazomib, carfilzomib (Kyprolis®), marizomib;

Glutaminase inhibitors, such as CB-839;

Vaccines, such as peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131; bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, stapuldencel-T, eltrapuldencel-T, SL-701, BSK01TM, rocapuldencel-T (AGS-003), DCVAC, CVac$^{rm}$, stapuldencel-T, eltrapuldencel-T, SL-701, BSK01™, ADXS31-142; oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, PF-06753512, VBI-1901, TG-4010, ProscaVax™; tumor cell vaccines, such as Vigil® (1ND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000;

anti-DLL4 (delta like ligand 4) antibodies, such as demcizumab;

STAT-3 inhibitors, such as napabucasin (BBI-608);

ATPase p97 inhibitors, such as CB-5083;

smoothened (SMO) receptor inhibitors, such as Odomzo® (sonidegib, formerly LDE-225), LEQ506, vismodegib (GDC-0449), BMS-833923, glasdegib (PF-04449913), LY2940680, and itraconazole;

interferon alpha ligand modulators, such as interferon alpha-2b, interferon alpha-2a biosimilar (Biogenomics), ropeginterferon alfa-2b (AOP-2014, P-1101, PEG IFN alpha-2b), Multiferon (Alfanative, Viragen), interferon alpha 1b, Roferon-A (Canferon, Ro-25-3036), interferon alfa-2a follow-on biologic (Biosidus)(Inmutag, Inter 2A), interferon alfa-2b follow-on biologic (Biosidus-Bioferon, Citopheron, Ganapar, Beijing Kawin Technology—Kaferon), Alfaferone, pegylated interferon alpha-1b, peginterferon alfa-2b follow-on biologic (Amega), recombinant human interferon alpha-1b, recombinant human interferon alpha-2a, recombinant human interferon alpha-2b, veltuzumab-IFN alpha 2b conjugate, Dynavax (SD-101), and interferon alfa-nl (Humoferon, SM-10500, Sumiferon);

interferon gamma ligand modulators, such as interferon gamma (OH-6000, Ogamma 100);

IL-6 receptor modulators, such as tocilizumab, siltuximab, AS-101 (CB-06-02, IVX-Q-101);

Telomerase modulators, such as, tertomotide (GV-1001, HR-2802, Riavax) and imetelstat (GRN-163, JNJ-63935937);

DNA methyltransferases inhibitors, such as temozolomide (CCRG-81045), decitabine, guadecitabine (S-110, SGI-110), KRX-0402, RX-3117, RRx-001, and azacitidine;

DNA gyrase inhibitors, such as pixantrone and sobuzoxane;

Bcl-2 family protein inhibitors, such as ABT-263, venetoclax (ABT-199), ABT-737, and AT-101;

Notch inhibitors, such as LY3039478 (crenigacestat), tarextumab (anti-Notch2/3), BMS-906024;

anti-myostatin inhibitors, such as landogrozumab;

hyaluronidase stimulators, such as PEGPH-20;

Wnt pathway inhibitors, such as SM-04755, PRI-724, WNT-974;

gamma-secretase inhibitors, such as PF-03084014, MK-0752, RO-4929097;

Grb-2 (growth factor receptor bound protein-2) inhibitors, such as BP1001;

TRAIL pathway-inducing compounds, such as ONC201, ABBV-621;

Focal adhesion kinase inhibitors, such as VS-4718, defactinib, GSK2256098;

hedgehog inhibitors, such as saridegib, sonidegib (LDE225), glasdegib and vismodegib;

Aurora kinase inhibitors, such as alisertib (MLN-8237), and AZD-2811,AMG-900, barasertib, ENMD-2076;

HSPB1 modulators (heat shock protein 27, HSP27), such as brivudine, apatorsen;

ATR inhibitors, such as BAY-937, AZD6738, AZD6783, VX-803, VX-970 (berzosertib) and VX-970;

mTOR inhibitors, such as sapanisertib and vistusertib (AZD2014), ME-344;

mTOR/PI3K inhibitors, such as gedatolisib, GSK2141795, omipalisib, RG6114;

Hsp90 inhibitors, such as AUY922, onalespib (AT13387), SNX-2112, SNX5422;

Murine double minute (mdm2) oncogene inhibitors, such as DS-3032b, RG7775, AMG-232, HDM201, and idasanutlin (RG7388);

CD137 agonists, such as urelumab, utomilumab (PF-05082566);

STING agonists, such as ADU-S100 (MIW-815), SB-11285, MK-1454, SR-8291, AdVCA0848, GSK-532, SYN-STING, MSA-1, SR-8291;

FGFR inhibitors, such as FGF-401, 1NCB-054828, BAY-1163877, AZD4547, JNJ-42756493, LY2874455, Debio-1347;

fatty acid synthase (FASN) inhibitors, such as TVB-2640;

Anti-KIR monoclonal antibodies, such as lirilumab (IPH-2102), IPH-4102;

Antigen CD19 inhibitors, such as MOR208, MEDI-551, AFM-11, inebilizumab;

CD44 binders, such as A6;

protein phosphatease 2A (PP2A) inhibitors, such as LB-100;

CYP17 inhibitors, such as seviteronel (VT-464), ASN-001, ODM-204, CFG920, abiraterone acetate;

RXR agonists, such as IRX4204;

hedgehog/smoothened (hh/Smo) antagonists, such as taladegib, patidegib;

complement $C_3$ modulators, such as Imprime PGG;

IL-15 agonists, such as ALT-803, NKTR-255, and hetIL-15;

EZH2 (enhancer of zeste homolog 2) inhibitors, such as tazemetostat, CPI-1205, GSK-2816126;

Oncolytic viruses, such as pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301;

DOT1L (histone methyltransferase) inhibitors, such as pinometostat (EPZ-5676);

toxins such as Cholera toxin, ricin, *Pseudomonas* exotoxin, *Bordetella pertussis* adenylate cyclase toxin, diphtheria toxin, and caspase activators;

DNA plasmids, such as BC-819

PLK inhibitors of PLK 1, 2, and 3, such as volasertib (PLK1);

WEE1 inhibitors, such as AZD1775 (adavosertib);

Rho kinase (ROCK) inhibitors, such as AT13148, KD025;

ERK inhibitors, such as GDC-0994, LY3214996, MK-8353;

IAP inhibitors, such as ASTX660, debio-1143, birinapant, APG-1387, LCL-161;

RNA polymerase inhibitors, such has lurbinectedin (PM-1183), CX-5461;

Tubulin inhibitors, such as PM-184, BAL-101553 (lisavanbulin), and OXI-4503, fluorapacin (AC-0001), plinabulin;

Toll-like receptor 4 (TL4) agonists, such as G100, GSK1795091, and PEPA-10;

Elongation factor 1 alpha 2 inhibitors, such as plitidepsin;

CD95 inhibitors, such as APG-101, APO-010, asunercept;

WT1 inhibitors, such as DSP-7888;

splicing factor 3B subunitl (SF3B1) inhibitors, such as H3B-8800

PDGFR alpha/KIT mutant-specific inhibitors such as BLU-285;

SHP-2 inhibitors, such as TNO155 (SHP-099), RMC-4550; and retinoid Z receptor gamma (RORy) agonists, such as LYC-55716.

In some embodiments, provided herein are methods of treating or preventing a hyperproliferative disorder or cancer in a human or animal having or at risk of having the hyperproliferative disorder or cancer is provided, comprising administering to the human or animal a therapeutically effective amount of a compound of Formula (J), (I), (Ia), (IIa), (IIIa), (IIIb), (IIIc), (IVa), (IVb), and/or (IVc) as disclosed herein, or a pharmaceutically acceptable salt thereof, in combination with a therapeutically effective amount of one or more (e.g., one, two, three, one or two, or one to three) additional therapeutic agents selected from the group consisting of apoptosis signal-regulating kinase (ASK) inhibitors; Bruton's tyrosine kinase (BTK) inhibitors; cluster of differentiation 47 (CD47) inhibitors; cyclin-dependent kinase (CDK) inhibitors; discoidin domain receptor (DDR) inhibitors; histone deacetylase (HDAC) inhibitors; indoleamine-pyrrole-2,3-dioxygenase (IDO1) inhibitors; Janus kinase (JAK) inhibitors; lysyl oxidase-like protein (LOXL) inhibitors; matrix metalloprotease (MMP) inhibitors; mitogen-activated protein kinase (MEK) inhibitors; phosphatidylinositol 3-kinase (PI3K) inhibitors; spleen tyrosine kinase (SYK) inhibitors; toll-like receptor 8 (TLR8) inhibitors; toll-like receptor 9 (TLR9) inhibitors; tyrosine-kinase inhibitors (TKIs), and any combination thereof, or a pharmaceutically acceptable salt thereof. Non-limiting examples include:

Apoptosis Signal-Regulating Kinase (ASK) Inhibitors: ASK inhibitors include ASK1 inhibitors. Examples of ASK1 inhibitors include, but are not limited to, those described in WO 2011/008709 (Gilead Sciences) and WO 2013/112741 (Gilead Sciences);

Bruton's Tyrosine Kinase (BTK) Inhibitors: Examples of BTK inhibitors include, but are not limited to, (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib, M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315;

Cluster of Differentiation 47 (CD47) inhibitors: Examples of CD47 inhibitors include, but are not limited to anti-CD47 mAbs (Vx-1004), anti-human CD47 mAbs (CNTO-7108), CC-90002, CC-90002-ST-001, humanized anti-CD47 antibody (Hu5F9-G4), NI-1701, NI-1801, RCT-1938, and TTI-621;

Cyclin-dependent Kinase (CDK) Inhibitors: CDK inhibitors include inhibitors of CDK 1, 2, 3, 4, 6, 7 and 9, such as abemaciclib, alvocidib (HMR-1275,flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02;

Discoidin Domain Receptor (DDR) Inhibitors: DDR inhibitors include inhibitors of DDR1 and/or DDR2. Examples of DDR inhibitors include, but are not limited to, those disclosed in WO 2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO 2013/034933 (Imperial Innovations);

Histone Deacetylase (HDAC) Inhibitors: Examples of HDAC inhibitors include, but are not limited to, abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, entinostat;

Indoleamine-pyrrole-2,3-dioxygenase (IDO1) inhibitors: Examples of IDO1 inhibitors include, but are not limited to, BLV-0801, epacadostat, F-001287, GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916;

Janus Kinase (JAK) Inhibitors: JAK inhibitors inhibit JAK1, JAK2, and/or JAK3. Examples of JAK inhibitors include, but are not limited to, AT9283, AZD1480, baricitinib, BMS-911543, fedratinib, filgotinib (GLPG0634), gandotinib (LY2784544), INCB039110

(itacitinib), lestaurtinib, momelotinib (CYT0387), NS-018, pacritinib (SB1518), peficitinib (ASP015K), ruxolitinib, tofacitinib (formerly tasocitinib), INCB052793, and XL019;

Lysyl Oxidase-Like Protein (LOXL) Inhibitors: LOXL inhibitors include inhibitors of LOXL1, LOXL2, LOXL3, LOXL4, and/or LOXL5. Examples of LOXL inhibitors include, but are not limited to, the antibodies described in WO 2009/017833 (Arresto Biosciences). Examples of LOXL2 inhibitors include, but are not limited to, the antibodies described in WO 2009/017833 (Arresto Biosciences), WO 2009/035791 (Arresto Biosciences), and WO 2011/097513 (Gilead Biologics);

Matrix Metalloprotease (MMP) Inhibitors: MMP inhibitors include inhibitors of MMP1 through 10. Examples of MMP9 inhibitors include, but are not limited to, marimastat (BB-2516), cipemastat (Ro 32-3555), GS-5745 (andecaliximab) and those described in WO 2012/027721 (Gilead Biologics);

Mitogen-activated Protein Kinase (MEK) Inhibitors: MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LTT462, AS703988, CC-90003, refametinib;

Phosphatidylinositol 3-kinase (PI3K) Inhibitors: PI3K inhibitors include inhibitors of PI3Kγ, PI3K6, PI3K (3, PI3Ka, and/or pan-PI3K. Examples of PI3K inhibitors include, but are not limited to, ACP-319, AEZA-129, AMG-319, AS252424, AZD8186, BAY 10824391, BEZ235, buparlisib (BKM120), BYL719 (alpelisib), CH5132799, copanlisib (BAY 80-6946), duvelisib, GDC-0032, GDC-0077, GDC-0941, GDC-0980, GSK2636771, GSK2269557, idelalisib (Zydelig®), INCB50465, IPI-145, IPI-443, IPI-549, KAR4141, LY294002, LY3023414, MLN1117, OXY111A, PA799, PX-866, RG7604, rigosertib, RP5090, RP6530, SRX3177, taselisib, TG100115, TGR-1202 (umbralisib), TGX221, WX-037, X-339, X-414, XL147 (SAR245408), XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences);

Spleen Tyrosine Kinase (SYK) Inhibitors: Examples of SYK inhibitors include, but are not limited to, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), and those described in U.S. Pat. No. 8,450,321 (Gilead Conn.) and those described in U.S. 2015/0175616;

Toll-like receptor 8 (TLR8) inhibitors: Examples of TLR8 inhibitors include, but are not limited to, E-6887, IMO-4200, IMO-8400, IMO-9200, MCT-465, MEDI-9197, motolimod, resiquimod, VTX-1463, and VTX-763;

Toll-like receptor 9 (TLR9) inhibitors: Examples of TLR9 inhibitors include, but are not limited to, AST-008, IMO-2055, IMO-2125, lefitolimod, litenimod, MGN-1601, and PUL-042; and Tyrosine-kinase Inhibitors (TKIs): TKIs may target epidermal growth factor receptors (EGFRs) and receptors for fibroblast growth factor (FGF), platelet-derived growth factor (PDGF), and vascular endothelial growth factor (VEGF). Examples of TKIs include, but are not limited to, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, tivoanib, and TH-4000, MEDI-575 (anti-PDGFR antibody).

As used herein, the term "chemotherapeutic agent" or "chemotherapeutic" (or "chemotherapy" in the case of treatment with a chemotherapeutic agent) is meant to encompass any non-proteinaceous (i.e., non-peptidic) chemical compound useful in the treatment of cancer. Examples of chemotherapeutic agents include but are not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, especially bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlomaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammall and calicheamicin phil1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carrninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-tricUorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylomithine (DFMO); retinoids such as retinoic acid; capecitabine; NUC-1031; FOLFIRI (fluorouracil, leucovorin, and irinotecan); and pharmaceutically acceptable salts, acids, or derivatives of any of the above.

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Anti-Hormonal Agents

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

Examples of progesterone receptor antagonist include onapristone.

Anti-Angiogenic Agents

Anti-angiogenic agents include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inbibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cis-hydroxyproline, d,I-3,4-dehydroproline, thiaproline, α,α'-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy amino-imidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

Anti-fibrotic agents include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Immunotherapeutic Agents

The immunotherapeutic agents include and are not limited to therapeutic antibodies suitable for treating subjects. Some examples of therapeutic antibodies include abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, namatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, and 3F8. Rituximab can be used for treating indolent B-cell cancers, including marginal-zone lymphoma, WM, CLL and small lymphocytic lymphoma. A combination of Rituximab and chemotherapy agents is especially effective.

The exemplified therapeutic antibodies may be further labeled or combined with a radioisotope particle such as indium-111, yttrium-90 (90Y-clivatuzumab), or iodine-131.

Cancer Gene Therapy and Cell Therapy

Cancer Gene Therapy and Cell Therapy includes the insertion of a normal gene into cancer cells to replace a mutated or altered gene; genetic modification to silence a mutated gene; genetic approaches to directly kill the cancer cells; including the infusion of immune cells designed to replace most of the subject's own immune system to enhance the immune response to cancer cells, or activate the subject's own immune system (T cells or Natural Killer cells) to kill cancer cells, or find and kill the cancer cells; genetic approaches to modify cellular activity to further alter endogenous immune responsiveness against cancer.

Gene Editors

Examples of genome editing system include a CRISPR/Cas9 system, a zinc finger nuclease system, a TALEN system, a homing endonucleases system, and a meganuclease system.

CAR-T Cell Therapy and TCR-T Cell Therapy

CAR-T cell therapy includes a population of immune effector cells engineered to express a chimeric antigen receptor (CAR), wherein the CAR comprises a tumor antigen-binding domain. The immune effector cell is a T cell or an NK cell. TCR-T cell therapy includes TCR-T cells that are engineered to target tumor derived peptides present on the surface of tumor cells. Cells can be autologous or allogeneic.

In some embodiments, the CAR comprises an antigen binding domain, a transmembrane domain, and an intracellular signalling domain.

In some embodiments, the intracellular domain comprises a primary signaling domain, a costimulatory domain, or both of a primary signaling domain and a costimulatory domain.

In some embodiments, the primary signaling domain comprises a functional signaling domain of one or more proteins selected from the group consisting of CD3 zeta, CD3 gamma,CD3 delta, CD3 epsilon, common FcR gamma (FCERIG), FcR beta (Fc Epsilon Rlb), CD79a,CD79b, Fcgamma RIIa, DAP10, and DAP12.

In some embodiments, the costimulatory domain comprises a functional domain of one or more proteins selected from the group consisting of CD27, CD28, 4-1BB (CD137), OX40, CD30, CD40, PD-1, ICOS, lymphocyte function-associated antigen-1 (LFA-I), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRFI), CD160, CD19, CD4, CD8alpha, CD8beta, IL2R beta, IL2R gamma, IL7R alpha, ITGA4, VLAl, CD49a, ITGA4, IA4, CD49D, ITGA6, VLA-6, CD49f, ITGAD, CD 1 ld, ITGAE, CD103, ITGAL, CD 1 la, LFA-1, ITGAM, CD1 lb, ITGAX, CD1 lc, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R u, ITGA1, VLAl, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and NKG2C.

In some embodiments, the antigen binding domain binds a tumor antigen.

In some embodiments, the tumor antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (aNeuSAc(2-8)aNeuSAc(2-3)bD-Gaip(1-4)bDGIcp(1-1)Cer); TNF receptor family member B cell maturation (BCMA); Tn antigen ((Tn Ag) or (GalNAcu-Ser/Thr)); prostate-specific membrane antigen (PSMA); Receptor tyrosine kinase-like orphan receptor 1 (RORI); Fms-Like, Tyrosine Kinase 3 (FLT3); Tumor-associated glycoprotein 72 (TAG72); CD38; CD44v6; Carcinoembryonic antigen (CEA); Epithelial cell adhesion molecule (EP-CAM); B7H3 (CD276); KIT (CD117); Interleukin-13 receptor subunit alpha-2 (IL-13R$_a$2 or CD213A2); Mesothelin; Interleukin 11 receptor alpha (IL-11R$_a$); prostate stem cell antigen (PSCA); Protease Serine 21 (Testisin or PRSS21); vascular endothelial growth factor receptor 2 (VEGFR2); Lewis(Y)antigen; CD24; Platelet-derived growth factor receptor beta (PDGFR-beta); Stage-specificembryonic antigen-4 (SSEA-4); CD20; delta like 3 (DLL3); Folate receptor alpha; Receptor tyrosine-protein kinase, ERBB2 (Her2/neu); Mucin 1, cell surface associated (MUC1); epidermal growth factor receptor (EGFR); neural cell adhesion molecule (NCAM); Prostase; prostatic acid phosphatase (PAP);

elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murineleukemia viral oncogene homolog 1 (Abl) (bcr-abl); tyrosinase; ephrin type-A receptor 2 (EphA2); Fucosyl GM1; sialyl Lewis adhesion molecule (sLe); ganglioside GM3 (aNeuSAc(2-3)bDGalp(1-4)bDGlcp(1-1)Cer); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanomaassociated antigen 1 (MAGE-A1); ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1 (CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like modulecontaining mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

In some embodiments, the tumor antigen is selected from CD150, 5T4, ActRIIA, B7, BMCA, CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, GD2, GD3, HER1-HER2 in combination, HER2-HER3 in combination, HERV-K, HIV-1 envelope glycoprotein gp120, HIV-1 envelope glycoprotein gp41, HLA-DR, HM1.24, HMW-MAA, Her2, Her2/neu, IGF-1R, IL-11Ralpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-i, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-RI (DR4), TRAIL-R$^2$ (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acethycholine e receptor, folate binding protein, gp100, hepatitis B surface antigen, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

Non limiting examples of cell therapies include Algenpantucel-L, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, CryoStim, AlloStim, lentiviral transduced huCART-meso cells, CART-22 cells, EGFRt/19-28z/4-1BBL CAR T cells, autologous 4H11-28z/fIL-12/EGFRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502,CMD-601, CMD-602, CSG-005.

In some embodiments, the tumor targeting antigen includes: Alpha-fetoprotein, such as ET-1402, and AFP-TCR; Anthrax toxin receptor 1, such as anti-TEM8 CAR T-cell therapy; B cell maturation antigens (BCMA), such as bb-2121, UCART-BCMA, ET-140, KITE-585, MCM-998, LCAR-B38M, CART-BCMA, SEA-BCMA, BB212, UCART-BCMA, ET-140, P-BCMA-101, AUTO-2 (APRIL-CAR); Anti-CLL-1 antibodies, such as KITE-796; B7 homolog 6, such as CAR-NKp30 and CAR-B7H6; B-lymphocyte antigen CD19, such as TBI-1501, CTL-119 huCART-19 T cells, JCAR-015 U.S. Pat. No. 7,446,190, JCAR-014, JCAR-017, (WO2016196388, WO2016033570, WO2015157386), axicabtagene ciloleucel (KTE-C$_{19}$), U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T; B-lymphocyte antigen CD20, such as ATTCK-20; B-lymphocyte cell adhesion, such as UCART-22, JCAR-018 WO2016090190; NY-ESO-1, such as GSK-3377794, TBI-1301; Carbonic anhydrase, such as DC-Ad-GMCAIX; Caspase 9 suicide gene, such as CaspaCIDe DLI, BPX-501; CCR5, such as SB-728; CDw123, such as MB-102, UCART-123; CD20m such as CBM-C20.1; CD4, such as ICG-122; CD30, such as CART30 (CBM-C30.1; CD33, such as CIK-CAR.CD33; CD38, such as T-007, UCART-38; CD40 ligand, such as BPX-201; CEACAM protein 4 modulators, such as MG7-CART; Claudin 6, such as CSG-002; EBV targeted, such as CMD-003; EGFR, such as autologous 4H11-28z/flL-12/EFGRt T cell; Endonuclease, such as PGN-514, PGN-201; Epstein-Barr virus specific T-lymphocytes, such as TT-10; Erbb2, such as CST-102, CIDeCAR; Ganglioside (GD2), such as 4SCAR-GD2; Glutamate carboxypeptidase II, such as CIK-CAR.PSMA, CART-PSMA-TGFBRDN, P-PSMA-101; Glypican-3 (GPC3), such as TT-16, GLYCAR; Hemoglobin, such as PGN-236; Hepatocyte growth factor receptor, such as anti-cMet RNA CAR T; Human papillomavirus E7 protein, such as KITE-439; Immunoglobulin gamma Fc receptor III, such as ACTR087; IL-12, such as DC-RTS-IL-12; IL-12 agonist/mucin 16, such as JCAR-020; IL-13 alpha 2, such as MB-101; IL-2, such as CST-101; K-Ras GTPase, such as anti-KRAS G12V mTCR cell therapy; Neural cell adhesion molecule L1 L1CAM (CD171), such as JCAR-023; Latent membrane protein 1/Latent membrane protein 2, such as Ad5f35-LMPdl-2-transduced autologous dendritic cells; Melanoma associated antigen 10, such as MAGE-A10$C_{796}$T MAGE-A10 TCR; Melanoma associated antigen 3/Melanoma associated antigen 6 (MAGE A3/A6) such as KITE-718; Mesothelin, such as CSG-MESO, TC-210; NKG2D, such as NKR-2; Ntrkrl tyrosine kinase receptor, such as JCAR-024; T cell receptors, such as BPX-701, IMCgp100; T-lymphocyte, such as TT-12; Tumor infiltrating lymphocytes, such as LN-144, LN-145; and Wilms tumor protein, such as JTCR-016, WT1-CTL.

Lymphoma or Leukemia Combination Therapy

In some embodiments, the additional therapeutic agents are suitable for treating lymphoma or leukemia. These agents include aldesleukin, alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541, bortezomib (VELCADE®), bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17-AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R-MCP (rituximab and MCP), R-roscovitine (seliciclib, CYC202), sargramostim, sildenafil citrate, simvastatin, sirolimus, styryl sulphones, tacrolimus, tanespimycin, temsirolimus (CC1-779), thalidomide, therapeutic allogeneic lymphocytes, thiotepa, tipifamib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The abovementioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

In some embodiments, the additional therapeutic agents are suitable for treating non-Hodgkin's lymphomas (NHL), especially those of B cell origin, which include monoclonal antibodies, standard chemotherapy approaches (e.g., CHOP, CVP, FCM, MCP, and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP, R-FCM, R-CVP, and R-MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

In some embodiments, the additional therapeutic agents are suitable for treating mantle cell lymphoma (MCL), which include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

Other examples of therapeutic agents suitable for treating MCL include:
- immunotherapy, such as monoclonal antibodies (like rituximab) and cancer vaccines, such as GTOP-99, which are based on the genetic makeup of an individual subject's tumor;
- radioimmunotherapy, wherein a monoclonal antibody is combined with a radioisotope particle, such as iodine-131 tositumomab (BEXXAR®), yttrium-90 ibritumomab tiuxetan (ZEVALIN®), and BEXXAR® in sequential treatment with CHOP;
- autologous stem cell transplantation coupled with high-dose chemotherapy, administering proteasome inhibitors such as bortezomib (VELCADE® or PS-341), or administering antiangiogenesis agents such as thalidomide, especially in combination with rituximab;
- drugs that lead to the degradation of Bcl-2 protein and increase cancer cell sensitivity to chemotherapy, such as oblimersen, in combination with other chemotherapeutic agents;
- mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents;
- other agents such as flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CC1-779), everolimus (RAD001), BMS-345541, curcumin, SAHA, thalidomide, lenalidomide (REVLIMID®, CC-5013), and geldanamycin (17-AAG).

Waldenstrom's Macroglobulinemia Combination Therapy

In some embodiments, the additional therapeutic agents are suitable for treating Waldenstrom's Macroglobulinemia (WM), which include aldesleukin, alemtuzumab, alvocidib, amifostine trihydrate, aminocamptothecin, antineoplaston A10, antineoplaston AS2-1, anti-thymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Other examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

In some embodiments, the additional therapeutic agents are suitable for treating diffuse large B-cell lymphoma (DLBCL), which include cyclophosphamide, doxorubicin, vincristine, prednisone, anti-CD20 monoclonal antibodies, etoposide, bleomycin, many of the agents listed for WM, and any combination thereof, such as ICE and R-ICE.

Chronic Lymphocytic Leukemia Combination Therapy

In some embodiments, the additional therapeutic agents are suitable for treating chronic lymphocytic leukemia (CLL), which include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

In some embodiments, the additional therapeutic agents are suitable for treating myelofibrosis, which include hedgehog inhibitors, histone deacetylase (HDAC) inhibitors, and tyrosine kinase inhibitors. Non-limiting examples of hedgehog inhibitors are saridegib and vismodegib.

Examples of HDAC inhibitors include, but are not limited to, pracinostat and panobinostat.

Non-limiting examples of tyrosine kinase inhibitors are lestaurtinib, bosutinib, imatinib, gilteritinib, radotinib, and cabozantinib.

Hyperproliferative Disease Combination Therapy

In some embodiments, the additional therapeutic agents are suitable for treating a hyperproliferative disease, which include gemcitabine, nab-paclitaxel, and gemcitabine/nab-paclitaxel with a JAK inhibitor and/or PI3Kδ inhibitor.

Bladder Cancer Combination Therapy

In some embodiments, the additional therapeutic agents are suitable for treating bladder cancer, which include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof.

Breast Cancer Combination Therapy

In some embodiments, the additional therapeutic agents are suitable for treating breast cancer, which include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof.

Triple Negative Breast Cancer Combination Therapy

In some embodiments, the additional therapeutic agents are suitable for treating triple negative breast cancer, which include cyclophosphamide, docetaxel, doxorubicin, epirubicin, fluorouracil, paclitaxel, and combinations thereof.

Colorectal Cancer Combination Therapy

In some embodiments, the additional therapeutic agents are suitable for treating colorectal cancer, which include bevacizumab, capecitabine, cetuximab, fluorouracil, irinotecan, leucovorin, oxaliplatin, panitumumab, ziv-aflibercept, and any combinations thereof.

Castration-Resistant Prostate Cancer Combination Therapy

In some embodiments, the additional therapeutic agents are suitable for treating castration-resistant prostate cancer, which include abiraterone, cabazitaxel, docetaxel, enzalutamide, prednisone, sipuleucel-T, and any combinations thereof.

Esophageal and Esophagogastric Junction Cancer Combination Therapy

In some embodiments, the additional therapeutic agents are suitable for treating esophageal and esophagogastric junction cancer, which include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof.

Gastric Cancer Combination Therapy

In some embodiments, the additional therapeutic agents are suitable for treating gastric cancer, which include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head & Neck Cancer Combination Therapy

In some embodiments, the additional therapeutic agents are suitable for treating head & neck cancer, which include afatinib, bleomycin, capecitabine, carboplatin, cetuximab, cisplatin, docetaxel, fluorouracil, gemcitabine, hydroxyurea, methotrexate, nivolumab, paclitaxel, pembrolizumab, vinorelbine, and any combinations thereof.

Hepatobiliary Cancer Combination Therapy

In some embodiments, the additional therapeutic agents are suitable for treating hepatobiliary cancer, which include capecitabine, cisplatin, fluoropyrimidine, 5-fluorourcil, gemecitabine, oxaliplatin, sorafenib, and any combinations thereof.

Hepatocellular Carcinoma Combination Therapy

In some embodiments, the additional therapeutic agents are suitable for treating hepatocellular carcinoma, which include capecitabine, doxorubicin, gemcitabine, sorafenib, and any combinations thereof.

Non-Small Cell Lung Cancer Combination Therapy

In some embodiments, the additional therapeutic agents are suitable for treating non-small cell lung cancer (NSCLC), which include afatinib, albumin-bound paclitaxel, alectinib, bevacizumab, bevacizumab, cabozantinib, carboplatin, cisplatin, crizotinib, dabrafenib, docetaxel, erlotinib, etoposide, gemcitabine, nivolumab, paclitaxel, pembrolizumab, pemetrexed, ramucirumab, trametinib, trastuzumab, vandetanib, vemurafenib, vinblastine, vinorelbine, and any combinations thereof.

Small Cell Lung Cancer Combination Therapy

In some embodiments, the additional therapeutic agents are suitable for treating small cell lung cancer (SCLC), which include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof.

Melanoma Combination Therapy

In some embodiments, the additional therapeutic agents are suitable for treating melanoma, which include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, pembrolizumab, pilimumab, temozolomide, trametinib, vemurafenib, vinblastine, and any combinations thereof.

Ovarian Cancer Combination Therapy

In some embodiments, the additional therapeutic agents are suitable for treating ovarian cancer, which include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcibabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Pancreatic Cancer Combination Therapy

In some embodiments, the additional therapeutic agents are suitable for treating pancreatic cancer, which include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof.

Renal Cell Carcinoma Combination Therapy

In some embodiments, the additional therapeutic agents are suitable for treating renal cell carcinoma, which include axitinib, bevacizumab, cabozantinib, erlotinib, everolimus, levantinib, nivolumab, pazopanib, sorafenib, sunitinib, temsirolimus, and any combinations thereof.

VIII. Kits

The present disclosure provides a kit comprising a compound of the present disclosure or a pharmaceutically acceptable salt thereof. The kit may further comprise instructions for use, e.g., for use in treating a viral infection. The instructions for use are generally written instructions, although electronic storage media (e.g., magnetic diskette or optical disk) containing instructions are also acceptable.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

IX. Examples

The embodiments are also directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the disclosed compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or diastereomerically pure.

Representative syntheses of compounds of the present disclosure are described in schemes below, and the particular examples that follow.

Example 1. General Synthetic Method

The specific 3'3'-cyclic dinucleotides detailed in the Examples were synthesized according to the general synthetic method described below. Compounds were named using ChemDraw Professional ver. 17.0.0.206 (121) (PerkinElmer Informatics, Inc., Cambridge, Mass. USA) unless otherwise indicated.

The abbreviations used in the Examples shown below include the following:

| | Abbreviations |
|---|---|
| TEAB | triethylammonium bicarbonate |
| CPG | controlled pore glass |
| Bz | benzoyl |
| DBU | 1,8-diazabicyclo[5.4.0]undec-7-en |
| DCM | dichloromethane |
| DMTr | 4,4-dimethoxytrityl |
| DMSO | dimethylsulfoxide |
| EtOH | ethanol |
| iPr | isopropyl |
| LCAA | long chain aminoalkyl |
| ACN | acetonitrile |
| MeOH | methanol |
| MeIm | 1-methylimidazole |
| MOP | 4-methoxy-1-oxide-2-pyridylmethanol |
| CDDO | 2-chloro-5,5-dimethyl-1,3,2-dioxaphosphorinane-2-oxide |
| NMMNO | 4-methylmorpholine-4-oxide |
| TBDMSCl | tert-butyldimethylsilyl chloride |
| TIPSCl | triisopropylbenzenesulfonyl chloride |
| THF | tetrahydrofuran |
| tBuOOH | tert-butyl hydroperoxide |
| FBS | fetal bovine serum |
| HEPES | 4-(2-hydroxyethyl)-1-piperazineethanesulfonic acid |
| BSA | bovine serum albumin |
| ETT | ethylthiotetrazole |

Example 2. Preparation of monomers derived from 4'-phosphonomethoxy nucleosides

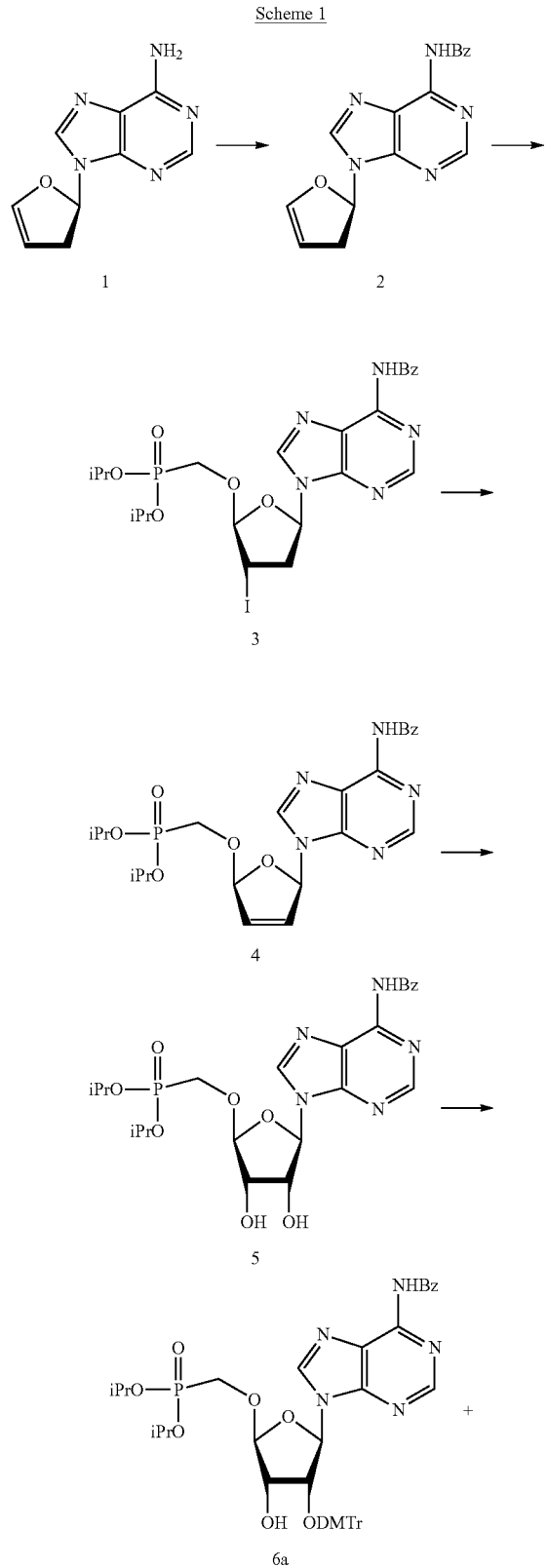

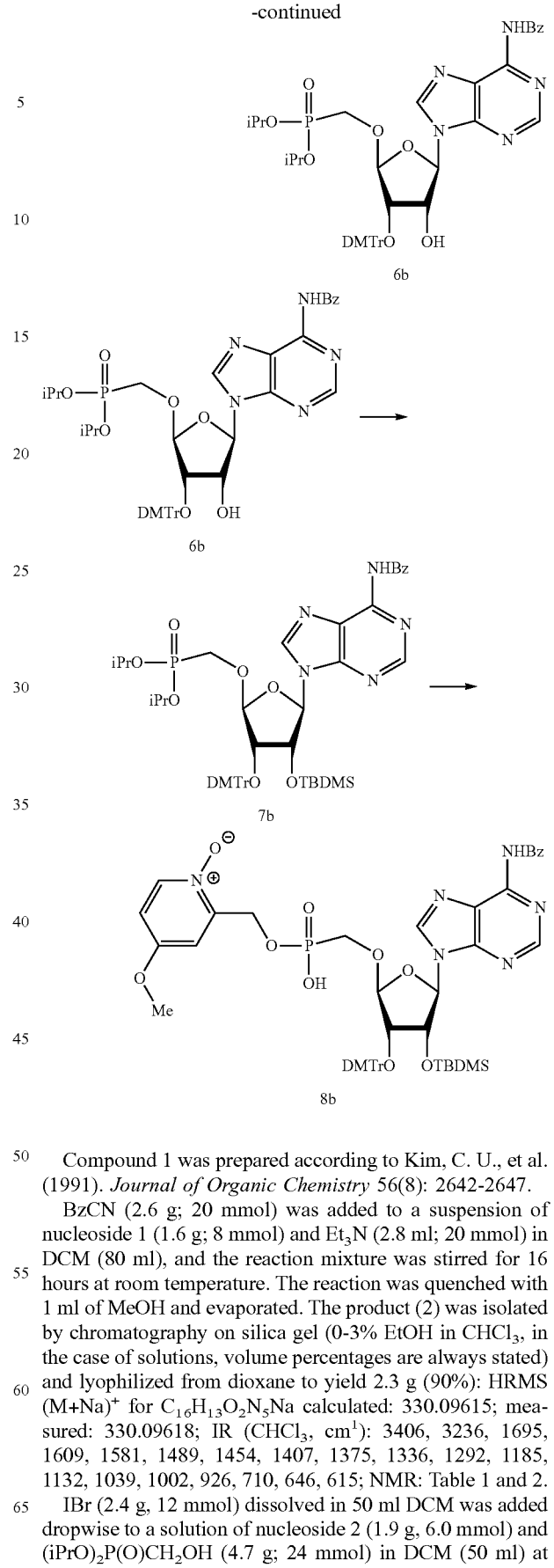

Compound 1 was prepared according to Kim, C. U., et al. (1991). *Journal of Organic Chemistry* 56(8): 2642-2647.

BzCN (2.6 g; 20 mmol) was added to a suspension of nucleoside 1 (1.6 g; 8 mmol) and $Et_3N$ (2.8 ml; 20 mmol) in DCM (80 ml), and the reaction mixture was stirred for 16 hours at room temperature. The reaction was quenched with 1 ml of MeOH and evaporated. The product (2) was isolated by chromatography on silica gel (0-3% EtOH in $CHCl_3$, in the case of solutions, volume percentages are always stated) and lyophilized from dioxane to yield 2.3 g (90%): HRMS $(M+Na)^+$ for $C_{16}H_{13}O_2N_5Na$ calculated: 330.09615; measured: 330.09618; IR ($CHCl_3$, $cm^1$): 3406, 3236, 1695, 1609, 1581, 1489, 1454, 1407, 1375, 1336, 1292, 1185, 1132, 1039, 1002, 926, 710, 646, 615; NMR: Table 1 and 2.

IBr (2.4 g, 12 mmol) dissolved in 50 ml DCM was added dropwise to a solution of nucleoside 2 (1.9 g, 6.0 mmol) and $(iPrO)_2P(O)CH_2OH$ (4.7 g; 24 mmol) in DCM (50 ml) at −25° C. The mixture was stirred for 2 h at −25° C. and quenched with 1.7 ml of Et$_3$N. It was then extracted between chloroform (300 ml) and Na$_2$S$_2$O$_3$ solution (3×50 ml) followed by NaHCO$_3$ (3×50 ml). The organic phase was dried over Na$_2$SO$_4$ and the product (3) was isolated by chromatography on silica gel (0-7% EtOH in CHCl$_3$) and lyophilized from dioxane to yield 2.0 g (53%): HRMS (M+Na)$^+$ for C$_{23}$H$_{29}$O$_6$N$_5$INaP calculated: 652.07923; measured: 652.07941; IR (CHCl$_3$, cm$^{-1}$): 3088, 3066, 2980, 1695, 1608, 1601, 1580, 1512, 1512, 1490, 1452, 1418, 1386, 1375, 1337, 1251, 1236, 1178, 1142, 1098, 1070, 1002, 989, 812, 798, 710, 692, 640, 586, 502; NMR: Table 1 and 2.

A solution of phosphonate 3 (2.0 g, 3.2 mmol) and DBU (0.9 ml, 6 mmol) in THF (30 ml) was heated at 65° C. After 50 minutes, the heterogeneous mixture was concentrated, diluted with chloroform, and extracted between chloroform (100 ml) and 10% citric acid solution (3×50 ml). The organic phase was dried over Na$_2$SO$_4$ and the product (4) was isolated by chromatography on silica gel (0-7% EtOH in CHCl$_3$) and lyophilized from dioxane to yield 1.4 g (90%): HRMS (M+Na)$^+$ for C$_{23}$H$_{28}$O$_6$N$_5$NaP calculated: 524.16694; measured: 524.16696; IR (CHCl$_3$, cm$^{-1}$): 3411, 3224, 3087, 3066, 1694, 1607, 1601, 1579, 1512, 1512, 1491, 1452, 1386, 1376, 1332, 1287, 1251, 1178, 1142, 1103, 1073, 1002, 991, 835, 820, 798, 710, 691; NMR: Table 1 and 2.

NMMNO (1.2 g, 10.5 mmol) and 4% water solution of OsO$_4$ (1 ml) was added to a solution of phosphonate 4 (2.6 g, 5.1 mmol) in acetone (35 ml) and water (15 ml). After 16 hours at room temperature, the reaction was quenched by the addition of Na$_2$S$_2$O$_3$ (0.5 g), the reaction mixture was then concentrated diluted with chloroform (100 ml) and extracted between chloroform (300 ml) and water (3×100 ml). The organic phase was dried over Na$_2$SO$_4$ and the product (5) was isolated by chromatography on silica gel (0-10% MeOH in CHCl$_3$) and lyophilized from dioxane to yield 2.5 g (90%): HRMS (M+Na)$^+$ for C$_{23}$H$_{30}$O$_8$N$_5$NaP calculated: 558.17242; measured: 558.17226; IR (CHCl$_3$, cm$^{-1}$): 3279, 2981, 1702, 1614, 1601, 1583, 1514, 1514, 1488, 1458, 1387, 1376, 1353, 1335, 1296, 1248, 1177, 1140, 1134, 1103, 1007, 995, 995, 848, 798, 709, 691, 640; NMR: Table 1 and 2.

DMTr-Cl (1.9 g, 5.5 mmol) was added to a solution of phosphonate 5 (2.4 g, 4.6 mmol) and DBU (0.9 ml, 6 mmol) in DCM (50 ml), the reaction mixture was stirred for 16 hours at room temperature. The reaction was quenched by the addition of MeOH (1 ml) and the reaction mixture was concentrated, diluted with chloroform (150 ml) and extracted between chloroform (300 ml) and water (3×100 ml). The organic phase was dried over Na$_2$SO$_4$. The product (6) was isolated by chromatography on silica gel (0-50% acetone in toluene). The mixture of regioisomers 6a and 6b was separated by C$_{18}$ reverse phase chromatography and isocratic elution with 75% MeOH/H$_2$O, pure products were lyophilized from dioxane in a yield of 1.8 g (46%) for 6a (faster eluting regioisomer) and 1.0 g (26%) for 6b (slower elution regioisomer): 6a: HRMS (M+Na)$^+$ for C$_{44}$H$_{48}$O$_{10}$N$_5$NaP calculated: 860.30310; measured: 860.30341; IR (CHCl$_3$, cm$^{-1}$): 3300, 3127, 2980, 2935, 2837, 1703, 1609, 1582, 1510, 1491, 1454, 1412, 1406, 1386, 1376, 1335, 1300, 1252, 1177, 1132, 1103, 1074, 1055, 992, 798, 727, 643; NMR: Table 1 and 2. 6b: HRMS (M+Na)$^+$ for C$_{44}$H$_{48}$O$_{10}$N$_5$NaP calculated: 860.30310; measured: 860.30330; IR (CHCl$_3$, cm$^{-1}$): 3287, 3178, 2980, 2931, 2837, 1703, 1609, 1583, 1510, 1473, 1457, 1403, 1386, 1376, 1332, 1299, 1252, 1178, 1156, 1102, 1056, 990, 798; NMR: Table 1 and 2.

TBDMSCl (0.8 g; 5.6 mmol) was added to a solution of phosphonate 6b (0.9 g; 1.1 mmol) and DBU (0.9 ml; 5.6 mmol) in DCM (10 ml) and the mixture was stirred for 16 hours at room temperature. The reaction was quenched by the addition of MeOH (1 ml) and the reaction mixture was extracted between chloroform (300 ml) and water (3×100 ml). The organic phase was dried over Na$_2$SO$_4$. The product (7b) was isolated by chromatography on silica gel (0-50% ethyl acetate in toluene) and lyophilized from dioxane to yield 1.0 g (90%): HRMS (M+Na)$^+$ pro C$_{50}$H$_{62}$O$_{10}$N$_5$NaPS calculated: 974.38958; measured: 974.38991; IR (CHCl$_3$, cm$^{-1}$): 3412, 3178, 2978, 2956, 2932, 2838, 1701, 1608, 1582, 1510, 1491, 1471, 1453, 1453, 1415, 1406, 1386, 1376, 1335, 1300, 1253, 1178, 1155, 1103, 1072, 1027, 990, 934, 837, 782, 726, 677, 649, 584; NMR: Table 1 and 2.

Bromotriethylsilane (0.6 ml; 4.5 mmol) was added to a solution of diisopropyl phosphonate 7b (1.1 g; 1.1 mmol) and 2,6-lutidine (1.0 mL; 9 mmol) in ACN (15 ml). The reaction mixture was stirred for 16 hours at room temperature, concentrated, diluted with chloroform (200 ml), and extracted with 0.2 mol·l$^{-1}$ TEAB (3×30 ml). The organic phase was dried over Na$_2$SO$_4$, concentrated and co-distilled with dioxane and pyridine. For the next step, crude phosphonic acid was used without further purification.

CDDO (0.6 g; 3.4 mmol) was added to a mixture of phosphonic acid, 4-methoxy-1-oxido-2-pyridylmethanol (0.4 g; 2.8 mmol) and 4-methoxy-1-oxido-2-pyridine (0.3 g; 2.6 mmol) in pyridine (15 ml). The reaction was stirred for 16 hours at room temperature, quenched by the addition of 2M TEAB (5 ml) and the reaction mixture was evaporated. The concentrate was diluted with chloroform (200 ml) and extracted with 0.2 M TEAB (3×30 ml). The organic phase was dried over Na$_2$SO$_4$, concentrated and co-distilled with dioxane. For the next step, crude diMOP ester of phosphonic acid was used without further purification.

Et$_3$N (1.4 ml) and benzenethiol (1 ml) were added to a solution of diMOP phosphonate in dioxane (10 ml). The reaction mixture was stirred for 1 hour at room temperature to give the 8b monoester. It was then diluted with ethyl acetate (50 ml) and directly applied to a column of Et$_3$N-buffered silica gel. The product (8b) was isolated by chromatography on silica gel (0-100% of ethyl acetate/ethanol/acetone/water 4:1:1:1 in ethyl acetate) and lyophilized from dioxane to yield 0.8 g (61%): HRMS (M+Na)$^+$ C$_{51}$H$_{57}$O$_{12}$N$_6$NaPSi calculated: 1027.34336; measured: 1027.34374; IR (CHCl$_3$, cm$^{-1}$): 1696, 1608, 1581, 1509, 1506, 1471, 1419, 1333, 1301, 1252, 1221, 1177, 1158, 1035, 1035, 870, 837, 706, 678, 594, 585; NMR: Table 1 and 2.

TABLE 1

$^1$H NMR data in DMSO-d$_6$. Interaction constants are given in brackets J(H, P).

| | H-1' | H-2' | H-2" | H-3' | H-4' | P—CH$_2$—O | H-2 & H-8 |
|---|---|---|---|---|---|---|---|
| 1 $^a$ | 6.74 dd (4.4; 9.6) | 3.10 dddd (4.4; 16.9; 2.6; 2.0) | 3.21 dddd (9.6; 16.9; 2.1; 2.8) | 5.28 ddd (2.6; 2.1; 2.8) | 6.60 td (2.8; 2.8; 2.0) | — | — | 8.17 s  8.18 s |

TABLE 1-continued $^1$H NMR data in DMSO-$d_6$. Interaction constants are given in brackets J(H, P).

| | H-1' | H-2' | H-2" | H-3' | H-4' | P—CH$_2$—O | | H-2 & H-8 | |
|---|---|---|---|---|---|---|---|---|---|
| 2 [b] | 6.91 dd (4.3; 9.5) | 3.19 dddd (4.3; 9.5; 17.0; 2.6) | 3.27 dddd (9.5; 17.0; 2.2; 2.7) | 5.34 ddd (2.6; 2.2; 2.8) | 6.64 td (2.0; 2.7; 2.8) | — | — | 8.78 s | 8.53 s |
| 3 [c] | 6.72 dd (7.0; 6.6) | 3.34 ddd (7.0; 15.2; 6.3) | 2.94 ddd (6.6; 15.2; 2.6) | 4.42 ddd (6.3; 2.6; 1.2) | 5.64 d (1.2) | 3.88 dd (13.8; 8.7) | 3.77 dd (13.8; 9.1) | 8.78 s | 8.54 s |
| 4 [d] | 7.02 ddd (1.8; 1.5; 0.7) | 6.54 ddd (1.8; 5.9; 1.2) | — | 6.64 ddd (1.5; 5.9; 1.1) | 5.99 ddd (0.7; 1.2; 1.1) | 3.84 m (2H) | | 8.79 s | 8.24 s |
| 5 [e] | 6.24 d (6.7) | 4.80 dd (6.7; 4.4) | — | 4.06 d (4.4) | 5.10 s | 3.84 dd (13.8; 9.2) | 3.81 dd (13.8; 8.9) | 8.75 s | 8.53 s |
| 6a [f] | 6.52 d (6.8) | 4.64 dd (6.8; 4.1) | — | 2.91 br dd (4.1; 5.1) | 4.97 s | 3.73 dd (13.6; 9.3) | 3.69 dd (13.6; 8.7) | 8.76 s | 8.21 s |
| 6b [g] | 6.43 d (7.0) | 4.77 td (7.0; 6.9; 4.8) | — | 4.06 d (4.8) | 3.37 s | 3.50 dd (10.0; 13.1) | 3.02 dd (10.0; 13.3) | 8.79 s | 8.49 s |
| 7b [h] | 6.49 d (6.9) | 4.92 dd (6.9; 4.5) | — | 3.90 d (4.5) | 3.73 s | 3.62 dd (13.5; 9.7) | 3.22 dd (13.5; 9.1) | 8.79 s | 8.57 s |
| 8b [i] | 6.41 d (6.8) | 4.89 dd (6.8; 4.5) | — | 3.82 br d (4.5) | 2.78 s | 3.15 dd (11.0; 9.6) | 2.72 dd (11.0; 9.6) | 8.78 s | 9.12 s |

Other signals:

[a] 6-NH$_2$: 7.32 br;

[b] 6-NHBz: 11.23 br (NH), 8.04 m (2x o- ArH), 7.55 (2x m- ArH), 7.65 (p- ArH);

[c] 6-NHBz: 11.24 br (NH), 8.04 m (2x o- ArH), 7.55 (2x m- ArH), 7.65 (p- ArH); —P(=O)(O-iPr)$_2$: 4.59 m (2x O—CH<), 1.24 d, J = 6.2 Hz, 1.23 d, J = 6.2 Hz, 1.22 d, J = 6.2 Hz, 1.20 d, J = 6.2 Hz (4x —CH$_3$);

[d] 6-NHBz: 11.25 br (NH), 8.04 m (2x o- ArH), 7.55 (2x m- ArH), 7.65 (p- ArH); —P(=O)(O-iPr)$_2$: 4.53 m (2x O—CH<), 1.20 d, J = 6.2 Hz, 1.185 d, J = 6.2 Hz, 1.18 d, J = 6.2 Hz, 1.13 d, J = 6.2 Hz (4x —CH$_3$);

[e] 6-NHBz: 11.23 br (NH), 8.05 m (2x o- ArH), 7.55 (2x m- ArH), 7.64 (p- ArH); —P(=O)(O-iPr)$_2$: 4.63 m (2x O—CH<), 1.263 d, J = 6.2 Hz, 1.259 d, J = 6.2 Hz, 1.246 d, J = 6.2 Hz, 1.243 d, J = 6.2 Hz (4x —CH$_3$);

[f] 6-NHBz: 11.32 br (NH), 8.07 m (2x o- ArH), 7.57 (2x m- ArH), 7.66 (p- ArH); 2'-ODMTr: 7.27 m (2x m- ArH), 7.16 m (2x o- ArH), 7.12 m (2x o- ArH a p-ArH), 7.02 m (2x o- ArH), 6.70 m (2x m- ArH), 6.57 m (2x m- ArH), 3.69 s a 3.65 s (2x OCH$_3$); —P(=O)(O-iPr)$_2$: 4.55 m (2x O—CH<), 1.217 d, J = 6.2 Hz, 1.211 d, J = 6.2 Hz, 1.174 d, J = 6.2 Hz, 1.160 d, J = 6.2 Hz (4x —CH$_3$);

[g] 6-NHBz: 11.29 br (NH), 8.05 m (2x o- ArH), 7.55 (2x m- ArH), 7.65 (p- ArH); 2'—OH: 6.21 br d, J = 6.9 Hz; 3'-ODMTr: 7.62 m (2x o- ArH), 7.49 m (2x o- ArH), 7.43 m (2x m- ArH), 7.36 m (2x m- ArH), 7.28 m (p-ArH), 6.94 m (2x m- ArH), 6.93 m (2x m- ArH), 3.756 s a 3.752 s (2x OCH$_3$); —P(=O)(O-iPr)$_2$: 4.54 m (2x O—CH<), 1.216 d, J = 6.2 Hz, 1.206 d, J = 6.2 Hz, 1.172 d, J = 6.2 Hz. 1.168 d, J = 6.2 Hz (4x —CH$_3$);

[h] 6-NHBz: 11.29 br (NH), 8.04 m (2x o- ArH), 7.55 (2x m- ArH), 7.64 (p- ArH); 2'-OTBDMS: 0.77 s (t-Bu), −0.08 s (—CH$_3$), −0.57 (—CH$_3$); 3'-ODMTr: 7.57 m (2x o- ArH), 7.41 m (2x o- ArH), 7.39 m (2x o- ArH), 7.35 m (2x m- ArH), 7.28 m (p-ArH), 6.93 m (2x m- ArH), 6.91 m (2x m- ArH), 3.75 s (2x OCH$_3$); —P(=O)(O-iPr)$_2$: 4.56 m (2x O—CH<), 1.222 d, J = 6.2 Hz. 1.212 d, J = 6.2 Hz, 1.179 d, J = 6.2 Hz, 1.165 d, J = 6.2 Hz (4x —CH$_3$);

[i] 6-NHBz: 11.27 br (NH), 8.05 m (2x o- ArH), 7.54 (2x m- ArH), 7.64 (p- ArH); 2'-OTBDMS: 0.81 s (t-Bu), 0.07 s (—CH$_3$), −0.76 s (—CH$_3$); 3'-ODMTr: 7.52 m (2x o- ArH), 7.33 m (2x m- ArH), 7.31 m (4x o- ArH), 7.28 m (p-ArH), 6.88 m (4x m- ArH), 3.752 s a 3.743 s (2x OCH$_3$); —P(=O)-Pic: 4.94 dd, J = 17.8, 8.0 Hz a 4.72 dd, J = 17.8, 7.5 Hz (P—OCH$_2$), 8.01 d, J = 7.1 Hz (o- ArH), 6.75 dd, J = 7.1 a 3.5 Hz (m- ArH), 7.06 br d, J = 3.5 Hz (m- ArH), 3.63 s (OCH$_3$);

TABLE 2

$^{13}$C NMR data in DMSO-$d_6$. Interaction constants are given in brackets J(H, P).

| | C-1' | C-2' | C-3' | C-4' | P—CH$_2$—O | C-2 | C-4 | C-5 | C-6 | C-8 |
|---|---|---|---|---|---|---|---|---|---|---|
| 1 | 83.24 | 34.42 | 100.30 | 144.35 | — | 153.10 | 149.22 | 118.86 | 156.26 | 138.60 |
| 2 [a] | 83.64 | 34.36 | 100.53 | 144.39 | — | 152.15 | 152.02 | 125.70 | 150.62 | 142.48 |
| 3 [b] | 83.84 | 40.44 | 22.19 | 111.45 (12.1) | 61.33 (166.2) | 152.02 | 152.34 | 125.56 | 150.64 | 142.60 |
| 4 [c] | 85.95 | 132.07 | 130.58 | 108.77 (13.6) | 61.84 (166.7) | 152.09 | 152.03 | 125.58 | 150.77 | 142.17 |
| 5 [d] | 86.92 | 74.48 | 73.92 | 108.35 (11.8) | 61.31 (167.1) | 152.14 | 152.80 | 125.69 | 151.19 | 142.36 |
| 6a [e] | 85.73 | 77.39 | 72.67 | 108.43 (12.1) | 61.03 (167.3) | 152.09 | 152.62 | 125.56 | 150.81 | 142.33 |
| 6b [f] | 87.24 | 73.48 | 76.51 | 106.85 (14.8) | 62.25 (168.5) | 152.16 | 152.89 | 125.72 | 150.78 | 142.31 |
| 7b [g] | 87.47 | 75.31 | 76.72 | 105.91 (13.3) | 62.02 (167.6) | 152.26 | 152.70 | 125.60 | 150.95 | 142.42 |

TABLE 2-continued

<sup>13</sup>C NMR data in DMSO-d$_6$. Interaction constants are given in brackets J(H, P).

| | C-1' | C-2' | C-3' | C-4' | P—CH$_2$—O | C-2 | C-4 | C-5 | C-6 | C-8 |
|---|---|---|---|---|---|---|---|---|---|---|
| 8b [h] | 86.77 | 76.85 | 76.62 | 106.08 (13.2) | 64.38 (157.5) | 152.13 | 153.05 | 125.09 | 150.54 | 143.64 |

Other signals:

[a] 6-NHBz: 165.81 (C=O), 133.49 (i- ArC), 128.68 (2x o- a 2x m- ArC), 132.68 (p- ArC);

[b] 6-NHBz: 165.84 (C=O), 133.55 (i- ArC), 128.66 (2x o- ArC), 128.64 (2x m- ArC), 132.62 (p- ArC); —P(=O)(O-iPr)$_2$: 70.75 d, J = 6.3 Hz (O—CH<), 70.74 d, J = 6.3 Hz (O—CH<), 23.83 d, J = 3.5 Hz (—CH$_3$), 23.86 d, J = 3.5 Hz (—CH$_3$), 23.92 d, J = 3.8 Hz (—CH$_3$), 23.97 d, J = 3.7 Hz (—CH$_3$);

[c] 6-NHBz: 165.89 (C=O), 133.61 (i- ArC), 128.66 (2x o- ArC), 128.63 (2x m- ArC), 132.59 (p- ArC); —P(=O)(O-iPr)$_2$: 70.57 d, J = 6.2 Hz (O—CH<), 70.54 d, J = 6.3 Hz (O—CH<), 23.90 d, J = 4.5 Hz (—CH$_3$), 23.87 d, J = 4.5 Hz (—CH$_3$), 23.79 d, J = 4.6 Hz (—CH$_3$), 23.71 d, J = 4.4 Hz (—CH$_3$);

[d] 6-NHBz: 166.07 (C=O), 133.89 (i- ArC), 128.71 (2x o- ArC), 128.63 (2x m- ArC), 132.53 (p- ArC); —P(=O)(O-iPr)$_2$: 70.77 d, J = 6.2 Hz (O—CH<), 70.72 d, J = 6.2 Hz (O—CH<), 24.02 d, J = 3.6 Hz (—CH$_3$), 23.99 d, J = 3.7 Hz (—CH$_3$), 23.91 d, J = 4.5 Hz (—CH$_3$), 23.89 d, J = 4.5 Hz (—CH$_3$);

[e] 6-NHBz: 165.91 (C=O), 133.66 (i- ArC), 128.75 (2x o- ArC a 2x m- ArC), 132.73 (p- ArC); 2'-ODMTr: 158.46 (p- ArC), 158.28 (p- ArC), 145.16 (i- ArC), 135.40 (i- ArC), 135.21 (i- ArC), 130.14 (2x o- ArC), 129.59 (2x o- ArC), 127.85 (2x o- ArC), 127.62 (2x m- ArC), 127.00 (p- ArC), 113.20 (2x m- ArC), 113.10 (2x m- ArC), 86.85 (>C<), 55.20 a 55.13 (2x OCH$_3$), —P(=O)(O-iPr)$_2$: 70.82 d, J = 6.3 Hz (O—CH<), 70.78 d, J = 6.3 Hz (O—CH<), 24.00 d, J = 3.8 Hz (—CH$_3$), 23.97 d, J = 3.8 Hz (—CH$_3$), 23.88 d, J = 4.0 Hz (—CH$_3$), 23.85 d, J = 4.0 Hz (—CH$_3$);

[f] 6-NHBz: 165.97 (C=O), 133.57 (i- ArC), 128.75 (2x o- ArC), 128.73(2x m- ArC), 132.73 (p- ArC); 2'-ODMTr: 158.67 (p- ArC), 158.63 (p- ArC), 145.25 (i- ArC), 136.13 (i- ArC), 135.76 (i- ArC), 130.32 (2x o- ArC), 130.24 (2x o- ArC), 128.23 (2x m- ArC), 128.14 (2x o- ArC), 127.23 (p- ArC), 113.66 (2x m- ArC), 113.64 (2x m- ArC), 87.01 (>C<), 55.33 a 55.32 (2x OCH$_3$), —P(=O)(O-iPr)$_2$: 70.84 d, J = 6.4 Hz (O—CH<), 70.79 d, J = 6.4 Hz (O—CH<), 23.96 d, J = 3.8 Hz (2x —CH$_3$), 23.87 d, J = 4.7 Hz (—CH$_3$), 23.82 d, J = 4.4 Hz (—CH$_3$);

[g] 6-NHBz: 165.95 (C=O), 133.59 (i- ArC), 128.78 (2x o- ArC), 128.74 (2x m- ArC), 132.75 (p- ArC); 2'-OTBDMS: 26.68 a 17.82 (t-Bu), −4.70 (—CH$_3$), −5.62 (—CH$_3$); 3'-ODMTr: 158.78 (p- ArC), 158.71 (p- ArC), 145.41 (i- ArC), 136.29 (i- ArC), 135.60 (i- ArC), 128.26 (2x m-ArC), 127.96 (2x o-ArC), 127.37 (p- ArC), 113.68 (4x m- ArC), 86.85 (>C<), 55.37 a 55.36 (2x OCH$_3$), —P(=O)(O-iPr)$_2$: 70.90 d, J = 6.3 Hz (O—CH<), 70.82 d, J = 6.3 Hz (O—CH<), 23.97 d, J = 3.6 Hz (2x —CH$_3$), 23.84 d, J = 4.6 Hz (—CH$_3$), 23.82 d, J = 4.2 Hz (—CH$_3$);

[h] 6-NHBz: 165.84 (C=O), 133.56 (i- ArC), 128.74 (2x o- ArC a 2x m- ArC), 132.73 (p- ArC); 2'-OTBDMS: 25.74 a 17.73 (t-Bu), −4.66 (—CH$_3$), −5.98 (—CH$_3$); 3'-ODMTr: 158.85 (p- ArC), 158.70 (p- ArC), 145.22 (i- ArC), 136.59 (i- ArC), 135.60 (i- ArC), 130.36 (2x o- ArC), 129.79 (2x o- ArC), 128.29 (2x m- ArC), 127.91 (2x o- ArC), 127.31 (p- ArC), 113.58 (2x m- ArC), 113.36 (2x m- ArC), 86.60 (>C<), 55.44 a 55.41 (2x OCH$_3$), —P(=O)-Pic): 61.20 d, J = 3 Hz (P—OCH$_2$), 156.70 (p- ArC), 151.12 (o- ArC), 139.36 (o- ArC), 109.70 (m- ArC), 109.03 (m- ArC), 56.18 (OCH$_3$).

Alternatively, 4'-phosphonomethoxy nucleosides were obtained according to the method shown in Scheme 2.

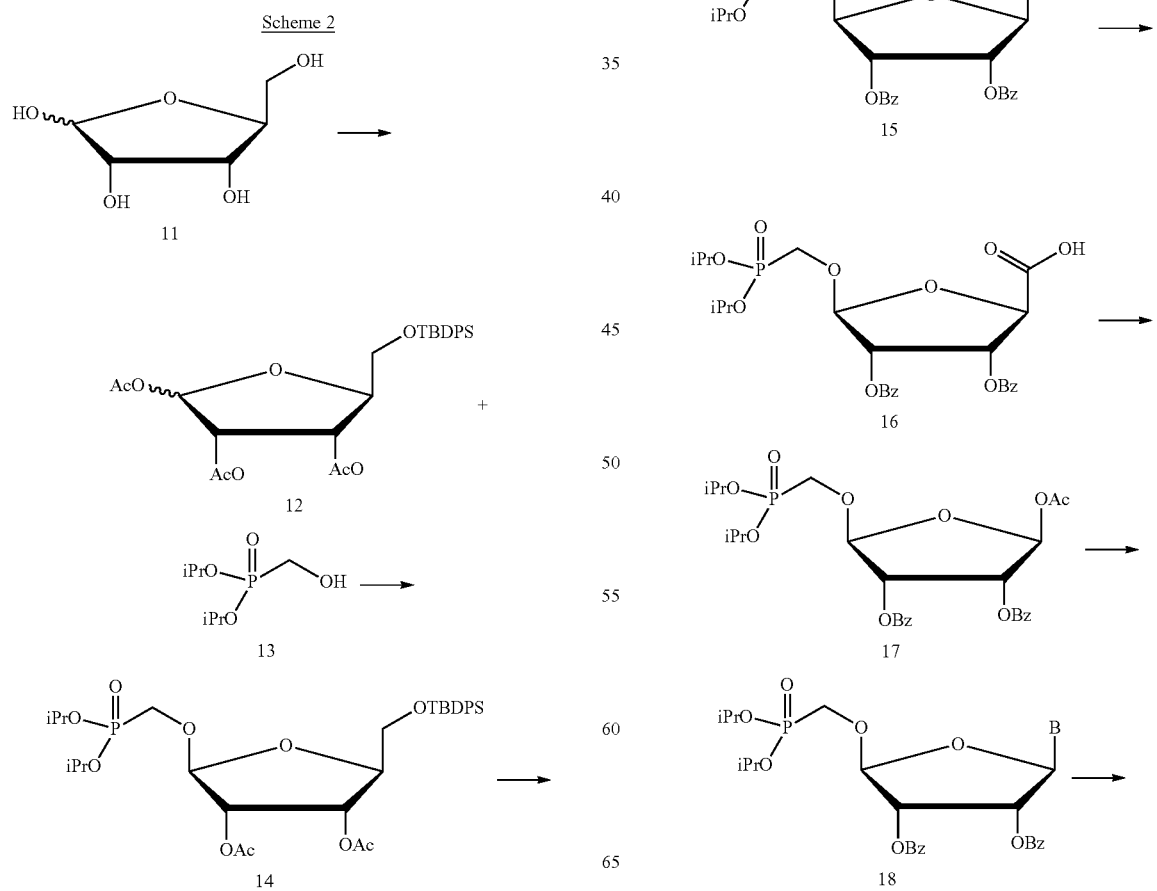

Scheme 2

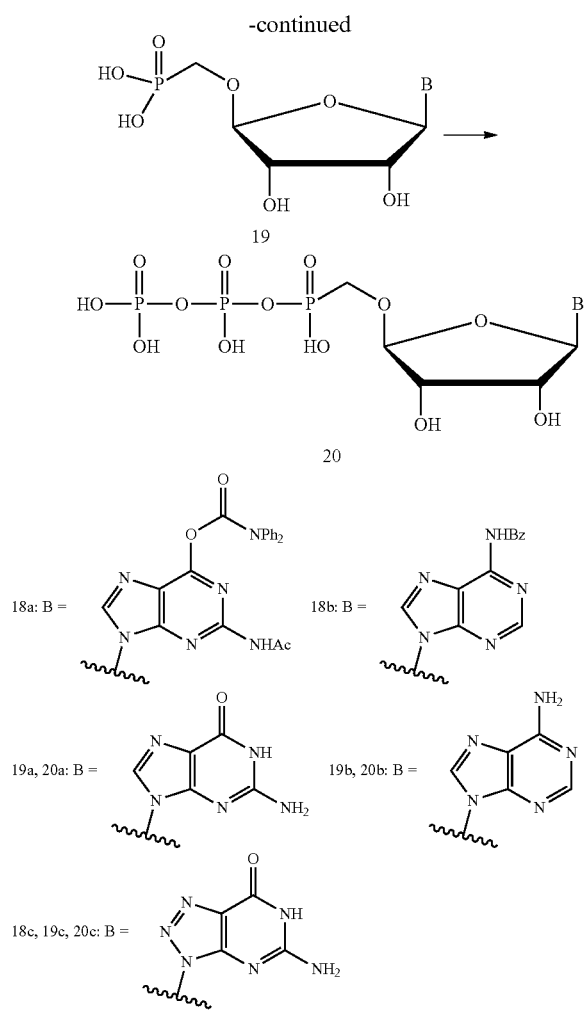

Product 12 tert-Butyldimethylsilyl chloride (91 ml; 350 mmol) was added dropwise to a solution of L-ribose 11 (48 g; 320 mmol) in pyridine (700 ml) and the reaction mixture was stirred for 16 hours at room temperature. After L-ribose (11) vanished, Ac$_2$O (122 ml; 1.28 mol) was added dropwise and reaction was stirred 16 hours at room temperature. The reaction was quenched with 100 ml of MeOH and concentrated, diluted with Et$_2$O (500 ml) and extracted between Et$_2$O (500 ml) and water (600 ml) followed by NaHCO$_3$ (2×500 ml). The organic phase was dried over Na$_2$SO$_4$ and the product (2) was isolated by chromatography on silica gel (0-10% ethyl acetate in toluene) in a yield of 106 g (65%): HRMS (M+Na)$^+$ for C$_{27}$H3$_4$O$_8$NaSi calculated: 537.19152; measured: 537.19154; IR (CHCl$_3$, cm$^{-1}$): 1751, 1589, 1488, 1473, 1464, 1390, 1370, 1220, 1178, 1075, 1028, 1010, 823, 703, 505; NMR: Table 3 and 4.

Product 13

Compound 13 was prepared according to Kelley, J. L.; Linn, J. A.; McLean, E. W.; Tuttle, J. V., *J. Med. Chem.* 1993, 36 (22), 3455-63.

Product 14

Hexamethyldisilazane (100 ml) and catalytic amount of saccharin was added to alcohol 13 (20 g; 100 mmol) and stirred 8 hours at 100° C. Hexamethyldisilazane was evaporated and silylated alcohol 13 was codestilated with toluene. Then compound 12 (33.6 g; 65 mmol) was added to silylated alcohol 13 in 500 ml ACN and finally SnCl$_4$ (24 ml; 200 mmol) was added. Reaction mixture was stirred 1 hour. The reaction mixture was quenched with 16 ml of pyridine, filtrated and concentrated. The product 14 was isolated by chromatography on silica gel (0-50% ethyl acetate in toluene) in a yield of 27.5 g (63%): HRMS (M+Na)$^+$ for C$_{42}$H$_{51}$O$_{10}$NaPSi calculated: 673.25683; measured: 673.25691; IR (CHCl$_3$, cm$^{-1}$): 1754, 1469, 1462, 1386, 1374, 1241, 1219, 1141, 1106, 1081, 988, 863, 823, 703; NMR: Table 3 and 4.

Product 15

Phosphonate 14 (27.5 g; 42 mmol) in saturated NH$_3$ in MeOH (400 ml) was stirred for 16 hours at room temperature. Mixture was then concentrated and codestilated with toluene. Residue was diluted with pyridine (400 ml) and BzCl (12 ml; 100 mmol) was added dropwise. Mixture was then stirred for 16 hours at room temperature. The reaction was quenched with 50 ml of water and concentrated, diluted with Et$_2$O (500 ml) and extracted between Et$_2$O (500 ml) and water (600 ml) followed by NaHCO$_3$ (2×500 ml). The organic phase was dried over Na$_2$SO$_4$, filtrated and concentrated. The residue was diluted with THF (400 ml), TBAF× 3H$_2$O was added (16 g; 51 mmol) and mixture was stirred 1 hour at room temperature. The reaction was quenched adding 20 ml of water, concentrated, diluted with Et$_2$O (500 ml) and extracted between Et$_2$O (500 ml) and saturated aqueous NH$_4$Cl (3×300 ml). The organic phase was dried over Na$_2$SO$_4$, filtrated and concentrated. The product 15 was isolated by chromatography on silica gel (0-50% ethyl acetate in toluene) in a yield of 17.5 g (78%): HRMS (M+Na)$^+$ for C$_{42}$H$_{51}$O$_{10}$NaPSi calculated: 797.28813; measured: 797.28842; IR (CHCl$_3$, cm$^{-1}$): 2978, 2892, 1732, 1602, 1585, 1491, 1472, 1464, 1452, 1428, 1386, 1375, 1362, 1316, 1276, 1178, 1125, 1113, 1070, 1028, 991, 938, 889, 708, 615, 505; NMR: Table 3 and 4.

Product 17

2,2,6,6-Tetramethylpiperidine 1-oxyl (156 mg; 1 mmol) and (diacetoxyiodo)benzene (6.5 g; 20 mmol) were added to phosphonate 15 (5.3 g; 10 mmol) in 30% water in ACN (100 ml) and the mixture was stirred 16 hours at room temperature. The reaction was quenched adding 20 ml of EtOH, evaporated and codestilated with water (5×50 ml) and then with toluene (3×30 ml). The acid 16 was used for next step without further purification.

Pb(OAc)$_4$ (5.5 g, 12.3 mmol) was added to acid 16 in 100 ml THF. Reaction was stirred 2 hours at room temperature, filtrated and concentrated. The product 17 was isolated by chromatography on silica gel (0-30% ethyl acetate in toluene) in a yield of 2.95 g (53% over two steps): HRMS (M+Na)$^+$ for C$_{27}$H$_{33}$O$_{11}$NaP calculated: 587.16527; measured: 587.16534; IR (CHCl$_3$, cm$^{-1}$): 2981, 2878, 1734, 1602, 1492, 1467, 1452, 1386, 1375, 1364, 1281, 1263, 1224, 1179, 1163, 1123, 1071, 1024, 991, 981, 888, 711; NMR: Table 3 and 4.

Product 18a

Bis(trimethylsilyl)acetamide (1.1 ml; 4.5 mmol) was added to N2-acetyl-06-(diphenylcarbamoyl)guanine (550 mg; 1.4 mmol) in 1,2-dichloroethane (14 ml) and stirred 1 hour at 60° C. The mixture was concentrated, codestilated with dry toluene (2×20 ml), added to the acetate 17 (565 mg, 1 mmol) in ACN (10 ml) and finally SnCl$_4$ (600 μl; 5.1 mmol) was added and mixture was stirred 2 hours at room temperature. The reaction was then quenched adding 1 ml of pyridine, filtrated and concentrated. The product 18a was isolated by chromatography on silica gel (0-100% ethyl acetate in toluene) in a yield of 340 mg (42%); HRMS (M+Na)$^+$ for C$_{45}$H45012N6NaP calculated: 915.27253;

measured: 915.27259; IR (CHCl$_3$, cm$^{-1}$): 3318, 3185, 1737, 1699, 1618, 1598, 1591, 1519, 1511, 1492, 1452, 1386, 1374, 1315, 1298, 1273, 1219, 1180, 1168, 1123, 1106, 1023, 989, 907, 887, 805, 728, 719, 713, 641, 531; NMR: Table 3 and 4.

Product 18b

Bis(trimethylsilyl)acetamide (1.1 ml; 4.5 mmol) was added to N-benzoyladenine (335 mg; 1.4 mmol) in 1,2-dichloroethane (14 ml) and stirred 1 hour at 60° C. The mixture was concentrated, codestilated with dry toluene (2×20 ml), added to the acetate 7 (565 mg, 1 mmol) in ACN (10 ml) and finally SnCl$_4$ (600 µl; 5.1 mmol) was added and mixture was stirred 2 hours at room temperature. The reaction was then quenched adding 1 ml of pyridine, filtrated and concentrated. The product 18b was isolated by chromatography on silica gel (0-5% methanol in chloroform) in a yield of 160 mg (50%).

Product 18c

Bis(trimethylsilyl)acetamide (3 ml; 12 mmol) was added to 8-azaguanine (400 mg; 2.6 mmol) in 1,2-dichloroethane (18 ml) and stirred 1 hour at 60° C. The mixture was concentrated, codestilated with dry toluene (2×20 ml), added to the acetate 7 (1.5 g, 2.6 mmol) in ACN (20 ml) and finally SnCl$_4$ (2 ml; 17 mmol) was added in one portion and mixture was stirred 2 hours at room temperature. The reaction was then quenched adding 3 ml of pyridine, filtrated and concentrated. The product 18c was isolated by chromatography on silica gel (0-100% ethyl acetate in toluene) in a yield of 160 mg (10%): HRMS (M+Na)$^+$ for C$_{29}$H$_{33}$O$_{10}$N$_6$NaP calculated: 679.18880; measured: 679.18901; IR (CHCl$_3$, cm$^{-1}$): 3319, 3165, 2980, 2875, 1733, 1706, 1643, 1601, 1493, 1466, 1452, 1386, 1376, 1316, 1274, 1243, 1179, 1121, 1106, 1026, 996, 891, 774, 712, 685; NMR: Table 3 and 4.

Product 19a

Bromotrimethylsilane (490 µl; 3.7 mmol) was added to 18a (330 mg; 0.37 mmol) in pyridine (5 ml) and the mixture was stirred 6 hours and concentrated. Residue was diluted with saturated NH$_3$ in 50% MeOH/H$_2$O (20 ml) and stirred 16 hours at room temperature, then concentrated and nucleotide 19a was isolated by reverse phase chromatography (first 15 min of isocratic elution with 0.1 mol·l$^{-1}$ TEAB, then 35 min gradient 0-15% ACN in 0.1 mol·l$^{-1}$ TEAB) in a yield of 138 mg (80%): HRMS (M-H)$^-$ for C$_{10}$H$_{13}$O$_8$N$_5$P calculated: 362.05072; measured: 362.05020; IR (CHCl$_3$, cm$^{-1}$): 3402, 3153, 2823, 2739, 2680, 2492, 1693, 1645, 1605, 1571, 1480, 1451, 1398, 1229, 1162, 1093, 1038, 999, 965, 783, 682, 574; NMR: Table 3 and 4.

Product 19b

Bromotrimethylsilane (490 µl; 3.7 mmol) was added to 18b (275 mg; 0.37 mmol) in pyridine (5 ml) and the mixture was stirred 6 hours and concentrated. Residue was diluted with saturated NH$_3$ in 50% MeOH/H$_2$O (20 ml) and stirred 16 hours at room temperature, then concentrated and nucleotide 19b was isolated by reverse phase chromatography (first 15 min of isocratic elution with 0.1 mol·l$^{-1}$ TEAB, then 35 min gradient 0-15% ACN in 0.1 mol·l$^{-1}$ TEAB) in a yield of 134 mg (80%): HRMS (M-H)$^-$ for C$_{10}$H$_{13}$O$_7$N$_5$P calculated: 346.05581; measured: 346.05585; IR (CHCl$_3$, cm$^{-1}$): 3411, 3342, 3268, 2728, 2679, 2593, 1649, 1610, 1603, 1577, 1423, 1377, 1337, 1296, 1247, 1135, 1073, 1070, 1038, 907, 795, 655; NMR: Table 3 and 4.

Product 19c

Bromotrimethylsilane (330 µl; 2.5 mmol) was added to 18c (160 mg; 0.24 mmol) in pyridine (5 ml) and the mixture was stirred 6 hours and concentrated. Residue was diluted with saturated NH$_3$ in 50% MeOH/H$_2$O (10 ml) and stirred 16 hours at room temperature, then concentrated and nucleotide 19c was isolated by reverse phase chromatography (first 15 min of isocratic elution with 0.1 mol·l$^{-1}$ TEAB, then 35 min gradient 0-15% ACN in 0.1 mol·l$^{-1}$ TEAB) in a yield of 100 mg (90%; Et$_3$NH$^+$ salt): HRMS (M-H)$^-$ for C$_9$H$_{12}$O$_8$N$_6$P calculated: 363.04597; measured: 363.04563; IR (CHCl$_3$, cm$^{-1}$): 3419, 3167, 2686, 2491, 1711, 1639, 1532, 1457, 1240, 1112, 1056, 1039, 788, 682; NMR: Table 3 and 4.

Product 20a

Triethylammonium salt of phosphonate 19a (76 mg; 0.16 mmol) was converted to pyridinium salt (DOWEX™ WX 8 in pyridinium cycle), and dried by the co-evaporation with anhydrous pyridine. The mixture of pyridinium salt, imidazole (130 mg; 1.92 mmol), and tri-n-octylamine (0.35 ml; 0.8 mmol) was dried by the co-evaporation with anhydrous DMF (2×10 ml). The semi-solid residue was dissolved in anhydrous DMF (8 ml), triphenylphosphine (210 mg; 0.8 mmol), and 2,2'-dipyridyldisulfide (Aldrithiol™, 176 mg; 0.8 mmol) was added and the mixture was stirred over night at the room temperature. The course of the reaction was checked by the LCMS.

The reaction mixture was added drop-wise to the precipitation solution-sodium perchlorate monohydrate (702 mg, 5 mmol) and triethylamine (4 ml) in peroxide free mixture of acetone (60 ml) and diethylether (36 ml) at 0° C. The solution was let to precipitate at 0° C. for ca 30 minutes, and the precipitate was then separated by the centrifugation (10000 RPM, 3° C., 20 min), and washed by another part of the precipitation solution and with the dry diethylether, successively. Solid imidazolide was dried in vacuo. Tributylammonium pyrophosphate (0.5 M solution in DMSO, 1.2 ml; 0.6 mmol) was added to the imidazolide and the solution was kept at the room temperature for 48 hrs. Resulted triphosphate was purified by the column chromatography on reversed phase (Phenomenex Luna C18 5 tm), using linear gradient of acetonitrile (0-5%) in triethylamine bicarbonate buffer (0.1 M).

Triethylammonium salt of the product was converted to sodium salt (DOWEX™ WX 8 Na$^+$), yielded 71 mg (78%) of desired isosteric triphosphate analogue 20a (Na$_2$ salt): HRMS (M-H)$^-$ for C$_{10}$H$_{15}$O$_{14}$N$_5$P$_3$ calculated: 521.98338; measured: 521.98242; NMR: Table 3 and 4.

Product 20b

Triethylammonium salt of phosphonate 19b (74 mg; 0.2 mmol) was converted to pyridinium salt (DOWEX™ WX 8 in pyridinium cycle), and dried by the co-evaporation with anhydrous pyridine. The mixture of pyridinium salt, imidazole (163 mg; 2.4 mmol), and tri-n-octylamine (0.44 ml; 1 mmol) was dried by the co-evaporation with anhydrous DMF (2×10 ml). The semi-solid residue was dissolved in anhydrous DMF (12 ml), triphenylphosphine (262 mg; 1 mmol), and 2,2'-dipyridyldisulfide (Aldrithiol™, 220 mg; 1 mmol) was added and the mixture was stirred over night at the room temperature. The course of the reaction was checked by the LCMS.

The reaction mixture was added drop-wise to the precipitation solution-sodium perchlorate monohydrate (702 mg; 5 mmol) and triethylamine (4 ml) in peroxide free mixture of acetone (60 ml) and diethylether (36 ml) at 0° C. The solution was let to precipitate at 0° C. for ca 30 minutes, and the precipitate was then separated by the centrifugation (10000 RPM, 3° C., 20 min), and washed by another part of the precipitation solution and with the dry diethylether, successively. Solid imidazolide was dried in vacuo. Tributylammonium pyrophosphate (0.5 M solution in DMSO, 1.2 ml; 0.6 mmol) was added to the imidazolide and the solution was kept at the room temperature for 48 hrs. Resulted triphosphate was purified by the column chromatography on reversed phase (Phenomenex Luna C18 5 µm), using linear gradient of acetonitrile (0-5%) in triethylamine bicarbonate buffer (0.1 M).

Triethylammonium salt of the product was converted to sodium salt (DOWEX™ WX 8 Na⁺), yielded 50 mg (45%) of desired isosteric triphosphate analogue 20b (Na$_2$ salt): ESI-MS (M-H)⁻ for $C_{10}H_{16}N_5O_{13}P_3$ calculated: 506.0; measured: 506.0.

Product 20c

Triethylammonium salt of phosphonate 19c (100 mg; 0.2 mmol) was converted to pyridinium salt (DOWEX™ WX 8 in pyridinium cycle), and dried by the co-evaporation with anhydrous pyridine. The mixture of pyridinium salt, imidazole (163 mg; 2.4 mmol), and tri-n-octylamine (0.44 ml; 1 mmol) was dried by the co-evaporation with anhydrous DMF (2×10 ml). The semi-solid residue was dissolved in anhydrous DMF (12 ml), triphenylphosphine (262 mg; 1 mmol), and 2,2'-dipyridyldisulfide (Aldrithiol™, 220 mg; 1 mmol) was added and the mixture was stirred over night at the room temperature. The course of the reaction was checked by the LCMS.

The reaction mixture was added drop-wise to the precipitation solution-sodium perchlorate monohydrate (702 mg; 5 mmol) and triethylamine (4 ml) in peroxide free mixture of acetone (60 ml) and diethylether (36 ml) at 0° C. The solution was let to precipitate at 0° C. for ca 30 minutes, and the precipitate was then separated by the centrifugation (10000 RPM, 3° C., 20 min), and washed by another part of the precipitation solution and with the dry diethylether, successively. Solid imidazolide was dried in vacuo. Tributylammonium pyrophosphate (0.5 M solution in DMSO, 1.2 ml; 0.6 mmol) was added to the imidazolide and the solution was kept at the room temperature for 48 hrs. Resulted triphosphate was purified by the column chromatography on reversed phase (Phenomenex Luna C18 5 μm), using linear gradient of acetonitrile (0-5%) in triethylamine bicarbonate buffer (0.1 M).

Triethylammonium salt of the product was converted to sodium salt (DOWEX™ WX 8 Na⁺), yielded 100 mg (80%) of desired isosteric triphosphate analogue 20c (Na$_2$ salt): HRMS (M-H)⁻ for $C_9H_{14}O_{14}N_6P_3$ calculated: 522.97863; measured: 522.97760; IR (KBr, cm⁻¹): 3402, 3387, 3163, 2493, 1709, 1644, 1533, 1456, 1227, 1109, 1070, 1036, 1001, 930, 788, 682; NMR: Table 3 and 4.

TABLE 3

¹H NMR data of compounds 12, 14, 15, 17, 18a, 18c, 19a, 19b, 19c, 20a and 20c (coupling constant values are given in brackets).

| Compound | Solvent | H-1' | H-2' | H-3' | H-4' | Base |
|---|---|---|---|---|---|---|
| 12 [a] 1α-OAc | DMSO-d$_6$ | 6.36 d (4.7) | 5.325 dd (4.7; 6.6) | 5.425 dd (6.6; 2.6) | 4.32 q (2.6; 3.0; 3.0) | — |
| 12 1β-OAc | DMSO-d$_6$ | 6.07 d (1.6) | 5.32 dd (1.6; 4.7) | 5.46 dd (4.7; 6.5) | 4.25 dt (6.5; 3.3; 3.2) | — |
| 14 [b] | DMSO-d$_6$ | 5.17 d (1.8) | 5.14 dd (1.8; 5.0) | 5.28 dd (5.0; 6.2) | 4.185 dt (6.2; 4.8; 4.9) | — |
| 15 [c] | DMSO-d$_6$ | 5.44 d (1.7) | 5.54 dd (1.7; 5.0) | 5.67 dd (5.0; 6.0) | 4.52 m | — |
| 17 [d] | DMSO-d$_6$ | 6.46 d (2.4) | 5.67 dd (2.4; 5.1) | 5.60 dd (5.1; 2.1) | 5.65 d (2.1) | — |
| 18a [e] | DMSO-d$_6$ | 6.71 d (5.7) | 6.46 dd (5.7; 5.0) | 5.94 dd (5.0; 1.2) | 5.68 d (1.2) | H-8: 8.64 s NH: 10.76 s |
| 18c [f] | DMSO-d$_6$ | 6.59 d (4.7) | 6.521 (4.7; 4.8) | 5.93 dd (4.8; 2.1) | 5.72 d (2.1) | NH: 11.15 s |
| 19a [g] | D$_2$O | 6.025 d (6.5) | 4.97 ddd (6.5; 4.4; 0.6) | 4.37 dt (4.4; 0.6; 0.6) | 5.21 t (0.6; 0.6) | H-8: 8.09 s |
| 19b [h] | D$_2$O | 6.21 dd (6.3; 0.4) | 5.02 ddd (6.3; 4.4; 0.5) | 4.405 ddd (4.4; 0.8; 0.4) | 5.25 ddd (0.8; 0.5) | H-2: 8.18 s H-8: 8.41 s |
| 19c [i] | D$_2$O | 6.20 d (6.1) | 5.39 dd (6.1; 4.6) | 4.46 dd (4.6; 0.8) | 5.27 d (0.8) | — |
| 20a [j] | D$_2$O | 6.58 d (5.8) | 5.46 dd (5.8; 4.6) | 4.52 dd (4.6; 1.3) | 5.39 d (1.3) | — |
| 20c [k] | D$_2$O | 6.24 d (6.6) | 5.43 dd (6.6; 4.6) | 4.49 br d (4.6; <1) | 5.34 br s (<1) | — |

Other peaks:

[a] H-5'a: 3.805 dd, J = 11.5; 3.0 Hz and 3.80 dd, J = 11.5; 3.2 Hz; H-5'b: 3.72 dd, J = 11.5; 3.0 Hz and 3.69 dd, J = 11.5; 3.3 Hz; OAc: 2.094 s, 2.081 s, 2.076 s, 2.032 s, 2.031 s, 1.917 s; OTBDPS: 7.62 m, 7.47 m, 7.43 m (Ar—H), 1.01 s, 1.00 s (t-Bu);

[b] H-5'a: 3.76 dd, J = 11.0; 4.8 Hz; H-5'b: 3.72 dd, J = 11.0; 4.9 Hz; OAc: 2.00 s, 1.98 s; O—CH$_2$—P=O(OiPr)$_2$: 3.795 dd, J = 13.8; 8.9 Hz and 3.76 dd, J = 13.8; 8.7 Hz (P—CH$_2$—O), 4,54 m, 1.20 d, J = 6.2 Hz, 1.19 d, J = 6.2 Hz, 1.18 d, J = 6.1 Hz, 1.16 d, J = 6.2 Hz (2x OiPr); OTBDPS: 7.62 m, 7.48 m, 7.44 m (Ar—H), 0.99 s (t-Bu);

[c] H-5'a and H-5'b: 3.88 m (2H); OBz: 7.88 m, 7.655 m, 7.465 m; O—CH$_2$—P=O(OiPr)$_2$: 3.89 m (P—CH$_2$—O), 4.58 m, 1.21 d, J = 6.2 Hz, 1.20 d, J = 6.2 Hz, 1.18 d, J = 6.2 Hz (2x OiPr); OTBDPS: 7.65 m, 7.62 m, 7.44 m, 7.41 m, 7.37 m (Ar—H), 0.96 s (t-Bu);

[d] OAc 2.13 s; OBz: 7.895 m, 7.84 m, 7.67 m, 7.64 m, 7.49 m, 7.44 m; O—CH$_2$—P=O(OiPr)$_2$: 3.95 dd, J = 13.7; 9.0 Hz and 3.92 dd, J = 13.7; 9.3 Hz (P—CH$_2$—O), 4.64 m, 1.270 d, J = 6.3 Hz, 1.266 d, J = 6.2 Hz, 1.260 d, J = 6.2 Hz, 1.250 d, J = 6.0 Hz (2x OiPr);

[e] NAc: 2.215 s; OBz: 8.005 m, 7.80 m, 7.71 m, 7.61 m, 7.56 m, 7.41 m; O—CH$_2$—P=O(OiPr)$_2$: 3.97 d, J = 9.4 Hz (P—CH$_2$—O), 4.65 m, 1.273 d, J = 6.0 Hz, 1.263 d, J = 6.0 Hz, 1.256 d, J = 6.2 Hz, 1.236 d, J = 6.2 Hz (2x OiPr); O—CO—N(C$_6$H$_5$)$_2$: 7.505 m, 7.44 m, 7.32 m;

[f] OBz: 7.97 m, 7.85 m, 7.70 m, 7.64 m, 7.53 m, 7.45 m; O—CH$_2$—P=O(OiPr)$_2$: 3.88 br d, J = 9.0 Hz (P—CH$_2$—O), 4.58 m, 1.222 d, J = 6.2 Hz, 1.209 d, J = 6.2 Hz, 1.196 d, J = 6.2 Hz (2x OiPr);

[g] O—CH$_2$—P=O(OH)$_2$: 3.75 dd, J = 12.8; 8.6 Hz and 3.50 dd, J = 12.8; 9.8 Hz;

[h] O—CH$_2$—P=O(OH)$_2$: 3.78 dd, J = 12.8; 8.8 Hz and 3.58 dd, J = 12.8; 9.7 Hz;

[i] O—CH$_2$—P=O(OH)$_2$: 3.67 dd, J = 13.1; 8.1 Hz and 3.46 dd, J = 13.1; 9.7 Hz;

[j] O—CH$_2$—P=O(OH)—O—P=O(OH)—O—P=O(OH)$_2$: 3.78 dd, J = 13.9; 8.8 Hz and 3.75 dd, J = 13.9; 7.7 Hz;

[k] O—CH$_2$—P=O(OH)—O—P=O(OH)—O—P=O(OH)$_2$: 3.88 dd, J = 13.6; 7.4 Hz and 3.76 dd, J = 13.6; 9.9 Hz.

TABLE 4

$^{13}C$ and $^{31}P$ NMR data of compounds 12, 14, 15, 17, 18a, 18c, 19a, 19b, 19c, 20a and 20c (coupling constant J(C, P) are given in brackets).

| Compound | Solvent | C-1' | C-2' | C-3' | C-4' | Base | $^{31}P$ |
|---|---|---|---|---|---|---|---|
| 12 [a] 1α-OAc | DMSO-$d_6$ | 93.98 | 70.15 | 69.63 | 84.05 | — | — |
| 12 1β-OAc | DMSO-$d_6$ | 97.84 | 74.09 | 69.74 | 81.81 | — | — |
| 14 [b] | DMSO-$d_6$ | 105.27 (12.1) | 73.91 | 71.39 | 80.93 | — | 19.60 |
| 15 [c] | DMSO-$d_6$ | 105.44 (8.2) | 74.83 | 72.50 | 81.09 | — | 19.51 |
| 17 [d] | DMSO-$d_6$ | 98.82 | 75.29 | 74.63 | 106.98 (13.1) | — | 18.03 |
| 18a [e] | DMSO-$d_6$ | 86.12 | 73.82 | 74.43 | 106.34 (13.4) | C-2: 152.70<br>C-4: 154.72<br>C-5: 120.36<br>C-6: 165.53<br>C-8: 144.24 | 19.42 |
| 18c [f] | DMSO-$d_6$ | 86.13 | 73.22 | 74.63 | 106.54 (12.9) | C-2: 155.69<br>C-4: 152.30<br>C-5: 124.66<br>C-6: 156.25 | 19.06 |
| 19a [g] | $D_2O$ | 89.27 | 77.15 | 76.56 | 111.95 (11.8) | C-2: 156.79<br>C-4: 154.74<br>C-5: 118.76<br>C-6: 161.68<br>C-8: 140.52 | 14.35 |
| 19b [h] | $D_2O$ | 89.58 | 77.59 | 76.63 | 112.08 (11.9) | C-2: 155.57<br>C-4: 151.98<br>C-5: 121.15<br>C-6: 158.23<br>C-8: 142.96 | 15.19 |
| 19c [i] | $D_2O$ | 91.09 | 76.23 | 76.57 | 112.17 (10.9) | C-2: 158.82<br>C-4: 155.02<br>C-5: 127.40<br>C-6: 160.97 | 15.38 |
| 20a [j] | $D_2O$ | 94.14 | 75.62 | 76.54 | 112.63 (9.5) | C-2: 163.20<br>C-4: 157.43<br>C-5: 117.34<br>C-6: 157.90 | −9.21<br>−22.24<br>8.82 |
| 20c [k] | $D_2O$ | 91.54 | 74.86 | 76.42 | 111.97 (10.5) | C-2: 160.91<br>C-4: 154.97<br>C-5: 127.55<br>C-6: 158.64 | −9.84<br>−22.30<br>9.21 |

Other peaks:

[a] C-5': 63.52, 63.06; OAc: 170, 10, 169.78, 169.74, 169,58, 169.39, 169.18, 21.08, 20.90, 20.68, 20.52, 20.49, 20.33; OTBDPS: 135.39, 135.27, 135.23, 132.70, 132.57, 132.55, 132.50, 130.24, 130.17, 123,20, 128.17, 128.16, 128.10 (Ar—C), 23.68, 23,65, 18.99, 18.94 (t-Bu);

[b] C-5': 64.66; OAc: 169.70, 169.59, 20.51, 20.50; O—CH$_2$—P=O(OiPr)$_2$: 61.28 (J = 166.9 Hz)(P—CH$_2$—O), 70.64 (J = 6.3 Hz), 70.57 (J = 6.4 Hz), 23.93 (J = 3.5 Hz), 23.91 (J = 3.5 Hz), 23.80 (J =4.4 Hz), 23.78 (J = 4.4 Hz) (2x OiPr); OTBDPS: 135.24, 132.73, 132.69, 130.21, 130.17, 128.16, 128.15 (Ar—C), 26.69, 18.94 (t-Bu);

[c] C-5': 64.84; OBz: 164.93, 164.76, 134.13, 133.98, 129.48, 129.39, 129.04, 128.89, 128.80, 128.70; O—CH$_2$—P=O (OiPr)$_2$: 61.50 (J = 166.8 Hz) (P—CH$_2$—O), 70.66 (J = 6.4 Hz), 70.60 (J = 6.2 Hz), 23.94 (J = 3.2 Hz), 23.92 (J = 3.5 Hz), 23.82 (J = 4.3 Hz), 23.80 (J = 4.4 Hz) (2x OiPr); OTBDPS: 135.25, 135.23, 132.71, 132.68, 130.15, 130.14, 128.11, 128.10 (Ar—C), 26.69, 18.90 (t-Bu);

[d] OAc: 169.39, 20.95; OBz: 164.67, 164.62, 134.25, 134.21, 129.56, 129.50, 129.03, 129.00, 128.42, 128.41; O—CH$_2$—P=O(OiPr)$_2$: 61.88 (J = 166.0 Hz) (P—CH$_2$—O), 70.83 (J = 6.3 Hz), 70.77 (J = 6.3 Hz), 23.97 (J = 3.1 Hz), 23.96 (J = 3.5 Hz), 23.81 (J = 4.6 Hz) (2x OiPr);

[e] NAc: 169.06, 24.76; OBz: 164.63, 164.61, 134.36, 134.20, 129.60, 129.58, 129.18, 128.93, 128.56, 128.32; O—CH$_2$—P=O(OiPr)$_2$: 61.97 (J = 167.1 Hz) (P—CH$_2$—O), 71.09 (J = 6.3 Hz), 70.99 (J = 6.3 Hz), 23.94 (J = 3.6 Hz), 23.81 (J = 4.4 Hz), 23.79 (J = 4.4 Hz) (2x OiPr); O—CO—N(C$_6$H$_5$)$_2$: 150.23, 141.76, 129.60, 127.54, 127.12;

[f] OBz: 164.69, 164.66, 134.34, 134.27, 129.61, 129.56, 129.14, 129.03, 128.49, 128.33; O—CH$_2$—P=O (OiPr)$_2$: 61.94 (J = 164.2 Hz)(P—CH$_2$—O), 70.92 (J = 6.2 Hz), 70.87 (J = 6.2 Hz), 23.94 (J = 3.9 Hz), 23.93 (J = 3.8 Hz), 23.78 (J = 4.6 Hz) and 23.75 (J = 4.7 Hz)(2x OiPr);

[g] O—CH$_2$—P=O (OH)$_2$: 67.95 (J = 154.5 Hz);

[h] O—CH$_2$—P=O (OH)$_2$: 67.64 (J = 155.0 Hz);

[i] O—CH$_2$—P=O (OH)$_2$: 67.37 (J = 154.8 Hz);

[j] O—CH$_2$—P=O(OH)—O—P=O(OH)—O—P=O(OH)$_2$: 66.53 (J = 163.7 Hz);

[k] O—CH$_2$—P=O(OH)—O—P=O(OH)—O—P=O(OH)$_2$: 66.26 (J = 164.2 Hz)

Example 3. Synthesis of Dinucleotides

Preparation of a Modified Solid Support CE-CPG

The solid support (LCAA-CPG) modified with 12-cyano-13-[(4,4'-dimethoxytrityl)oxy]-3,6,9-trioxatridecane hydrogensuccinate (CE-CPG) was prepared according to Pǎces, O., et al. (2008). *Collection of Czechoslovak Chemical Communications* 73(1): 32-43.

CE-CPG

Scheme 3. Example of the synthesis of CDN derived from 4'-phosphonomethoxy nucleoside

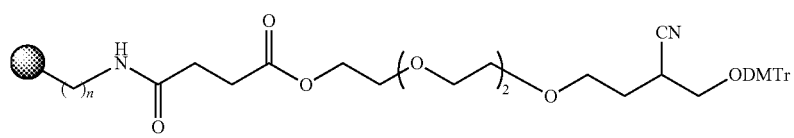

Synthesis of dinucleotides derived from 4'-phosphonomethoxy nucleosides

Dinucleotides were synthesized by "trityl off" method in a 1 μmol scale in the 5'→3' direction using the CE-CPG solid support (20 mg), see Scheme 3. The synthesis protocols using phosphotriester and phosphoramidite methods are shown in Table 5. The average yield of the condensation was in the range 93-95% (conductivity detector, DMTr+).

TABLE 5

Protocols for the synthesis of dinucleotides

| Operation | Agent | Volume (ml) | Time (s) |
|---|---|---|---|
| *Phosphotriester condensation method* | | | |
| 1. Detritylation | 3% CHCl$_2$COOH in DCM | 3 | 135 |
| 2. Condensation | 0.1 mol · l$^{-1}$ monomer in pyridine | 0.1 | 600 |
| | 0.3 mol · l$^{-1}$ TIPSCl in pyridine | 0.1 | |
| 3. Capping | Ac$_2$O/pyridine/THF 1:1:8 | 0.1 | 150 |
| | 1-MeIm/THF 1:9 | 0.1 | |
| *Phosphoramidite condensation method* | | | |
| 1. Detritylation | 3% CHCl$_2$COOH in DCM | 3 | 135 |
| 2. Condensation | 0.1 mol · l$^{-1}$ monomer in ACN | 0.1 | 600 |
| | 0.3 mol · l$^{-1}$ ETT in ACN | 0.1 | |
| 3. Capping | Ac$_2$O/pyridine/THF 1:1:8 | 0.1 | 150 |
| | 1-MeIm/THF 1:9 | 0.1 | |
| 4. Oxidation | tBuOOH/DCM 1:4 | 0.2 | 180 |

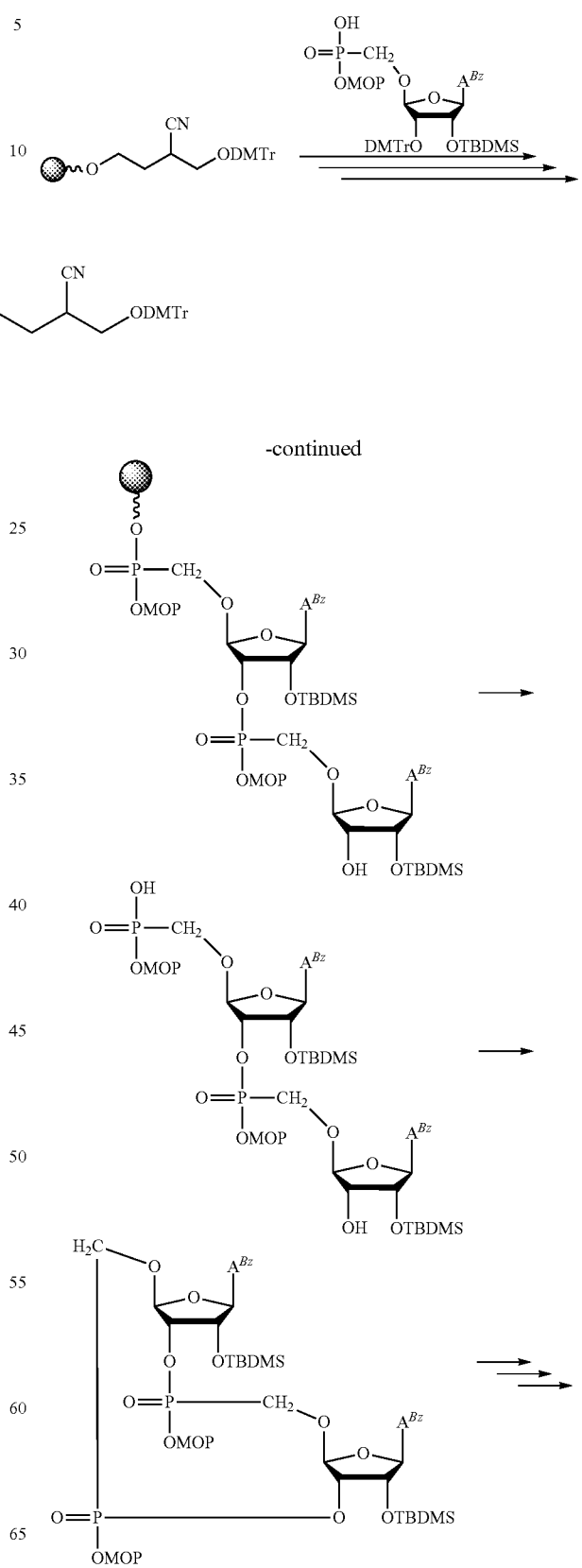

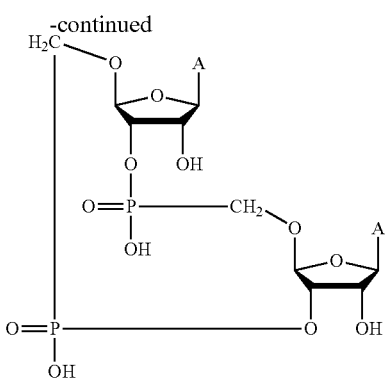

Preparation of monomers derived from nucleoside-5'-methylphosphonates

Phosphonate and phosphoramidite monomers were prepared according to Páv, O; Košiová, I.; Barvik, I.; Pohl, R.; Buděšinský, M.; Rosenberg, I. Synthesis of oligoribonucleotides with phosphonate-modified linkages. *Org. Biomol. Chem.* 2011, 9, 6120-6126 and Piv, O.; Panova, N.; Snášel, J.; Zbomiková, E.; Rosenberg I. Activation of human RNase L by 2'- and 5'-O-methylphosphonate-modified oligoadenylates. *Bioorg. Med. Chem. Lett.* 2012, 22, 181-185.

Synthesis of Dinucleotides Derived from Nucleoside-5'-Methylphosphonates

The dinucleotides were synthesized by "trityl off" method in a 1 μmol scale in the 5'→3' direction using the CE-CPG (20 mg), see Scheme 4. The synthesis protocols by phosphotriester and phosphoramidite methods were the same as those shown in Table 3 above. The average yield of the coupling step was in the range 93-95% (conductivity detector, DMTr+).

Scheme 4
Example of the synthesis of CDN derived from nucleoside-5'-methylphosphonates.

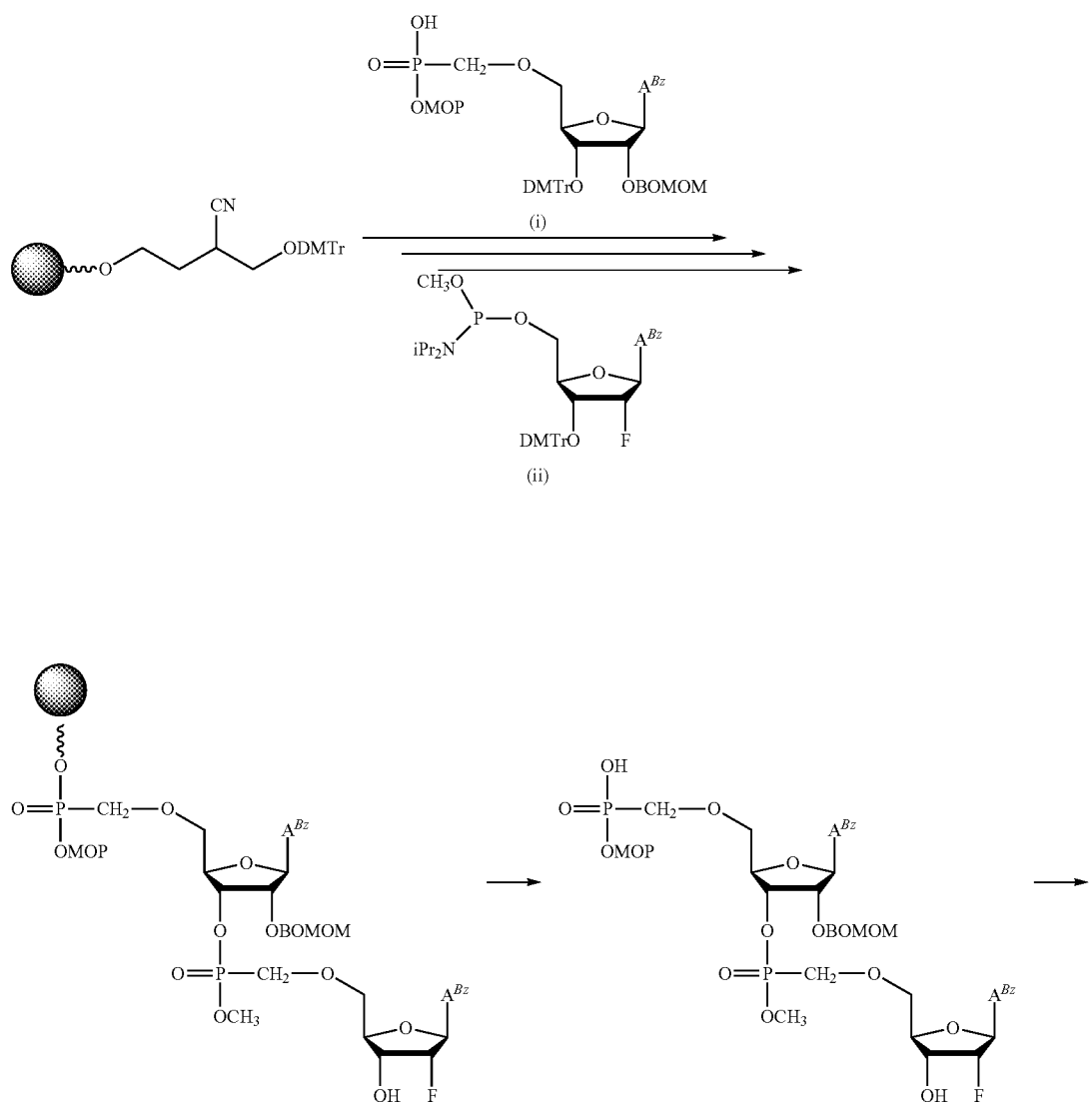

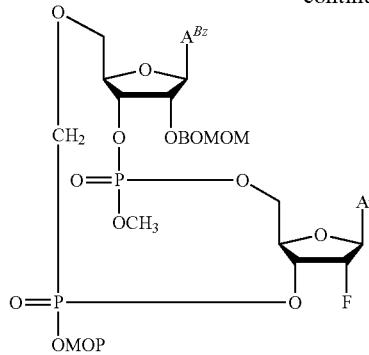 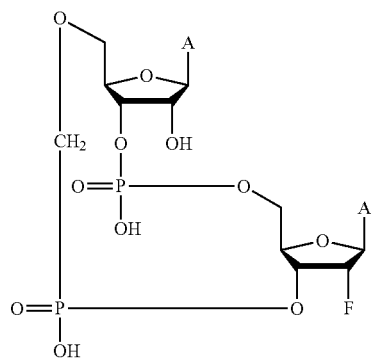

Example 4. Cyclization, Deprotection and Purification of Dinucleotides

4'-Phosphonomethoxy Nucleosides

An exemplary synthesis is depicted in Scheme 3 above. A 10% solution of Et$_2$NH in ACN (500 µl) was added to the linear dimer bound to CE-CPG solid support and the heterogeneous mixture was shaken on an Eppendorf Thermomixer comfort shaker for 2 h at room temperature. The solvents were evaporated and a solution of CDDO (18 mg) in pyridine (400 µl) was added to the solid support. The heterogeneous mixture was shaken for 2 hours at room temperature. Then, 10 µl of Et$_3$N and 266 µl of water were added to the reaction mixture and the shaking continued for 16 hours at 65° C. The reaction mixture was evaporated.

A solution of 33% MeNH$_2$ in EtOH (300 µl) and 50% MeOH/water (600 µl) was added to the reaction mixture, followed by shaking for 8 hours at room temperature. The solvents were then evaporated. 50% Aqueous MeOH (600 µl) was added to the reaction mixture and the solid support was separated from the solution by decantation and washed several times with 50% aqueous MeOH. The methanolic solutions were combined and evaporated. The residue was dissolved in 10% ACN/0.1 mol·l$^{-1}$ TEAB (1.5 ml) and loaded onto a SEP-PAK column. The column was washed with 0.1 mol·l$^{-1}$ TEAB (5 ml). The product was then eluted with 80% ACN/water solution (5 ml). The eluent was evaporated and the residue was co-distilled with iPrOH (3×200 µl).

The silylated dinucleotide was dissolved in a mixture of DMSO (115 µl), Et$_3$N (60 µl) and Et$_3$N.3HF (75 µl) and the reaction mixture was heated at 65° C. for 3 h. The solution was diluted with 1 mol·l$^{-1}$ ammonium acetate (385 µl) and water (0.5 ml) and loaded onto a semipreparative C18 column (Luna 5 tm C18 250×10 mm). Cyclic dinucleotide was isolated by reverse phase chromatography (first 15 min of isocratic elution with 0.1 mol·l$^{-1}$ TEAB, then 35 min gradient 0-15% ACN in 0.1 mol·l$^{-1}$ TEAB).

5'-methylphosphonates

An exemplary synthesis is depicted in Scheme 4 above. 10% solution of Et$_2$NH in ACN (500 µl) was added to the CE-CPG solid support with bound linear dimer, and the heterogeneous mixture was shaken on an Eppendorf Thermomixer comfort shaker for 2 h at room temperature. The solvents were evaporated and a solution of CDDO (18 mg) in pyridine (400 µl) was added to the carrier. The heterogeneous mixture was shaken for 2 hours at room temperature. Then, 10 µl of Et$_3$N and 266 µl of water were added to the reaction mixture and the shaking was continued for 16 hours at 65° C. The reaction mixture was evaporated.

50% Aqueous MeOH (600 µl) was added to the reaction mixture and the solid support was separated from the solution by decantation and washed with 50% aqueous MeOH (3×200 µl). A solution of 33% MeNH$_2$ in EtOH (600 µl) was added to the methanolic solution and the mixture was shaken for 8 hours at room temperature. The solvents were then evaporated. The residue was dissolved in 0.1 mol·l$^{-1}$ TEAB (1.5 ml) and applied to a semipreparative C18 column (Luna 5 µm C18 250×10 mm). Cyclic dinucleotide was isolated by reverse phase chromatography (first 15 min isocratic elution with 0.1 mol·l$^{-1}$ TEAB, then 35 min gradient 0-15% ACN in 0.1 mol·l$^{-1}$ TEAB).

Enzymatic Preparation of 3'3' CDNs

Araadenosine-5'-Triphosphate (cat. #N-1048), 2-Aminopurine-riboside-5'-Triphosphate (cat. #N-1067), 7-Deazaguanosine-5'-Triphosphate (cat. #N-1044), 2'-Deoxyadenosine-5'-Triphosphate (cat. #N-2510), Adenosine-5'-O-(1-Thiotriphosphate) (cat. #N-8005), O$^6$-Methylguanosine-5'-Triphosphate (cat. #N-1031), and N$^6$-Methyladenosine-5'-Triphosphate (cat. #N-1013) were purchased from TriLink Biotechnologies (San Diego, USA). Adenosine 5'-Triphosphate (cat. #NU-1010-10G), Guanosine 5'-Triphosphate (cat.#NU-1012-10G), and 6-Methylthio-Inosine-5'-Triphosphate (cat. #NU-1131S) were from Jena Bioscience (Jena, Germany). 2'-Deoxy-2,2'-Difluoro-Adenosine 5'-Triphosphate (cat. #107-01), 2'-Deoxy-2-Fluoroadenosine 5'-Triphosphate (cat. #107-02), 2-Fluoro Araadenosine-5'-Triphosphate (cat. #107-03), 6-Methylthio-GTP (cat. #NU-1131S), and 2'-Deoxy-2-Chloroadenosine 5'-Triphosphate (cat. #107-04) were obtained from Metkinen Chemistry (Kuopio, Finland). Other nucleoside triphosphates were prepared from commercially available nucleosides following a standard protocol (Gillerman, I.; Fisher, B., Nucleos. Nucleot. Nucl. 2010; 29, 245-256).

A recombinant DNA encoding Vibrio cholerae DncV/ VCO179 was prepared by GenScript (Piscataway, N.J.) and subcloned into vector pHisGB2 by the use of Gibson Assembly Master Mix (New England Biolabs, Ipswich, USA). The resulting construct enabled expression of DncV/VCO179 protein containing N terminal 6×His/GB1/TEV-site tag. The protein was overexpressed in E. coli BL21 (DE3) (ThermoFisher, Waltham, USA). Bacterial pellet was resuspended in ice cold lysis buffer containing 20 mM sodium phosphate buffer (pH 7.4), 500 mM NaCl, 10% glycerol, and 20 mM imidazole using Dounce homogenizer. DNase I and RNase A were added (final concentration 50 µg/ml) together with MgCl$_2$ (final concentration 5 mM) to the homogenate and bacteria were lysed using MSE Soniprep 150 (3 mm Tip Solid Titanium Exponential Probe, 2 min, 50% power, amplitude 12 microns). The lysate was spun 30,000×g for 20 minutes at 4° C. and supernatant was loaded onto equilibrated 5 mL HisTrap column (GE Healthcare BioSciences, Pittsburgh, USA). The column was washed with 50 ml lysis buffer and DncV protein was eluted with 5 ml 20 mM sodium phosphate buffer (pH 7.4) buffer containing 500 mM NaCl; 10% glycerol, and 300 mM imidazole. The GB1 tag was then cleaved off using TEV protease (approximate molar ratio 1:50) at 4° C. for 16 hours. DncV enzyme was further purified by size exclusion chromatography using HiLoad 16/60 Superdex 75 column in buffer containing 150 mM NaCl; 50 mM Tris (pH 7.4), and 10% glycerol. The elution buffer was exchanged for 50% glycerol, 50 mM Tris (pH 7.6), 100 mM NaCl, 1 mM DTT, 1 mM EDTA with Amicon® Ultra-15 10 K Device (Merck Millipore Ltd.), and enzyme was flash frozen in liquid nitrogen and stored at −80° C.

DncV protein sequence including GB1-tag, His-tag and TEV cleavage site (SEQ ID NO: 11)
MNSSHHHHHHMQYKLILNGKTLKGETTTEAVDAATAEKVLKQYANDNGVD

GEWTYDDATKTFTVTENNNNNNNNNNNENLYFQGMRMTWNFHQYYTNRNDG

LMGKLVLTDEEKNNLKALRKIIRLRTRDVFEEAKGIAKAVKKSALTFEII

QEKVSTTQIKHLSDSEQREVAKLIYEMDDDARDEFLGLTPRFWTQGSFQY

DTLNRPFQPGQEMDIDDGTYMPMPIFESEPKIGHSLLILLVDASLKSLVA

ENHGWKFEAKQTCGRIKIEAEKTHIDVPMYAIPKDEFQKKQIALEANRSF

VKGAIFESYVADSITDDSETYELDSENVNLALREGDRKWINSDPKIVEDW

FNDSCIRIGKHLRKVCRFMKAWRDAQWDVGGPSSISLMAATVNILDSVAH

DASDLGETMKIIAKHLPSEFARGVESPDSTDEKPLFPPSYKHGPREMDIM

SKLERLPEILSSAESADSKSEALKKINMAFGNRVTNSELIVLAKALPAFA

QE

1 µmol of the appropriate nucleoside triphosphate and 1 µmol of 4'-phosphonomethoxynucleotide diphosphate 20a, 20b or 20c as described above were dissolved in 500 µl 50 mM HEPES buffer pH 8.0 containing 10 mM $MgCl_2$; 100 mM NaCl; 1 mM DTT; 2 and 2 µM Vibrio Cholerae dinucleotide cyclase (DncV/VCO179) and incubated at 37° C. overnight on a shaker. The reaction mixtures were spun 25,000 g for 20 minutes and supernatants were passed through 3,000 Da filter concentrator (cat. #88512, ThermoFisher, Waltham, USA). Triethyl ammonium bicarbonate buffer (TEAB, cat. #T7408, Sigma Aldrich, Czech Republic) was added to the flow through fractions to 0.1 M final concentration. The samples were then purified on semi-preparative C18 column (Luna 5 tm C18 250×10 mm) using 50 min gradient of 0-10% ACN in 0.1M TEAB (3 mL/min). TEAB was removed from the collected fractions by 3 cycles of evaporation/dissolving in 50% methanol and evaporates were dissolved in endotoxin free water (cat. #TMS-011-A, Merck Millipore, Prague, Czech Republic). The identification of CDNs was performed on Alliance HT chromatographic system (2795 separation module, 2996 PDA detector, Micromass ZQ mass detector, Waters, Milford, USA) using SeQuant ZIC-pHILIC column (cat #150461, 150×4.6 mm, 5 m polymer, Merck Millipore, Prague, Czech Republic) and 10 mM ammonium acetate buffer pH 7.0 with linear gradient of acetonitrile (90% to 50% in 20 min; flow 0.6 mL per minute). Negative ESI method was used for ionization; negatively charged and double-negatively charged ions of CDNs were detected.

BMB171 Diadenylate Cyclase

A recombinant codon optimized cDNA encoding diadenylate cyclase BMB171 from *Bacillus* sp. was chemically synthesized and cloned between NcoI and XhoI sites of vector pET-28b(+) by GenScript (Piscataway, N.J.). The protein was overexpressed in *E. coli* BL21 (DE3) (ThermoFisher, Waltham, USA). Bacterial pellet was re-suspended in ice-cold lysis buffer containing 20 mM Phosphate Na buffer (pH 7.4), 500 mM NaCl, 10% glycerol, and 20 mM imidazol using Dounce homogenizer. DNase I and RNase A were added (final concentration 50 µg/ml) together with $MgCl_2$ (final concentration 5 mM) to the homogenate and bacteria were lysed using MSE Soniprep 150 (3 mm Tip Solid Titanium Exponential Probe, 2 min, 50% power, amplitude 12 microns). The lysate was spun 30,000×g for 20 minutes and supernatant was loaded onto 5 mL HisTrap column (GE Healthcare BioSciences, Pittsburgh, USA). The resin was washed with 50 ml lysis buffer and 50 ml wash buffer (20 mM Phosphate Na buffer (pH 7.4), 500 mM NaCl, 10% glycerol, and 125 mM imidazol) and BMB171 was eluted with 15 ml 20 mM Na-Phosphate buffer (pH7.4) buffer containing 500 mM NaCl; 10% glycerol, and 300 mM imidazol. The protein was further purified by size exclusion chromatography using HiLoad 16/60 Superdex 75 in buffer containing 150 mM NaCl; 50 mM Tris (pH 7.4), and 10% glycerol. The protein buffer was exchanged for 50% glycerol, 50 mM Tris (pH 7.6), 100 mM NaCl, 1 mM DTT, 1 mM EDTA with Amicon® Ultra-15 10 K Device (Merck Millipore Ltd.), and BMB171 was flash frozen in liquid $N_2$.

BMB171 amino acid sequence including C-terminal His-tag (SEQ ID NO: 12)
MEENKQRVKSMINILQLVAPGTPLREGIDNVLRAQTGGLIVLGYNEQIKS

IVDGGFHINCAFSPASLYELAKMDGALILNETGSKILIANAQLVPDSSID

SIETGMRHRTAERVAKQTGSLVVAISQRRNVITLYQGNLRYTLKDIGVIL

TKANQAIQTLEKYKAVWNDGITNLGILEFEEVVTMSEVVHVLHSVEMVLR

IKNEILSYIHELGTEGRLIRLQLTELLADLEAEAALLIKDYHQEKTQDHH

QILKKLQDLANTQLLEDSDLVKLLGYPGQTSLEESVTPRGYRITSKISRV

PPLIIENLINRFKTLQGVCRATINELDDVEGIGEVRAKKIREGLKRIQEH

LYMSRHNLEHHHHHH.

Alternative Enzymatic Preparation of CDNs

2 µmol of the appropriate nucleoside triphosphate and 2 µmol of 4'-phosphonomethoxynucleotide diphosphate 20b as described above were dissolved in 500 µl 50 mM HEPES K buffer containing pH 8.0, 10 mM $MgCl_2$, 100 mM NaCl, 1 mM DTT, 20 µM BMB171 Diadenylate Cyclase and incubated at 50° C. overnight on a shaker. The reaction mixtures were spun 25,000 g for 20 minutes and supernatants were passed through 3,000 Da filter concentrator (cat. #88512, ThermoFisher, Waltham, USA). Triethyl ammonium bicarbonate buffer (TEAB, cat. #T7408, Sigma Aldrich, Czech Republic) was added to the flow through fractions to 0.1 M final concentration. The samples were then purified on semipreparative C18 column (Luna 5 m C18 250×10 mm) using 50 min gradient of 0-10% ACN in 0.1M TEAB (3 mL/min). TEAB was removed from the collected fractions by 3 cycles of evaporation/dissolving in 50% methanol and evaporates were dissolved in endotoxin free water (cat. #TMS-011-A, Merck Millipore, Prague, Czech Republic). The identification of CDNs was performed on Alliance HT chromatographic system (2795 separation module, 2996 PDA detector, Micromass ZQ mass detector, Waters, Milford, USA) using SeQuant ZIC-pHILIC column (cat #150461, 150×4.6 mm, 5 μm polymer, Merck Millipore, Prague, Czech Republic) and 10 mM ammonium acetate buffer pH 7.0 with linear gradient of acetonitrile (90% to 50% in 20 min; flow 0.6 mL per minute). Negative ESI method was used for ionization; negatively charged and double-negatively charged ions of CDNs were detected.

Example 5. Compound 31: (2R,3R,3aS,7aR,9R,10R,10aS,14aR)-2,9-bis(6-amino-9H-purin-9-yl)-3,5,10,12-tetrahydroxydecahydrodifuro[2,3-e:2',3'-k][1,4,7,10]tetraoxa[2,8]diphosphacyclododecine 5,12-dioxide

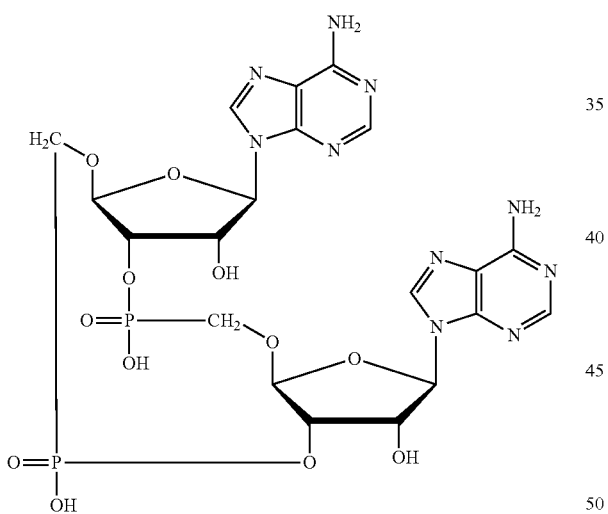

The titled compound was prepared according to Scheme 3 described above. HRMS (M-H)⁻ for $C_{20}H_{23}O_{12}N_{10}P_2$ calculated: 657.1; measured: 657.1.

¹H NMR (D₂O) δ 8.30 (s, 2H), 8.19 (s, 2H), 6.19 (d, J=4.1 Hz, 2H), 5.41 (d, J=2.6 Hz, 2H), 4.84 (ddd, J=9.1, 4.6, 2.6 Hz, 2H), 4.82 (dd, J=4.9, 4.1 Hz, 2H), 3.95 (dd, J=13.6, 5.7 Hz, 2H), 3.78 (dd, J=13.6, 11.5 Hz, 2H); ³¹P NMR (D₂O) δ 16.64.

¹³C NMR (D₂O) δ 155.1, 152.4, 148.5, 139.7, 118.6, 108.7, 88.0, 77.8, 73.2, 64.8.

Example 6. Compound 32: (2R,3R,3aS,7aR,9R,10R,10aS,14aR)-2,9-bis(6-amino-9H-purin-9-yl)-3,5,10,12-tetrahydroxydecahydrodifuro[3,2-d:3',2'-i][1,3,6,9]tetraoxa[2,8]diphosphacyclododecine 5,12-dioxide

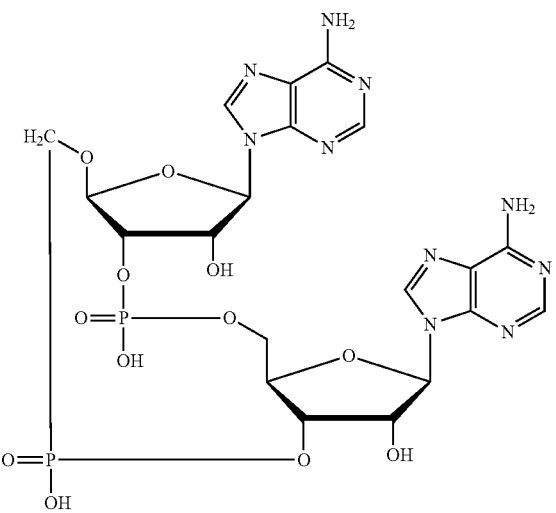

The titled compound was prepared according to the general protocol shown in Scheme 3 above. ESI-MS (M-H)⁻ for $C_{20}H_{23}O_{12}N_{10}P_2$ calculated: 657.1; measured: 657.1.

Example 7. Compound 33: (2R,3R,3aS,7aR,9R,10R,10aR,14aR)-2,9-bis(6-amino-9H-purin-9-yl)-10-fluoro-3,5,12-trihydroxydecahydrodifuro[3,2-d:3',2'-i][1,3,6,9]tetraoxa[2,8]diphosphacyclododecine 5,12-dioxide

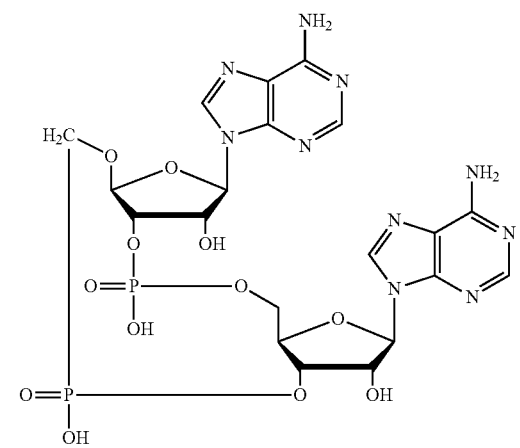

The titled compound was prepared according to the general protocol shown in Scheme 3 above. ESI-MS (M-H)⁻ for $C_{20}H_{22}FO_{11}N_{10}P_2$ calculated: 659.1; measured: 659.1.

¹H NMR (D₂O) δ 8.41 (s, 1H), 8.30 (s, 1H), 8.26 (s, 1H), 8.255 (s, 1H), 6.47 (d, J=17.2 Hz, 1H), 6.26 (d, J=1.6 Hz, 1H), 5.53 (d, J=4.2 Hz, 1H), 5.45 (dd, J=51.7, 4.4 Hz, 1H), 5.20 (dddd, J=22.5, 9.0, 5.8, 4.4 Hz, 1H), 4.77 (dd, J=4.9, 1.6 Hz, 1H), 4.75 (ddd, J=11.1, 4.9, 4.2 Hz, 2H), 4.51 (m, 1H), 4.42 (dt, J=12.0, 2.1 Hz, 1H), 4.17 (ddd, J=12.0, 2.8, 0.9 Hz, 1H), 4.10 (dd, J=12.8, 6.5 Hz, 1H), 3.91 (dd, J=12.8, 12.4 Hz, 1H); ³¹P NMR (D₂O) δ 16.67, 0.35.

Example 8. Compound 34: (2R,3R,3aS,7aR,9R,10R,10aR,15aR)-2,9-bis(6-amino-9H-purin-9-yl)-10-fluoro-3,5,12-trihydroxydecahydro-2H-difuro[2,3-e:2',3'-l][1,3,7,10]tetraoxa[2,8]diphosphacyclotridecine 5,12-dioxide

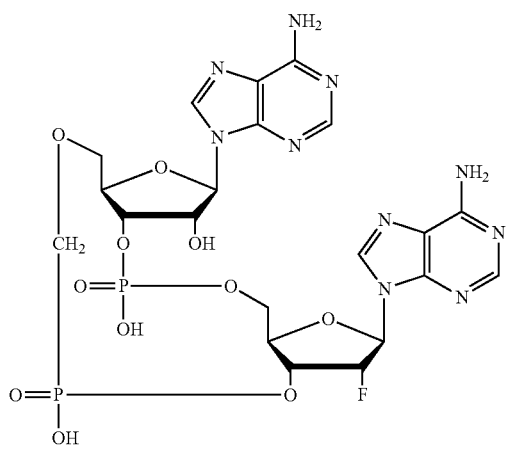

Compound 34 was prepared according to the protocol described in Scheme 4 above. ESI-MS (M-H)⁻ for $C_{21}H_{24}FO_{11}N_{10}P_2$ calculated: 673.1; measured: 673.1.

Example 9. Compound 35: 2-amino-9-((2R,3R,3aS,7aR,9R,10R,10aR,15aR)-9-(6-amino-9H-purin-9-yl)-10-fluoro-3,5,12-trihydroxy-5,12-dioxidodecahydro-2H-difuro[2,3-e:2',3'-l][1,3,7,10]tetraoxa[2,8]diphosphacyclotridecin-2-yl)-1,9-dihydro-6H-purin-6-one

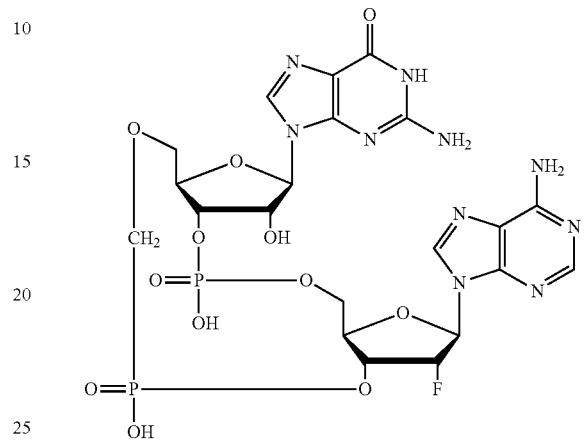

Compound 34 was prepared according to the protocol described in Scheme 4 above. ESI-MS (M-H)⁻ for $C_{21}H_{24}FO_{12}N_{10}P_2$ calculated: 689.1; measured: 689.1.

Example 10. Compounds 36-54

The following compounds were synthesized according to the general protocols described above. Solid phase synthesis protocols of Examples 3 and 4 were used unless otherwise indicated. Compounds 45 and 54 were prepared according to the enzymatic 3'3'-CDN preparation described in Example 4. Compounds 46-53 were prepared according to the alternative enzymatic CDN preparation described in Example 4.

| Compound | Structure/Name | (M − H)⁻ calc'd/found |
|---|---|---|
| 36 | 9,9'-((2R,3R,3aS,7aR,9R,10R,10aS,14aR)-3,5,10,12-tetrahydroxy-5,12-dioxidodecahydrodifuro[2,3-e:2',3'-k][1,4,7,10]tetraoxa[2,8]diphosphacyclododecine-2,9-diyl)bis(2-amino-1,9-dihydro-6H-purin-6-one) | 689.1/689.1 |

| Compound | Structure/Name | (M − H)⁻ calc'd/found |
|---|---|---|
| 37 | 2-amino-9-((2R,3R,3aS,7aR,9R,10R,10aS,14aR)-9-(6-amino-9H-purin-9-yl)-3,5,10,12-tetrahydroxy-5,12-dioxidodecahydrodifuro[3,2-d:3',2'-j][1,3,6,9]tetraoxa[2,8]diphosphacyclododecin-2-yl)-1,9-dihydro-6H-purin-6-one) | 673.1/673.1 |

37: $^1$H NMR (D$_2$O) δ 8.46 (s, 1H), 8.25 (s, 1H), 7.95 (s, 1H), 6.20 (d, J = 1.5 Hz, 1H), 6.04 (d, J = 1.7 Hz, 1H), 5.47 (d, J = 5.0 Hz, 1H), 5.10 (ddd, J = 8.5, 6.9, 4.8 Hz, 1H), 4.86 (dt, J = 11.5, 5.1 Hz, 1H), 4.72 (dd, J = 5.2, 1.7 Hz, 1H), 4.67 (dd, J = 4.8, 1.5 Hz, 1H), 4.46 (dddd, J = 8.5, 3.0, 2.7, 1.6 Hz, 1H), 4.37 (dd, J = 11.8, 2.7 Hz, 1H), 4.14 (ddd, J = 11.8, 2.6, 1.6 Hz, 1H), 4.06 (dd, J = 12.8, 7.0 Hz, 1H), 3.87 (t, J = 12.8 Hz, 1H); $^{31}$P NMR (D$_2$O) δ 16.73, 0.40.

| Compound | Structure/Name | (M − H)⁻ calc'd/found |
|---|---|---|
| 38 | 2-amino-9-((2R,3R,3aS,7aR,9R,10R,10aS,14aR)-9-(6-amino-9H-purin-9-yl)-3,5,10,12-tetrahydroxy-5,12-dioxidodecahydrodifuro[2,3-e:2',3'-k][1,4,7,10]tetraoxa[2,8]diphosphacyclododecin-2-yl)-1,9-dihydro-6H-purin-6-one | 673.1/673.1 |

38: $^1$H NMR (D$_2$O) δ 8.26 (s, 1H), 8.01 (s, 2H), 6.27 (d, J = 4.1 Hz, 1H), 6.07 (d, J = 4.6 Hz, 1H), 5.49 (d, J = 2.6 Hz, 1H), 5.44 (d, J = 2.4 Hz, 1H), 4.95 (ddd, J = 9.2, 5.0, 2.4 Hz, 1H), 4.92 (ddd, J = 9.1, 4.9, 2.6 Hz, 1H), 4.89 (dd, J = 4.9, 4.1 Hz, 1H), 4.88 (dd, J = 5.0, 4.6 Hz, 1H), 4.04 (dd, J = 13.6, 5.9 Hz, 1H), 4.01 (dd, J = 13.7, 5.4 Hz, 1H), 3.93 (dd, J = 13.7, 11.5 Hz, 1H), 3.86 (dd, J = 13.6, 11.5 Hz, 1H); $^{31}$P NMR (D$_2$O) δ 16.76, 16.53.

| Compound | Structure/Name | (M − H)⁻ calc'd/found |
|---|---|---|
| 39 | 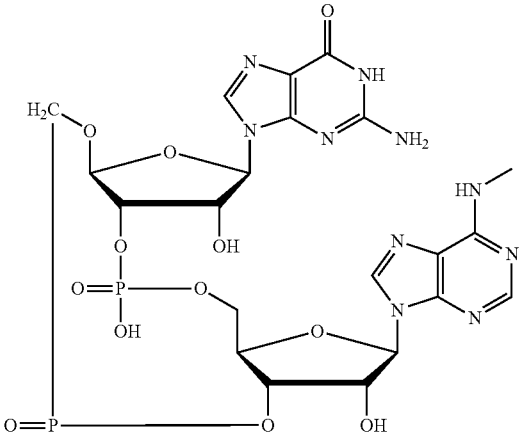<br>2-amino-9-((2R,3R,3aS,7aR,9R,10R,10aS,14aR)-3,5,10,12-tetrahydroxy-9-(6-(methylamino)-9H-purin-9-yl)-5,12-dioxidodecahydrodifuro[3,2-d:3′,2′-j][1,3,6,9]tetraoxa[2,8]diphosphacyclododecin-2-yl)-1,9-dihydro-6H-purin-6-one | 687.1/687.1 |

39: $^1$H NMR (D$_2$O) δ 8.41 (s, 1H), 8.26 (s, 1H), 7.95 (s, 1H), 6.19 (d, J = 1.4 Hz, 1H), 6.04 (d, J = 1.7 Hz, 1H), 5.46 (d, J = 5.1 Hz, 1H), 5.10 (ddd, J = 8.5, 6.9, 4.9 Hz, 1H), 4.85 (dt, J = 11.3, 5.1 Hz, 1H), 4.71 (dd, J = 5.1, 1.7 Hz, 1H), 4.66 (dd, J = 4.9, 1.4 Hz, 1H), 4.45 (dtd, J = 8.5, 3.0, 1.6 Hz, 1H), 4.37 (ddd, J = 11.8, 3.0, 2.7 Hz, 1H), 4.14 (ddd, J = 11.8, 3.0, 1.6 Hz, 1H), 4.06 (dd, J = 12.8, 7.1 Hz, 1H), 3.88 (t, J = 12.6 Hz, 1H); $^{31}$P NMR (D$_2$O) δ 16.67, 0.39.

| 40 | 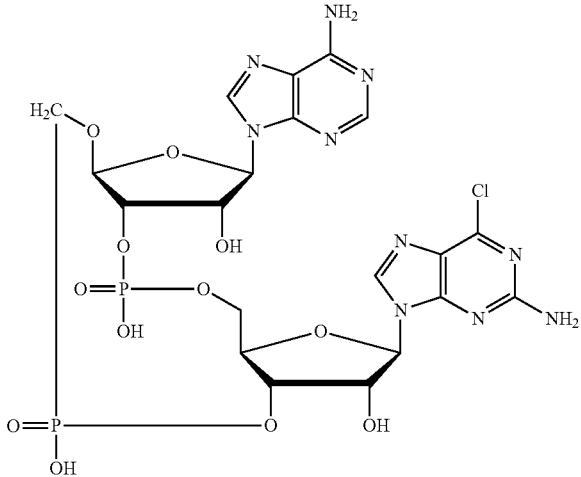<br>(2R,3R,3aS,7aR,9R,10R,10aS,14aR)-9-(2-amino-6-chloro-9H-purin-9-yl)-2-(6-amino-9H-purin-9-yl)-3,5,10,12-tetrahydroxydecahydrodifuro[3,2-d:3′,2′-j][1,3,6,9]tetraoxa[2,8]diphosphacyclododecine 5,12-dioxide | 691.1/691.1 |

| Compound | Structure/Name | (M − H)⁻ calc'd/found |
|---|---|---|
| 41 | 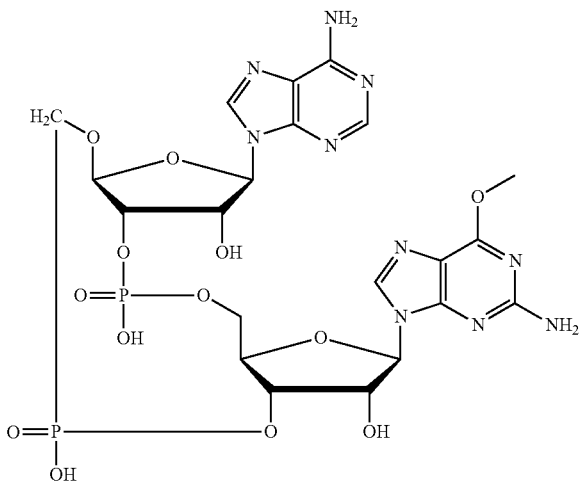<br>(2R,3R,3aS,7aR,9R,10R,10aS,14aR)-9-(2-amino-6-methoxy-9H-purin-9-yl)-2-(6-amino-9H-purin-9-yl)-3,5,10,12-tetrahydroxydecahydrodifuro[3,2-d:3′,2′-j][1,3,6,9]tetraoxa[2,8]diphosphacyclododecine 5,12-dioxide | 687.1/687.1 |
| 42 | 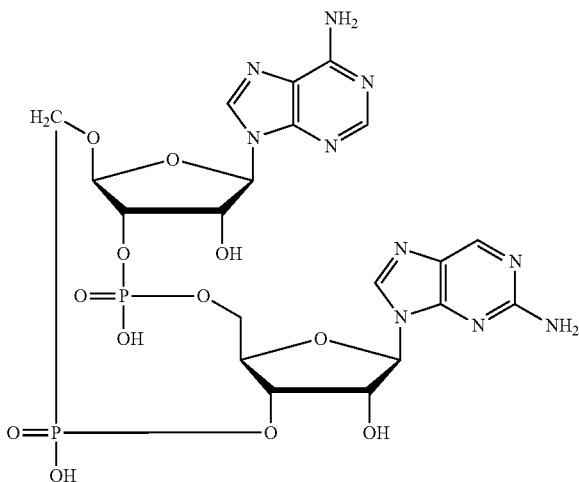<br>(2R,3R,3aS,7aR,9R,10R,10aS,14aR)-9-(2-amino-9H-purin-9-yl)-2-(6-amino-9H-purin-9-yl)-3,5,10,12-tetrahydroxydecahydrodifuro[3,2-d:3′,2′-j][1,3,6,9]tetraoxa[2,8]diphosphacyclododecine 5,12-dioxide | 657.1/657.1 |

| Compound | Structure/Name | (M − H)⁻ calc'd/found |
|---|---|---|
| 43 | 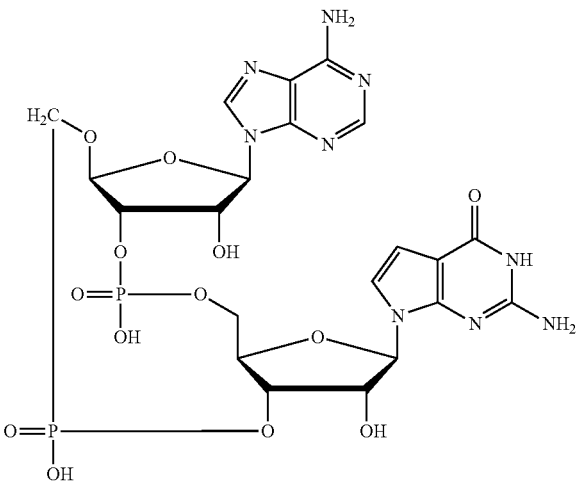<br>2-amino-7-((2R,3R,3aS,7aR,9R,10R,10aS,14aR)-2-(6-amino-9H-purin-9-yl)-3,5,10,12-tetrahydroxy-5,12-dioxidodecahydrodifuro[3,2-d:3',2'-j][1,3,6,9]tetraoxa[2,8]diphosphacyclododecin-9-yl)-3,7-dihydro-4H-pyrrolo[2,3-d]pyrimidin-4-one | 672.1/672.1 |
| 44 | 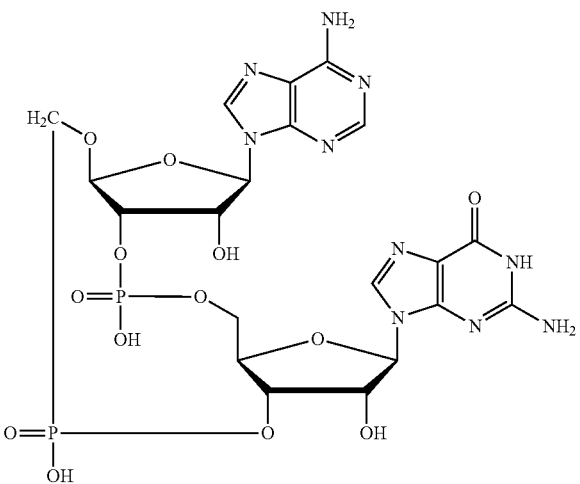<br>2-amino-9-((2R,3R,3aS,7aR,9R,10R,10aS,14aR)-2-(6-amino-9H-purin-9-yl)-3,5,10,12-tetrahydroxy-5,12-dioxidodecahydrodifuro[3,2-d:3',2'-j][1,3,6,9]tetraoxa[2,8]diphosphacyclododecin-9-yl)-1,9-dihydro-6H-purin-6-one | 673.1/673.1 |

44: $^1$H NMR (D$_2$O) δ 8.33 (s, 1H), 8.27 (s, 1H), 8.09 (s, 1H), 6.26 (br s, 1H), 5.99 (br s, 1H), 5.54 (d, J = 4.5 Hz, 1H), 5.12 (m, 1H), 4.76 (m, 1H), 4.74 (m, 1H), 4.68 (d, J = 4.0 Hz, 1H), 4.88 (dd, J = 5.0, 4.6 Hz, 1H), 4.41 (d, J = 7.5 Hz, 1H), 4.34 (d, J = 11.5 Hz, 1H), 4.12 (d, J = 11.5 Hz, 1H), 4.115 (t, J = 12.5 Hz, 1H), 3.91 (d, J = 12.5 Hz, 1H); $^{31}$P NMR (D$_2$O) δ 16.57, 0.47.

| Compound | Structure/Name | $(M-H)^-$ calc'd/found |
|---|---|---|
| 45 | (2R,3R,3aS,7aR,9R,10R,10aS,14aR)-9-(2-amino-6-(methylthio)-9H-purin-9-yl)-2-(6-amino-9H-purin-9-yl)-3,5,10,12-tetrahydroxydecahydrodifuro[3,2-d:3′,2′-j][1,3,6,9]tetraoxa[2,8]diphosphacyclododecine 5,12-dioxide | 703.1/703.1 |
| 46 | 5-amino-3-((2R,3R,3aS,7aR,9R,10R,10aS,14aR)-9-(6-amino-9H-purin-9-yl)-3,5,10,12-tetrahydroxy-5,12-dioxidodecahydrodifuro[2,3-e:2′,3′-k][1,4,7,10]tetraoxa[2,8]diphosphacyclododecin-2-yl)-3,6-dihydro-7H-[1,2,3]triazolo[4,5-d]pyrimidin-7-one | 689.1/689.1 |

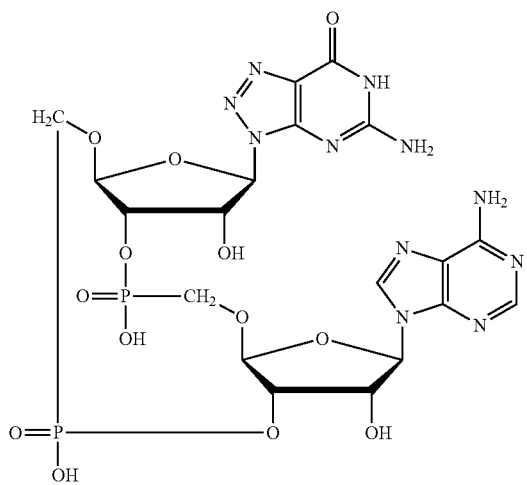

46: $^1$H NMR (D$_2$O) δ 8.38 (s, 1H), 8.27 (s, 1H), 6.28 (d, J = 3.5 Hz, 1H), 6.26 (d, J = 4.1 Hz, 1H), 5.46 (dd, J = 2.8, 1.9 Hz, 2H), 5.21 (ddd, J = 9.1, 5.0, 2.8 Hz, 1H), 5.19 (dd, J = 5.0, 3.5 Hz, 1H), 4.92 (m, 1H), 4.90 (m, 1H), 4.02 (dd, J = 13.7, 5.4 Hz, 1H), 3.87 (dd, J = 13.5, 5.6 Hz, 1H), 3.85 (dd, J = 13.7, 11.2 Hz, 1H), 3.74 (dd, J = 13.5, 11.8 Hz, 1H); $^{31}$P NMR (D$_2$O) δ 16.92, 16.63.

| Compound | Structure/Name | (M − H)⁻ calc'd/found |
|---|---|---|
| 47 | 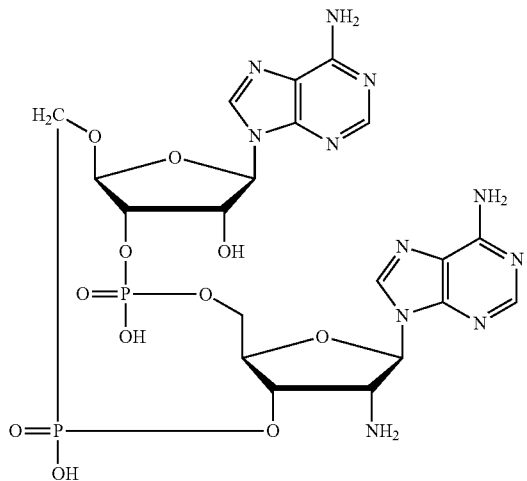 (2R,3R,3aS,7aR,9R,10R,10aS,14aR)-10-amino-2,9-bis(6-amino-9H-purin-9-yl)-3,5,12-trihydroxydecahydrodifuro[3,2-d:3',2'-j][1,3,6,9]tetraoxa[2,8]diphosphacyclododecine 5,12-dioxide | 656.1/656.1 |

47: $^1$H NMR (D$_2$O) δ 8.46 (s, 1H), 8.33 (s, 1H), 8.25 (s, 2H), 6.27 (d, J = 1.5 Hz, 1H), 6.05 (d, J = 4.4 Hz, 1H), 5.55 (d, J = 4.9 Hz, 1H), 5.15 (td, J = 7.5, 6.2 Hz, 1H), 4.78 (m, 1H), 4.73 (dd, J = 4.9, 1.5 Hz, 1H), 4.46 (ddt, J = 6.4, 3.5, 2.5 Hz, 1H), 4.23 (dt, J = 11.7, 3.8 Hz, 1H), 4.14 (m, 2H), 4.10 (dd, J = 6.1, 4.4 Hz, 1H), 3.94 (t, J = 12.5 Hz, 1H); $^{31}$P NMR (D$_2$O) δ 16.36, 0.45.

| Compound | Structure/Name | (M − H)⁻ calc'd/found |
|---|---|---|
| 48 | 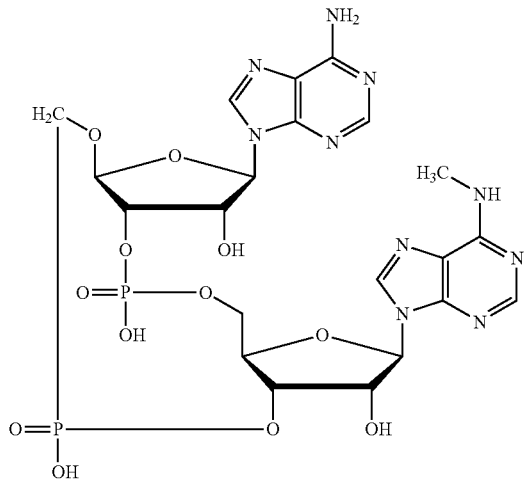 (2R,3R,3aS,7aR,9R,10R,10aS,14aR)-2-(6-amino-9H-purin-9-yl)-3,5,10,12-tetrahydroxy-9-(6-(methylamino)-9H-purin-9-yl)decahydrodifuro[3,2-d:3',2'-j][1,3,6,9]tetraoxa[2,8]diphosphacyclododecine 5,12-dioxide | 671.1/671.1 |

48: $^1$H NMR (D$_2$O) δ 8.41 (s, 1H), 8.29 (s, 1H), 8.26 (s, 1H), 8.24 (s, 1H), 6.25 (d J = 1.0 Hz, 1H), 6.19 (d, J = 1.5 Hz, 1H), 5.54 (d, J = 4.7 Hz, 1H), 5.12 (ddd, J = 8.6, 6.8, 4.8 Hz, 1H), 4.74 (m, 1H), 4.72 (m, 1H), 4.67 (dd, J = 4.8, 1.5 Hz, 1H), 4.46 (ddt, J = 8.6, 3.0, 1.5 Hz, 1H), 4.38 (ddd, J = 11.8, 2.7 Hz, 1H), 4.15 (ddd, J = 11.8, 2.8, 1.5 Hz, 1H), 4.11 (dd, J = 12.6, 7.2 Hz, 1H), 3.93 (t, J = 12.6 Hz, 1H), 3.06 (s, 3H); $^{31}$P NMR (D$_2$O) δ 16.40, 0.36.

| Compound | Structure/Name | (M − H)⁻ calc'd/found |
|---|---|---|
| 49 | (2R,3R,3aS,7aR,9R,10R,10aS,14aR)-2,9-bis(6-amino-9H-purin-9-yl)-3,10,12-trihydroxy-5-mercaptodecahydrodifuro[3,2-d:3',2'-j][1,3,6,9]tetraoxa[2,8]diphosphacyclododecine 5,12-dioxide | 673.1/673.1 |

49: $^1$H NMR (D$_2$O) δ 8.63 (s, 1H), 8.30 (s, 1H), 8.25 (s, 1H), 8.23 (s, 1H), 6.26 (d J = 1.3 Hz, 1H), 6.20 (d, J = 1.3 Hz, 1H), 5.57 (d, J = 5.0 Hz, 1H), 5.12 (ddd, J = 8.4, 6.8, 4.6 Hz, 1H), 4.90 (q, J = 5.0 Hz, 1H), 4.78 (m, 1H), 4.67 (dd, J = 4.6, 1.3 Hz, 1H), 4.47 (ddd, J = 8.4, 3.3, 1.3 Hz, 1H), 4.43 (dt, J = 11.7, 3.3 Hz, 1H), 4.12 (m, 2H), 3.93 (t, J = 12.6 Hz, 1H); $^{31}$P NMR (D$_2$O) δ 58.41, 16.35.

| 50 | (2R,3R,3aS,7aR,9R,10R,10aS,14aR)-9-(4-amino-7H-pyrrolo[2,3-d]pyrimidin-7-yl)-2-(6-amino-9H-purin-9-yl)-3,5,10,12-tetrahydroxydecahydrodifuro[3,2-d:3',2'-j][1,3,6,9]tetraoxa[2,8]diphosphacyclododecine 5,12-dioxide | 656.1/656.1 |

50: $^1$H NMR (D$_2$O) δ 8.34 (s, 1H), 8.26 (s, 1H), 8.16 (s, 1H), 7.48 (d, J = 3.8 Hz, 1H), 6.62 (d, J = 3.8 Hz, 1H), 6.32 (d, J = 2.5 Hz, 1H), 6.27 (d, J = 1.6 Hz, 1H), 5.56 (d, J = 4.7 Hz, 1H), 5.15 (dt, J = 7.5, 5.3 Hz, 1H), 4.78 (m, 1H), 4.76 (m, 1H), 4.54 (dd, J = 5.3, 2.5 Hz, 1H), 4.39 (m, 1H), 4.29 (dt, J = 11.7, 3.0 Hz, 1H), 4.13 (ddd, J = 11.7, 3.8, 1.8 Hz, 1H), 4.125 (dd, J = 12.9, 6.8 Hz, 1H), 3.93 (dd, J = 12.9, 12.3 Hz, 1H); $^{31}$P NMR (D$_2$O) δ 16.53, 0.50.

| Compound | Structure/Name | (M − H)⁻ calc'd/found |
|---|---|---|
| 51 | 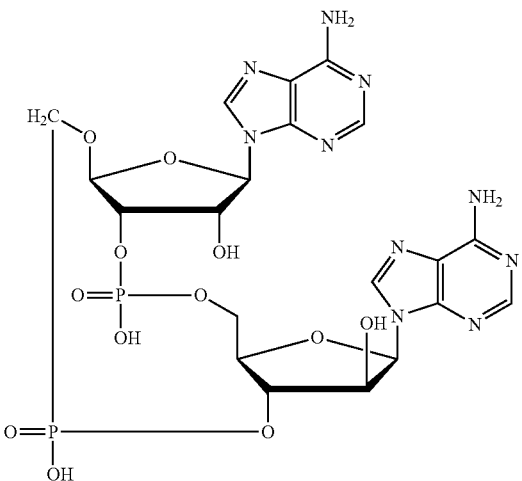<br>(2R,3R,3aS,7aR,9R,10S,10aS,14aR)-2,9-bis(6-amino-9H-purin-9-yl)-3,5,10,12-tetrahydroxydecahydrodifuro[3,2-d:3',2'-j][1,3,6,9]tetraoxa[2,8]diphosphacyclododecine 5,12-dioxide | 657.1/657.1 |

51: $^1$H NMR (D$_2$O) δ 8.46 (s, 1H), 8.30 (s, 1H), 8.26 (s, 1H), 8.24 (s, 1H), 6.50 (d J = 6.0 Hz, 1H), 6.26 (d, J = 1.8 Hz, 1H), 5.55 (d, J = 4.5 Hz, 1H), 5.12 (q, J = 6.5 Hz, 1H), 4.81 (m, 1H), 4.78 (m, 1H), 4.76 (m, 1H), 4.35 (ddt, J = 6.9, 3.5, 2.4 Hz, 1H), 4.29 (dt, J = 11.6, 3.3 Hz, 1H), 4.18 (ddd, J = 11.6, 3.5, 2.2 Hz, 1H), 4.14 (dd, J = 12.9, 6.9 Hz, 1H), 3.93 (dd, J = 12.9, 12.1 Hz, 1H); $^{31}$P NMR (D$_2$O) δ 16.92, 0.45.

| Compound | Structure/Name | (M − H)⁻ calc'd/found |
|---|---|---|
| 52 | 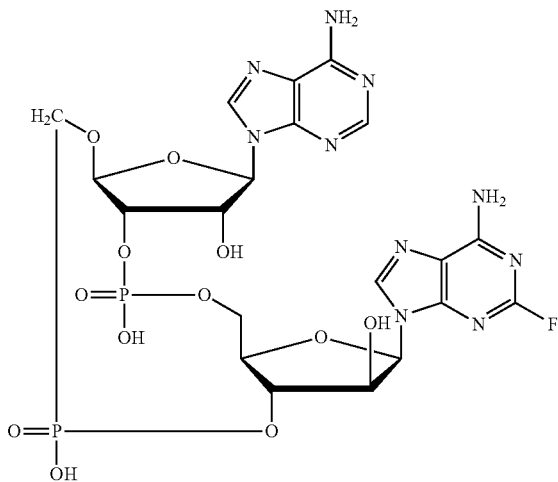<br>(2R,3R,3aS,7aR,9R,10S,10aS,14aR)-9-(6-amino-2-fluoro-9H-purin-9-yl)-2-(6-amino-9H-purin-9-yl)-3,5,10,12-tetrahydroxydecahydrodifuro[3,2-d:3',2'-j][1,3,6,9]tetraoxa[2,8]diphosphacyclododecine 5,12-dioxide | 675.1/675.1 |

52: $^1$H NMR (D$_2$O) δ 8.40 (s, 1H), 8.35 (s, 1H), 8.25 (s, 1H), 6.38 (d, J = 6.1 Hz, 1H), 6.28 (d, J = 1.6 Hz, 1H), 5.55 (d, J = 4.4 Hz, 1H), 5.12 (dt, J = 7.4, 6.2 Hz, 1H), 4.80 (m, 1H), 4.78 (m, 1H), 4.75 (m, 1H), 4.34 (ddt, J = 7.4, 3.2, 2.3 Hz, 1H), 4.29 (dt, J = 11.6, 3.3 Hz, 1H), 4.18 (ddd, J = 11.6, 3.3, 2.1 Hz, 1H), 4.15 (dd, J = 12.8, 7.0 Hz, 1H), 3.93 (dd, J = 12.8, 12.2 Hz, 1H); $^{31}$P NMR (D$_2$O) δ 16.95, 0.45.

| Compound | Structure/Name | (M − H)⁻ calc'd/found |
|---|---|---|
| 53 | 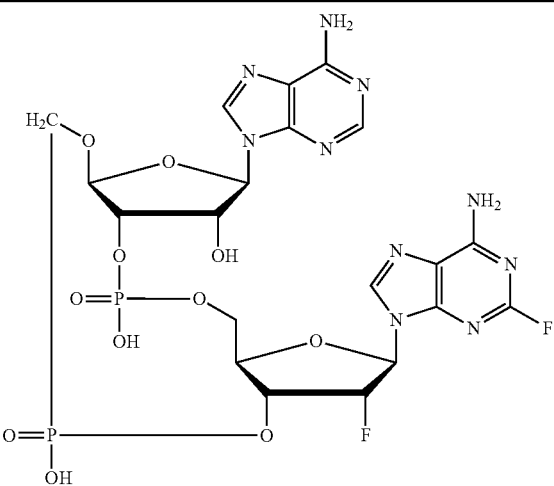<br>(2R,3R,3aS,7aR,9R,10R,10aR,14aR)-9-(6-amino-2-fluoro-9H-purin-9-yl)-2-(6-amino-9H-purin-9-yl)-10-fluoro-3,5,12-trihydroxydecahydrodifuro[3,2-d:3',2'-j][1,3,6,9]tetraoxa[2,8]diphosphacyclododecine 5,12-dioxide<br>53: $^1$H NMR (D$_2$O) δ 8.37 (s, 1H), 8.31 (s, 1H), 8.22 (s, 1H), 6.38 (d, J = 16.6 Hz, 1H), 6.27 (d, J = 1.6 Hz, 1H), 5.55 (d, J = 4.7 Hz, 1H), 5.43 (dd, J = 51.6, 4.2 Hz, 1H), 5.22 (dddd, J = 9.4, 3.5, 2.1, 1.0 Hz, 1H), 4.78 (m, 1H), 4.74 (m, 1H), 4.51 (dddd, J = 9.4, 3.5, 2.1, 1.0 Hz, 1H), 4.42 (dt, J = 11.8, 2.1 Hz, 1H), 4.19 (ddd, J = 11.8, 2.8, 1.0 Hz, 1H), 4.15 (dd, J = 12.8, 6.9 Hz, 1H), 3.95 (t, J = 12.8 Hz, 1H); $^{31}$P NMR (D$_2$O) δ 16.59, 0.34; $^{19}$F NMR (D$_2$O) δ −198.3, −118.5. | 677.1/677.1 |
| 54 | 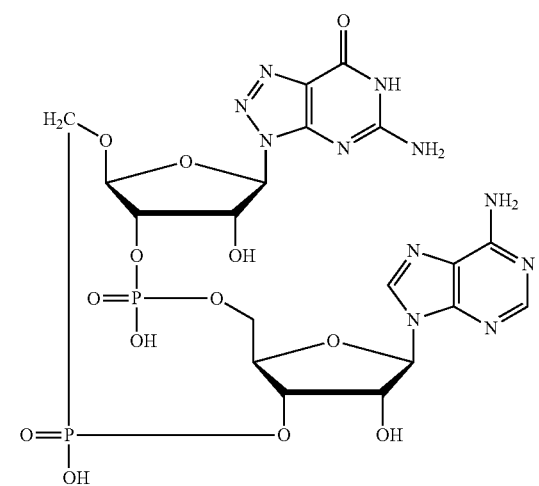<br>5-amino-3-((2R,3R,3aS,7aR,9R,10R,10aS,14aR)-9-(6-amino-9H-purin-9-yl)-3,5,10,12-tetrahydroxy-5,12-dioxidodecahydrodifuro[3,2-d:3',2'-j][1,3,6,9]tetraoxa[2,8]diphosphacyclododecine-2-yl)-3,6-dihydro-7H-[1,2,3]triazolo[4,5-d]pyrimidin-7-one<br>54: $^1$H NMR (D$_2$O) δ 8.50 (s, 1H), 8.26 (s, 1H), 6.25 (d, J = 1.3 Hz, 1H), 6.20 (d, J = 1.5 Hz, 1H), 5.49 (d, J = 5.0 Hz, 1H), 5.24 (dt, J = 11.3, 5.1 Hz, 1H), 5.10 (ddd, J = 8.5, 7.0, 5.0 Hz, 1H), 4.96 (dd, J = 5.1, 1.3 Hz, 1H), 4.64 (dd, J = 5.0, 1.5 Hz, 1H), 4.44 (ddd, J = 8.5, 7.0, 2.7, 1.8 Hz, 1H), 4.37 (dt, J = 12.0, 2.7 Hz, 1H), 4.14 (ddd, J = 12.0, 2.7, 1.8 Hz, 1H), 3.87 (dd, J = 13.3, 6.8 Hz, 1H), 3.73 (dd, J = 13.3, 12.9 Hz, 1H); $^{31}$P NMR (D$_2$O) δ 16.88, 0.45. | 674.1/674.1 |

Example 11. Biological Evaluation

A cyclic dinucleotide was determined to be a STING agonist: (A) if it demonstrated binding to the AQ allelic form of human STING protein with thermal shift of >0.5° C. in the STING Differential Scanning Fluorimetry Assay (DSF), and (B) if it demonstrated STING activation through IRF-3 dependent expression of firefly luciferase reporter with $EC_{50} < 100$ μmol·l$^{-1}$.

ISRE Reporter Plasmid (pGL64.27-4×ISRE)

Two complementary oligonucleotides of the sequence AAAGATCTTGGAAAGTGAAACCTTG-GAAAACGAAACTGGACAAAGGGAAACTG CAGAAACTGAAACAAAGCTTAA (SEQ ID NO: 1) and TTAAGCTTTGTTTCAGTTTCTGCAGTTTCCCTTTG-TCCAGTTTCGTTTTCCAAGGTT TCACTTTCCAA-GATCTTT (SEQ ID NO:2) containing four interferon-sensitive response elements (ISRE) were synthesized by Sigma Aldrich (Czech Republic, Prague). The oligonucleotides were mixed in equal molar amounts, hybridized, and cleaved by restriction endonucleases HindIII (cat. #. R0104S, NEB, Ipswich, USA) and BglII (cat. #R0144S, NEB, Ipswich, USA). Ultimately, they were ligated into plasmid pGL4.27 (cat. #E6651, Promega, Madison, USA) linearized with the same enzymes. As result the sequence with four ISRE sites was placed upstream of the minimum promoter of firefly luciferase reporter gene.

293T wtSTING-FL Reporter Cells

293T cells (cat. #CRL-3216, ATCC, Manassas, USA) were seeded a day before transfection at density 125,000 cells per cm$^2$ onto poly-D-lysine (cat. #P6407, Sigma Aldrich, Czech Republic) coated six well plates in antibiotic free DMEM with high glucose (cat. #D5796, Sigma Aldrich, Czech Republic) supplemented with 10% heat inactivated FBS (cat. #S1520, Biowest, Riverside, USA). On the day of transfection, 2.5 μg of the plasmid pUNO1-hSTING-WT (cat. #punol-hstingwt, InvivoGen, San Diego, USA) encoding human wild type STING (WT STING) was diluted in 125 μL OptiMEM medium (cat. #31985062, ThermoFisher, Waltham, USA) and mixed with 125 μL of the same medium containing 12.5 μL of Lipofectamine 2000 (cat. #11668019, ThermoFisher, Waltham, USA). After 5 minutes incubation at room temperature (RT), 250 μL of the mixture was added dropwise to the cells in one well. Cells were incubated 36 hours at 37° C. with 5% CO$_2$, and then detached with 0.05% Trypsin and 0.22 g/L EDTA (both cat. #L0941, Biowest, Riverside, USA).

Transfected cells were seeded onto poly-D-lysine coated six well plates at density 50,000 cells per 1 cm$^2$ in DMEM medium with high glucose containing 10% heat inactivated FBS, 30 μg/mL blasticidin (cat. #ant-bl-05, InvivoGen, San Diego, USA), 0.06 mg/ml Penicillin G and 0.1 mg/ml Streptomycin Sulfate (both cat. #. L0018, Biowest, Riverside, USA). The medium was replenished every 3-4 days until visible colonies of cells resistant to blasticidin were formed.

Blasticidin resistant cells stably expressing WT STING were further transfected with pGL64.27-4×ISRE plasmid following the same procedure as described above. The transfected cells were selected for the resistance to 300 μg/mL hygromycin (cat. #. 10687010, ThermoFisher, Waltham, USA) in DMEM with high glucose containing 10% heat inactivated FBS, 30 μg/mL blasticidin, 0.06 mg/ml Penicillin G and 0.1 mg/ml Streptomycin Sulfate. Homogeneous culture of stably double transfected cells was prepared by limiting dilution of cells in 96 well plates and wells with cells were selected that originated from a single cell. These cells were expanded, and expression of WT STING was confirmed by western blot using monoclonal mouse anti STING antibodies (cat. #. MAB7169, 1:1000 dilution; 20 antibody cat. #. HAF007, 1:2000 dilution, both from R&D Systems, Minneapolis, USA), and by induction of firefly luciferase expression in the presence of 50 μM STING agonist 2'3' cGAMP (cat. #tlrl-nacga23, InvivoGen, San Diego, USA). Genomic DNA from the transfected cells was amplified with primers pUNO1_Seq_F (TGCTTGCT-CAACTCTACGTC) (SEQ ID NO:3) and pUNO1_Seq_R (GTGGTTTGTCCAAACTCATC) (SEQ ID NO:4) that were complementary to pUNO1 plasmid and the presence of WT STING gene in the transfected cells was confirmed by DNA sequencing.

Digitonin Assay Using 293T wtSTING-FL Reporter Cells

293T wtSTING-FL cells were seeded at density of 250,000 cells per cm$^2$ onto 96 well poly-D-lysine coated plates in 100 μl DMEM with high glucose supplemented with 10% heat inactivated FBS. The medium was removed next day and three fold serial dilutions of compounds in Digitonin buffer containing 50 mmol·l$^{-1}$ HEPES (cat. #H3375, Sigma Aldrich, Czech Republic) pH 7.0, 100 mmol·l$^{-1}$ KCl, 3 mmol·l$^{-1}$ MgCl$_2$, 0.1 mmol·l$^{-1}$ DTT (cat. #D0632, Sigma Aldrich, Czech Republic), 85 mmol·l$^{-1}$ Sucrose (cat. #S7903, Sigma Aldrich, Czech Republic), 0.2% BSA (cat. #A2153, Sigma Aldrich, Czech Republic), 1 mmol·l$^{-1}$ ATP (cat. #A1852, Sigma Aldrich, Czech Republic), 0.1 mmol·l$^{-1}$ GTP (cat. #G8877, Sigma Aldrich, Czech Republic), and 10 μg/mL Digitonin A (cat. #D141, Sigma Aldrich, Czech Republic) were added to the cells. The buffer was removed after 30 minutes incubation at 37° C. with 5% CO$_2$, the cells were washed once with 100 μl of cultivation medium, and 100 μl of medium was added to each well. The plates with cells were incubated for 5 hours at 37° C. with 5% CO$_2$, 50 μl of the medium was removed and 30 μl of ONE-Glo™ Luciferase Assay System reagent (cat. #E6120, Promega, Madison, USA) was added to each well. Luminescence was read on Synergy H1 (Biotek, Winooski, USA). GrafPad Prism (La Jolla, USA) was used to calculate the 50% effective concentration ($EC_{50}$) from an 8-point dose-response curve. Control compounds 3'3'-c-di-GMP (cat. #tlrl-nacdg), 3'3'-c-di-AMP (cat. #tlrl-nacda), 3'3'-cGAMP (cat. #tlrl-nacga), 2'3'-cGAMP (cat. #tlrl-nacga23), and 2'2'-cGAMP (cat. #tlrl-nacga22) were purchased from Invivogen (San Diego, USA).

WT STING and AQ STING Proteins

Both WT and AQ human STING (G230A-R293Q) cDNA were amplified by the use of PCR (Phusion® High-Fidelity DNA Polymerase, cat. #M0530S, NEB, Ipswich, USA) using oligonucleotides hSTING140-BamH-For (GTGG-GATCCGCCCCAGCTGAGATCTCTGCAG) (SEQ ID NO:5) and hSTING379-Not-Rev3 (TATGCGGCCGCCT-ATTACACAGTAACCTCTTCCTTTTC) (SEQ ID NO:6) from pUNO1-hSTING-WT (cat. #punol-hstingwt, Invivo-Gen, San Diego, USA) and pUNO1-hSTING-HAQ plasmids (punol-hsting-haq, InvivoGen, San Diego, USA). Purified PCR products were cleaved with restriction enzymes BamHI (cat. #R0136S, NEB, Ipswich, USA) and NotI (cat. #R0189S, NEB, Ipswich, USA) and cloned into the pSUMO vector linearized with the identical enzymes. Plasmid pSUMO was created by introducing 8-His-SUMO sequence between NdeI and BamHI sites of pHis-parallel2 plasmid (Clontech, Moutain View, USA). pSUMO-STING WT or pSUMO-STING AQ plasmids thus encoded truncated human WT STING or AQ STING (amino acid residues 140-343) with N-terminal 8×His and SUMO tag.

The recombinant WT STING and AQ STING proteins were overexpressed in Rosetta-gami B (DE3) competent cells (cat. #71136-3, Merck Millipore, Billerica, USA). Bacterial pellets were re-suspended in ice-cold lysis buffer containing 50 mmol·l$^{-1}$ TrisCl (cat. #T1503, Sigma Aldrich, Czech Republic) pH 8.0, 300 mmol·l$^{-1}$ NaCl, 3 mmol·l$^{-1}$ β-mercaptoethanol (cat. #M6250, Sigma Aldrich, Czech Republic), 10% glycerol (cat. #G5516, Sigma Aldrich, Czech Republic) and 20 mmol·l$^{-1}$ imidazole (cat. #15513, Sigma Aldrich, Czech Republic) using Dounce homogenizer. DNase I (cat. #D5025, Sigma Aldrich, Czech Republic) and RNase A (cat. #R6513, Sigma Aldrich, Czech Republic) were added (final concentration 50 µg/ml) together with MgCl$_2$ (final concentration 5 mmol·l$^{-1}$) to the homogenate and bacteria were lysed using French Press G-M™ High-Pressure Cell Press Homogenizer (1500 psi, 3 cycles). Lysate was spun 30,000 g for 20 minutes and supernatant was gently stirred with Ni-NTA resin (cat. #745400.25 Macherey-Nagel, Duren, Germany) for 30 minutes. The resin was poured into a chromatography column, washed with 50 ml buffer A (50 mmol·l$^{-1}$ TrisCl (pH 8.0), 800 mmol·l$^{-1}$ NaCl, 3 mmol·l$^{-1}$ 3-mercaptol; 10% glycerol; 20 mmol·l$^{-1}$ imidazole) and 8-His-SUMO tagged STING proteins were eluted with 15 ml buffer A containing 300 mmol·l$^{-1}$ imidazole. The eluted proteins were cleaved with recombinant SUMO protease (80 µg/ml of protein solution, cat. #12588018, ThermoFisher, Waltham, USA). The proteins were further purified by size exclusion chromatography using HiLoad 16/60 Superdex 75 (cat. #28989333, GE Healthcare Bio-Sciences, Pittsburgh, USA) in 50 mmol·l$^{-1}$ Tris Cl buffer pH 7.4 containing 150 mmol·l$^{-1}$ NaCl, and 10% glycerol. Proteins were concentrated with Amicon® Ultra-15 10 K device (cat. #UFC901008, Merck Millipore, Billerica, USA) and flash frozen in liquid N$_2$.

DNA sequence of 8-His-SUMO (SEQ ID NO: 7)
ATGTCGCATCACCATCATCATCACCACCATGGGATGTCGGACTCAGAAGT

CAATCAAGAAGCTAAGCCAGAGGTCAAGCCAGAAGTCAAGCCTGAGACTC

ACATCAATTTAAAGGTGTCCGATGGATCTTCAGAGATCTTCTTCAAGATC

AAAAAGACCACTCCTTTAAGAAGGCTGATGGAAGCGTTCGCTAAAAGACA

GGGTAAGGAAATGGACTCCTTAAGATTCTTGTACGACGGTATTAGAATTC

AAGCTGATCAGACCCCTGAAGATTTGGACATGGAGGATAACGATATTATT

GAGGCTCACCGCGAACAGATTGGTGGATCC.

Amino acid sequence of 8-His-SUMO (SEQ ID NO: 8)
MSHHHHHHHHGMSDSEVNQEAKPEVKPEVKPETHINLKVSDGSSEIFFKI

KKTTPLRRLMEAFAKRQGKEMDSLRFLYDGIRTQADQTPEDLDMEDNDIT

EAHREQIGGS.

Amino acid sequence of truncated WT STING (SEQ ID NO: 9)
APAEISAVCEKGNFNVAHGLAWSYYIGYLRLILPELQARIRTYNQHYNNL

LRGAVSQRLYILLPLDCGVPDNLSMADPNIRFLDKLPQQTGDRAGIKDRV

YSNSIYELLENGQRAGTCVLEYATPLQTLFAMSQYSQAGFSREDRLEQAK

LFCRTLEDILADAPESQNNCRLIAYQEPADDSSFSLSQEVLRHLRQEEKE

EVTV.

Amino acid sequence of truncated AQ STING (SEQ ID NO: 10)
APAEISAVCEKGNFNVAHGLAWSYYIGYLRLILPELQARIRTYNQHYNNL

LRGAVSQRLYILLPLDCGVPDNLSMADPNIRFLDKLPQQTADRAGIKDRV

YSNSIYELLENGQRAGTCVLEYATPLQTLFAMSQYSQAGFSREDRLEQAK

LFCQTLEDILADAPESQNNCRLIAYQEPADDSSFSLSQEVLRHLRQEEKE

EVTV.

Differential Scanning Fluorimetry (DSF) with WT STING and AQ STING

WT and AQ allelic forms of STING protein were diluted to the final concentration 0.1 mg/ml in 100 mmol·l$^{-1}$ TrisCl buffer pH 7.4 containing, 150 mmol·l$^{-1}$ NaCl, 1:500 SYPRO Orange (cat. #S6650, ThermoFisher, Waltham, USA) and 150 µM CDN or water. 20 µL solutions of the reaction mixtures were pipetted in triplicates into 96 well optical reaction plates and thermal denaturation of samples were performed on real time PCR cycler (LightCycler R 480 Instrument II—Roche, Basel, Switzerland). The first derivative of the thermal denaturation curves was performed to calculate denaturing temperatures of STING-CDN complexes and STING apoproteins. The thermal shift for each CDN was calculated by subtracting the average denaturing temperature of STING apoprotein from the average denaturing temperature of STING CDN complex.

TABLE 6

| | Biological Data | | |
|---|---|---|---|
| | DSF ΔTm (° C.) | | Digitonin assay EC$_{50}$ (µmol·l$^{-1}$) |
| Compound | WT STING | AQ STING | WT STING |
| 31 | 0.1 | 2.5 | 19.2 |
| 32 | 0.8 | 6.4 | 1.2 |
| 33 | 5.7 | 12.0 | 0.11 |
| 34 | 0.2 | 4.3 | 19.6 |
| 35 | 2.3 | 9.0 | 2.4 |
| 36 | 0.6 | 5.6 | 8.1 |
| 37 | 7.6 | 15.9 | 0.005 |
| 38 | 1.9 | 9.5 | 0.2 |
| 39 | 2.9 | 8 | 0.12 |
| 40 | 0.4 | 2.1 | 7.5 |
| 41 | 0.1 | 1.6 | 17.6 |
| 42 | 0.7 | 6.6 | 0.6 |
| 43 | 0.6 | 3.3 | 4.7 |
| 44 | 4.5 | 11.2 | 0.09 |
| 45 | 0 | 1.1 | 20.8 |
| 46 | 0.3 | 5.9 | 3.2 |
| 47 | 0.1 | 2.1 | 20.8 |
| 48 | 0.6 | 4.4 | 1.5 |
| 49 | 0.5 | 4.2 | 1.5 |
| 50 | 0.4 | 2.0 | 8.6 |
| 51 | 4.0 | 10.6 | 0.17 |
| 52 | 1.1 | 6.3 | 2.2 |
| 53 | 3.0 | 8.8 | 0.9 |
| 54 | 3.9 | 12.2 | 0.06 |
| 3'3'c-di-GMP | 2.6 | 7.7 | 5.8 |
| 3'3'c-di-AMP | 2.6 | 9.3 | 0.3 |
| 3'3'cGAMP | 5.1 | 13.3 | 0.16 |
| 2'2'-cGAMP | 11.5 | 19.4 | 0.03 |
| 2'3'-cGAMP | 15.2 | 22.7 | 0.03 |

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound of formula (J):

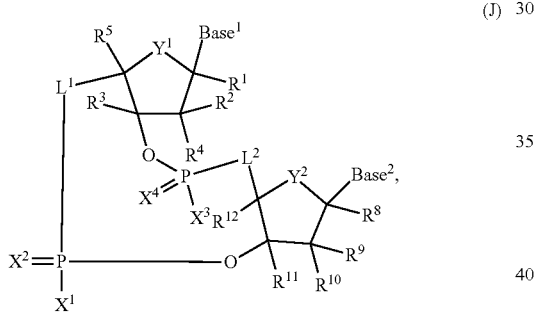

or pharmaceutically acceptable salt thereof, wherein $L^1$ is —C(R$^6$R$^7$)—O— and $L^2$ is —C(R$^{13}$R$^{14}$)—O—,
$L^1$ is —C(R$^6$R$^7$)—O— and $L^2$ is —O—C(R$^{13}$R$^{14}$)—,
$L^1$ is —O—C(R$^6$R$^7$)— and $L^2$ is —C(R$^{13}$R$^{14}$)—O—,
$L^1$ is —C(R$^6$R$^7$)—K$^1$—C(R$^6$R$^7$)— and $L^2$ is —O—C(R$^{13}$R$^{14}$)—,
$L^1$ is —O—C(R$^6$R$^7$)— and $L^2$ is —C(R$^{13}$R$^{14}$)—K$^1$—C(R$^{13}$R$^{14}$)—, $Y^1$ and $Y^2$ are each independently —O—, —S—, or —CH$_2$—;

$X^1$ and $X^3$ are each independently OH, SH, OR$^{15}$, SR$^{15}$, or N(R$^{15}$)$_2$;

$X^2$ and $X^4$ are each independently O or S;

$R^1$, $R^5$, $R^8$ and $R^{12}$ are each independently H, CN, N$_3$, F, Cl, Br, I, COOR$^{15}$, CON(R$^{15}$)$_2$, C$_1$-C$_6$ alkyl, C$_2$-C$_6$ alkenyl, C$_2$-C$_6$ alkynyl, OR$^{15}$, SR$^{15}$, or N(R$^{15}$)$_2$;

$R^2$, $R^3$, $R^4$, $R^9$, $R^{10}$ and $R^{11}$ are each independently H, OH, F, Cl, Br, I, CN, N$_3$, C$_1$-C$_6$ alkyl, C$_2$-C$_6$ alkenyl, C$_2$-C$_6$ alkynyl, OR$^{15}$, SR$^{15}$, or N(R$^{15}$)$_2$;

$R^6$, $R^7$, $R^{13}$ and $R^{14}$ are each independently H, CN, N$_3$, F, Cl, Br, I, COOR$^{15}$, CON(R$^{15}$)$_2$, OR$^{15}$, SR$^{15}$, N(R$^{15}$)$_2$, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_{10}$ heteroaryl;

each $R^{15}$ is independently H, —C(=Z)R$^{16}$, —C(=Z)OR$^{16}$, —C(=Z)SR$^{16}$, —C(=Z)N(R$^{16}$)$_2$, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_{10}$ heteroaryl;

each $R^{16}$ is independently H, C$_1$-C$_6$ alkyl, C$_2$-C$_6$ alkenyl, C$_2$-C$_6$ alkynyl, C$_3$-C$_7$ cycloalkyl, C$_2$-C$_{10}$ heterocycloalkyl, C$_6$-C$_{10}$ aryl, or C$_2$-C$_{10}$ heteroaryl;

each Z is independently O, S, or NR$^{15}$;

$K^1$ is a variable that represents —O—, —S—, —S(O)—, —S(O)$_2$—, —NH—, or —NR$^{15}$—;

Base$^1$ and Base$^1$ are each independently:

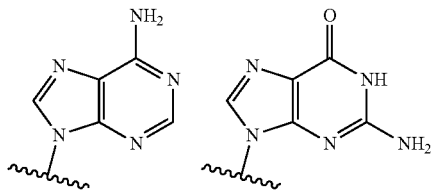

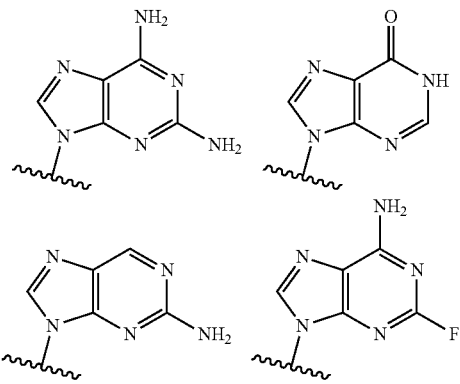

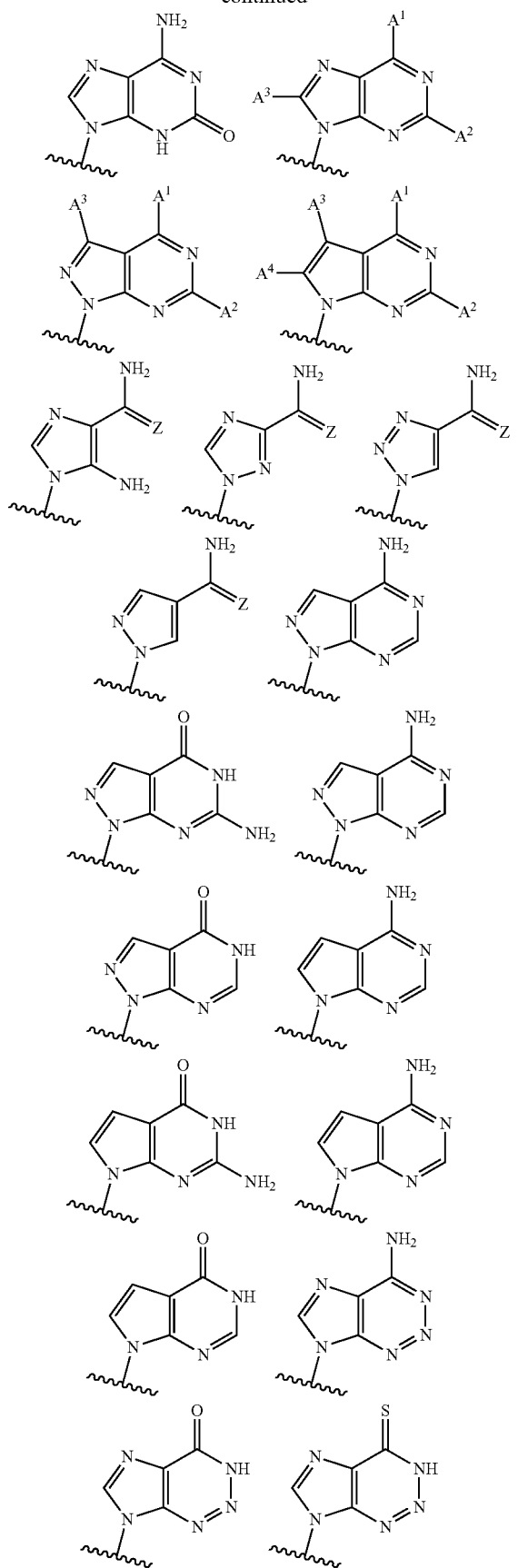
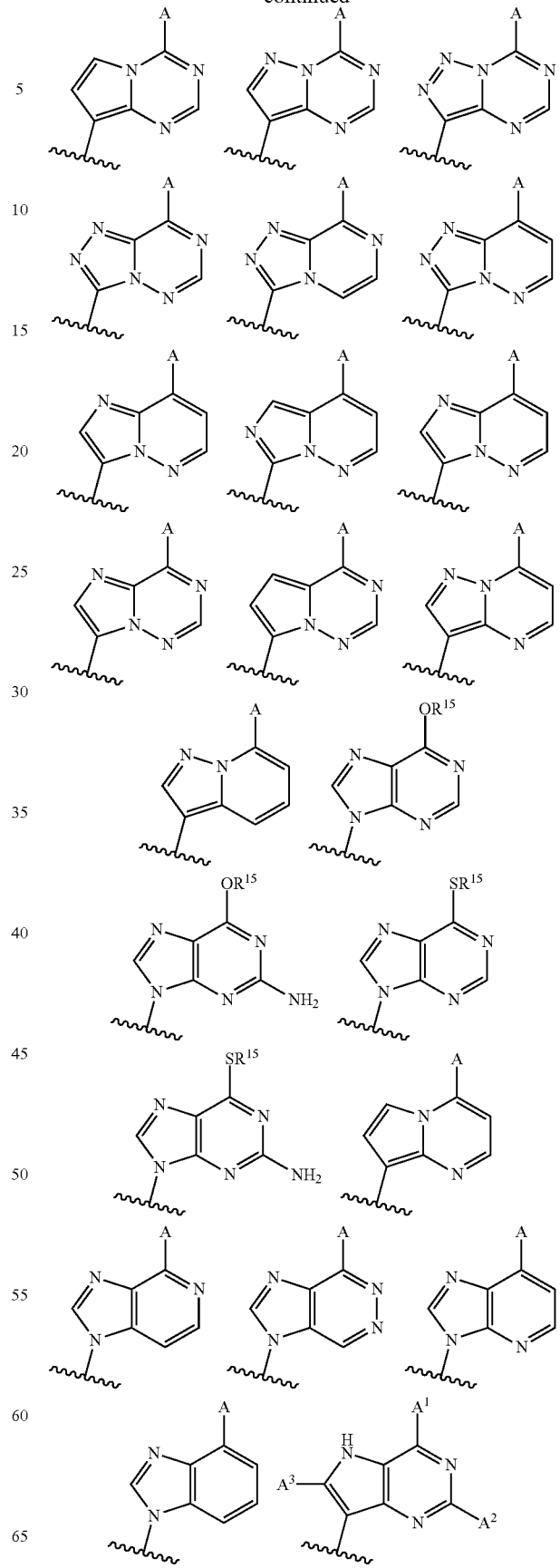

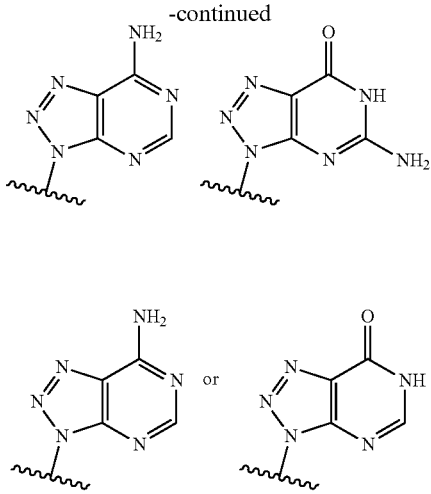

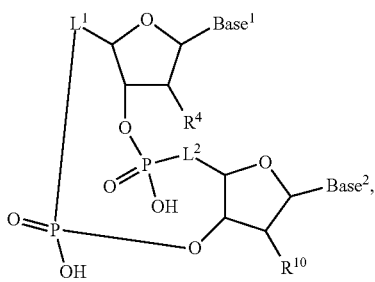

or pharmaceutically acceptable salt thereof.

5. The compound of claim 1 that has a structure of formula (Ia):

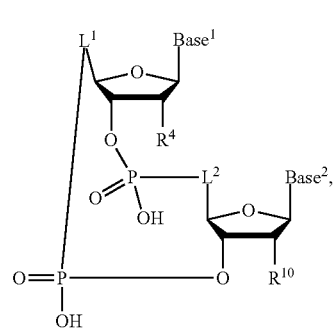

wherein

A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$; and wherein the $C_1$-$C_6$ alkyl, $C_2$-$C_6$ alkenyl, $C_2$-$C_6$ alkynyl, $C_2$-$C_{10}$ heterocycloalkyl, $C_6$-$C_{10}$ aryl, or $C_2$-$C_{10}$ heteroaryl independently in each instance is optionally substituted with 1, 2, or 3 —OH; —SH; —$NH_2$; =O; =NH; =S; halogen; —$N_3$; $C_6$-$C_{10}$ aryl optionally substituted with 1, 2, or 3 —OH, —CN, —O(C=O)$OR^B$, —O(C=O)$R^B$, or —COO$R^B$, unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino;

unsubstituted $C_1$-$C_6$ dialkylamino; —CN; —O(C=O)$OR^B$ —O(C=O)$R^B$; or —COO$R^B$; wherein $R^B$ is H or unsubstituted $C_1$-$C_6$ alkyl.

2. The compound of claim 1 that has a structure of formula (I):

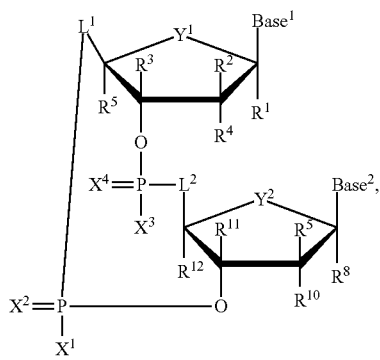

or pharmaceutically acceptable salt thereof.

3. The compound of claim 1 wherein $R^1$, $R^2$, $R^3$, $R^5$, $R^8$, $R^9$, $R^{11}$, and $R^{12}$ are each independently H, OH, F, CN, or $C_1$-$C_6$ alkyl.

4. The compound of claim 1 that has a structure of formula (IIa):

or pharmaceutically acceptable salt thereof.

6. The compound of claim 1, wherein $L^1$ is —C($R^6R^7$)—O— and $L^2$ is —O—C($R^{13}R^{14}$)—, $L^1$ is —C($R^6R^7$)—O— and $L^2$ is —C($R^{13}R^{14}$)—O—, or $L^1$ is —C($R^6R^7$)—$K^1$—C($R^6R^7$)— and $L^2$ is —O—C($R^{13}R^{14}$)—.

7. The compound of claim 1 that has a structure of formula (IIIa):

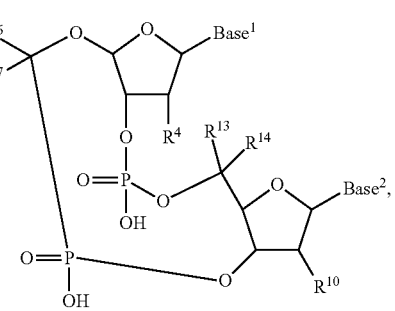

or pharmaceutically acceptable salt thereof.

8. The compound of claim 1 that has a structure of formula (IVa):

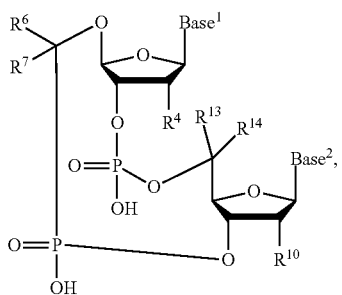

(IVa)

or pharmaceutically acceptable salt thereof.

9. The compound of claim 1 that has a structure of formula (IVb):

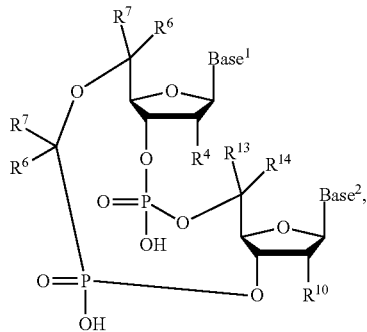

(IVb)

or pharmaceutically acceptable salt thereof.

10. The compound of claim 1 that has a structure of formula (IIIc):

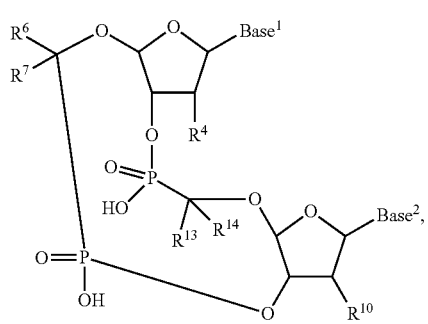

(IIIc)

or pharmaceutically acceptable salt thereof.

11. The compound of claim 1 that has a structure of formula (IVc):

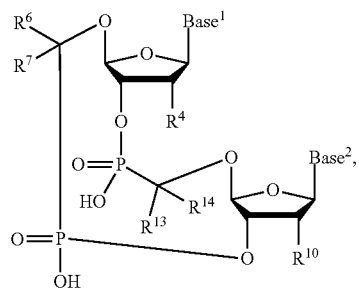

(IVc)

or pharmaceutically acceptable salt thereof.

12. The compound of claim 1, wherein $R^6$, $R^7$, $R^{13}$ and $R^{14}$ are each H.

13. The compound of claim 1, wherein $R^4$ and $R^{10}$ are each independently H, OH, or F.

14. The compound of claim 1, wherein Base$^1$ and Base$^2$ are each independently:

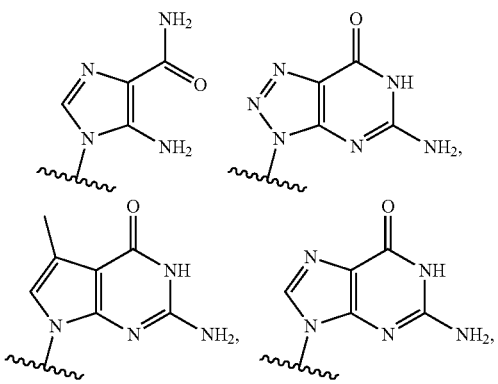

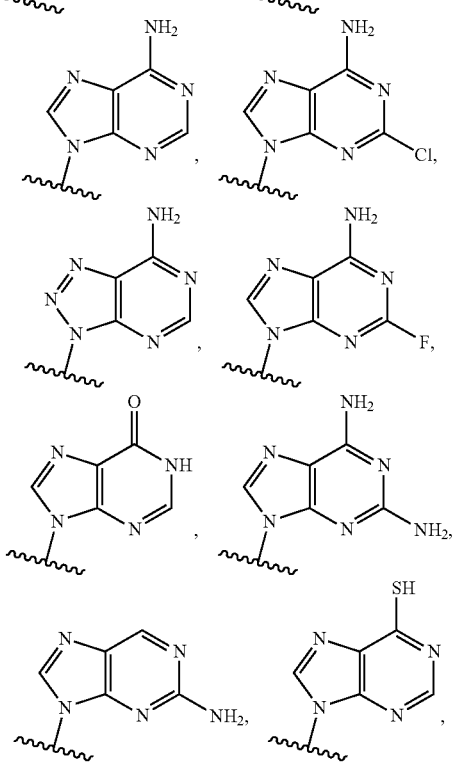

-continued
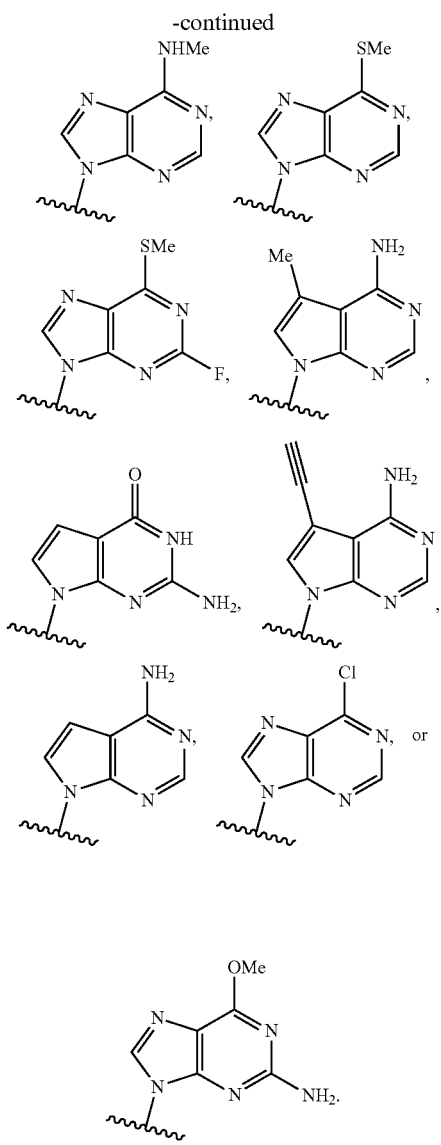
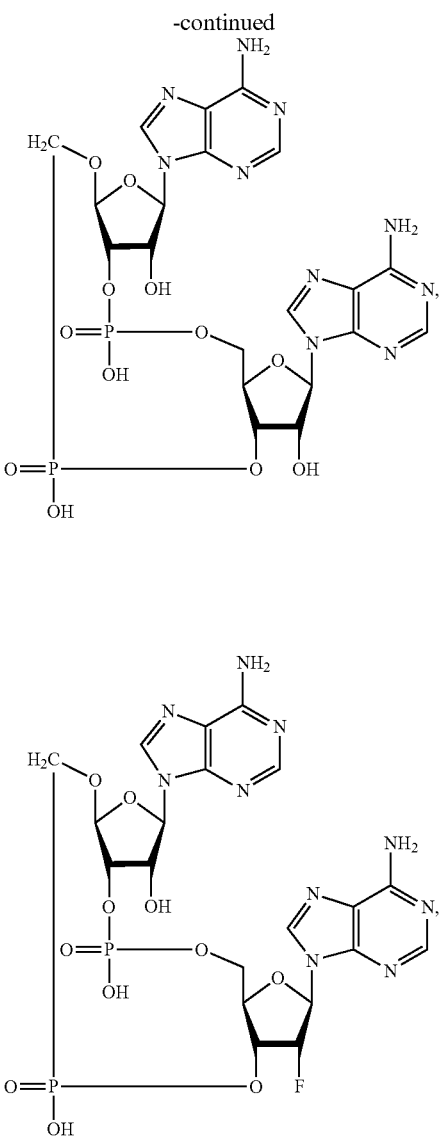
15. The compound of claim 1 that has a structure:
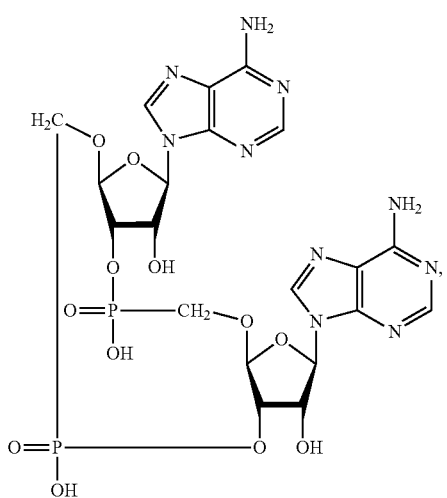
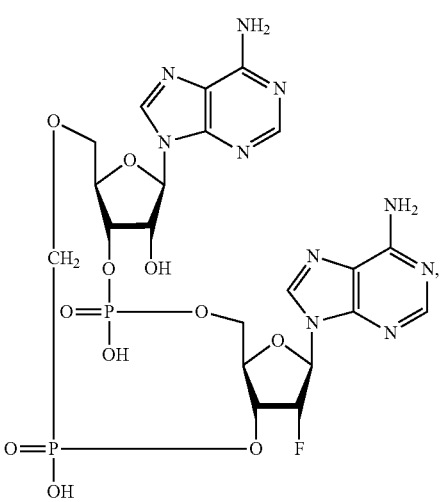

-continued
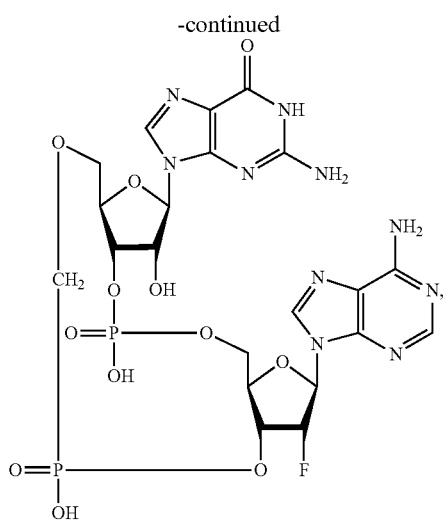
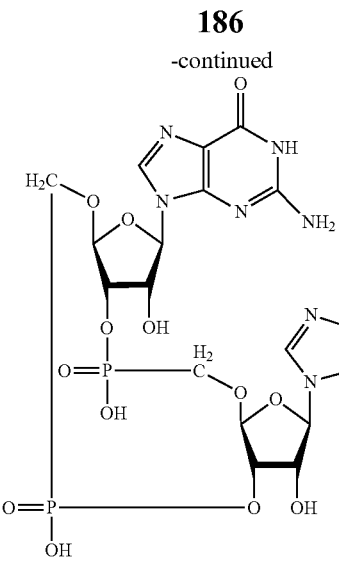
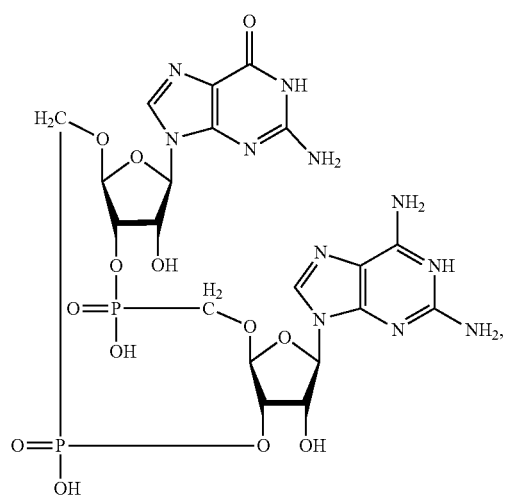
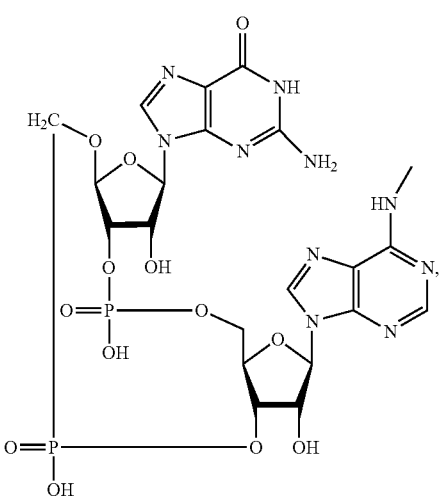
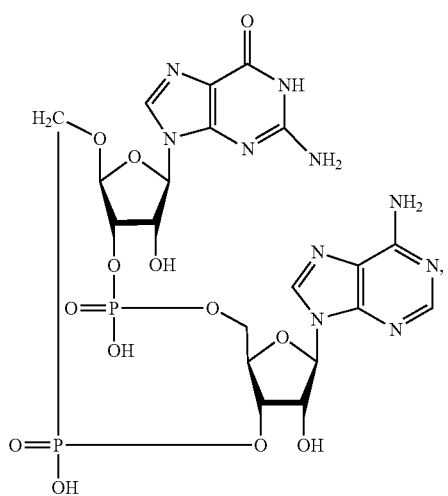
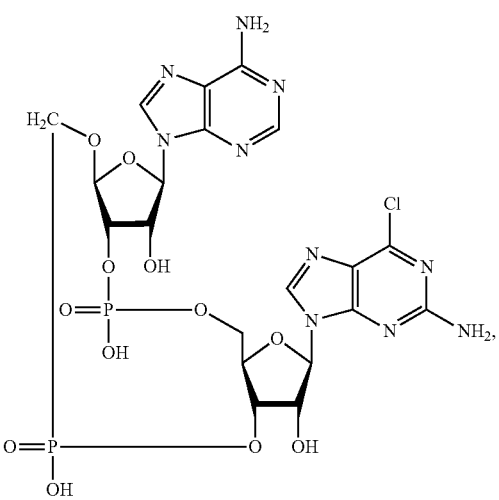

187
-continued
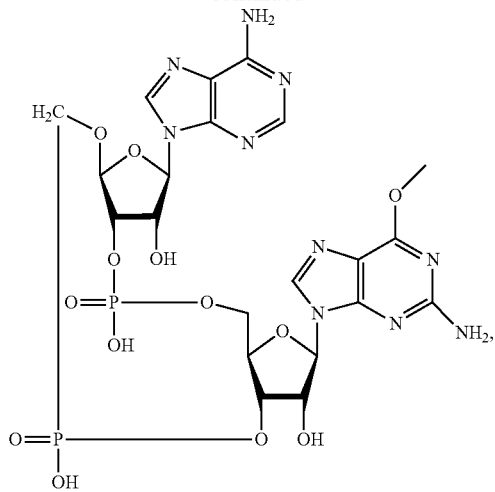
188
-continued
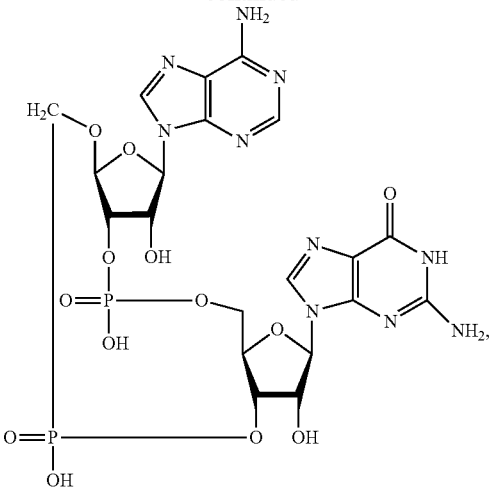
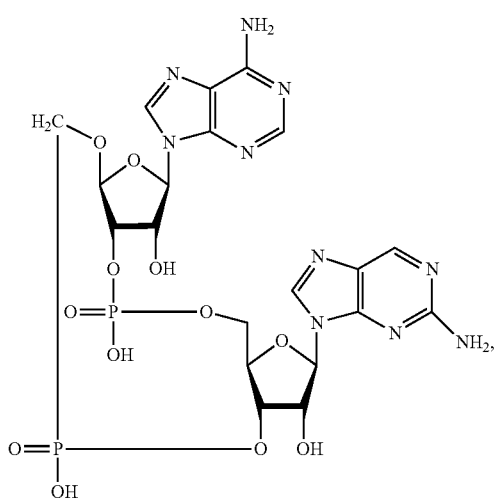
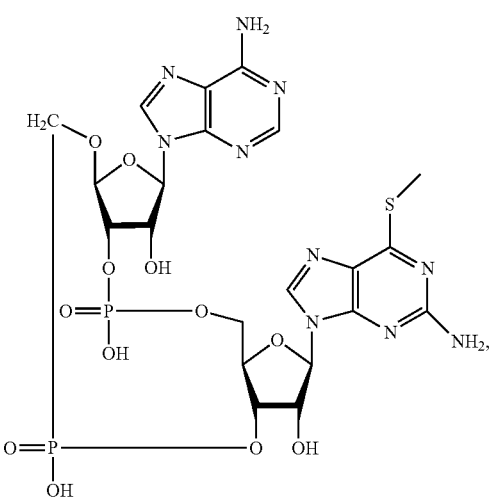
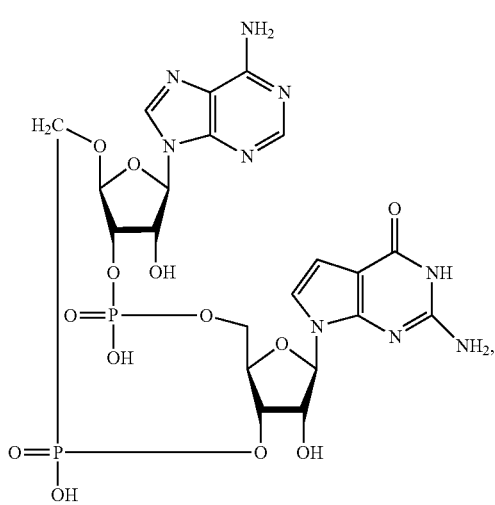
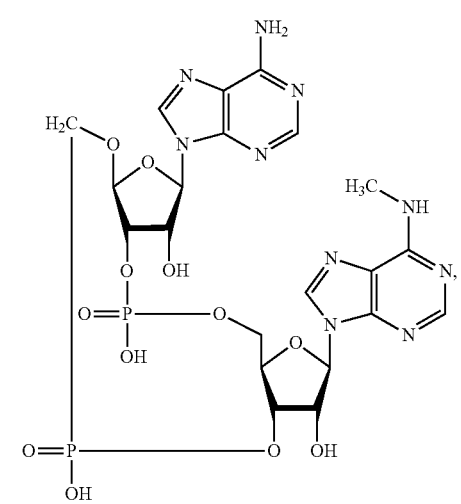

189
-continued
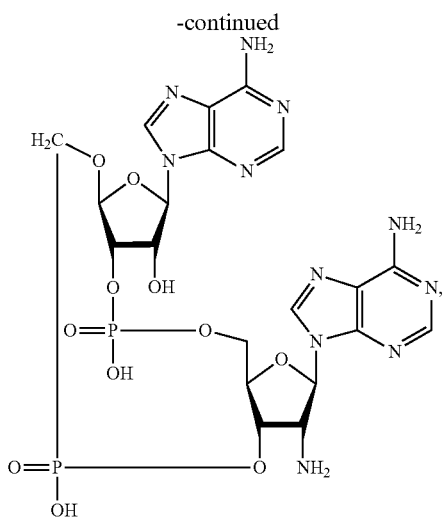
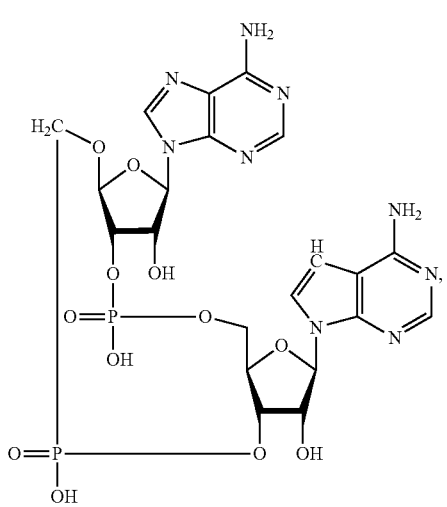
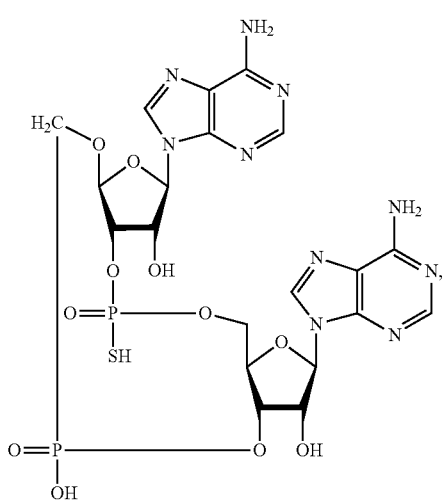
190
-continued
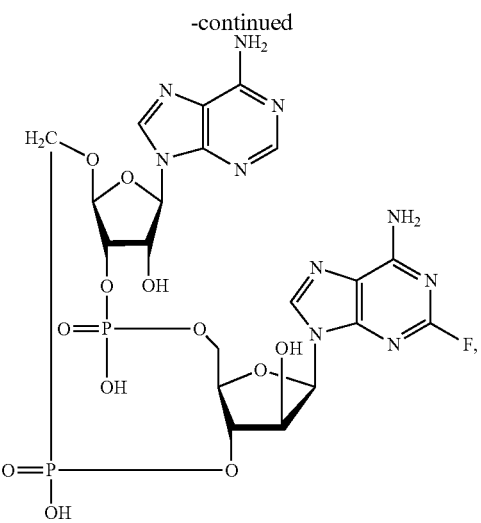
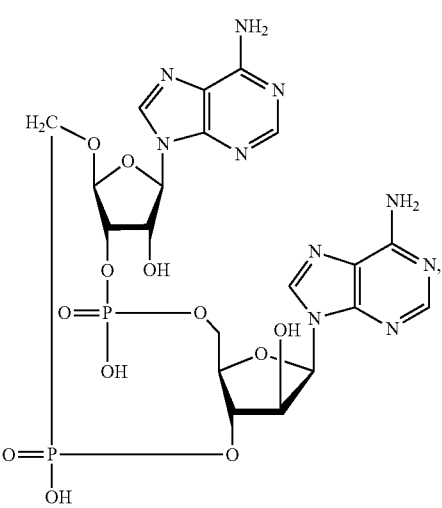
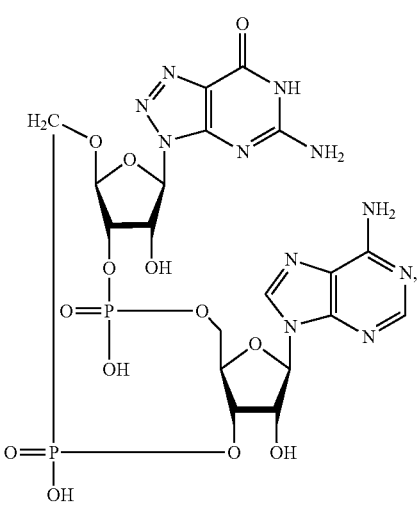

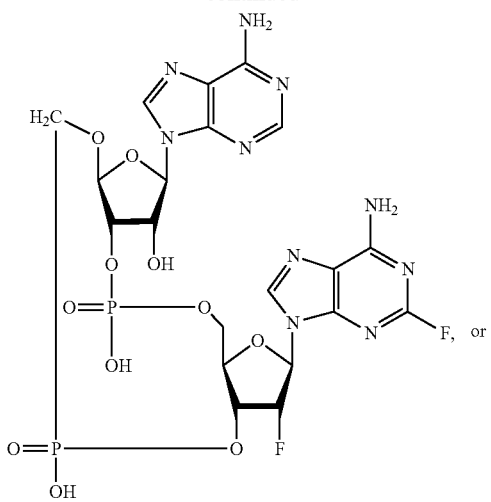

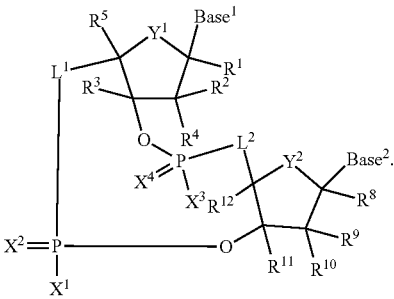

or pharmaceutically acceptable salt thereof.

16. A pharmaceutical composition comprising the compound of claim 1, or pharmaceutically acceptable salt thereof, and a pharmaceutically acceptable carrier, excipient, and/or diluent.

17. A method of treating a disease or disorder selected from the group consisting of psoriasis, actinic keratoses, seborrheic keratoses, warts, keloids, eczema, solid cancers, lymphomas, and viral infection caused by Hepadnaviridae virus, retrovirus or lentivirus in a human or animal, the method comprising administering to the human or animal in need thereof a therapeutically effective amount of a compound of formula (J):

or pharmaceutically acceptable salt thereof;
wherein
$L^1$ is —C($R^6R^7$)—O— and $L^2$ is —C($R^{13}R^{14}$)—O—,
$L^1$ is —C($R^6R^7$)—O— and $L^2$ is —O—C($R^{13}R^{14}$)—,
$L^1$ is —O—C($R^6R^7$)— and $L^2$ is —C($R^{13}R^{14}$)—O—,
$L^1$ is —C($R^6R^7$)—$K^1$—C($R^6R^7$)— and $L^2$ is —O—C($R^{13}R^{14}$)—,
$L^1$-O—C($R^6R^7$)— and $L^2$ is —C($R^{13}R^{14}$)—$K^1$—C($R^{13}R^{14}$)—,
$Y^1$ and $Y^2$ are each independently —O—, —S—, or —$CH_2$—;
$X^1$ and $X^3$ are each independently OH, SH, $OR^{15}$, $SR^{15}$, or $N(R^{15})_2$;
$X^2$ and $X^4$ are each independently O or S;
$R^1$, $R^5$, $R^8$ and $R^{12}$ are each independently H, CN, $N_3$, F, Cl, Br, I, $COOR^{15}$, $CON(R^{15})_2$, $C_1$-$C_6$ alkyl, $C_2$-$C_6$ alkenyl, $C_2$-$C_6$ alkynyl, $OR^{15}$, $SR^{15}$, or $N(R^{15})_2$;
$R^2$, $R^3$, $R^4$, $R^9$, $R^{10}$ and $R^{11}$ are each independently H, OH, F, Cl, Br, I, CN, $N_3$, $C_1$-$C_6$ alkyl, $C_2$-$C_6$ alkenyl, $C_2$-$C_6$ alkynyl, $OR^{15}$, $SR^{15}$, or $N(R^{15})_2$;
$R^6$, $R^7$, $R^{13}$ and $R^{14}$ are each independently H, CN, $N_3$, F, Cl, Br, I, $COOR^{15}$, $CON(R^{15})_2$, $OR^{15}$, $SR^{15}$, $N(R^{15})_2$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;
each $R^{15}$ is independently H, —C(=Z)$R^{16}$ —C(=Z)$OR^{16}$, —C(=Z)$SR^{16}$, —C(=Z)$N(R^{16})_2$, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;
each $R^{16}$ is independently H, $C_1$-$C_6$ alkyl, $C_2$-$C^6$ alkenyl, $C_2$-$C_6$ alkynyl, $C_3$-$C_7$ cycloalkyl, $C_7$-$C_{10}$ heterocycloalkyl, $C_6$-$C_{10}$ aryl, or $C_2$-$C_{10}$ heteroaryl;
each Z is independently O, S or $NR^{15}$;
$K^1$ is a variable that represents —O—, —S—, —S(O)—, —S(O)$_2$—, —NH—, or —$NR^{15}$—;
Base$^1$ and Base$^2$ are each independently;

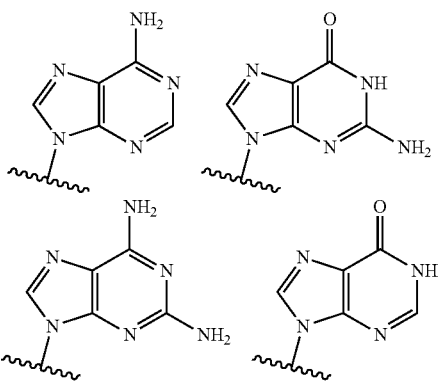

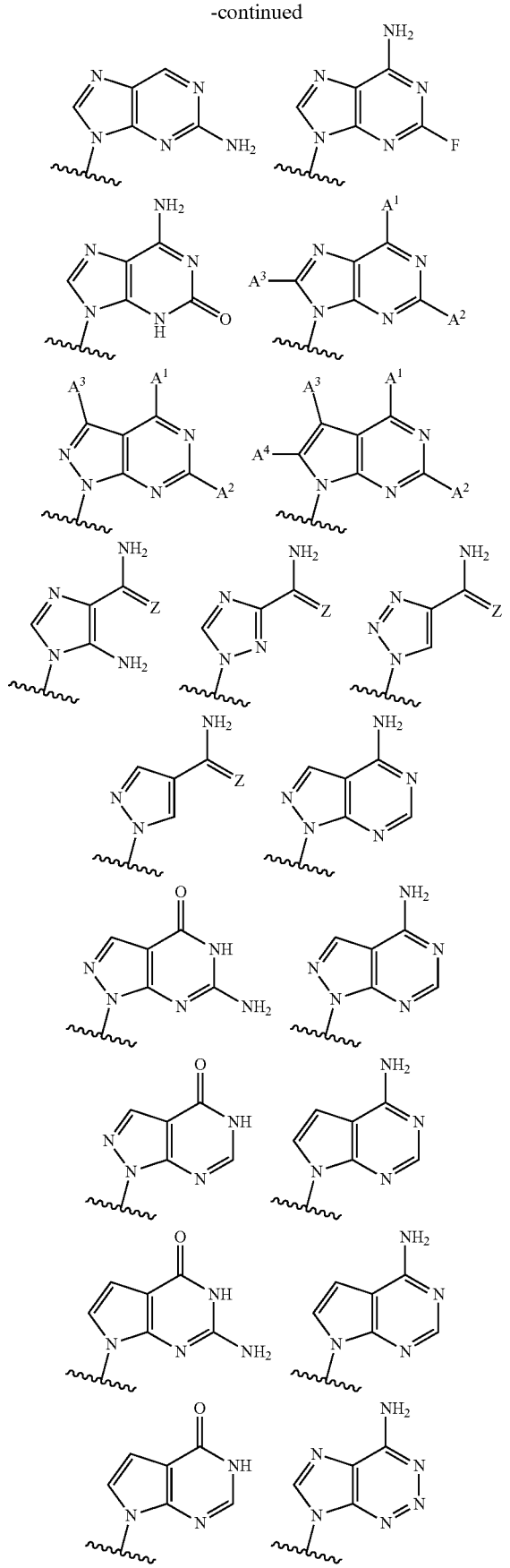
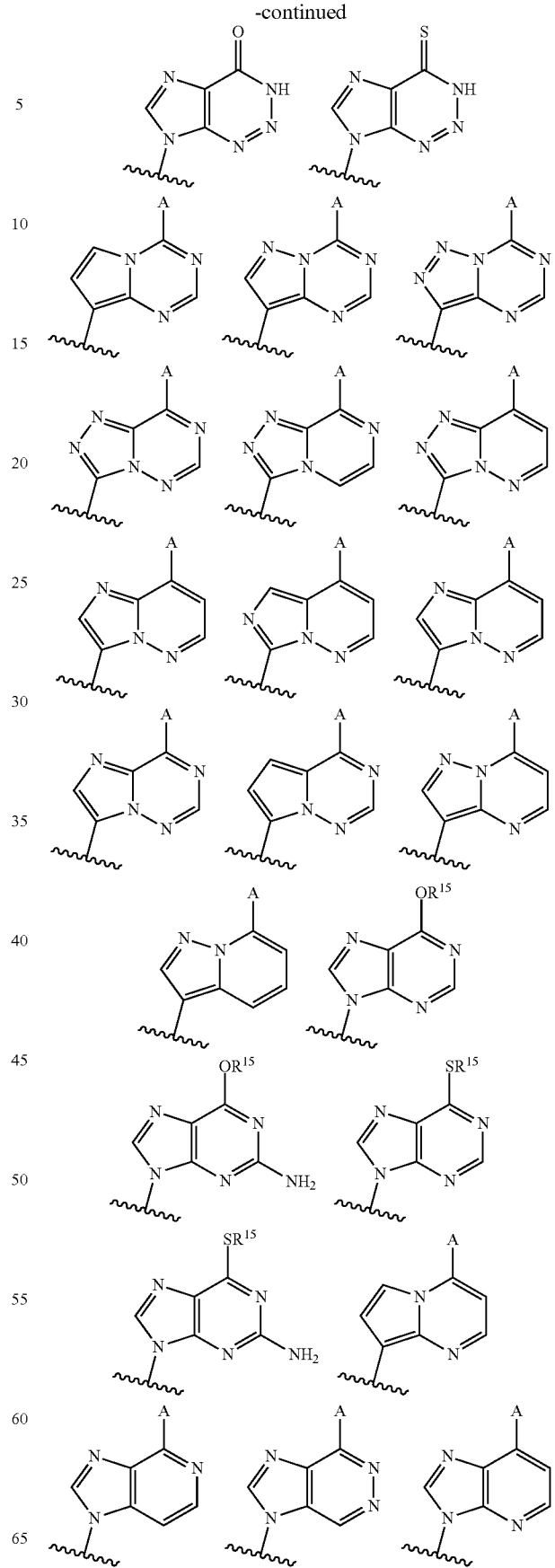

-continued

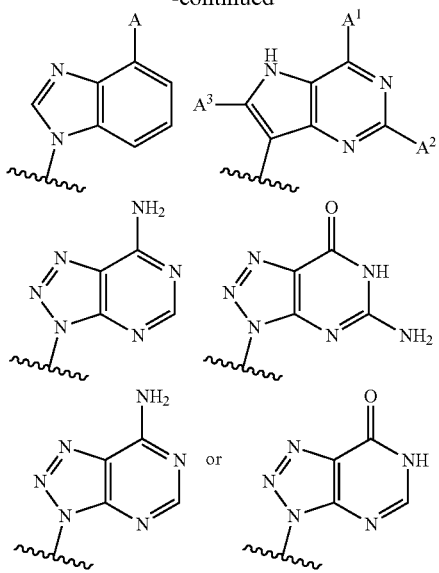

wherein
A, A¹, A², A³ and A⁴ are each independently H, OH, SH, F, Cl, Br, I, NH₂, OR¹⁵, SR¹⁵, NHR¹⁵, N(R¹⁵)₂, or R¹⁶; and wherein the $C_1$-$C_6$ alkyl, $C_2$-$C_6$ alkenyl, $C_2$-$C_6$ alkynyl, $C_2$-$C_{10}$ heterocycloalkyl, $C_6$-$C_{10}$ aryl, or $C_2$-$C_{10}$ heteroaryl independently in each instance is optionally substituted with 1, 2 or 3 —OH; —SH; —NH₂; =O; =NH; =S; halogen; —N₃; $C_6$-$C_{10}$ aryl optionally substituted with 1, 2 or 3 —OH, —CN, —O(C=O)OR$^B$, —O(C=O)R$^B$, or —COOR$^B$, unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)OR$^B$; O(C=O)R$^B$, or —COOR$^B$; wherein R$^B$ is H or unsubstituted $C_1$-$C_6$ alkyl.

18. A method of inducing the activity of STING adaptor protein, the method comprising administering a therapeutically effective amount of a compound of formula (J):

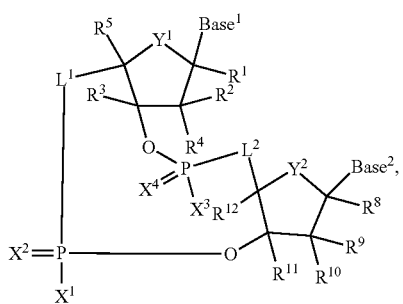

(J)

or pharmaceutically acceptable salt thereof,
wherein
L¹ is —C(R⁶R⁷)—O— and L² is —C(R¹³R¹⁴)—O—,
L¹ is —C(R⁶R⁷)—O— and L² is —O—C(R¹³R¹⁴)—,
L¹ is —O—C(R⁶R⁷)— and L² is —C(R¹³R¹⁴)—O—,
L¹ is —C(R⁶R⁷)—O— and L² is —C(R¹³R¹⁴)—O—,
L¹ is —C(R⁶R⁷)—K¹—C(R⁶R⁷)— and L² is —O—C(R¹³R¹⁴)—, L¹-O—C(R⁶R⁷)— and L² is —C(R¹³R¹⁴)—K¹—C(R¹³R¹⁴)—, Y¹ and Y² are each independently —O—, —S—, or —CH₂—;

X¹ and X³ are each independently OH, SH, OR¹⁵, SR¹⁵, or N(R¹⁵)₂;

X² and X⁴ are each independently O or S;

R¹, R⁵, R⁸ and R¹² are each independently H, CN, N₃, F, Cl, Br, I, COOR¹⁵, CON(R¹⁵)₂, $C_1$-$C_6$ alkyl, $C_2$-$C_6$ alkenyl, $C_2$-$C_6$ alkynyl, OR¹⁵, SR¹⁵, or N(R¹⁵)₂;

R², R³, R⁴, R⁹, R¹⁰ and R¹¹ are each independently H, OH, F, Cl, Br, I, CN, N₃, $C_1$-$C_6$, alkyl, $C_2$-$C_6$ alkenyl, $C_2$-$C_6$ alkynyl, OR¹⁵, SR¹⁵, or N(R¹⁵)₂;

R⁶, R⁷, R¹³ and R¹⁴ are each independently H, CN, N₃, F, Cl, Br, I, COOR¹⁵, CON(R¹⁵)₂, OR¹⁵, SR¹⁵, N(R¹⁵)₂, $C_1$-$C_6$ alkyl, $C_2$-$C_6$ alkenyl, $C_2$-$C_6$ alkynyl, $C_3$-$C_7$ cycloalkyl, $C_2$-$C_{10}$ heterocycloalkyl, $C_6$-$C_{10}$ aryl, or $C_2$-$C_{10}$ heteroaryl;

each R¹⁵ is independently H, —C(=Z)R¹⁶ —C(=Z)OR¹⁶, —C(=Z)SR¹⁶, —C(=Z)N(R¹⁶)₂, $C_1$-$C_6$ alkyl, $C_2$-$C_6$ alkenyl, $C_2$-$C_6$ alkynyl, $C_3$-$C_7$ cycloalkyl, $C_2$-$C^{10}$ heterocycloalkyl, $C_6$-$C_{10}$ aryl, or $C_2$-$C_{10}$ heteroaryl;

each R¹⁶ is independently H, $C_1$-$C_6$ alkyl, $C_2$-$C^6$ alkenyl, $C_2$-$C_6$ alkynyl, $C_3$-$C_7$ cycloalkyl, $C_7$-$C_{10}$ heterocycloalkyl, $C_6$-$C_{10}$ aryl, or $C_2$-$C_{10}$ heteroaryl;

each Z is independently O, S or NR¹⁵;

K¹ is a variable that represents —O—, —S—, —S(O)—, —S(O)₂—, —NH—, or —NR¹⁵—;

Base¹ and Base² are each independently;

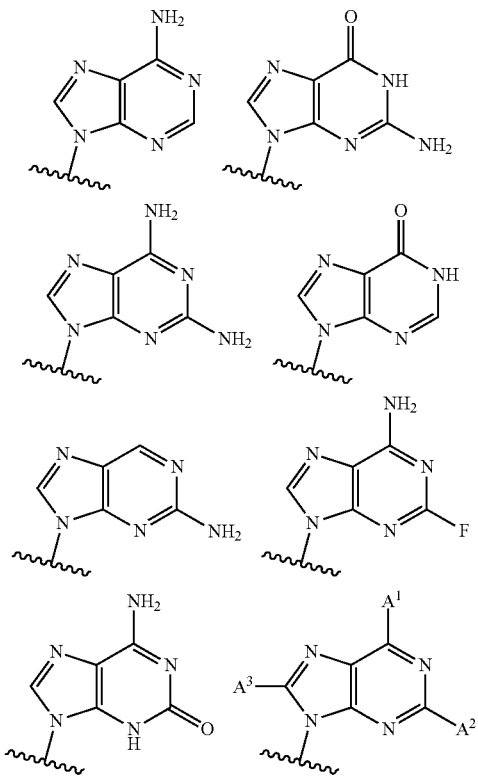

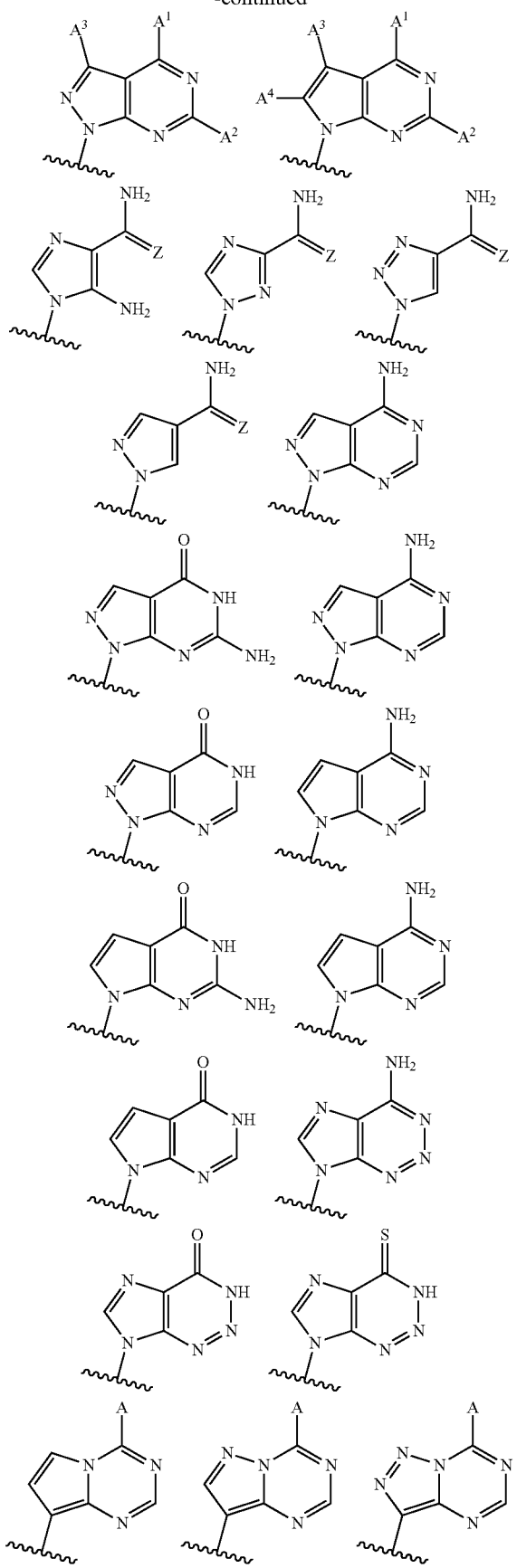
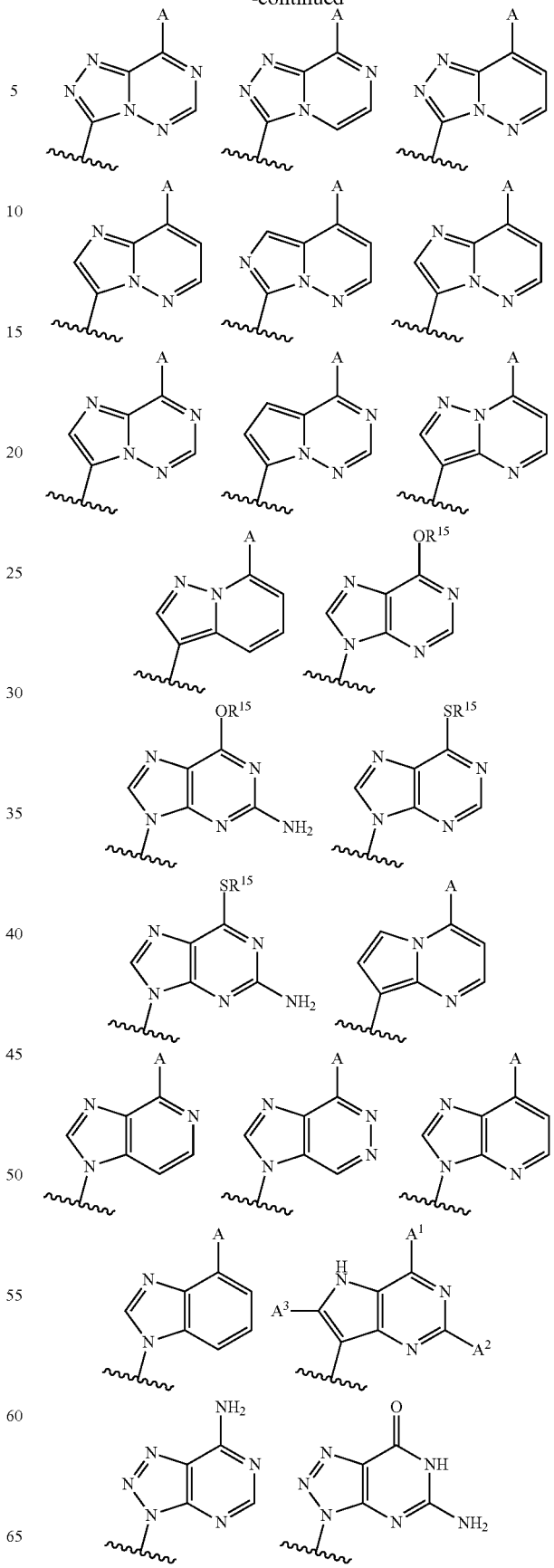

-continued

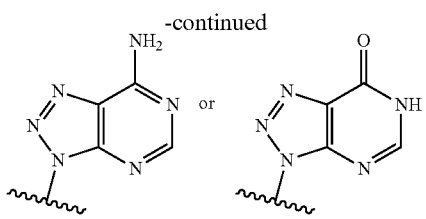

wherein
A, $A^1$, $A^2$, $A^3$ and $A^4$ are each independently H, OH, SH, F, Cl, Br, I, $NH_2$, $OR^{15}$, $SR^{15}$, $NHR^{15}$, $N(R^{15})_2$, or $R^{16}$; and
wherein the $C_1$-$C_6$ alkyl, $C_2$-$C_6$ alkenyl, $C_2$-$C_6$ alkynyl, $C_2$-$C_{10}$ heterocycloalkyl, $C_6$-$C_{10}$ aryl, or $C_2$-$C_{10}$ heteroaryl independently in each instance is optionally substituted with 1, 2 or 3 —OH; —SH; —$NH_2$; =O; =NH; =S; halogen; —$N_3$; $C_6$-$C_{10}$ aryl optionally substituted with 1, 2 or 3 —OH, —CN, —O(C=O)$OR^B$, —O(C=O)$R^B$, or —COO$R^B$, unsubstituted $C_1$-$C_6$ alkyl; unsubstituted $C_1$-$C_6$ alkoxy; unsubstituted $C_1$-$C_6$ alkylthio; unsubstituted $C_1$-$C_6$ alkylamino; unsubstituted $C_1$-$C_6$ dialkylamino; —CN; —O(C=O)$OR^B$; O(C=O)$R^B$, or —COO$R^B$; wherein $R^B$ is H or unsubstituted $C_1$-$C_6$ alkyl.

19. The method of claim 17, wherein the viral infection is selected from the group consisting of hepatitis B, infections caused by Rous sarcoma virus, simian retrovirus, bovine leukemia virus, human T-lymphotrophic virus including HTLV-1, HTLV-2, and HTLV-3, murine leukemia virus, feline leukemia virus, human immunodeficiency virus including HIV-1 and HIV-2, simian immunodeficiency virus, equine infectious anemia virus, bovine immunodeficiency virus, rabbit endogenous lentivirus type K, and feline immunodeficiency virus.

20. The method of claim 17, cancer is selected from the group consisting of adrenal cancer, bladder cancer, bone cancer, brain cancer, breast cancer, colon cancer, colorectal cancer, eye cancer, head-and-neck cancer, kidney cancer, renal cell carcinoma, liver cancer, lung cancer, non-small cell lung cancer, ovarian cancer, pancreatic cancer, prostate cancer, squamous cell carcinoma, melanoma, thyroid cancer, uterine cancer, vaginal cancer, Burkitt's lymphoma, Hodgkin's lymphoma, non-Hodgkin's lymphoma, indolent non-Hodgkin's lymphoma, refractory indolent non-Hodgkin's lymphoma, multiple myeloma, chronic myeloid leukemia, acute lymphocytic leukemia, B-cell acute lymphocytic leukemia, acute myeloid leukemia, chronic lymphocytic leukemia, small lymphocytic lymphoma, myelodysplastic syndrome, mantle cell lymphoma, follicular lymphoma, Waldestrom's macroglobulinemia, T-cell lymphoma, B-cell lymphoma, diffuse large B-cell lymphoma, and marginal zone lymphoma.

* * * * *

SEQUENCE LISTING

<160> NUMBER OF SEQ ID NOS: 12

<210> SEQ ID NO 1
<211> LENGTH: 75
<212> TYPE: DNA
<213> ORGANISM: Artificial Sequence
<220> FEATURE:
<223> OTHER INFORMATION: Synthetic construct

<400> SEQUENCE: 1
aaagatcttg gaaagtgaaa ccttggaaaa cgaaactgga caaagggaaa ctgcagaaac    60
tgaaacaaag cttaa    75

<210> SEQ ID NO 2
<211> LENGTH: 75
<212> TYPE: DNA
<213> ORGANISM: Artificial Sequence
<220> FEATURE:
<223> OTHER INFORMATION: Synthetic construct

<400> SEQUENCE: 2
ttaagctttg tttcagtttc tgcagtttcc ctttgtccag tttcgttttc caaggtttca    60
ctttccaaga tcttt    75

<210> SEQ ID NO 3
<211> LENGTH: 20
<212> TYPE: DNA
<213> ORGANISM: Artificial Sequence
<220> FEATURE:
<223> OTHER INFORMATION: Synthetic construct

<400> SEQUENCE: 3
tgcttgctca actctacgtc    20

<210> SEQ ID NO 4
<211> LENGTH: 20
<212> TYPE: DNA
<213> ORGANISM: Artificial Sequence
<220> FEATURE:
<223> OTHER INFORMATION: Synthetic construct

<400> SEQUENCE: 4
gtggtttgtc caaactcatc    20

<210> SEQ ID NO 5
<211> LENGTH: 31
<212> TYPE: DNA
<213> ORGANISM: Artificial Sequence
<220> FEATURE:
<223> OTHER INFORMATION: Synthetic construct

<400> SEQUENCE: 5
gtgggatccg ccccagctga gatctctgca g    31

<210> SEQ ID NO 6
<211> LENGTH: 38
<212> TYPE: DNA
<213> ORGANISM: Artificial Sequence

```
<220> FEATURE:
<223> OTHER INFORMATION: Synthetic construct

<400> SEQUENCE: 6
tatgcggccg cctattacac agtaacctct tccttttc                              38

<210> SEQ ID NO 7
<211> LENGTH: 330
<212> TYPE: DNA
<213> ORGANISM: Artificial Sequence
<220> FEATURE:
<223> OTHER INFORMATION: Synthetic construct

<400> SEQUENCE: 7
atgtcgcatc accatcatca tcaccaccat gggatgtcgg actcagaagt caatcaagaa      60
gctaagccag aggtcaagcc agaagtcaag cctgagactc acatcaattt aaaggtgtcc    120
gatggatctt cagagatctt cttcaagatc aaaaagacca ctcctttaag aaggctgatg    180
gaagcgttcg ctaaaagaca gggtaaggaa atggactcct taagattctt gtacgacggt    240
attagaattc aagctgatca gacccctgaa gatttggaca tggaggataa cgatattatt    300
gaggctcacc gcgaacagat tggtggatcc                                      330

<210> SEQ ID NO 8
<211> LENGTH: 110
<212> TYPE: PRT
<213> ORGANISM: Artificial Sequence
<220> FEATURE:
<223> OTHER INFORMATION: Synthetic construct

<400> SEQUENCE: 8
```

Met Ser His His His His His His His Gly Met Ser Asp Ser Glu
1               5                   10                  15

Val Asn Gln Glu Ala Lys Pro Glu Val Lys Pro Glu Val Lys Pro Glu
            20                  25                  30

Thr His Ile Asn Leu Lys Val Ser Asp Gly Ser Ser Glu Ile Phe Phe
        35                  40                  45

Lys Ile Lys Lys Thr Thr Pro Leu Arg Arg Leu Met Glu Ala Phe Ala
50                  55                  60

Lys Arg Gln Gly Lys Glu Met Asp Ser Leu Arg Phe Leu Tyr Asp Gly
65                  70                  75                  80

Ile Arg Ile Gln Ala Asp Gln Thr Pro Glu Asp Leu Asp Met Glu Asp
                85                  90                  95

Asn Asp Ile Ile Glu Ala His Arg Glu Gln Ile Gly Gly Ser
            100                 105                 110

```
<210> SEQ ID NO 9
<211> LENGTH: 204
<212> TYPE: PRT
<213> ORGANISM: Artificial Sequence
<220> FEATURE:
<223> OTHER INFORMATION: Synthetic construct

<400> SEQUENCE: 9
```

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
            20                  25                  30

Leu Pro Glu Leu Gln Ala Arg Ile Arg Thr Tyr Asn Gln His Tyr Asn
        35                  40                  45

```
Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Gly Asp Arg Ala Gly Ile
                85                  90                  95

Lys Asp Arg Val Tyr Ser Asn Ser Ile Tyr Glu Leu Leu Glu Asn Gly
                100                 105                 110

Gln Arg Ala Gly Thr Cys Val Leu Glu Tyr Ala Thr Pro Leu Gln Thr
                115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Arg Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
                180                 185                 190

His Leu Arg Gln Glu Glu Lys Glu Glu Val Thr Val
                195                 200

<210> SEQ ID NO 10
<211> LENGTH: 204
<212> TYPE: PRT
<213> ORGANISM: Artificial Sequence
<220> FEATURE:
<223> OTHER INFORMATION: Synthetic construct

<400> SEQUENCE: 10

Ala Pro Ala Glu Ile Ser Ala Val Cys Glu Lys Gly Asn Phe Asn Val
1               5                   10                  15

Ala His Gly Leu Ala Trp Ser Tyr Tyr Ile Gly Tyr Leu Arg Leu Ile
                20                  25                  30

Leu Pro Glu Leu Gln Ala Arg Ile Arg Thr Tyr Asn Gln His Tyr Asn
            35                  40                  45

Asn Leu Leu Arg Gly Ala Val Ser Gln Arg Leu Tyr Ile Leu Leu Pro
    50                  55                  60

Leu Asp Cys Gly Val Pro Asp Asn Leu Ser Met Ala Asp Pro Asn Ile
65                  70                  75                  80

Arg Phe Leu Asp Lys Leu Pro Gln Gln Thr Ala Asp Arg Ala Gly Ile
                85                  90                  95

Lys Asp Arg Val Tyr Ser Asn Ser Ile Tyr Glu Leu Leu Glu Asn Gly
                100                 105                 110

Gln Arg Ala Gly Thr Cys Val Leu Glu Tyr Ala Thr Pro Leu Gln Thr
                115                 120                 125

Leu Phe Ala Met Ser Gln Tyr Ser Gln Ala Gly Phe Ser Arg Glu Asp
    130                 135                 140

Arg Leu Glu Gln Ala Lys Leu Phe Cys Gln Thr Leu Glu Asp Ile Leu
145                 150                 155                 160

Ala Asp Ala Pro Glu Ser Gln Asn Asn Cys Arg Leu Ile Ala Tyr Gln
                165                 170                 175

Glu Pro Ala Asp Asp Ser Ser Phe Ser Leu Ser Gln Glu Val Leu Arg
                180                 185                 190

His Leu Arg Gln Glu Glu Lys Glu Glu Val Thr Val
                195                 200
```

<210> SEQ ID NO 11
<211> LENGTH: 502
<212> TYPE: PRT
<213> ORGANISM: Artificial Sequence
<220> FEATURE:
<223> OTHER INFORMATION: Synthetic construct

<400> SEQUENCE: 11

```
Met Asn Ser Ser His His His His His His Met Gln Tyr Lys Leu Ile
1               5                   10                  15

Leu Asn Gly Lys Thr Leu Lys Gly Glu Thr Thr Thr Glu Ala Val Asp
            20                  25                  30

Ala Ala Thr Ala Glu Lys Val Leu Lys Gln Tyr Ala Asn Asp Asn Gly
        35                  40                  45

Val Asp Gly Glu Trp Thr Tyr Asp Asp Ala Thr Lys Thr Phe Thr Val
    50                  55                  60

Thr Glu Asn Asn Asn Asn Asn Asn Asn Asn Glu Asn Leu Tyr
65                  70                  75                  80

Phe Gln Gly Met Arg Met Thr Trp Asn Phe His Gln Tyr Tyr Thr Asn
                85                  90                  95

Arg Asn Asp Gly Leu Met Gly Lys Leu Val Leu Thr Asp Glu Glu Lys
            100                 105                 110

Asn Asn Leu Lys Ala Leu Arg Lys Ile Ile Arg Leu Arg Thr Arg Asp
        115                 120                 125

Val Phe Glu Glu Ala Lys Gly Ile Ala Lys Ala Val Lys Lys Ser Ala
    130                 135                 140

Leu Thr Phe Glu Ile Ile Gln Glu Lys Val Ser Thr Thr Gln Ile Lys
145                 150                 155                 160

His Leu Ser Asp Ser Glu Gln Arg Glu Val Ala Lys Leu Ile Tyr Glu
                165                 170                 175

Met Asp Asp Asp Ala Arg Asp Glu Phe Leu Gly Leu Thr Pro Arg Phe
            180                 185                 190

Trp Thr Gln Gly Ser Phe Gln Tyr Asp Thr Leu Asn Arg Pro Phe Gln
        195                 200                 205

Pro Gly Gln Glu Met Asp Ile Asp Asp Gly Thr Tyr Met Pro Met Pro
    210                 215                 220

Ile Phe Glu Ser Glu Pro Lys Ile Gly His Ser Leu Leu Ile Leu Leu
225                 230                 235                 240

Val Asp Ala Ser Leu Lys Ser Leu Val Ala Glu Asn His Gly Trp Lys
                245                 250                 255

Phe Glu Ala Lys Gln Thr Cys Gly Arg Ile Lys Ile Glu Ala Glu Lys
            260                 265                 270

Thr His Ile Asp Val Pro Met Tyr Ala Ile Pro Lys Asp Glu Phe Gln
        275                 280                 285

Lys Lys Gln Ile Ala Leu Glu Ala Asn Arg Ser Phe Val Lys Gly Ala
    290                 295                 300

Ile Phe Glu Ser Tyr Val Ala Asp Ser Ile Thr Asp Asp Ser Glu Thr
305                 310                 315                 320

Tyr Glu Leu Asp Ser Glu Asn Val Asn Leu Ala Leu Arg Glu Gly Asp
                325                 330                 335

Arg Lys Trp Ile Asn Ser Asp Pro Lys Ile Val Glu Asp Trp Phe Asn
            340                 345                 350

Asp Ser Cys Ile Arg Ile Gly Lys His Leu Arg Lys Val Cys Arg Phe
        355                 360                 365
```

```
Met Lys Ala Trp Arg Asp Ala Gln Trp Asp Val Gly Gly Pro Ser Ser
            370                 375                 380

Ile Ser Leu Met Ala Ala Thr Val Asn Ile Leu Asp Ser Val Ala His
385                 390                 395                 400

Asp Ala Ser Asp Leu Gly Glu Thr Met Lys Ile Ala Lys His Leu
                405                 410                 415

Pro Ser Glu Phe Ala Arg Gly Val Glu Ser Pro Asp Ser Thr Asp Glu
                420                 425                 430

Lys Pro Leu Phe Pro Pro Ser Tyr Lys His Gly Pro Arg Glu Met Asp
                435                 440                 445

Ile Met Ser Lys Leu Glu Arg Leu Pro Glu Ile Leu Ser Ser Ala Glu
    450                 455                 460

Ser Ala Asp Ser Lys Ser Glu Ala Leu Lys Lys Ile Asn Met Ala Phe
465                 470                 475                 480

Gly Asn Arg Val Thr Asn Ser Glu Leu Ile Val Leu Ala Lys Ala Leu
                485                 490                 495

Pro Ala Phe Ala Gln Glu
            500

<210> SEQ ID NO 12
<211> LENGTH: 365
<212> TYPE: PRT
<213> ORGANISM: Artificial sequence
<220> FEATURE:
<223> OTHER INFORMATION: Synthetic polypeptide

<400> SEQUENCE: 12

Met Glu Glu Asn Lys Gln Arg Val Lys Ser Met Ile Asn Ile Leu Gln
1               5                   10                  15

Leu Val Ala Pro Gly Thr Pro Leu Arg Glu Gly Ile Asp Asn Val Leu
                20                  25                  30

Arg Ala Gln Thr Gly Gly Leu Ile Val Leu Gly Tyr Asn Glu Gln Ile
            35                  40                  45

Lys Ser Ile Val Asp Gly Gly Phe His Ile Asn Cys Ala Phe Ser Pro
    50                  55                  60

Ala Ser Leu Tyr Glu Leu Ala Lys Met Asp Gly Ala Leu Ile Leu Asn
65                  70                  75                  80

Glu Thr Gly Ser Lys Ile Leu Ile Ala Asn Ala Gln Leu Val Pro Asp
                85                  90                  95

Ser Ser Ile Asp Ser Ile Glu Thr Gly Met Arg His Arg Thr Ala Glu
                100                 105                 110

Arg Val Ala Lys Gln Thr Gly Ser Leu Val Val Ala Ile Ser Gln Arg
            115                 120                 125

Arg Asn Val Ile Thr Leu Tyr Gln Gly Asn Leu Arg Tyr Thr Leu Lys
    130                 135                 140

Asp Ile Gly Val Ile Leu Thr Lys Ala Asn Gln Ala Ile Gln Thr Leu
145                 150                 155                 160

Glu Lys Tyr Lys Ala Val Trp Asn Asp Gly Ile Thr Asn Leu Gly Ile
                165                 170                 175

Leu Glu Phe Glu Glu Val Val Thr Met Ser Glu Val Val His Val Leu
                180                 185                 190

His Ser Val Glu Met Val Leu Arg Ile Lys Asn Glu Ile Leu Ser Tyr
            195                 200                 205

Ile His Glu Leu Gly Thr Glu Gly Arg Leu Ile Arg Leu Gln Leu Thr
    210                 215                 220
```

| | | | | | | | | | | | | | | |
|---|---|---|---|---|---|---|---|---|---|---|---|---|---|---|
| Glu 225 | Leu | Leu | Ala | Asp 230 | Leu | Glu | Ala | Glu | Ala 235 | Ala | Leu | Leu | Ile | Lys Asp 240 |
| Tyr | His | Gln | Glu | Lys 245 | Thr | Gln | Asp | His | His 250 | Gln | Ile | Leu | Lys | Lys Leu 255 |
| Gln | Asp | Leu | Ala | Asn 260 | Thr | Gln | Leu | Leu | Glu 265 | Asp | Ser | Asp | Leu 270 | Val Lys |
| Leu | Leu | Gly 275 | Tyr | Pro | Gly | Gln | Thr 280 | Ser | Leu | Glu | Glu | Ser 285 | Val | Thr Pro |
| Arg | Gly 290 | Tyr | Arg | Ile | Thr | Ser 295 | Lys | Ile | Ser | Arg | Val 300 | Pro | Pro | Leu Ile |
| Ile 305 | Glu | Asn | Leu | Ile | Asn 310 | Arg | Phe | Lys | Thr | Leu 315 | Gln | Gly | Val | Cys Arg 320 |
| Ala | Thr | Ile | Asn | Glu 325 | Leu | Asp | Asp | Val | Glu 330 | Gly | Ile | Gly | Glu 335 | Val Arg |
| Ala | Lys | Lys | Ile 340 | Arg | Glu | Gly | Leu | Lys 345 | Arg | Ile | Gln | Glu 350 | His | Leu Tyr |
| Met | Ser | Arg 355 | His | Asn | Leu | Glu | His 360 | His | His | His | His 365 | | | |